(12) United States Patent
Cisar et al.

(10) Patent No.: US 9,994,537 B2
(45) Date of Patent: *Jun. 12, 2018

(54) PIPERAZINE CARBAMATES AND METHODS OF MAKING AND USING SAME

(71) Applicant: Abide Therapeutics, Inc., San Diego, CA (US)

(72) Inventors: Justin S. Cisar, San Diego, CA (US); Cheryl A. Grice, Encinitas, CA (US); Todd K. Jones, Solana Beach, CA (US); Olivia D. Weber, San Diego, CA (US); Dong-Hui Wang, San Diego, CA (US)

(73) Assignee: ABIDE THERAPEUTICS, INC., San Diego, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/672,165

(22) Filed: Aug. 8, 2017

(65) Prior Publication Data

US 2017/0334874 A1   Nov. 23, 2017

Related U.S. Application Data

(63) Continuation of application No. 15/072,229, filed on Mar. 16, 2016, now Pat. No. 9,771,341.

(60) Provisional application No. 62/135,072, filed on Mar. 18, 2015.

(51) Int. Cl.

| | |
|---|---|
| *C07D 295/205* | (2006.01) |
| *C07D 207/08* | (2006.01) |
| *C07D 471/10* | (2006.01) |
| *C07D 417/04* | (2006.01) |
| *C07D 403/04* | (2006.01) |
| *C07D 401/04* | (2006.01) |
| *C07D 295/26* | (2006.01) |
| *C07D 265/30* | (2006.01) |
| *C07D 207/12* | (2006.01) |
| *C07D 211/38* | (2006.01) |
| *C07D 211/58* | (2006.01) |
| *C07D 207/14* | (2006.01) |
| *C07D 211/14* | (2006.01) |
| *C07D 498/08* | (2006.01) |
| *C07D 211/62* | (2006.01) |
| *C07D 487/04* | (2006.01) |
| *C07D 207/16* | (2006.01) |

(52) U.S. Cl.
CPC ....... *C07D 295/205* (2013.01); *C07D 207/08* (2013.01); *C07D 207/12* (2013.01); *C07D 207/14* (2013.01); *C07D 207/16* (2013.01); *C07D 211/14* (2013.01); *C07D 211/38* (2013.01); *C07D 211/58* (2013.01); *C07D 211/62* (2013.01); *C07D 265/30* (2013.01); *C07D 295/26* (2013.01); *C07D 401/04* (2013.01); *C07D 403/04* (2013.01); *C07D 417/04* (2013.01); *C07D 471/10* (2013.01); *C07D 487/04* (2013.01); *C07D 498/08* (2013.01)

(58) Field of Classification Search
CPC .. C07D 207/08; C07D 207/12; C07D 207/14; C07D 207/16; C07D 211/14; C07D 211/38; C07D 211/58; C07D 211/62; C07D 265/30; C07D 295/205; C07D 295/26; C07D 401/04; C07D 403/04; C07D 417/04; C07D 471/10; C07D 487/04; C07D 498/08

See application file for complete search history.

(56) References Cited

U.S. PATENT DOCUMENTS

| | | |
|---|---|---|
| 9,133,148 B2 | 9/2015 | Cisar et al. |
| 9,487,495 B2 | 11/2016 | Cisar et al. |
| 2011/0275650 A1 | 11/2011 | Cravatt et al. |
| 2014/0357693 A1 | 12/2014 | Shaul et al. |
| 2016/0272602 A1 | 9/2016 | Cisar et al. |
| 2017/0073320 A1 | 3/2017 | Cisar et al. |

FOREIGN PATENT DOCUMENTS

| | | |
|---|---|---|
| DE | 1802739 A1 | 6/1969 |
| JP | S6183073 A | 4/1986 |
| JP | 2000500448 A | 1/2000 |
| JP | 2008500270 A | 1/2008 |
| JP | 2008521768 A | 6/2008 |
| JP | 2009523729 A | 6/2009 |
| JP | 2010513447 A | 4/2010 |
| RU | 2167150 C2 | 5/2001 |
| WO | WO-8911794 A1 | 12/1989 |
| WO | WO-9311097 A1 | 6/1993 |
| WO | WO-9517439 A2 | 6/1995 |
| WO | WO-9800408 A1 | 1/1998 |
| WO | WO-0125188 A1 | 4/2001 |
| WO | WO-0234382 A1 | 5/2002 |
| WO | WO-2005063698 A1 | 7/2005 |

(Continued)

OTHER PUBLICATIONS

Berge et al. Pharmaceutical Salts. Journal of Pharmaceutical Sciences 66(1):1-19 (Jan. 1977).

(Continued)

*Primary Examiner* — Umamaheswari Ramachandran
(74) *Attorney, Agent, or Firm* — Wilson, Sonsini, Goodrich & Rosati

(57) ABSTRACT

Provided herein are piperazine carbamates and pharmaceutical compositions comprising said compounds. The subject compounds and compositions are useful as modulators of MAGL and/or ABHD6. Furthermore, the subject compounds and compositions are useful for the treatment of pain.

16 Claims, No Drawings

(56) References Cited

FOREIGN PATENT DOCUMENTS

| | | |
|---|---|---|
| WO | WO-2005070910 A2 | 8/2005 |
| WO | WO-2005080363 A1 | 9/2005 |
| WO | WO-2006074025 A1 | 7/2006 |
| WO | WO-2008106047 A2 | 9/2008 |
| WO | WO-2009141238 A1 | 11/2009 |
| WO | WO-2010009207 A1 | 1/2010 |
| WO | WO-2010056309 | 5/2010 |
| WO | WO-2010111050 A1 | 9/2010 |
| WO | WO-2010129497 A1 | 11/2010 |
| WO | WO-2011054795 A1 | 5/2011 |
| WO | WO-2011151808 A1 | 12/2011 |
| WO | WO-2013102431 A1 | 7/2013 |
| WO | WO-2013103973 A1 | 7/2013 |
| WO | WO-2013142307 A1 | 9/2013 |

OTHER PUBLICATIONS

Blankman et al. A comprehensive profile of brain enzymes that hydrolyze the endocannabinoid 2-arachidonoylglycerol. Chem. Biol. 14:1347-1356 (2007).

Chang et al. Highly Selective Inhibitors of Monoacylglycerol Lipase Bearing a Reactive Group that is Bioisosteric with Endocannabinoid Substrates. ChemBiol 19(5):579-588 (2012).

Chang et al. Proteome-wide reactivity profiling identifies diverse carbamate chemotypes tuned for serine hydrolase inhibition. ACS Chem Biol 8:1590-1599 (2013).

Fowler. Monoacylglycerol lipase—a target for drug development? Br Pharmacol. 166:1568-1585 (2012).

King et al. URB602 inhibits monoacylglycerol lipase and selectively blocks 2-arachidonoylglycerol degradation in intact brain slices. Chem Biol 14(12):1357-1365 (2007).

Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).

Long et al. Characterization of tunable piperidine and piperazine carbamates as inhibitors of endocannabinoid hydrolases. J Med chem 53(4):1830-1842 (2010).

Long et al. Selective blockade of 2-arachidonoylglycerol hydrolysis produces cannabinoid behavioral effects. Nat Chem Biol. 5(1):37-44 (2009).

Meanwell et al. Synopsis of some recent tactical application of bioisosteres in drug design. J Med Chem 54(8):2529-2591 (2011).

Mukhamadieva et al. Search for New Drugs Synthesis and Biological Activity of O-Carbamoylated 1,1,1,3,3,3-Hexafluoroisopropanols As New Specific Inhibitors of Carboxylesterase. Pharmaceutical Chemistry Journal 46(8):461-464 (2012).

Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).

Patani et al. Bioisosterism: A Rational Approach in Drug Design. Chem. Rev. 96:3147-3176 (1996).

PCT/US2013/020551 International Preliminary Report on Patentability dated Jul. 17, 2014.

PCT/US2013/020551 International Search Report dated May 21, 2013.

PCT/US2016/022690 International Search Report and Written Opinion dated Aug. 30, 2016.

PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).

PubChem CID 3469875. http://pubchem.ncbi.nlm.nih.gov/summary/summary.cgi?cid=3469875Retrieved Mar. 4, 2013 Create Date: Sep. 8, 2005 (11 pgs.).

PubChem CID 669902 http://pubchem.ncbi.nlm.nih.gov/summary/summary.cgi?cid=669902 Retrieved May 1, 2013 Create Date: Jul. 8, 2005 (4 pgs.).

Rautio et al. Prodrugs: design and clinical applications. Nat Rev Drug Discov 7(3):255-270 (2008).

Science IP Report dated Dec. 11, 2014 (126 pgs.).

Silverman. The Organic Chemistry of Drug Design and Drug Action. Academic Press (pp. 15-22) (1992).

South. Synthesis and Reactions of Halogenated Thiazole Isocyanates. Journal of Heterocyclic Chemistry 28:1003-1011 (1991).

Studnev et al. Synthesis, Antibacterial and Immunotropic Activity of Poly(fluoroalkyl-N-arylcarbamates. Pharmaceutical Chemistry Journal 36(12):654-657 (2002).

Thornber. Isosterism and molecular modification in drug design. Chem Soc Rev 8:563-580 (1979).

Urry et al. Free-radical chain addition reactions of aldehydes with perfluoro ketones and chloro perfluoro ketones. J Org Chem 32(2):347-352 (1967).

U.S. Appl. No. 14/369,982 Office Action dated Mar. 8, 2016.

U.S. Appl. No. 14/369,982 Office Action dated Oct. 22, 2015.

U.S. Appl. No. 14/599,105 Office Action dated Apr. 8, 2015.

U.S. Appl. No. 15/072,229 First Action Interview dated Sep. 19, 2016.

U.S. Appl. No. 15/072,229 Office Action dated Jan. 10, 2017.

U.S. Appl. No. 15/272,313 Office Action dated Apr. 10, 2017.

U.S. Appl. No. 15/272,313 Office Action dated Aug. 25, 2017.

PIPERAZINE CARBAMATES AND METHODS OF MAKING AND USING SAME

CROSS-REFERENCE

This application is a continuation of U.S. patent application Ser. No. 15/072,229, filed Mar. 16, 2016, which claims benefit of U.S. Provisional Application No. 62/135,072, filed on Mar. 18, 2015, all of which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. The serine hydrolase α-β-hydrolase domain 6 (ABHD6) is another lipid mediator.

BRIEF SUMMARY OF THE INVENTION

This disclosure provides, for example, compounds and compositions which are modulators of MAGL and/or ABHD6, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL and/or ABHD6 activity in warm-blooded animals such as humans.

One embodiment provides a compound of Formula (I):

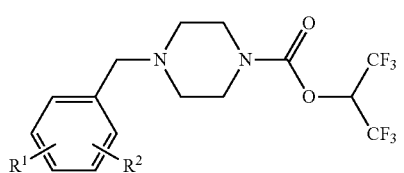

Formula (I)

wherein:
$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;
$R^2$ is —$NR^5R^6$, -alkyl($NR^{14}R^{15}$), or —$OR^7$;
each $R^3$ is independently selected from H, $C_{1-6}$ alkyl, haloalkyl, and aminoalkyl;
each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;
$R^5$ and $R^6$, together with the nitrogen to which they are attached, form
(i) a monocyclic heterocycle, a fused bicyclic heterocycle, or a spirocycle; or
(ii) a 7-8 membered bridged heterocyclic ring optionally containing an additional O, N, or S;
wherein the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle, the fused bicyclic heterocycle, or the spirocycle optionally contains an additional O, N, or S; and
the 7-8 membered bridged heterocyclic ring is optionally substituted with one or more substituents independently selected from halogen, —CN, oxo, optionally substituted $C_{1-6}$ alkyl, optionally substituted aryl, optionally substituted heteroaryl, optionally substituted heterocycle, optionally substituted cycloalkyl, —$S(O)_wR^{11}$, —$OR^3$, —$OR^7$, —$C(O)R^9$, —$C(O)OR^9$, —$C(O)NR^9R^{10}$, —$NR^9R^{10}$, —$NR^8C(O)R^9$, —$NR^8SO_2R^9$, —$NR^8C(O)OR^9$, and —$NR^8C(O)NR^9R^{10}$;
$R^7$ is alkynyl or (alkynyl)alkyl;
each $R^8$ is independently selected from H, optionally substituted alkyl, optionally substituted cycloalkyl, optionally substituted aryl, optionally substituted heteroaryl, and optionally substituted heterocycloalkyl;
each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;
each $R^{11}$ is independently selected from optionally substituted alkyl, optionally substituted cycloalkyl, optionally substituted aryl, optionally substituted heteroaryl, and optionally substituted heterocycloalkyl;
$R^{12}$ and $R^{13}$ together with the nitrogen to which they are attached form an optionally substituted heterocycle optionally containing an additional O, N, or S;
$R^{14}$ and $R^{15}$ together with the nitrogen to which they are attached form an optionally substituted heterocycle optionally containing an additional O, N, or S; and
w is 0, 1, or 2;
or a solvate, hydrate, tautomer, N-oxide, or pharmaceutically acceptable salt thereof.

Another embodiment provides a compound of Formula (Ia):

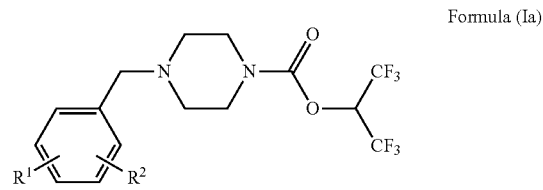

Formula (Ia)

wherein:
R$^1$ is halogen, —OR$^3$, —CN, aryl (optionally substituted by one, two, or three moieties each independently selected from R$^4$), aryloxy (optionally substituted by one, two, or three moieties each independently selected from R$^4$), heteroaryl (optionally substituted by one, two, or three moieties each independently selected from R$^4$), heteroaryloxy (optionally substituted by one, two, or three moieties each independently selected from R$^4$), heterocycle (optionally substituted by one, two, or three moieties each independently selected from R$^4$), cycloalkyl (optionally substituted by one, two, or three moieties each independently selected from R$^4$), optionally substituted C$_{1-6}$ alkyl, optionally substituted C$_{2-6}$ alkenyl, optionally substituted C$_{2-6}$ alkynyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, or —SH;

R$^2$ is —C(O)C(O)OR$^7$;

each R$^3$ is independently selected from H, C$_{1-6}$ alkyl, haloalkyl, and aminoalkyl;

each R$^4$ is independently selected from halogen, —OR$^3$, —CN, nitro, optionally substituted C$_{1-6}$ alkyl, optionally substituted C$_{1-6}$ alkenyl, optionally substituted C$_{1-6}$ alkynyl, cycloalkyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, and —SH;

R$^7$ is H or C$_{1-6}$ alkyl;

each R$^8$ is independently selected from H, optionally substituted alkyl, optionally substituted cycloalkyl, optionally substituted aryl, optionally substituted heteroaryl, and optionally substituted heterocycloalkyl;

each R$^9$ and R$^{10}$ is independently selected from H, optionally substituted alkyl, optionally substituted cycloalkyl, optionally substituted aryl, optionally substituted heteroaryl, and optionally substituted heterocycloalkyl; or R$^9$ and R$^{10}$ together with the nitrogen to which they are attached form an optionally substituted heterocycle optionally containing an additional O, N, or S;

each R$^{11}$ is independently selected from optionally substituted alkyl, optionally substituted cycloalkyl, optionally substituted aryl, optionally substituted heteroaryl, and optionally substituted heterocycloalkyl; and w is 0, 1, or 2;

or a solvate, hydrate, tautomer, N-oxide, or pharmaceutically acceptable salt thereof.

Another embodiment provides a compound of Formula (II):

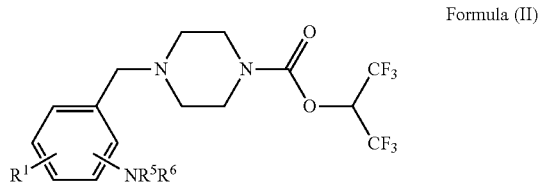

Formula (II)

wherein:
R$^1$ is halogen, —OR$^3$, —CN, aryl (optionally substituted by one, two, or three moieties each independently selected from R$^4$), aryloxy (optionally substituted by one, two, or three moieties each independently selected from R$^4$), heteroaryl (optionally substituted by one, two, or three moieties each independently selected from R$^4$), heteroaryloxy (optionally substituted by one, two, or three moieties each independently selected from R$^4$), heterocycle (optionally substituted by one, two, or three moieties each independently selected from R$^4$), cycloalkyl (optionally substituted by one, two, or three moieties each independently selected from R$^4$), optionally substituted C$_{1-6}$ alkyl, optionally substituted C$_{2-6}$ alkenyl, optionally substituted C$_{2-6}$ alkynyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, or —SH;

each R$^3$ is independently selected from H, C$_{1-6}$ alkyl, haloalkyl, and aminoalkyl;

each R$^4$ is independently selected from halogen, —OR$^3$, —CN, nitro, optionally substituted C$_{1-6}$ alkyl, optionally substituted C$_{1-6}$ alkenyl, optionally substituted C$_{1-6}$ alkynyl, cycloalkyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, and —SH;

R$^5$ and R$^6$, together with the nitrogen to which they are attached, form
(i) a monocyclic heterocycle, a fused bicyclic heterocycle, or a spirocycle; or
(ii) a 7-8 membered bridged heterocyclic ring optionally containing an additional O, N, or S;

wherein the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —OR$^7$, —NR$^{12}$R$^{13}$, —C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$; and the monocyclic heterocycle, the fused bicyclic heterocycle, or the spirocycle optionally contains an additional O, N, or S; and the 7-8 membered bridged heterocyclic ring is optionally substituted with one or more substituents independently selected from halogen, —CN, oxo, optionally substituted C$_{1-6}$ alkyl, optionally substituted aryl, optionally substituted heteroaryl, optionally substituted heterocycle, optionally substituted cycloalkyl, —S(O)$_w$R$^{11}$, —OR$^3$, —OR$^7$, —C(O)R$^9$, —C(O)OR$^9$, —C(O)NR$^9$R$^{10}$, —NR$^9$R$^{10}$, —NR$^8$C(O)R$^9$, —NR$^8$SO$_2$R$^9$, —NR$^8$C(O)OR$^9$, and —NR$^8$C(O)NR$^9$R$^{10}$;

R$^7$ is alkynyl or (alkynyl)alkyl;

each R$^8$ is independently selected from H, optionally substituted alkyl, optionally substituted cycloalkyl, optionally substituted aryl, optionally substituted heteroaryl, and optionally substituted heterocycloalkyl;

each R$^9$ and R$^{10}$ is independently selected from H, optionally substituted alkyl, optionally substituted cycloalkyl, optionally substituted aryl, optionally substituted heteroaryl, and optionally substituted heterocycloalkyl; or R$^9$ and R$^{10}$ together with the nitrogen to which they are attached form an optionally substituted heterocycle optionally containing an additional O, N, or S;

each R$^{11}$ is independently selected from optionally substituted alkyl, optionally substituted cycloalkyl, optionally substituted aryl, optionally substituted heteroaryl, and optionally substituted heterocycloalkyl;

R$^{12}$ and R$^{13}$ together with the nitrogen to which they are attached form an optionally substituted heterocycle optionally containing an additional O, N, or S; and w is 0, 1, or 2;

or a solvate, hydrate, tautomer, N-oxide, or pharmaceutically acceptable salt thereof.

Another embodiment provides a compound of Formula (IIa):

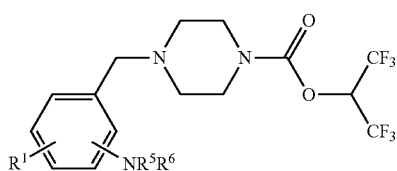

Formula (IIa)

wherein:

$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;

each $R^3$ is independently selected from H, $C_{1-6}$ alkyl, haloalkyl, and aminoalkyl;

each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;

$R^5$ and $R^6$, together with the nitrogen to which they are attached, form a monocyclic heterocycle, a fused bicyclic heterocycle, or a spirocycle; wherein the monocyclic heterocycle, the fused bicyclic heterocycle, or the spirocycle is substituted with hydroxyalkyl; and the monocyclic heterocycle, the fused bicyclic heterocycle, or the spirocycle optionally contains an additional O, N, or S;

each $R^8$ is independently selected from H, optionally substituted alkyl, optionally substituted cycloalkyl, optionally substituted aryl, optionally substituted heteroaryl, and optionally substituted heterocycloalkyl;

each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;

each $R^{11}$ is independently selected from optionally substituted alkyl, optionally substituted cycloalkyl, optionally substituted aryl, optionally substituted heteroaryl, and optionally substituted heterocycloalkyl; and w is 0, 1, or 2;

or a solvate, hydrate, tautomer, N-oxide, or pharmaceutically acceptable salt thereof.

Another embodiment provides a compound of Formula (III):

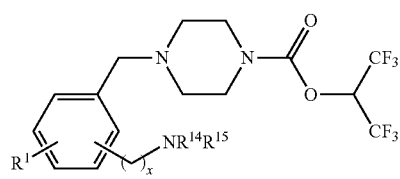

Formula (III)

wherein:

$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;

each $R^3$ is independently selected from H, $C_{1-6}$ alkyl, haloalkyl, and aminoalkyl;

each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;

each $R^8$ is independently selected from H, optionally substituted alkyl, optionally substituted cycloalkyl, optionally substituted aryl, optionally substituted heteroaryl, and optionally substituted heterocycloalkyl;

each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;

each $R^{11}$ is independently selected from optionally substituted alkyl, optionally substituted cycloalkyl, optionally substituted aryl, optionally substituted heteroaryl, and optionally substituted heterocycloalkyl;

$R^{14}$ and $R^{15}$ together with the nitrogen to which they are attached form an optionally substituted heterocycle optionally containing an additional O, N, or S;

w is 0, 1, or 2; and x is 1, 2, or 3;

or a solvate, hydrate, tautomer, N-oxide, stereoisomer, or pharmaceutically acceptable salt thereof.

Another embodiment provides a compound of Formula (IV):

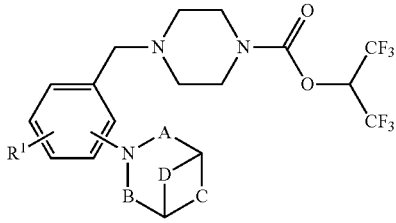

Formula (IV)

wherein:
A and B are independently a bond or $CR^{18}R^{19}$;
C is O or $CR^{18}R^{19}OCR^{20}R^{21}$;
D is $CR^{18}R^{19}$ or $CR^{18}R^{19}CR^{20}R^{21}$;
$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;
each $R^3$ is independently selected from H, $C_{1-6}$ alkyl, haloalkyl, and aminoalkyl;
each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;
each $R^8$ is independently selected from H, optionally substituted alkyl, optionally substituted cycloalkyl, optionally substituted aryl, optionally substituted heteroaryl, and optionally substituted heterocycloalkyl;
each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;
each $R^{11}$ is independently selected from optionally substituted alkyl, optionally substituted cycloalkyl, optionally substituted aryl, optionally substituted heteroaryl, and optionally substituted heterocycloalkyl;
$R^{17}$ is H, optionally substituted $C_{1-6}$ alkyl, optionally substituted aryl, optionally substituted heteroaryl, optionally substituted heterocycle, optionally substituted cycloalkyl, —$S(O)_wR^{11}$, —$C(O)R^9$, —$C(O)OR^9$, or —$C(O)NR^9R^{10}$;
each $R^{18}$, $R^{19}$, $R^{20}$, and $R^{21}$ is independently selected from H, optionally substituted $C_{1-6}$ alkyl, optionally substituted aryl, optionally substituted heteroaryl, optionally substituted heterocycle, optionally substituted cycloalkyl, —$C(O)R^9$, —$C(O)OR^9$, and —$C(O)NR^9R^{10}$; and
w is 0, 1, or 2;
or a solvate, hydrate, tautomer, N-oxide, stereoisomer, or pharmaceutically acceptable salt thereof.

Another embodiment provides a pharmaceutical composition comprising a piperazine carbamate described herein, or a solvate, hydrate, tautomer, N-oxide, stereoisomer, or a pharmaceutically acceptable salt thereof, and at least one pharmaceutically acceptable excipient.

Another embodiment provides a method of treating pain in a patient, comprising administering a therapeutically effective amount of a piperazine carbamate described herein to a patient in need thereof to treat said pain. In some embodiments, the pain is neuropathic pain.

DETAILED DESCRIPTION OF THE INVENTION

This disclosure is directed, at least in part, to MAGL and/or ABHD6 modulators or inhibitors. For example, provided herein are compounds capable of inhibiting MAGL and/or ABHD6.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.
"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In certain embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O) R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, $R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O) R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which includes fused or bridged ring systems. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, $R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O) R^a$, —$R^b$—$N(R^a)S(O)_t R^a$ (where t is 1 or 2), —$R^b$—$S(O)_t OR^a$ (where t is 1 or 2), —$R^b$—$S(O)_t R^a$ (where t is 1 or 2) and —$R^b$—$S(O)_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated. The terms "heterocyclyl" and "heterocycle" are used interchangeably.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Hetero aryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b] [1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, $R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O) R^a$, —$R^b$—$N(R^a)S(O)_t R^a$ (where t is 1 or 2), —$R^b$—$S(O)_t OR^a$ (where t is 1 or 2), —$R^b$—$S(O)_t R^a$ (where t is 1 or 2) and —$R^b$—$S(O)_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

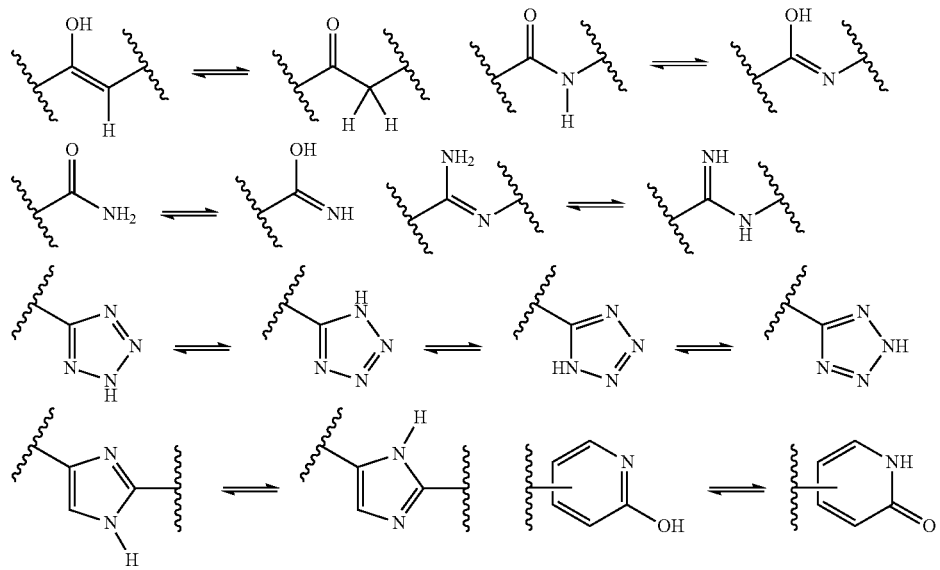

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the piperazine carbamates described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

Piperazine carbamates are described herein which are modulators of MAGL and/or ABHD6. These compounds, and compositions comprising these compounds, are useful for the treatment of pain.

One embodiment provides a compound of Formula (I):

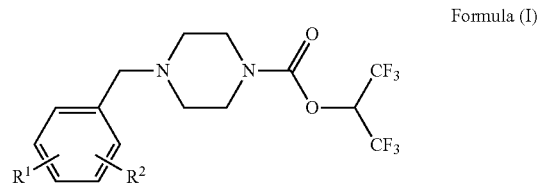

Formula (I)

wherein:
$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;

$R^2$ is —$NR^5R^6$, -alkyl($NR^{14}R^{15}$), or $OR^7$;

each $R^3$ is independently selected from H, $C_{1-6}$ alkyl, haloalkyl, and aminoalkyl;

each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;

$R^5$ and $R^6$, together with the nitrogen to which they are attached, form
  (i) a monocyclic heterocycle, a fused bicyclic heterocycle, or a spirocycle; or
  (ii) a 7-8 membered bridged heterocyclic ring optionally containing an additional O, N, or S;
  wherein the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle, the fused bicyclic heterocycle, or the spirocycle optionally contains an additional O, N, or S; and
  the 7-8 membered bridged heterocyclic ring is optionally substituted with one or more substituents independently selected from halogen, —CN, oxo, optionally substituted $C_{1-6}$ alkyl, optionally substituted aryl, optionally substituted heteroaryl, optionally substituted heterocycle, optionally substituted cycloalkyl, —$S(O)_wR^{11}$, —$OR^3$, —$OR^7$, —$C(O)R^9$, —$C(O)OR^9$, —$C(O)NR^9R^{10}$, —$NR^9R^{10}$, —$NR^8C(O)R^9$, —$NR^8SO_2R^9$, —$NR^8C(O)OR^9$, and —$NR^8C(O)NR^9R^{10}$;

$R^7$ is alkynyl or (alkynyl)alkyl;

each $R^8$ is independently selected from H, optionally substituted alkyl, optionally substituted cycloalkyl, optionally substituted aryl, optionally substituted heteroaryl, and optionally substituted heterocycloalkyl;

each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;

each $R^{11}$ is independently selected from optionally substituted alkyl, optionally substituted cycloalkyl, optionally substituted aryl, optionally substituted heteroaryl, and optionally substituted heterocycloalkyl;

$R^{12}$ and $R^{13}$ together with the nitrogen to which they are attached form an optionally substituted heterocycle optionally containing an additional O, N, or S;

$R^{14}$ and $R^{15}$ together with the nitrogen to which they are attached form an optionally substituted heterocycle optionally containing an additional O, N, or S; and w is 0, 1, or 2;

or a solvate, hydrate, tautomer, N-oxide, or pharmaceutically acceptable salt thereof.

In some embodiments of a compound of Formula (I), $R^2$ is —$NR^5R^6$. In some embodiments of a compound of Formula (I), $R^5$ and $R^6$, together with the nitrogen to which they are attached, form a monocyclic heterocycle, a fused bicyclic heterocycle, or a spirocycle, wherein: the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and monocyclic heterocycle, the fused bicyclic heterocycle, or the spirocycle optionally contains an additional O, N, or S. In some embodiments of a compound of Formula (I), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of a compound of Formula (I), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl, aryloxy, heteroaryl, heteroaryloxy, heterocycle, cycloalkyl, haloalkyl, $C_{1-6}$ alkyl, $C_{2-6}$ alkenyl, $C_{2-6}$ alkynyl, —$NR^9R^{10}$, —$NR^8C(O)R^9$, —$NR^8SO_2R^9$, —$NR^8C(O)OR^9$, —$S(O)_wR^{11}$—$NR^8C(O)NR^9R^{10}$, —$C(O)R^9$, —$C(O)OR^9$, and —$C(O)NR^9R^{10}$. In some embodiments of a compound of Formula (I), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl, aryloxy, haloalkyl, $C_{1-6}$ alkyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, $C(O)R^9$, —$C(O)OR^9$, and —$C(O)NR^9R^{10}$.

In some embodiments of a compound of Formula (I), $R^2$ is —$NR^5R^6$. In some embodiments of a compound of Formula (I), $R^5$ and $R^6$, together with the nitrogen to which they are attached, form a monocyclic heterocycle wherein the monocyclic heterocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, $C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle optionally contains an additional O, N, or S. In some embodiments of a compound of Formula (I), $R^5$ and $R^6$, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$, wherein the monocyclic heterocycle is selected from azetidine, pyrrolidine, piperidine, and morpholine. In some embodiments of a compound of Formula (I), $R^5$ and $R^6$, together with the nitrogen to which they are attached, form a monocyclic heterocycle substituted with one substituent selected from haloalkyl, —$OR^7$, —$C(O)OR^9$, —$C(O)NR^9R^{10}$, and —$NR^8SO_2R^9$, wherein the monocyclic heterocycle is selected from azetidine, pyrrolidine, piperidine, and morpholine. In some embodiments of a compound of Formula (I), $R^5$ and $R^6$, together with the nitrogen to which they are attached, form a monocyclic heterocycle substituted with one substituent selected from haloalkyl, —$OR^7$, —$C(O)OR^9$, —$C(O)NR^9R^{10}$, and —$NR^8SO_2R^9$, wherein the monocyclic heterocycle is selected from pyrrolidine, piperidine, and morpholine. In some embodiments of a compound of Formula (I), $R^5$ and $R^6$, together with the nitrogen to which they are attached, form a monocyclic heterocycle substituted with one substituent selected from —$C(O)OR^9$ and —$C(O)NR^9R^{10}$, wherein the monocyclic heterocycle is selected from pyrrolidine, piperidine, and morpholine. In some embodiments of a compound of Formula (I), $R^5$ and $R^6$, together with the nitrogen to which they are attached, form a monocyclic heterocycle substituted with one substituent selected from —$C(O)OR^9$ and —$C(O)NR^9R^{10}$, wherein the monocyclic heterocycle is selected from pyrrolidine, piperidine, and morpholine, and $R^9$ and $R^{10}$ is independently selected from H and unsubstituted alkyl. In some embodiments of a compound of Formula (I), $R^5$ and $R^6$, together with the nitrogen to which they are attached, form a monocyclic heterocycle substituted with one substituent selected from —$C(O)OR^9$ and —$C(O)NR^9R^{10}$, wherein the monocyclic heterocycle is pyrrolidine and $R^9$ and $R^{10}$ is independently selected from H and unsubstituted alkyl. In some embodiments of a compound of Formula (I), $R^5$ and $R^6$, together with the nitrogen to which they are attached, form a monocyclic heterocycle substituted with one substituent selected from —$C(O)OR^9$ and —$C(O)NR^9R^{10}$, wherein the monocyclic heterocycle is piperidine and $R^9$ and $R^{10}$ is independently selected from H and unsubstituted alkyl. In some embodiments of a compound of Formula (I), $R^5$ and $R^6$, together with the nitrogen to which they are attached, form a monocyclic heterocycle substituted with one substituent selected from —C(O)OR$^9$ and —C(O)NR$^9$R$^{10}$, wherein the monocyclic heterocycle is morpholine and R$^9$ and R$^{10}$ is independently selected from H and unsubstituted alkyl. In some embodiments of a compound of Formula (I), R$^5$ and R$^6$, together with the nitrogen to which they are attached, form a monocyclic heterocycle substituted with one or more substituents independently selected from substituted or unsubstituted aryl, substituted or unsubstituted heteroaryl, substituted or unsubstituted heterocycle, substituted or unsubstituted cycloalkyl, haloalkyl, —OR$^7$, —NR$^{12}$R$^{13}$, C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$, wherein the monocyclic heterocycle is azetidine. In some embodiments of a compound of Formula (I), R$^5$ and R$^6$, together with the nitrogen to which they are attached, form a monocyclic heterocycle substituted with one or more substituents independently selected from substituted or unsubstituted aryl, substituted or unsubstituted heteroaryl, substituted or unsubstituted heterocycle, substituted or unsubstituted cycloalkyl, haloalkyl, —OR$^7$, —NR$^{12}$R$^{13}$, —C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$, wherein the monocyclic heterocycle is pyrrolidine. In some embodiments of a compound of Formula (I), R$^5$ and R$^6$, together with the nitrogen to which they are attached, form a monocyclic heterocycle substituted with one or more substituents independently selected from substituted or unsubstituted aryl, substituted or unsubstituted heteroaryl, substituted or unsubstituted heterocycle, substituted or unsubstituted cycloalkyl, haloalkyl, —OR$^7$, —NR$^{12}$R$^{13}$, —C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$, wherein the monocyclic heterocycle is piperidine. In some embodiments of a compound of Formula (I), R$^5$ and R$^6$, together with the nitrogen to which they are attached, form a monocyclic heterocycle substituted with one or more substituents independently selected from substituted or unsubstituted aryl, substituted or unsubstituted heteroaryl, substituted or unsubstituted heterocycle, substituted or unsubstituted cycloalkyl, haloalkyl, —OR$^7$, —NR$^{12}$R$^{13}$, —C(O)OR$^9$, —C(O)NR$^9$R$^{10}$NR$^8$SO$_2$R$^9$, —NR$^8$C(O)OR$^9$, and —NR$^8$C(O)NR$^9$R$^{10}$, wherein the monocyclic heterocycle is morpholine.

In some embodiments of a compound of Formula (I), R$^2$ is —NR$^5$R$^6$. In some embodiments of a compound of Formula (I), R$^5$ and R$^6$, together with the nitrogen to which they are attached, form a fused bicyclic heterocycle wherein the fused bicyclic heterocycle is substituted with one or more substituents independently selected from optionally substituted aryl, optionally substituted heteroaryl, optionally substituted heterocycle, optionally substituted cycloalkyl, haloalkyl, —OR$^7$, —NR$^{12}$R$^{13}$, —C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$; and the fused bicyclic heterocycle optionally contains an additional O, N, or S. In some embodiments of a compound of Formula (I), R$^5$ and R$^6$, together with the nitrogen to which they are attached, form

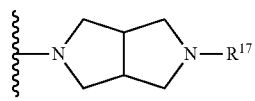

wherein R$^{17}$ is optionally substituted aryl, optionally substituted heteroaryl, optionally substituted heterocycle, optionally substituted cycloalkyl, haloalkyl, —C(O)OR$^9$, or —C(O)NR$^9$R$^{10}$. In further embodiments of a compound of Formula (I), R$^{17}$ is aryl, heteroaryl, heterocycle, cycloalkyl, haloalkyl, —C(O)OR$^9$, or —C(O)NR$^9$R$^{10}$. In still further embodiments of a compound of Formula (I), R$^{17}$ is cycloalkyl, haloalkyl, —C(O)OR$^9$, or —C(O)NR$^9$R$^{10}$.

In some embodiments of a compound of Formula (I), R$^2$ is —NR$^5$R$^6$. In some embodiments of a compound of Formula (I), R$^5$ and R$^6$, together with the nitrogen to which they are attached, form a spirocycle wherein the spirocycle is substituted with one or more substituents independently selected from optionally substituted aryl, optionally substituted heteroaryl, optionally substituted heterocycle, optionally substituted cycloalkyl, haloalkyl, —OR$^7$, —NR$^{12}$R$^{13}$, —C(O)OR$^9$, —C(O)NR$^9$R$^{10}$, —NR$^8$SO$_2$R$^9$, —NR$^8$C(O)OR$^9$, and —NR$^8$C(O)NR$^9$R$^{10}$; and the spirocycle optionally contains an additional O, N, or S. In some embodiments of a compound of Formula (I), R$^5$ and R$^6$, together with the nitrogen to which they are attached, form a spirocycle selected from

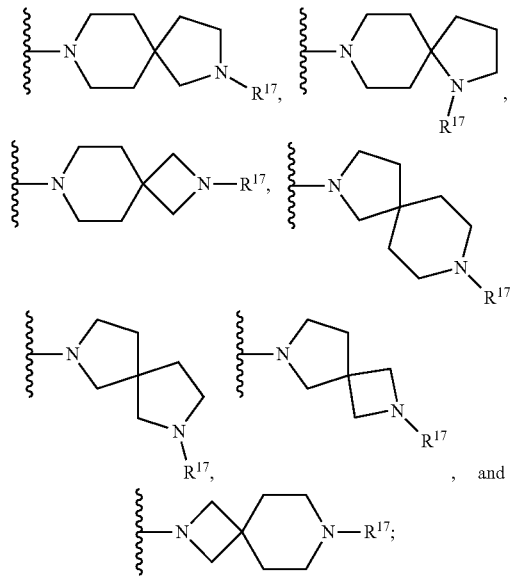

wherein R$^{17}$ is optionally substituted aryl, optionally substituted heteroaryl, optionally substituted heterocycle, optionally substituted cycloalkyl, haloalkyl, —C(O)OR$^9$, or —C(O)NR$^9$R$^{10}$. In further embodiments, R$^{17}$ is aryl, heteroaryl, heterocycle, cycloalkyl, haloalkyl, —C(O)OR$^9$, or —C(O)NR$^9$R$^{10}$. In still further embodiments, R$^{17}$ is cycloalkyl, haloalkyl, —C(O)OR$^9$, or —C(O)NR$^9$R$^{10}$.

In some embodiments of a compound of Formula (I), R$^2$ is —NR$^5$R$^6$. In some embodiments of a compound of Formula (I), R$^5$ and R$^6$, together with the nitrogen to which they are attached, form a 7-8 membered bridged heterocyclic ring optionally containing an additional O, N, or S, and optionally substituted with one or more substituents independently selected from halogen, —CN, oxo, optionally substituted C$_{1-6}$ alkyl, optionally substituted aryl, optionally substituted heteroaryl, optionally substituted heterocycle, optionally substituted cycloalkyl, —S(O)$_w$R$^{11}$, —OR$^3$, —C(O)R$^9$, —C(O)OR$^9$, —C(O)NR$^9$R$^{10}$, —NR$^9$R$^{10}$, —NR$^8$C(O)R$^9$, —NR$^8$SO$_2$R$^9$, —NR$^8$C(O)OR$^9$, and —NR$^8$C(O)NR$^9$R$^{10}$. In some embodiments of a compound of Formula (I), R$^5$ and R$^6$, together with the nitrogen to which which they are attached, form a 7-8 membered bridged heterocyclic ring containing an additional O, N, or S. In some embodiments of a compound of Formula (I), $R^5$ and $R^6$, together with the nitrogen to which they are attached, form an 8-membered bridged heterocyclic ring selected from

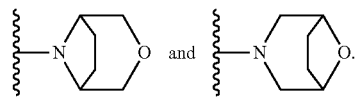

In some embodiments of a compound of Formula (I), $R^2$ is -alkyl($NR^{14}R^{15}$). In some embodiments of a compound of Formula (I), $R^{14}$ and $R^{15}$, together with the nitrogen to which they are attached, form a heterocycle optionally containing an additional O, N, or S; wherein the heterocycle is substituted with one or more substituents independently selected from halogen, oxo, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of a compound of Formula (I), $R^{14}$ and $R^{15}$, together with the nitrogen to which they are attached, form a substituted heterocycle; wherein the substituted heterocycle has one or more substituents independently selected from halogen, oxo, —$OR^3$, —CN, $C_{1-6}$ alkyl, haloalkyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of a compound of Formula (I), $R^{14}$ and $R^{15}$, together with the nitrogen to which they are attached, form an optionally substituted pyrrolidine, optionally substituted piperidine, optionally substituted morpholine, or optionally substituted piperazine. In some embodiments of a compound of Formula (I), $R^{14}$ and $R^{15}$, together with the nitrogen to which they are attached, form a substituted or unsubstituted pyrrolidine. In some embodiments of a compound of Formula (I), $R^{14}$ and $R^{15}$, together with the nitrogen to which they are attached, form a substituted or unsubstituted piperidine. In some embodiments of a compound of Formula (I), $R^{14}$ and $R^{15}$, together with the nitrogen to which they are attached, form a substituted or unsubstituted morpholine. In some embodiments of a compound of Formula (I), $R^{14}$ and $R^{15}$, together with the nitrogen to which they are attached, form a substituted or unsubstituted piperazine. In some embodiments of a compound of Formula (I), $R^{14}$ and $R^{15}$, together with the nitrogen to which they are attached, form an optionally substituted heterocycle selected from:

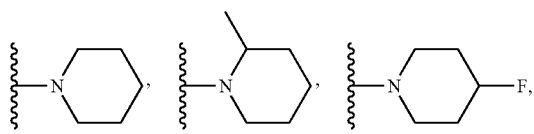

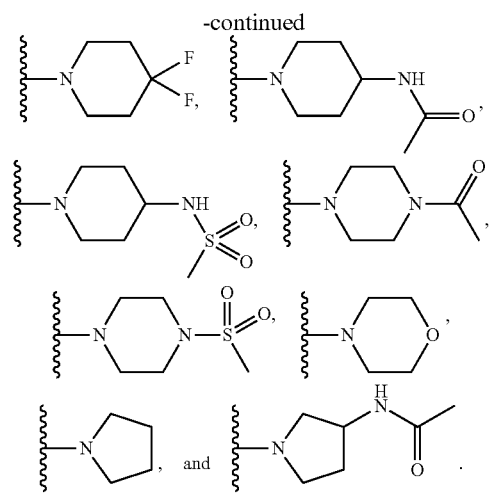

In some embodiments of a compound of Formula (I), $R^2$ is —$OR^7$.

In some embodiments of a compound of Formula (I), $R^1$ is halogen, —$CH_3$, —$CF_3$, —$OCH_3$, or —$OCF_3$. In some embodiments of a compound of Formula (I), $R^1$ is halogen. In some embodiments of a compound of Formula (I), $R^1$ is —Cl. In some embodiments of a compound of Formula (I), $R^1$ is —$CH_3$. In some embodiments of a compound of Formula (I), $R^1$ is —$CF_3$. In some embodiments of a compound of Formula (I), $R^1$ is —$OCH_3$. In some embodiments of a compound of Formula (I), $R^1$ is —$OCF_3$.

Another embodiment provides a compound of Formula (Ia):

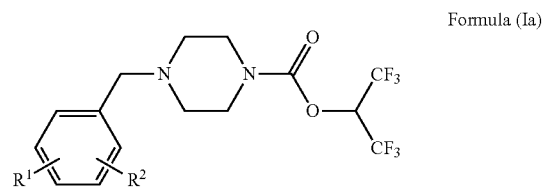

Formula (Ia)

wherein:
$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, or —SH;

$R^2$ is —$C(O)C(O)OR^7$;

each $R^3$ is independently selected from H, $C_{1-6}$ alkyl, haloalkyl, and aminoalkyl;

each $R^4$ is independently selected from halogen, —$OR^3$, —CN, nitro, optionally substituted $C_{1-6}$ alkyl, optionally substituted $C_{1-6}$ alkenyl, optionally substituted $C_{1-6}$ alkynyl, cycloalkyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, and —SH;

R$^7$ is H or C$_{1-6}$ alkyl;

each R$^8$ is independently selected from H, optionally substituted alkyl, optionally substituted cycloalkyl, optionally substituted aryl, optionally substituted heteroaryl, and optionally substituted heterocycloalkyl;

each R$^9$ and R$^{10}$ is independently selected from H, optionally substituted alkyl, optionally substituted cycloalkyl, optionally substituted aryl, optionally substituted heteroaryl, and optionally substituted heterocycloalkyl; or R$^9$ and R$^{10}$ together with the nitrogen to which they are attached form an optionally substituted heterocycle optionally containing an additional O, N, or S;

each R$^{11}$ is independently selected from optionally substituted alkyl, optionally substituted cycloalkyl, optionally substituted aryl, optionally substituted heteroaryl, and optionally substituted heterocycloalkyl; and w is 0, 1, or 2;

or a solvate, hydrate, tautomer, N-oxide, or pharmaceutically acceptable salt thereof.

In some embodiments of a compound of Formula (Ia), R$^2$ is —C(O)C(O)OR$^7$ and R$^7$ is H. In some embodiments of a compound of Formula (Ia), R$^2$ is —C(O)C(O)OR$^7$, R$^7$ is H, and R$^1$ is optionally substituted C$_{1-6}$ alkyl. In some embodiments of a compound of Formula (Ia), R$^2$ is —C(O)C(O)OR$^7$, R$^7$ is H, and R$^1$ is halogen, —CH$_3$, —CF$_3$, —OCH$_3$, or —OCF$_3$. In some embodiments of a compound of Formula (Ia), R$^2$ is —C(O)C(O)OR$^7$, R$^7$ is H, and R$^1$ is —CH$_3$. In some embodiments of a compound of Formula (Ia), R$^2$ is —C(O)C(O)OR$^7$, R$^7$ is H, and R$^1$ is —CF$_3$. In some embodiments of a compound of Formula (Ia), R$^2$ is —C(O)C(O)OR$^7$, R$^7$ is H, and R$^1$ is halogen. In some embodiments of a compound of Formula (Ia), R$^2$ is —C(O)C(O)OR$^7$, R$^7$ is H, and R$^1$ is —Cl. In some embodiments of a compound of Formula (Ia), R$^2$ is —C(O)C(O)OR$^7$, R$^7$ is H, and R$^1$ is —OCH$_3$. In some embodiments of a compound of Formula (Ia), R$^2$ is —C(O)C(O)OR$^7$, R$^7$ is H, and R$^1$ is —OCF$_3$.

In some embodiments of a compound of Formula (Ia), R$^2$ is —C(O)C(O)OR$^7$ and R$^7$ is C$_{1-6}$ alkyl. In some embodiments of a compound of Formula (Ia), R$^2$ is —C(O)C(O)OR$^7$, R$^7$ is C$_{1-6}$ alkyl, and R$^1$ is optionally substituted C$_{1-6}$ alkyl. In some embodiments of a compound of Formula (Ia), R$^2$ is —C(O)C(O)OR$^7$, R$^7$ is C$_{1-6}$ alkyl, and R$^1$ is halogen, —CH$_3$, —CF$_3$, —OCH$_3$, or —OCF$_3$. In some embodiments of a compound of Formula (Ia), R$^2$ is —C(O)C(O)OR$^7$, R$^7$ is C$_{1-6}$ alkyl, and R$^1$ is —CH$_3$. In some embodiments of a compound of Formula (Ia), R$^2$ is —C(O)C(O)OR$^7$, R$^7$ is C$_{1-6}$ alkyl, and R$^1$ is CF$_3$. In some embodiments of a compound of Formula (Ia), R$^2$ is —C(O)C(O)OR$^7$, R$^7$ is C$_{1-6}$ alkyl, and R$^1$ is halogen. In some embodiments of a compound of Formula (Ia), R$^2$ is —C(O)C(O)OR$^7$, R$^7$ is C$_{1-6}$ alkyl, and R$^1$ is —Cl. In some embodiments of a compound of Formula (Ia), R$^2$ is —C(O)C(O)OR$^7$, R$^7$ is C$_{1-6}$ alkyl, and R$^1$ is —OCH$_3$. In some embodiments of a compound of Formula (Ia), R$^2$ is —C(O)C(O)OR$^7$, R$^7$ is C$_{1-6}$ alkyl, and R$^1$ is —OCF$_3$.

In some embodiments of a compound of Formula (Ia), R$^2$ is —C(O)C(O)OR$^7$ and R$^7$ is —CH$_3$. In some embodiments of a compound of Formula (Ia), R$^2$ is —C(O)C(O)OR$^7$, R$^7$ is —CH$_3$, and R$^1$ is optionally substituted C$_{1-6}$ alkyl. In some embodiments of a compound of Formula (Ia), R$^2$ is —C(O)C(O)OR$^7$, R$^7$ is —CH$_3$, and R$^1$ is halogen, —CH$_3$, —CF$_3$, —OCH$_3$, or —OCF$_3$. In some embodiments of a compound of Formula (Ia), R$^2$ is —C(O)C(O)OR$^7$, R$^7$ is —CH$_3$, and R$^1$ is —CH$_3$. In some embodiments of a compound of Formula (Ia), R$^2$ is —C(O)C(O)OR$^7$, R$^7$ is —CH$_3$, and R$^1$ is CF$_3$. In some embodiments of a compound of Formula (Ia), R$^2$ is —C(O)C(O)OR$^7$, R$^7$ is —CH$_3$, and R$^1$ is halogen. In some embodiments of a compound of Formula (Ia), R$^2$ is —C(O)C(O)OR$^7$, R$^7$ is —CH$_3$, and R$^1$ is —Cl. In some embodiments of a compound of Formula (Ia), R$^2$ is —C(O)C(O)OR$^7$, R$^7$ is —CH$_3$, and R$^1$ is —OCH$_3$. In some embodiments of a compound of Formula (Ia), R$^2$ is —C(O) C(O)OR$^7$, R$^7$ is —CH$_3$, and R$^1$ is —OCF$_3$.

In some embodiments of a compound of Formula (Ia), R$^2$ is —C(O)C(O)OR$^7$ and R$^7$ is —CH$_2$CH$_3$. In some embodiments of a compound of Formula (Ia), R$^2$ is —C(O)C(O) OR$^7$, R$^7$ is —CH$_2$CH$_3$, and R$^1$ is optionally substituted C$_{1-6}$ alkyl. In some embodiments of a compound of Formula (Ia), R$^2$ is —C(O)C(O)OR$^7$, R$^7$ is —CH$_2$CH$_3$, and R$^1$ is halogen, —CH$_3$, —CF$_3$, —OCH$_3$, or —OCF$_3$. In some embodiments of a compound of Formula (Ia), R$^2$ is —C(O)C(O)OR$^7$, R$^7$ is —CH$_2$CH$_3$, and R$^1$ is —CH$_3$. In some embodiments of a compound of Formula (Ia), R$^2$ is —C(O)C(O)OR$^7$, R$^7$ is —CH$_2$CH$_3$, and R$^1$ is CF$_3$. In some embodiments of a compound of Formula (Ia), R$^2$ is —C(O)C(O)OR$^7$, R$^7$ is —CH$_2$CH$_3$, and R$^1$ is halogen. In some embodiments of a compound of Formula (Ia), R$^2$ is —C(O)C(O)OR$^7$, R$^7$ is —CH$_2$CH$_3$, and R$^1$ is —Cl. In some embodiments of a compound of Formula (Ia), R$^2$ is —C(O)C(O)OR$^7$, R$^7$ is —CH$_2$CH$_3$, and R$^1$ is —OCH$_3$. In some embodiments of a compound of Formula (Ia), R$^2$ is —C(O)C(O)OR$^7$, R$^7$ is —CH$_2$CH$_3$, and R$^1$ is —OCF$_3$ Another embodiment provides a compound of Formula (II):

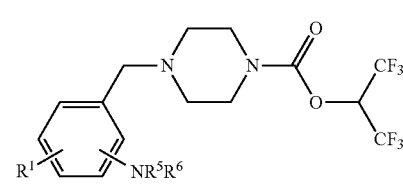

Formula (II)

wherein:

R$^1$ is halogen, —OR$^3$, —CN, aryl (optionally substituted by one, two, or three moieties each independently selected from R$^4$), aryloxy (optionally substituted by one, two, or three moieties each independently selected from R$^4$), heteroaryl (optionally substituted by one, two, or three moieties each independently selected from R$^4$), heteroaryloxy (optionally substituted by one, two, or three moieties each independently selected from R$^4$), heterocycle (optionally substituted by one, two, or three moieties each independently selected from R$^4$), cycloalkyl (optionally substituted by one, two, or three moieties each independently selected from R$^4$), optionally substituted C$_{1-6}$ alkyl, optionally substituted C$_{2-6}$ alkenyl, optionally substituted C$_{2-6}$ alkynyl, —NR$^9$R$^{10}$, —NR$^8$C(O)R$^9$, —NR$^8$SO$_2$R$^9$, —NR$^8$C(O)OR$^9$, —NR$^8$C(O)NR$^9$R$^{10}$, —C(O)R$^9$, —C(O)OR$^9$, —C(O)NR$^9$R$^{10}$, —S(O)$_w$R$^{11}$, or —SH;

each R$^3$ is independently selected from H, C$_{1-6}$ alkyl, haloalkyl, and aminoalkyl;

each R$^4$ is independently selected from halogen, —OR$^3$, —CN, nitro, optionally substituted C$_{1-6}$ alkyl, optionally substituted C$_{1-6}$ alkenyl, optionally substituted C$_{1-6}$ alkynyl, cycloalkyl, —NR$^9$R$^{10}$, —NR$^8$C(O)R$^9$, —$NR^8SO_2R^9$, —$NR^8C(O)OR^9$, —$NR^8C(O)NR^9R^{10}$, —$C(O)R^9$, —$C(O)OR^9$, —$C(O)NR^9R^{10}$, —$S(O)_wR^{11}$, and —SH;

$R^5$ and $R^6$, together with the nitrogen to which they are attached, form
  (i) a monocyclic heterocycle, a fused bicyclic heterocycle, or a spirocycle; or
  (ii) a 7-8 membered bridged heterocyclic ring optionally containing an additional O, N, or S;
  wherein the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle, the fused bicyclic heterocycle, or the spirocycle optionally contains an additional O, N, or S; and
  the 7-8 membered bridged heterocyclic ring is optionally substituted with one or more substituents independently selected from halogen, —CN, oxo, optionally substituted $C_{1-6}$ alkyl, optionally substituted aryl, optionally substituted heteroaryl, optionally substituted heterocycle, optionally substituted cycloalkyl, —$S(O)_wR^{11}$, —$OR^3$, —$OR^7$, —$C(O)R^9$, —$C(O)OR^9$, —$C(O)NR^9R^{10}$, —$NR^9R^{10}$, —$NR^8C(O)R^9$, —$NR^8SO_2R^9$, —$NR^8C(O)OR^9$, and —$NR^8C(O)NR^9R^{10}$;

$R^7$ is alkynyl or (alkynyl)alkyl;

each $R^8$ is independently selected from H, optionally substituted alkyl, optionally substituted cycloalkyl, optionally substituted aryl, optionally substituted heteroaryl, and optionally substituted heterocycloalkyl;

each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;

each $R^{11}$ is independently selected from optionally substituted alkyl, optionally substituted cycloalkyl, optionally substituted aryl, optionally substituted heteroaryl, and optionally substituted heterocycloalkyl;

$R^{12}$ and $R^{13}$ together with the nitrogen to which they are attached form an optionally substituted heterocycle optionally containing an additional O, N, or S; and w is 0, 1, or 2;

or a solvate, hydrate, tautomer, N-oxide, or pharmaceutically acceptable salt thereof.

In some embodiments of a compound of Formula (II), $R^5$ and $R^6$, together with the nitrogen to which they are attached, form a monocyclic heterocycle, a fused bicyclic heterocycle, or a spirocycle, wherein the monocyclic heterocycle, the fused bicyclic heterocycle, or the spirocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle, the fused bicyclic heterocycle, or the spirocycle optionally contains an additional O, N, or S. In some embodiments of a compound of Formula (II), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of a compound of Formula (II), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl, aryloxy, heteroaryl, heteroaryloxy, heterocycle, cycloalkyl, haloalkyl, $C_{1-6}$ alkyl, $C_{2-6}$ alkenyl, $C_{2-6}$ alkynyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, $C(O)OR^9$, and —$C(O)NR^9R^{10}$. In some embodiments of a compound of Formula (II), $R^{12}$ and $R^{13}$ together with the nitrogen to which they are attached form a heterocycle optionally containing an additional O, N, or S; wherein the heterocycle is substituted with one or more substituents independently selected from halogen, oxo, —$OR^3$, —CN, aryl, aryloxy, haloalkyl, $C_{1-6}$ alkyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$.

In some embodiments of a compound of Formula (II), $R^5$ and $R^6$, together with the nitrogen to which they are attached, form a monocyclic heterocycle wherein the monocyclic heterocycle is substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$; and the monocyclic heterocycle optionally contains an additional O, N, or S. In some embodiments of a compound of Formula (II), $R^5$ and $R^6$, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —$OR^7$, —$NR^{12}R^{13}$, —$C(O)OR^9$, —$C(O)NR^9R^{10}$, —$NR^8SO_2R^9$, —$NR^8C(O)OR^9$, and —$NR^8C(O)NR^9R^{10}$, wherein the monocyclic heterocycle is selected from azetidine, pyrrolidine, piperidine, and morpholine. In some embodiments of a compound of Formula (II), $R^5$ and $R^6$, together with the nitrogen to which they are attached, form a monocyclic heterocycle substituted with one substituent selected from haloalkyl, —$OR^7$, —$C(O)OR^9$, —$C(O)NR^9R^{10}$, and —$NR^8SO_2R^9$, wherein the monocyclic heterocycle is selected from azetidine, pyrrolidine, piperidine, and morpholine. In some embodiments of a compound of Formula (II), $R^5$ and $R^6$, together with the nitrogen to which they are attached, form a monocyclic heterocycle substituted with one substituent selected from haloalkyl, —$OR^7$, —$C(O)OR^9$, —$C(O)NR^9R^{10}$, and —NR⁸SO₂R⁹, wherein the monocyclic heterocycle is selected from pyrrolidine, piperidine, and morpholine. In some embodiments of a compound of Formula (II), R⁵ and R⁶, together with the nitrogen to which they are attached, form a monocyclic heterocycle substituted with one substituent selected from —C(O)OR⁹ and —C(O)NR⁹R¹⁰, wherein the monocyclic heterocycle is selected from pyrrolidine, piperidine, and morpholine. In some embodiments of a compound of Formula (II), R⁵ and R⁶, together with the nitrogen to which they are attached, form a monocyclic heterocycle substituted with one substituent selected from —C(O)OR⁹ and —C(O)NR⁹R¹⁰, wherein the monocyclic heterocycle is selected from pyrrolidine, piperidine, and morpholine, and R⁹ and R¹⁰ is independently selected from H and unsubstituted alkyl. In some embodiments of a compound of Formula (II), R⁵ and R⁶, together with the nitrogen to which they are attached, form a monocyclic heterocycle substituted with one substituent selected from —C(O)OR⁹ and —C(O)NR⁹R¹⁰, wherein the monocyclic heterocycle is pyrrolidine and R⁹ and R¹⁰ is independently selected from H and unsubstituted alkyl. In some embodiments of a compound of Formula (II), R⁵ and R⁶, together with the nitrogen to which they are attached, form a monocyclic heterocycle substituted with one substituent selected from —C(O)OR⁹ and —C(O)NR⁹R¹⁰, wherein the monocyclic heterocycle is piperidine and R⁹ and R¹⁰ is independently selected from H and unsubstituted alkyl. In some embodiments of a compound of Formula (II), R⁵ and R⁶, together with the nitrogen to which they are attached, form a monocyclic heterocycle substituted with one substituent selected from —C(O)OR⁹ and —C(O)NR⁹R¹⁰, wherein the monocyclic heterocycle is morpholine and R⁹ and R¹⁰ is independently selected from H and unsubstituted alkyl. In some embodiments of a compound of Formula (II), R⁵ and R⁶, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰, wherein the monocyclic heterocycle is azetidine. In some embodiments of a compound of Formula (II), R⁵ and R⁶, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰, wherein the monocyclic heterocycle is pyrrolidine. In some embodiments of a compound of Formula (II), R⁵ and R⁶, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰, wherein the monocyclic heterocycle is piperidine. In some embodiments of a compound of Formula (II), R⁵ and R⁶, together with the nitrogen to which they are attached, form a monocyclic heterocycle substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰, wherein the monocyclic heterocycle is morpholine.

In some embodiments of a compound of Formula (II), R⁵ and R⁶, together with the nitrogen to which they are attached, form a fused bicyclic heterocycle wherein the fused bicyclic heterocycle is substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰; and the fused bicyclic heterocycle optionally contains an additional O, N, or S. In some embodiments of a compound of Formula (II), R⁵ and R⁶, together with the nitrogen to which they are attached, form

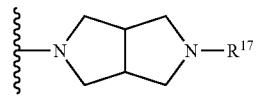

wherein R¹⁷ is optionally substituted aryl, optionally substituted heteroaryl, optionally substituted heterocycle, optionally substituted cycloalkyl, haloalkyl, —C(O)OR⁹, or —C(O)NR⁹R¹⁰. In further embodiments, R¹⁷ is aryl, heteroaryl, heterocycle, cycloalkyl, haloalkyl, —C(O)OR⁹, or —C(O)NR⁹R¹⁰. In still further embodiments, R¹⁷ is cycloalkyl, haloalkyl, —C(O)OR⁹, or —C(O)NR⁹R¹⁰.

In some embodiments of a compound of Formula (II), R⁵ and R⁶, together with the nitrogen to which they are attached, form a spirocycle wherein the spirocycle is substituted with one or more substituents independently selected from optionally substituted aryl, optionally substituted heteroaryl, optionally substituted heterocycle, optionally substituted cycloalkyl, haloalkyl, —OR⁷, —NR¹²R¹³, —C(O)OR⁹, —C(O)NR⁹R¹⁰, —NR⁸SO₂R⁹, —NR⁸C(O)OR⁹, and —NR⁸C(O)NR⁹R¹⁰; and the spirocycle optionally contains an additional O, N, or S. In some embodiments of a compound of Formula (II), R⁵ and R⁶, together with the nitrogen to which they are attached, form a spirocycle selected from

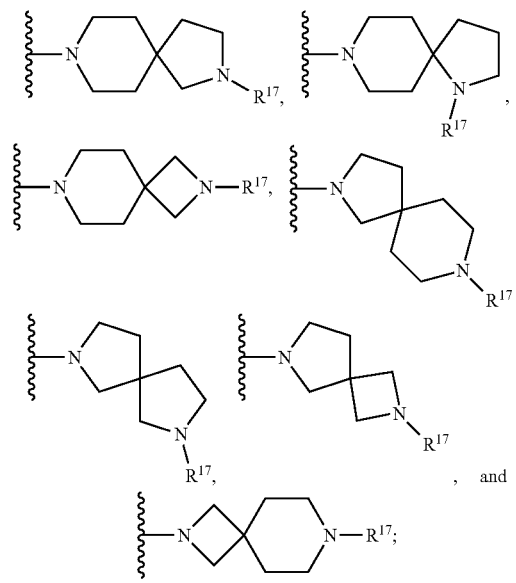

wherein R[17] is optionally substituted aryl, optionally substituted heteroaryl, optionally substituted heterocycle, optionally substituted cycloalkyl, haloalkyl, —C(O)OR[9], or —C(O)NR[9]R[10]. In further embodiments, R[17] is aryl, heteroaryl, heterocycle, cycloalkyl, haloalkyl, —C(O)OR[9], or —C(O)NR[9]R[10]. In still further embodiments, R[17] is cycloalkyl, haloalkyl, —C(O)OR[9], or —C(O)NR[9]R[10].

In some embodiments of a compound of Formula (II), R[5] and R[6], together with the nitrogen to which they are attached, form a 7-8 membered bridged heterocyclic ring optionally containing an additional O, N, or S, and optionally substituted with one or more substituents independently selected from halogen, —CN, oxo, optionally substituted C$_{1-6}$ alkyl, optionally substituted aryl, optionally substituted heteroaryl, optionally substituted heterocycle, optionally substituted cycloalkyl, —S(O)$_w$R[11], —OR[3], —OR[7], —C(O)R[9], —C(O)OR[9], —C(O)NR[9]R[10], —NR[9]R[10], —NR[8]C(O)R[9], —NR[8]SO$_2$R[9], —NR[8]C(O)OR[9], and —NR[8]C(O)NR[9]R[10]. In some embodiments of a compound of Formula (II), R[5] and R[6], together with the nitrogen to which they are attached, form a 7-8 membered bridged heterocyclic ring containing an additional O, N, or S. In some embodiments of a compound of Formula (II), R[5] and R[6], together with the nitrogen to which they are attached, form an 8-membered bridged heterocyclic ring selected from

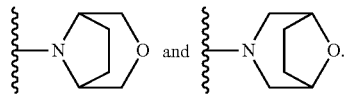

In some embodiments of a compound of Formula (II), R[1] is halogen, —CH$_3$, —CF$_3$, —OCH$_3$, or —OCF$_3$. In some embodiments of a compound of Formula (II), R[1] is halogen. In some embodiments of a compound of Formula (II), R[1] is —Cl. In some embodiments of a compound of Formula (II), R[1] is —CH$_3$. In some embodiments of a compound of Formula (II), R[1] is —CF$_3$. In some embodiments of a compound of Formula (II), R[1] is —OCH$_3$. In some embodiments of a compound of Formula (II), R[1] is —OCF$_3$.

Another embodiment provides a compound of Formula (IIa):

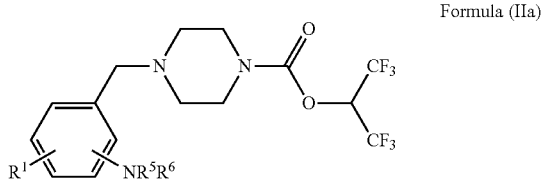

Formula (IIa)

wherein:
R[1] is halogen, —OR[3], —CN, aryl (optionally substituted by one, two, or three moieties each independently selected from R[4]), aryloxy (optionally substituted by one, two, or three moieties each independently selected from R[4]), heteroaryl (optionally substituted by one, two, or three moieties each independently selected from R[4]), heteroaryloxy (optionally substituted by one, two, or three moieties each independently selected from R[4]), heterocycle (optionally substituted by one, two, or three moieties each independently selected from R[4]), cycloalkyl (optionally substituted by one, two, or three moieties each independently selected from R[4]), optionally substituted C$_{1-6}$ alkyl, optionally substituted C$_{2-6}$ alkenyl, optionally substituted C$_{2-6}$ alkynyl, —NR[9]R[10], —NR[8]C(O)R[9], —NR[8]SO$_2$R[9], —NR[8]C(O)OR[9], —NR[8]C(O)NR[9]R[10], —C(O)R[9], —C(O)OR[9], —C(O)NR[9]R[10], —S(O)$_w$R[11], or —SH;

each R[3] is independently selected from H, C$_{1-6}$ alkyl, haloalkyl, and aminoalkyl;

each R[4] is independently selected from halogen, —OR[3], —CN, nitro, optionally substituted C$_{1-6}$ alkyl, optionally substituted C$_{1-6}$ alkenyl, optionally substituted C$_{1-6}$ alkynyl, cycloalkyl, —NR[9]R[10], —NR[8]C(O)R[9], —NR[8]SO$_2$R[9], —NR[8]C(O)OR[9], —NR[8]C(O)NR[9]R[10], —C(O)R[9], —C(O)OR[9], —C(O)NR[9]R[10], —S(O)$_w$R[11], and —SH;

R[5] and R[6], together with the nitrogen to which they are attached, form a monocyclic heterocycle, a fused bicyclic heterocycle, or a spirocycle; wherein the monocyclic heterocycle, the fused bicyclic heterocycle, or the spirocycle is substituted with hydroxyalkyl; and the monocyclic heterocycle, the fused bicyclic heterocycle, or the spirocycle optionally contains an additional O, N, or S;

each R[8] is independently selected from H, optionally substituted alkyl, optionally substituted cycloalkyl, optionally substituted aryl, optionally substituted heteroaryl, and optionally substituted heterocycloalkyl;

each R[9] and R[10] is independently selected from H, optionally substituted alkyl, optionally substituted cycloalkyl, optionally substituted aryl, optionally substituted heteroaryl, and optionally substituted heterocycloalkyl; or R[9] and R[10] together with the nitrogen to which they are attached form an optionally substituted heterocycle optionally containing an additional O, N, or S;

each R[11] is independently selected from optionally substituted alkyl, optionally substituted cycloalkyl, optionally substituted aryl, optionally substituted heteroaryl, and optionally substituted heterocycloalkyl; and w is 0, 1, or 2;

or a solvate, hydrate, tautomer, N-oxide, or pharmaceutically acceptable salt thereof.

In some embodiments of a compound of Formula (IIa), R[5] and R[6], together with the nitrogen to which they are attached, form a monocyclic heterocycle wherein the monocyclic heterocycle is substituted with hydroxyalkyl, and the monocyclic heterocycle optionally contains an additional O, N, or S. In some embodiments of a compound of Formula (IIa), R[5] and R[6], together with the nitrogen to which they are attached, form a monocyclic heterocycle wherein the monocyclic heterocycle is substituted with hydroxymethyl, and the monocyclic heterocycle optionally contains an additional O, N, or S. In some embodiments of a compound of Formula (IIa), R[5] and R[6], together with the nitrogen to which they are attached, form a piperidine, pyrrolidine, morpholine, or azetidine wherein the piperidine, pyrrolidine, morpholine, or azetidine is substituted with hydroxyalkyl. In some embodiments of a compound of Formula (IIa), R[5] and R[6], together with the nitrogen to which they are attached, form a piperidine, pyrrolidine, morpholine, or azetidine wherein the piperidine, pyrrolidine, morpholine, or azetidine is substituted with hydroxymethyl. In some embodiments of a compound of Formula (IIa), R[5] and R[6], together with the nitrogen to which they are attached, form a piperidine wherein the piperidine is substituted with hydroxyalkyl. In some embodiments of a compound of Formula (IIa), R[5] and R[6], together with the nitrogen to which they are attached, form a piperidine wherein the piperidine is substituted with hydroxymethyl. In some embodiments of a compound of Formula (IIa), R[5] and R[6], together with the nitrogen to which they are attached, form a pyrrolidine wherein the pyrrolidine is substituted with hydroxyalkyl. In some embodiments of a compound of Formula (IIa), R⁵ and R⁶, together with the nitrogen to which they are attached, form a pyrrolidine wherein the pyrrolidine is substituted with hydroxymethyl. In some embodiments of a compound of Formula (IIa), R⁵ and R⁶, together with the nitrogen to which they are attached, form a morpholine wherein the morpholine is substituted with hydroxyalkyl. In some embodiments of a compound of Formula (IIa), R⁵ and R⁶, together with the nitrogen to which they are attached, form a morpholine wherein the morpholine is substituted with hydroxymethyl. In some embodiments of a compound of Formula (IIa), R⁵ and R⁶, together with the nitrogen to which they are attached, form an azetidine wherein the azetidine is substituted with hydroxyalkyl. In some embodiments of a compound of Formula (IIa), R⁵ and R⁶, together with the nitrogen to which they are attached, form an azetidine wherein the azetidine is substituted with hydroxymethyl.

In some embodiments of a compound of Formula (IIa), R⁵ and R⁶, together with the nitrogen to which they are attached, form a fused bicyclic heterocycle wherein the fused bicyclic heterocycle is substituted with hydroxyalkyl, and the fused bicyclic heterocycle optionally contains an additional O, N, or S. In some embodiments of a compound of Formula (IIa), R⁵ and R⁶, together with the nitrogen to which they are attached, form a fused bicyclic heterocycle wherein the fused bicyclic heterocycle is substituted with hydroxymethyl, and the fused bicyclic heterocycle optionally contains an additional O, N, or S. In some embodiments of a compound of Formula (IIa), R⁵ and R⁶, together with the nitrogen to which they are attached, form

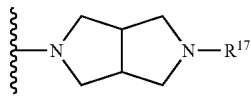

wherein R¹⁷ is hydroxyalkyl.

In some embodiments of a compound of Formula (IIa), R⁵ and R⁶, together with the nitrogen to which they are attached, form a spirocycle wherein the spirocycle is substituted with hydroxyalkyl, and the spirocycle optionally contains an additional O, N, or S. In some embodiments of a compound of Formula (IIa), R⁵ and R⁶, together with the nitrogen to which they are attached, form a spirocycle wherein the spirocycle is substituted with hydroxymethyl, and the spirocycle optionally contains an additional O, N, or S. In some embodiments of a compound of Formula (IIa), R⁵ and R⁶, together with the nitrogen to which they are attached, form a spirocycle selected from

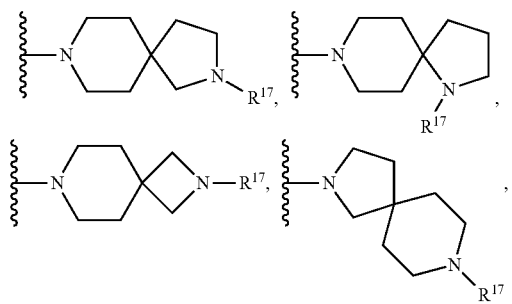

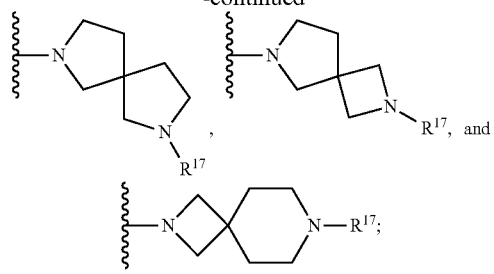

wherein R¹⁷ is hydroxyalkyl.

In some embodiments of a compound of Formula (IIa), R¹ is halogen, —CH₃, —CF₃, —OCH₃, or —OCF₃. In some embodiments of a compound of Formula (IIa), R¹ is halogen. In some embodiments of a compound of Formula (IIa), R¹ is —Cl. In some embodiments of a compound of Formula (IIa), R¹ is —CH₃. In some embodiments of a compound of Formula (IIa), R¹ is —CF₃. In some embodiments of a compound of Formula (IIa), R¹ is —OCH₃. In some embodiments of a compound of Formula (IIa), R¹ is —OCF₃.

Another embodiment provides a compound of Formula (III):

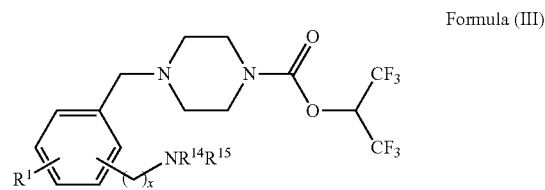

Formula (III)

wherein:
R¹ is halogen, —OR³, —CN, aryl (optionally substituted by one, two, or three moieties each independently selected from R⁴), aryloxy (optionally substituted by one, two, or three moieties each independently selected from R⁴), heteroaryl (optionally substituted by one, two, or three moieties each independently selected from R⁴), heteroaryloxy (optionally substituted by one, two, or three moieties each independently selected from R⁴), heterocycle (optionally substituted by one, two, or three moieties each independently selected from R⁴), cycloalkyl (optionally substituted by one, two, or three moieties each independently selected from R⁴), optionally substituted $C_{1-6}$ alkyl, optionally substituted $C_{2-6}$ alkenyl, optionally substituted $C_{2-6}$ alkynyl, —NR⁹R¹⁰, —NR⁸C(O)R⁹, —NR⁸SO₂R⁹, —NR⁸C(O)OR⁹, —NR⁸C(O)NR⁹R¹⁰, —C(O)R⁹, —C(O)OR⁹, —C(O)NR⁹R¹⁰, —S(O)_wR¹¹, or —SH;

each R³ is independently selected from H, $C_{1-6}$ alkyl, haloalkyl, and aminoalkyl;

each R⁴ is independently selected from halogen, —OR³, —CN, nitro, optionally substituted $C_{1-6}$ alkyl, optionally substituted $C_{1-6}$ alkenyl, optionally substituted $C_{1-6}$ alkynyl, cycloalkyl, —NR⁹R¹⁰, —NR⁸C(O)R⁹, —NR⁸SO₂R⁹, —NR⁸C(O)OR⁹, —NR⁸C(O)NR⁹R¹⁰, —C(O)R⁹, —C(O)OR⁹, —C(O)NR⁹R¹⁰, —S(O)_wR¹¹, and —SH;

each R⁸ is independently selected from H, optionally substituted alkyl, optionally substituted cycloalkyl, optionally substituted aryl, optionally substituted heteroaryl, and optionally substituted heterocycloalkyl;

each $R^9$ and $R^{10}$ is independently selected from H, optionally substituted alkyl, optionally substituted cycloalkyl, optionally substituted aryl, optionally substituted heteroaryl, and optionally substituted heterocycloalkyl; or $R^9$ and $R^{10}$ together with the nitrogen to which they are attached form an optionally substituted heterocycle optionally containing an additional O, N, or S;

each $R^{11}$ is independently selected from optionally substituted alkyl, optionally substituted cycloalkyl, optionally substituted aryl, optionally substituted heteroaryl, and optionally substituted heterocycloalkyl;

$R^{14}$ and $R^{15}$ together with the nitrogen to which they are attached form an optionally substituted heterocycle optionally containing an additional O, N, or S;

w is 0, 1, or 2; and x is 1, 2, or 3;

or a solvate, hydrate, tautomer, N-oxide, stereoisomer, or pharmaceutically acceptable salt thereof.

In some embodiments of a compound of Formula (III), $R^{14}$ and $R^{15}$, together with the nitrogen to which they are attached, form a heterocycle optionally containing an additional O, N, or S; wherein the heterocycle is substituted with one or more substituents independently selected from halogen, oxo, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of Formula (III), $R^{14}$ and $R^{15}$, together with the nitrogen to which they are attached, form a substituted heterocycle; wherein the substituted heterocycle has one or more substituents independently selected from halogen, oxo, —$OR^3$, —CN, $C_{1-6}$ alkyl, haloalkyl, —$NR^9R^{10}$, —$NR^8C(O)R^9$, —$NR^8SO_2R^9$, —$NR^8C(O)OR^9$, —$S(O)_wR^{11}$, —$NR^8C(O)NR^9R^{10}$, —$C(O)R^9$, —$C(O)OR^9$, and —$C(O)NR^9R^{10}$. In some embodiments of a compound of Formula (III), $R^{14}$ and $R^{15}$, together with the nitrogen to which they are attached, form an optionally substituted pyrrolidine, optionally substituted piperidine, optionally substituted morpholine, or optionally substituted piperazine. In some embodiments of a compound of Formula (III), $R^{14}$ and $R^{15}$, together with the nitrogen to which they are attached, form a substituted or unsubstituted pyrrolidine. In some embodiments of a compound of Formula (III), $R^{14}$ and $R^{15}$, together with the nitrogen to which they are attached, form a substituted or unsubstituted piperidine. In some embodiments of a compound of Formula (III), $R^{14}$ and $R^{15}$, together with the nitrogen to which they are attached, form a substituted or unsubstituted morpholine. In some embodiments of a compound of Formula (III), $R^{14}$ and $R^{15}$, together with the nitrogen to which they are attached, form a substituted or unsubstituted piperazine. In some embodiments of a compound of Formula (III), $R^{14}$ and $R^{15}$, together with the nitrogen to which they are attached, form an optionally substituted heterocycle selected from:

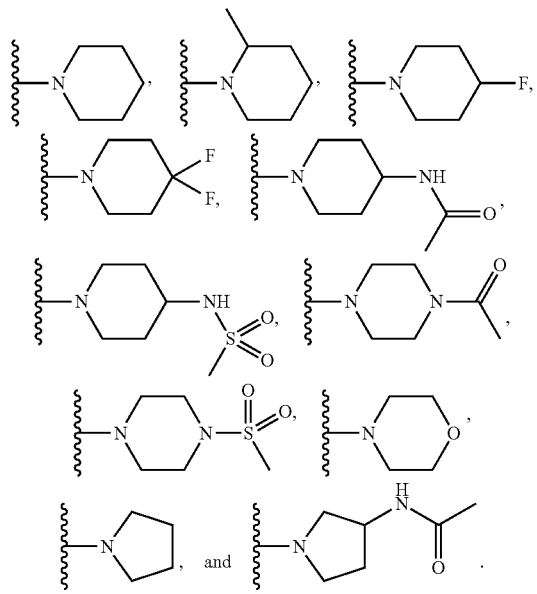

In some embodiments of a compound of Formula (III), $R^1$ is halogen, —$CH_3$, —$CF_3$, —$OCH_3$, or —$OCF_3$. In some embodiments of a compound of Formula (III), $R^1$ is halogen. In some embodiments of a compound of Formula (III), $R^1$ is —Cl. In some embodiments of a compound of Formula (III), $R^1$ is —$CH_3$. In some embodiments of a compound of Formula (III), $R^1$ is —$CF_3$. In some embodiments of a compound of Formula (III), $R^1$ is —$OCH_3$. In some embodiments of a compound of Formula (III), $R^1$ is —$OCF_3$.

Another embodiment provides a compound of Formula (IV):

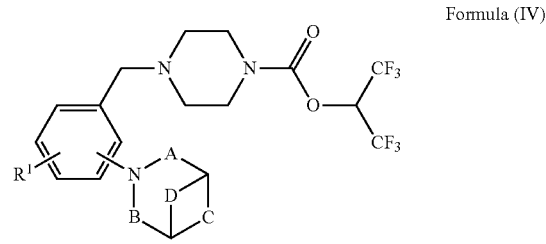

Formula (IV)

wherein:

A and B are independently a bond or $CR^{18}R^{19}$;

C is O or $CR^{18}R^{19}OCR^{20}R^{21}$;

D is $CR^{18}R^{19}$ or $CR^{18}R^{19}CR^{20}R^{21}$;

$R^1$ is halogen, —$OR^3$, —CN, aryl (optionally substituted by one, two, or three moieties each independently selected from $R^4$), aryloxy (optionally substituted by one, two, or three moieties each independently selected from $R^4$), heteroaryl (optionally substituted by one, two, or three moieties each independently selected from $R^4$), heteroaryloxy (optionally substituted by one, two, or three moieties each independently selected from $R^4$), heterocycle (optionally substituted by one, two, or three moieties each independently selected from $R^4$), cycloalkyl (optionally substituted by one, two, or three moieties each independently selected from $R^4$), optionally substituted $C_{1-6}$ alkyl, optionally substituted $C_{2-6}$ alkenyl, optionally substituted $C_{2-6}$ alkynyl, —$NR^9R^{10}$, —$NR^8C(O)R^9$, —$NR^8SO_2R^9$, —NR⁸C(O)OR⁹, —NR⁸C(O)NR⁹R¹⁰, —C(O)R⁹, —C(O)OR⁹, —C(O)NR⁹R¹⁰, —S(O)$_w$R¹¹, or —SH;

each R³ is independently selected from H, $C_{1-6}$ alkyl, haloalkyl, and aminoalkyl;

each R⁴ is independently selected from halogen, —OR³, —CN, nitro, optionally substituted $C_{1-6}$ alkyl, optionally substituted $C_{1-6}$ alkenyl, optionally substituted $C_{1-6}$ alkynyl, cycloalkyl, —NR⁹R¹⁰, —NR⁸C(O)R⁹, —NR⁸SO₂R⁹, —NR⁸C(O)OR⁹, —NR⁸C(O)NR⁹R¹⁰, —C(O)R⁹, —C(O)OR⁹, —C(O)NR⁹R¹⁰, —S(O)$_w$R¹¹, and —SH;

each R⁸ is independently selected from H, optionally substituted alkyl, optionally substituted cycloalkyl, optionally substituted aryl, optionally substituted heteroaryl, and optionally substituted heterocycloalkyl;

each R⁹ and R¹⁰ is independently selected from H, optionally substituted alkyl, optionally substituted cycloalkyl, optionally substituted aryl, optionally substituted heteroaryl, and optionally substituted heterocycloalkyl; or R⁹ and R¹⁰ together with the nitrogen to which they are attached form an optionally substituted heterocycle optionally containing an additional O, N, or S;

each R¹¹ is independently selected from optionally substituted alkyl, optionally substituted cycloalkyl, optionally substituted aryl, optionally substituted heteroaryl, and optionally substituted heterocycloalkyl;

R¹⁷ is H, optionally substituted $C_{1-6}$ alkyl, optionally substituted aryl, optionally substituted heteroaryl, optionally substituted heterocycle, optionally substituted cycloalkyl, —S(O)$_w$R¹¹, —C(O)R⁹, —C(O)OR⁹, or —C(O)NR⁹R¹⁰;

each R¹⁸, R¹⁹, R²⁰, and R²¹ is independently selected from H, optionally substituted $C_{1-6}$ alkyl, optionally substituted aryl, optionally substituted heteroaryl, optionally substituted heterocycle, optionally substituted cycloalkyl, —C(O)R⁹, —C(O)OR⁹, and —C(O)NR⁹R¹⁰; and w is 0, 1, or 2;

or a solvate, hydrate, tautomer, N-oxide, stereoisomer, or pharmaceutically acceptable salt thereof.

In some embodiments of a compound of Formula (IV), R¹⁸, R¹⁹, R²⁰, and R²¹ are H.

In some embodiments of a compound of Formula (IV), A and B are both bonds; D is CR¹⁸R¹⁹CR²⁰R²¹; and C is CR¹⁸R¹⁹OCR²⁰R²¹. In some embodiments of a compound of Formula (IV), A and B are both bonds; D is CH₂CH₂; and C is CH₂OCH₂.

In some embodiments of a compound of Formula (IV), A and B are both CR¹⁸R¹⁹; D is CR¹⁸R¹⁹CR²⁰R²¹; and C is O. In some embodiments of a compound of Formula (IV), A and B are both CH₂; D is CH₂CH₂; and C is O.

In some embodiments of a compound of Formula (IV), R¹ is halogen, —CH₃, —CF₃, —OCH₃, or —OCF₃. In some embodiments of a compound of Formula (IV), R¹ is halogen. In some embodiments of a compound of Formula (IV), R¹ is —Cl. In some embodiments of a compound of Formula (IV), R¹ is —CH₃. In some embodiments of a compound of Formula (IV), R¹ is —CF₃. In some embodiments of a compound of Formula (IV), R¹ is —OCH₃. In some embodiments of a compound of Formula (IV), R¹ is —OCF₃.

Further embodiments provided herein include combinations of one or more of the particular embodiments set forth above.

In some embodiments, the compound disclosed herein has the structure provided in Table 1.

TABLE 1

| Chemical Synthesis Example | Structure | Name |
|---|---|---|
| 1 | 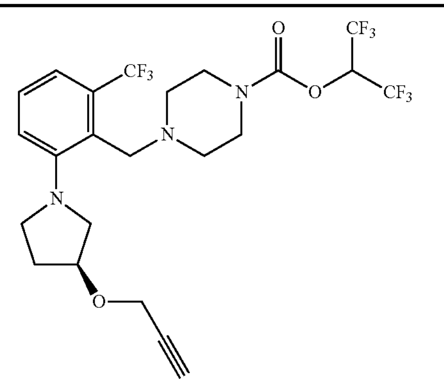 | 1,1,1,3,3,3-hexafluoropropan-2-yl (S)-4-(2-(3-(prop-2-yn-1-yloxy)pyrrolidin-1-yl)-6-(trifluoromethyl)benzyl)piperazine-1-carboxylate |
| 2 | 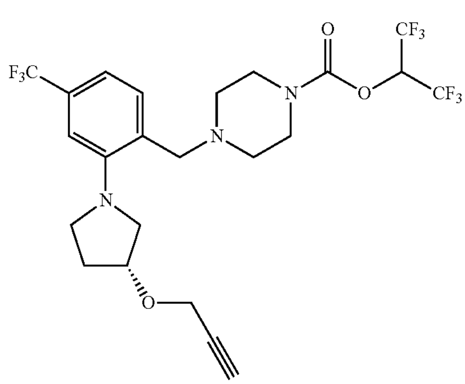 [SMILES: C#CCO[C@@H]1CCN(c2cc(C(F)(F)F)ccc2CN2CCN(C(=O)OC(C(F)(F)F)C(F)(F)F)CC2)C1] | 1,1,1,3,3,3-hexafluoropropan-2-yl (R)-4-(2-(3-(prop-2-yn-1-yloxy)pyrrolidin-1-yl)-4-(trifluoromethyl)benzyl)piperazine-1-carboxylate |

TABLE 1-continued

| Chemical Synthesis Example | Structure | Name |
|---|---|---|
| 3 | 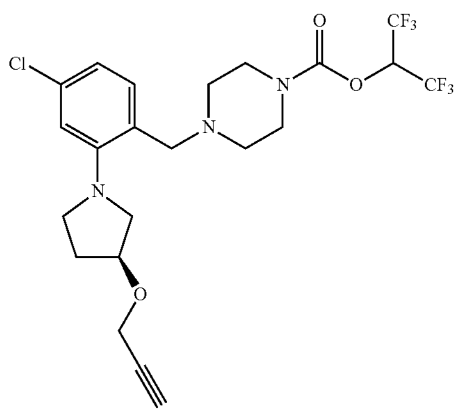 [SMILES: C#CCO[C@H]1CCN(c2cc(Cl)ccc2CN2CCN(C(=O)OC(C(F)(F)F)C(F)(F)F)CC2)C1] | 1,1,1,3,3,3-hexafluoropropan-2-yl (S)-4-(4-chloro-2-(3-(prop-2-yn-1-yloxy)pyrrolidin-1-yl)benzyl)piperazine-1-carboxylate |
| 4 | 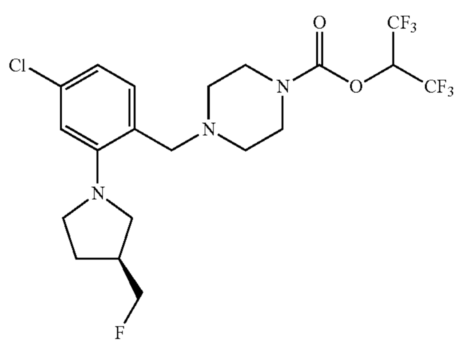 [SMILES: O=C(OC(C(F)(F)F)C(F)(F)F)N1CCN(Cc2ccc(Cl)cc2N2CC[C@H](CF)C2)CC1] | 1,1,1,3,3,3-hexafluoropropan-2-yl (S)-4-(4-chloro-2-(3-(fluoromethyl)pyrrolidin-1-yl)benzyl)piperazine-1-carboxylate |
| 5 | 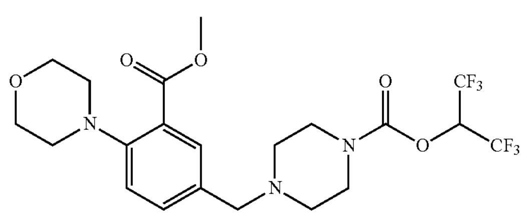 [SMILES: COC(=O)c1cc(CN2CCN(C(=O)OC(C(F)(F)F)C(F)(F)F)CC2)ccc1N1CCOCC1] | 1,1,1,3,33-hexafluoropropan-2-yl 4-(3-(methoxycarbonyl)-4-morpholinobenzyl)piperazine-1-carboxylate |
| 6 | 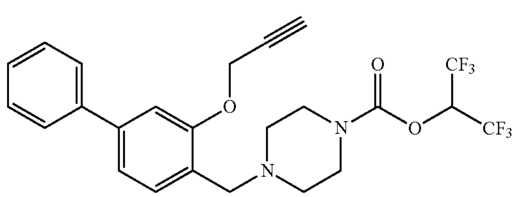 [SMILES: C#CCOc1cc(-c2ccccc2)ccc1CN1CCN(C(=O)OC(C(F)(F)F)C(F)(F)F)CC1] | 1,1,1,3,3,3-hexafluoropropan-2-yl 4-((3-(prop-2-yn-1-yloxy)-[1,1'-biphenyl]-4-yl)methyl)piperazine-1-carboxylate |
| 7 | 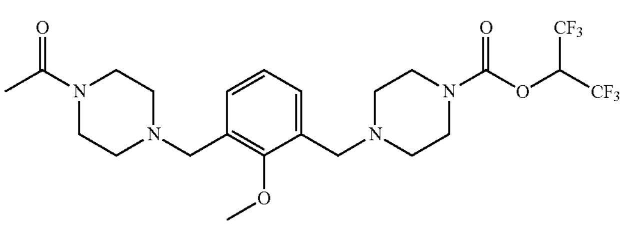 [SMILES: COc1c(CN2CCN(C(C)=O)CC2)cccc1CN1CCN(C(=O)OC(C(F)(F)F)C(F)(F)F)CC1] | 1,1,1,3,3,3-hexafluoropropan-2-yl 4-(3-((4-acetylpiperazin-1-yl)methyl)-2-methoxybenzyl)piperazine-1-carboxylate |

TABLE 1-continued

| Chemical Synthesis Example | Structure | Name |
|---|---|---|
| 8 | 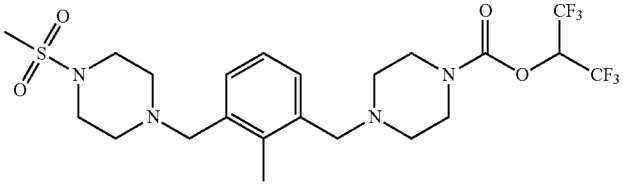 [SMILES: Cc1c(CN2CCN(C(=O)OC(C(F)(F)F)C(F)(F)F)CC2)cccc1CN1CCN(S(C)(=O)=O)CC1] | 1,1,1,3,3,3-hexafluoropropan-2-yl 4-(2-methyl-3-((4-(methylsulfonyl)piperazin-1-yl)methyl)benzyl)piperazine-1-carboxylate |
| 9 | 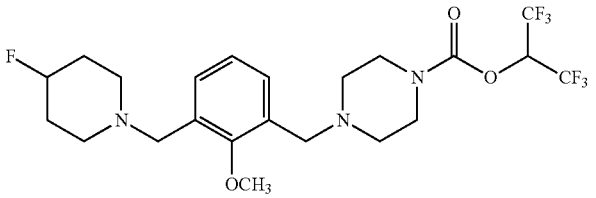 [SMILES: COc1c(CN2CCC(F)CC2)cccc1CN1CCN(C(=O)OC(C(F)(F)F)C(F)(F)F)CC1] | 1,1,1,3,3,3-hexafluoropropan-2-yl 4-(3-((4-fluoropiperidin-1-yl)methyl)-2-methoxybenzyl)piperazine-1-carboxylate |
| 10 | 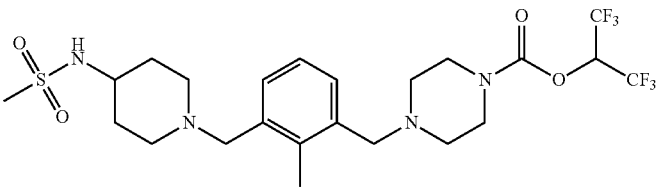 [SMILES: Cc1c(CN2CCC(NS(C)(=O)=O)CC2)cccc1CN1CCN(C(=O)OC(C(F)(F)F)C(F)(F)F)CC1] | 1,1,1,3,3,3-hexafluoropropan-2-yl 4-(2-methyl-3-((4-(methylsulfonamido)piperidin-1-yl)methyl)benzyl)piperazine-1-carboxylate |
| 11 | 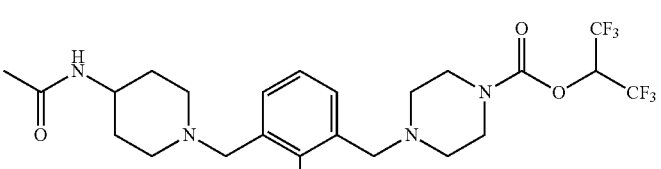 | 1,1,1,3,3,3-hexafluoropropan-2-yl 4-(3-((4-acetamidopiperidin-1-yl)methyl)-2-methylbenzyl)piperazine-1-carboxylate |
| 12 | 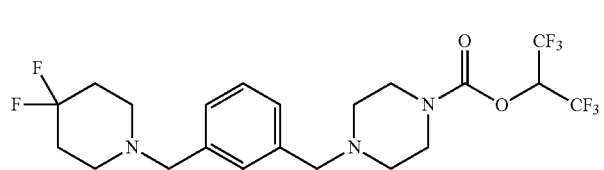 | 1,1,1,3,3,3-hexafluoropropan-2-yl 4-(3-((4,4-difluoropiperidin-1-yl)methyl)-2-methylbenzyl)piperazine-1-carboxylate |
| 13 | 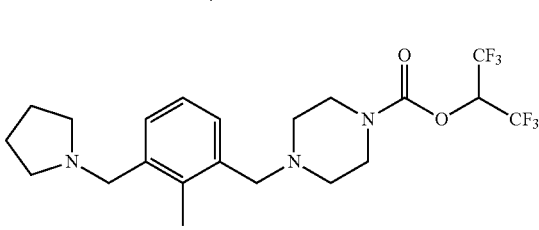 | 1,1,1,3,3,3-hexafluoropropan-2-yl 4-(2-methyl-3-(pyrrolidin-1-ylmethyl)benzyl)piperazine-1-carboxylate |
| 14 | 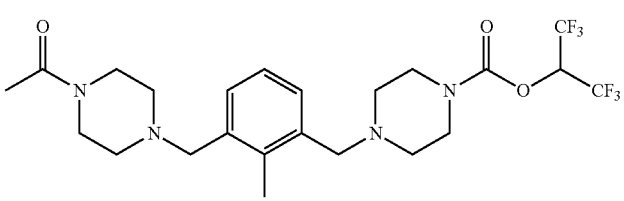 [SMILES: CC(=O)N1CCN(Cc2cccc(CN3CCN(C(=O)OC(C(F)(F)F)C(F)(F)F)CC3)c2C)CC1] | 1,1,1,3,3,3-hexafluoropropan-2-yl 4-(3-((4-acetylpiperazin-1-yl)methyl)-2-methylbenzyl)piperazine-1-carboxylate |

TABLE 1-continued

| Chemical Synthesis Example | Structure | Name |
|---|---|---|
| 15 | 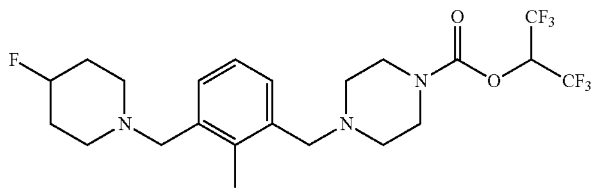 [SMILES: Cc1c(CN2CCC(F)CC2)cccc1CN1CCN(C(=O)OC(C(F)(F)F)C(F)(F)F)CC1] | 1,1,1,3,3,3-hexafluoropropan-2-yl 4-(3-((4-fluoropiperidin-1-yl)methyl)-2-methylbenzyl)piperazine-1-carboxylate |
| 16 | 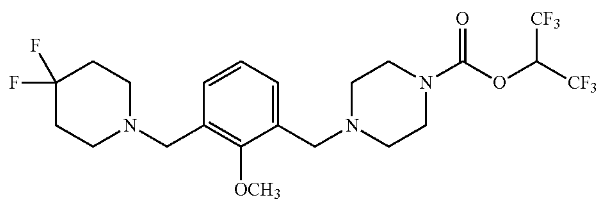 [SMILES: COc1c(CN2CCN(C(=O)OC(C(F)(F)F)C(F)(F)F)CC2)cccc1CN1CCC(F)(F)CC1] | 1,1,1,3,3,3-hexafluoropropan-2-yl 4-(3-((4,4-difluoropiperidin-1-yl)methyl)-2-methoxybenzyl)piperazine-1-carboxylate |
| 17 | 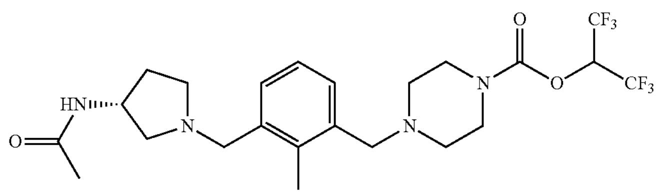 [SMILES: CC(=O)N[C@@H]1CCN(Cc2cccc(CN3CCN(C(=O)OC(C(F)(F)F)C(F)(F)F)CC3)c2C)C1] | 1,1,1,3,3,3-hexafluoropropan-2-yl (R)-4-(3-((3-acetamidopyrrolidin-1-yl)methyl)-2-methylbenzyl)piperazine-1-carboxylate |
| 18 | 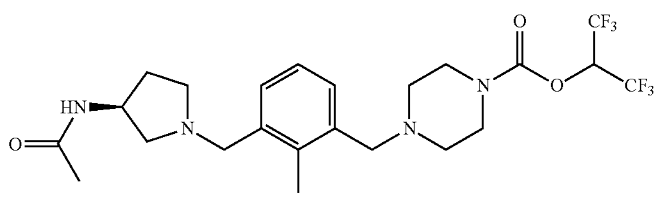 [SMILES: CC(=O)N[C@H]1CCN(Cc2cccc(CN3CCN(C(=O)OC(C(F)(F)F)C(F)(F)F)CC3)c2C)C1] | 1,1,1,3,3,3-hexafluoropropan-2-yl (S)-4-(3-((3-acetamidopyrrolidin-1-yl)methyl)-2-methylbenzyl)piperazine-1-carboxylate |
| 19 | 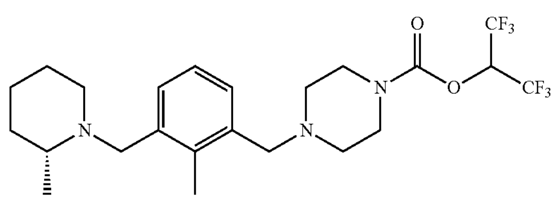 [SMILES: Cc1c(CN2CCN(C(=O)OC(C(F)(F)F)C(F)(F)F)CC2)cccc1CN1CCCC[C@H]1C] | 1,1,1,3,3,3-hexafluoropropan-2-yl (R)-4-(2-methyl-3-((2-methylpiperidin-1-yl)methyl)benzyl)piperazine-1-carboxylate |
| 20 | 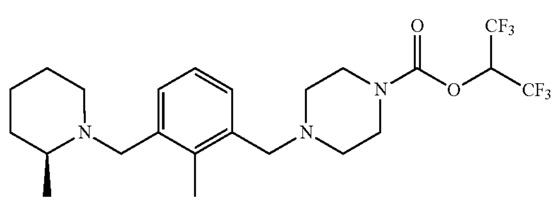 [SMILES: Cc1c(CN2CCN(C(=O)OC(C(F)(F)F)C(F)(F)F)CC2)cccc1CN1CCCC[C@@H]1C] | 1,1,1,3,3,3-hexafluoropropan-2-yl (S)-4-(2-methyl-3-((2-methylpiperidin-1-yl)methyl)benzyl)piperazine-1-carboxylate |
| 21 | 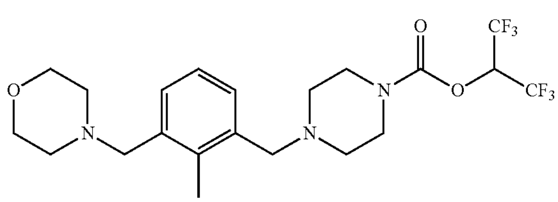 [SMILES: Cc1c(CN2CCOCC2)cccc1CN1CCN(C(=O)OC(C(F)(F)F)C(F)(F)F)CC1] | 1,1,1,3,3,3-hexafluoropropan-2-yl 4-(2-methyl-3-(morpholinomethyl)benzyl)piperazine-1-carboxylate |

TABLE 1-continued

| Chemical Synthesis Example | Structure | Name |
|---|---|---|
| 22 | 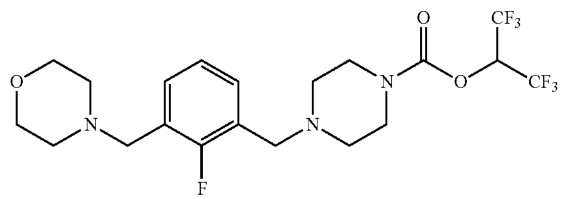 [SMILES: O=C(OC(C(F)(F)F)C(F)(F)F)N1CCN(Cc2cccc(CN3CCOCC3)c2F)CC1] | 1,1,1,3,3,3-hexafluoropropan-2-yl 4-(2-fluoro-3-(morpholinomethyl)benzyl)piperazine-1-carboxylate |
| 23 | 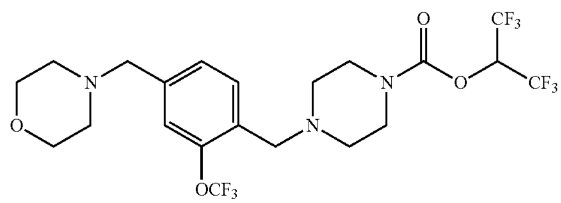 [SMILES: O=C(OC(C(F)(F)F)C(F)(F)F)N1CCN(Cc2ccc(CN3CCOCC3)cc2OC(F)(F)F)CC1] | 1,1,1,3,3,3-hexafluoropropan-2-yl 4-(4-(morpholinomethyl)-2-(trifluoromethoxy)benzyl)piperazine-1-carboxylate |
| 24 | 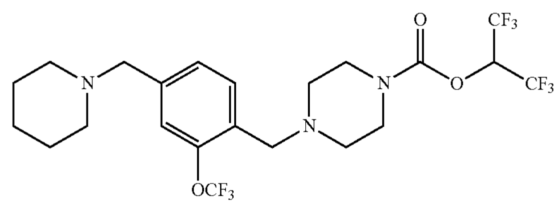 [SMILES: O=C(OC(C(F)(F)F)C(F)(F)F)N1CCN(Cc2ccc(CN3CCCCC3)cc2OC(F)(F)F)CC1] | 1,1,1,3,3,3-hexafluoropropan-2-yl 4-(4-(piperidin-1-ylmethyl)-2-(trifluoromethoxy)benzyl)piperazine-1-carboxylate |
| 25 | 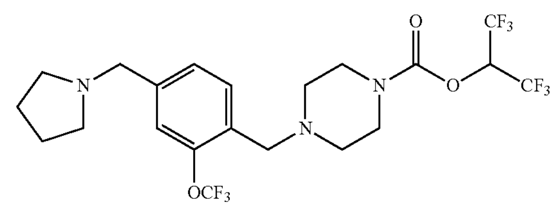 [SMILES: O=C(OC(C(F)(F)F)C(F)(F)F)N1CCN(Cc2ccc(CN3CCCC3)cc2OC(F)(F)F)CC1] | 1,1,1,3,3,3-hexafluoropropan-2-yl 4-(4-(pyrrolidin-1-ylmethyl)-2-(trifluoromethoxy)benzyl)piperazine-1-carboxylate |
| 26 | 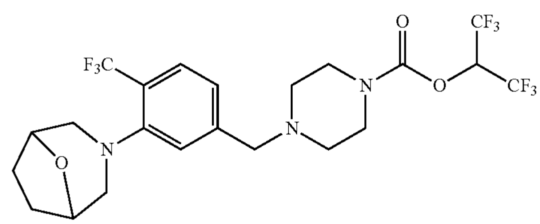 [SMILES: O=C(OC(C(F)(F)F)C(F)(F)F)N1CCN(Cc2ccc(C(F)(F)F)c(N3CC4CCC(C3)O4)c2)CC1] | 1,1,1,3,3,3-hexafluoropropan-2-yl 4-(3-(8-oxa-3-azabicyclo[3.2.1]octan-3-yl)-4-(trifluoromethyl)benzyl)piperazine-1-carboxylate |
| 27 | 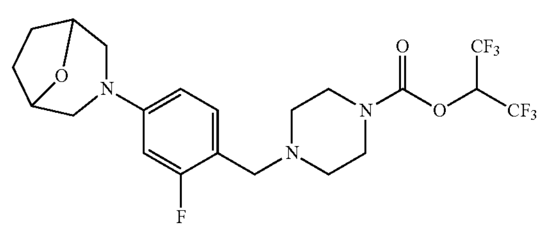 [SMILES: O=C(OC(C(F)(F)F)C(F)(F)F)N1CCN(Cc2ccc(N3CC4CCC(C3)O4)cc2F)CC1] | 1,1,1,3,3,3-hexafluoropropan-2-yl 4-(4-(8-oxa-3-azabicyclo[3.2.1]octan-3-yl)-2-fluorobenzyl)piperazine-1-carboxylate |
| 28 | 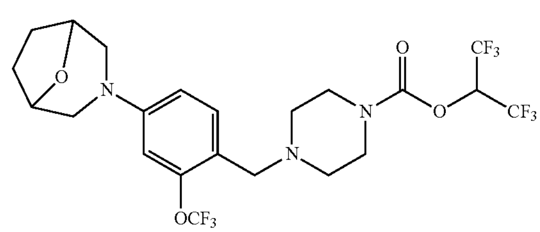 [SMILES: O=C(OC(C(F)(F)F)C(F)(F)F)N1CCN(Cc2ccc(N3CC4CCC(C3)O4)cc2OC(F)(F)F)CC1] | 1,1,1,3,3,3-hexafluoropropan-2-yl 4-(4-(8-oxa-3-azabicyclo[3.2.1]octan-3-yl)-2-(trifluoromethoxy)benzyl)piperazine-1-carboxylate |

TABLE 1-continued

| Chemical Synthesis Example | Structure | Name |
|---|---|---|
| 29 | 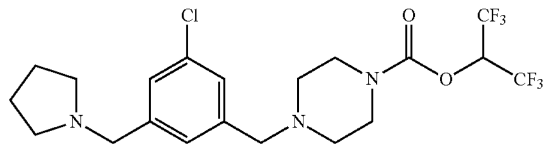 [SMILES: O=C(OC(C(F)(F)F)C(F)(F)F)N1CCN(Cc2cc(Cl)cc(CN3CCCC3)c2)CC1] | 1,1,1,3,3,3-hexafluoropropan-2-yl 4-(3-chloro-5-(pyrrolidin-1-ylmethyl)benzyl)piperazine-1-carboxylate |
| 30 | 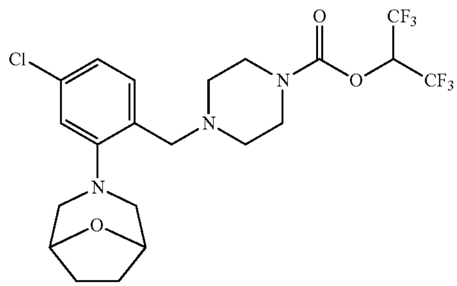 [SMILES: O=C(OC(C(F)(F)F)C(F)(F)F)N1CCN(Cc2ccc(Cl)cc2N2CC3CCC(C2)O3)CC1] | 1,1,1,3,3,3-hexafluoropropan-2-yl 4-(2-(8-oxa-3-azabicyclo[3.2.1]octan-3-yl)-4-chlorobenzyl)piperazine-1-carboxylate |
| 31 | 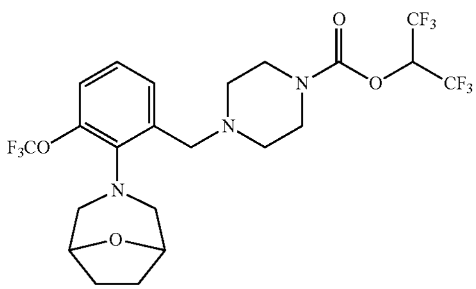 [SMILES: O=C(OC(C(F)(F)F)C(F)(F)F)N1CCN(Cc2cccc(OC(F)(F)F)c2N2CC3CCC(C2)O3)CC1] | 1,1,1,3,3,3-hexafluoropropan-2-yl 4-(2-(8-oxa-3-azabicyclo[3.2.1]octan-3-yl)-3-(trifluoromethoxy)benzyl)piperazine-1-carboxylate |
| 32 | 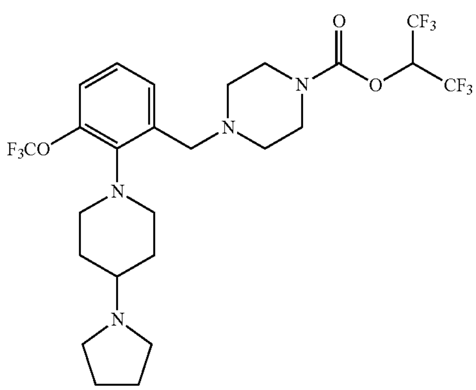 [SMILES: O=C(OC(C(F)(F)F)C(F)(F)F)N1CCN(Cc2cccc(OC(F)(F)F)c2N2CCC(N3CCCC3)CC2)CC1] | 1,1,1,3,3,3-hexafluoropropan-2-yl 4-(2-(4-(pyrrolidin-1-yl)piperidin-1-yl)-3-(trifluoromethoxy)benzyl)piperazine-1-carboxylate |
| 33 | 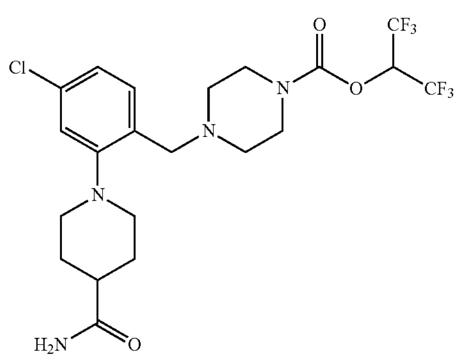 [SMILES: NC(=O)C1CCN(c2cc(Cl)ccc2CN2CCN(C(=O)OC(C(F)(F)F)C(F)(F)F)CC2)CC1] | 1,1,1,3,3,3-hexafluoropropan-2-yl 4-(2-(4-carbamoylpiperidin-1-yl)-4-chlorobenzyl)piperazine-1-carboxylate |

TABLE 1-continued

| Chemical Synthesis Example | Structure | Name |
|---|---|---|
| 34 | 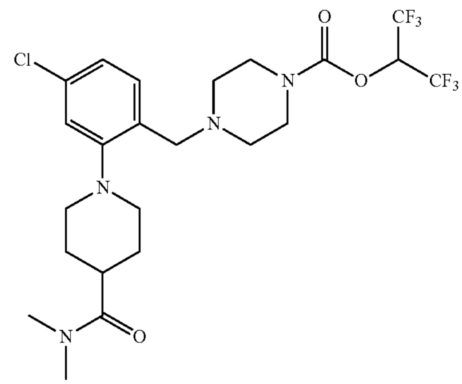 [SMILES: CN(C)C(=O)C1CCN(c2cc(Cl)ccc2CN2CCN(C(=O)OC(C(F)(F)F)C(F)(F)F)CC2)CC1] | 1,1,1,3,3,3-hexafluoropropan-2-yl 4-(4-chloro-2-(4-(dimethylcarbamoyl)piperidin-1-yl)benzyl)piperazine-1-carboxylate |
| 35 | 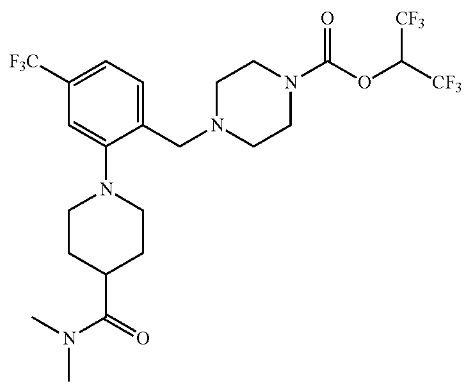 [SMILES: CN(C)C(=O)C1CCN(c2cc(C(F)(F)F)ccc2CN2CCN(C(=O)OC(C(F)(F)F)C(F)(F)F)CC2)CC1] | 1,1,1,3,3,3-hexafluoropropan-2-yl 4-(2-(4-(dimethylcarbamoyl)piperidin-1-yl)-4-(trifluoromethyl)benzyl)piperazine-1-carboxylate |
| 36 | 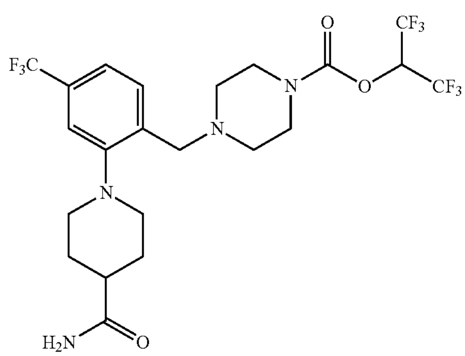 [SMILES: NC(=O)C1CCN(c2cc(C(F)(F)F)ccc2CN2CCN(C(=O)OC(C(F)(F)F)C(F)(F)F)CC2)CC1] | 1,1,1,3,3,3-hexafluoropropan-2-yl 4-(2-(4-carbamoylpiperidin-1-yl)-4-(trifluoromethyl)benzyl)piperazine-1-carboxylate |
| 37 | 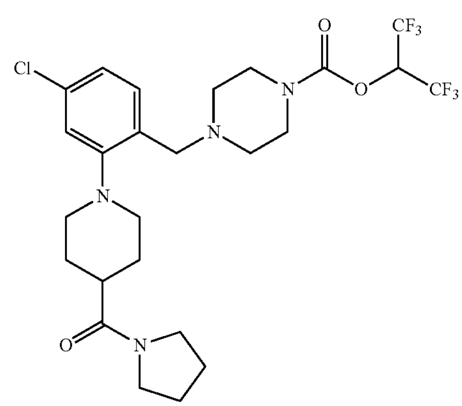 [SMILES: O=C(OC(C(F)(F)F)C(F)(F)F)N1CCN(Cc2ccc(Cl)cc2N2CCC(C(=O)N3CCCC3)CC2)CC1] | 1,1,1,3,3,3-hexafluoropropan-2-yl 4-(4-chloro-2-(4-(pyrrolidine-1-carbonyl)piperidin-1-yl)benzyl)piperazine-1-carboxylate |

TABLE 1-continued

| Chemical Synthesis Example | Structure | Name |
|---|---|---|
| 38 | 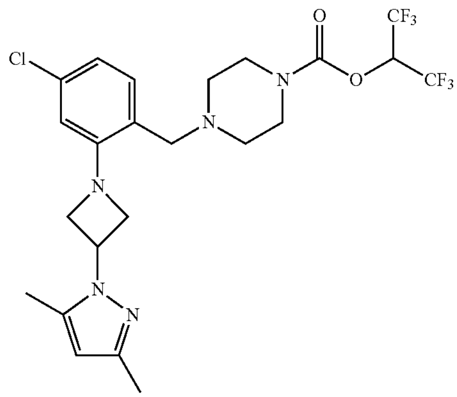 [SMILES: Cc1cc(C)n(C2CN(c3cc(Cl)ccc3CN3CCN(C(=O)OC(C(F)(F)F)C(F)(F)F)CC3)C2)n1] | 1,1,1,3,3,3-hexafluoropropan-2-yl 4-(4-chloro-2-(3-(3,5-dimethyl-1H-pyrazol-1-yl)azetidin-1-yl)benzyl)piperazine-1-carboxylate |
| 39 | 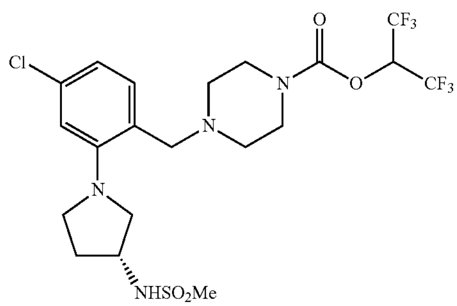 | 1,1,1,3,3,3-hexafluoropropan-2-yl (R)-4-(4-chloro-2-(3-(methylsulfonamido)pyrrolidin-1-yl)benzyl)piperazine-1-carboxylate |
| 40 | 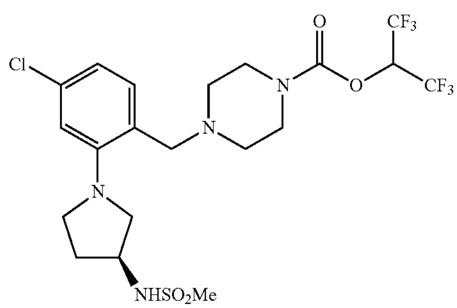 | 1,1,1,3,3,3-hexafluoropropan-2-yl (S)-4-(4-chloro-2-(3-(methylsulfonamido)pyrrolidin-1-yl)benzyl)piperazine-1-carboxylate |
| 41 | 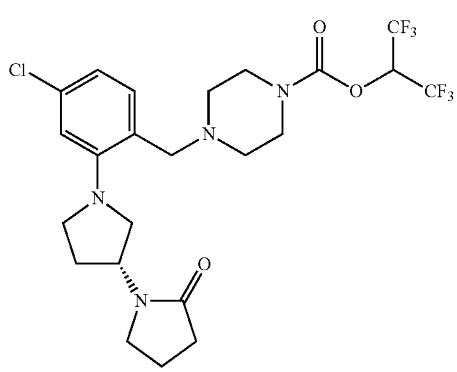 [SMILES: O=C(OC(C(F)(F)F)C(F)(F)F)N1CCN(Cc2ccc(Cl)cc2N2CC[C@@H](N3CCCC3=O)C2)CC1] | 1,1,1,3,3,3-hexafluoropropan-2-yl (R)-4-(4-chloro-2-(2-oxo-[1,3'-bipyrrolidin]-1'-yl)benzyl)piperazine-1-carboxylate |

TABLE 1-continued

| Chemical Synthesis Example | Structure | Name |
|---|---|---|
| 42 | 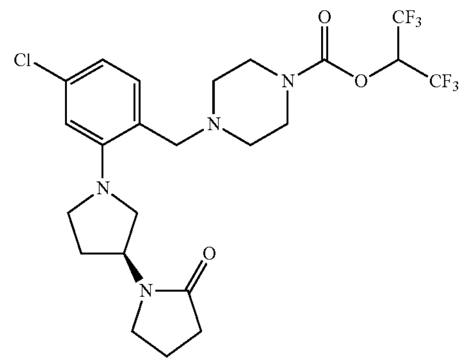 [SMILES: O=C(OC(C(F)(F)F)C(F)(F)F)N1CCN(Cc2ccc(Cl)cc2N2CC[C@H](N3CCCC3=O)C2)CC1] | 1,1,1,3,3,3-hexafluoropropan-2-yl (S)-4-(4-chloro-2-(2-oxo-[1,3'-bipyrrolidin]-1'-yl)benzyl)piperazine-1-carboxylate |
| 43 | 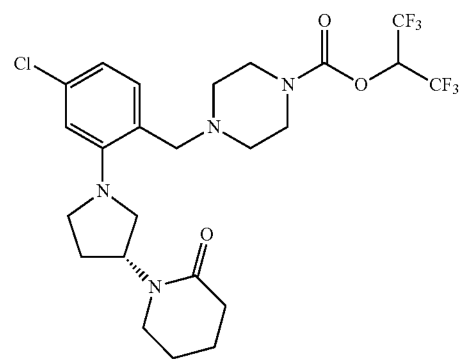 [SMILES: O=C(OC(C(F)(F)F)C(F)(F)F)N1CCN(Cc2ccc(Cl)cc2N2CC[C@@H](N3CCCCC3=O)C2)CC1] | 1,1,1,3,3,3-hexafluoropropan-2-yl (R)-4-(4-chloro-2-(3-(2-oxopiperidin-1-yl)pyrrolidin-1-yl)benzyl)piperazine-1-carboxylate |
| 44 | 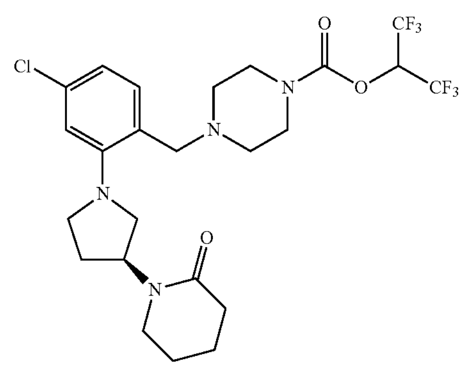 [SMILES: O=C(OC(C(F)(F)F)C(F)(F)F)N1CCN(Cc2ccc(Cl)cc2N2CC[C@H](N3CCCCC3=O)C2)CC1] | 1,1,1,3,3,3-hexafluoropropan-2-yl (S)-4-(4-chloro-2-(3-(2-oxopiperidin-1-yl)pyrrolidin-1-yl)benzyl)piperazine-1-carboxylate |
| 45 | 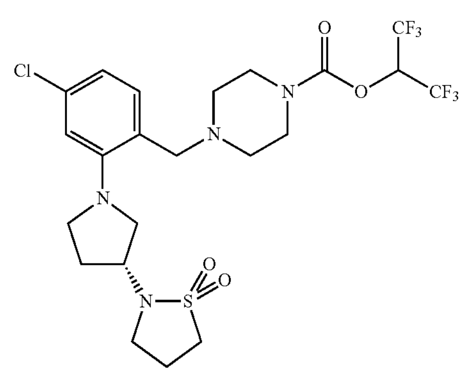 [SMILES: O=C(OC(C(F)(F)F)C(F)(F)F)N1CCN(Cc2ccc(Cl)cc2N2CC[C@@H](N3CCCS3(=O)=O)C2)CC1] | 1,1,1,3,3,3-hexafluoropropan-2-yl (R)-4-(4-chloro-2-(3-(1,1-dioxidoisothiazolidin-2-yl)pyrrolidin-1-yl)benzyl)piperazine-1-carboxylate |

TABLE 1-continued

| Chemical Synthesis Example | Structure | Name |
|---|---|---|
| 46 | 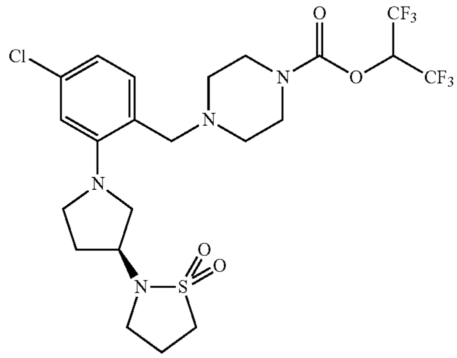 [SMILES: O=C(OC(C(F)(F)F)C(F)(F)F)N1CCN(Cc2ccc(Cl)cc2N2CC[C@H](N3CCCS3(=O)=O)C2)CC1] | 1,1,1,3,3,3-hexafluoropropan-2-yl (S)-4-(4-chloro-2-(3-(1,1-dioxidoisothiazolidin-2-yl)pyrrolidin-1-yl)benzyl)piperazine-1-carboxylate |
| 47 | 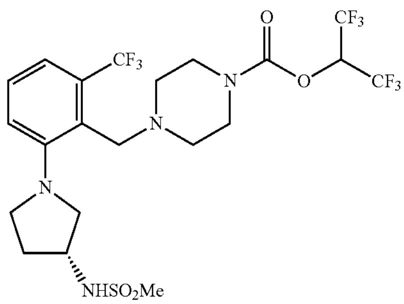 | 1,1,1,3,3,3-hexafluoropropan-2-yl (R)-4-(2-(3-(methylsulfonamido)pyrrolidin-1-yl)-6-(trifluoromethyl)benzyl)piperazine-1-carboxylate |
| 48 | 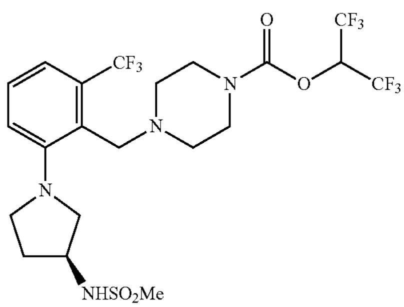 | 1,1,1,3,3,3-hexafluoropropan-2-yl (S)-4-(2-(3-(methylsulfonamido)pyrrolidin-1-yl)-6-(trifluoromethyl)benzyl)piperazine-1-carboxylate |
| 49 | 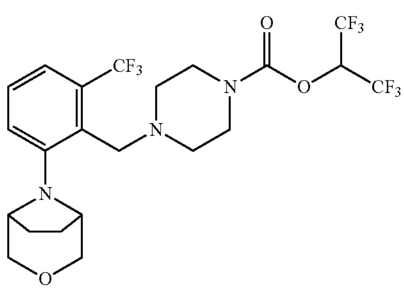 [SMILES: O=C(OC(C(F)(F)F)C(F)(F)F)N1CCN(Cc2c(N3C4CCC3COC4)cccc2C(F)(F)F)CC1] | 1,1,1,3,3,3-hexafluoropropan-2-yl 4-(2-(3-oxa-8-azabicyclo[3.2.1]octan-8-yl)-6-(trifluoromethyl)benzyl)piperazine-1-carboxylate |
| 50 | 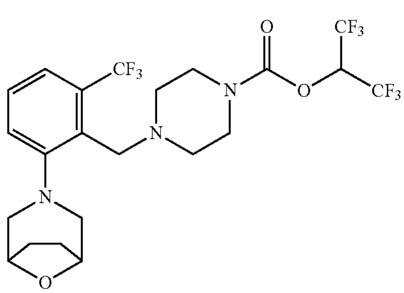 [SMILES: O=C(OC(C(F)(F)F)C(F)(F)F)N1CCN(Cc2c(N3CC4CCC(C3)O4)cccc2C(F)(F)F)CC1] | 1,1,1,3,3,3-hexafluoropropan-2-yl 4-(2-(8-oxa-3-azabicyclo[3.2.1]octan-3-yl)-6-(trifluoromethyl)benzyl)piperazine-1-carboxylate |

TABLE 1-continued

| Chemical Synthesis Example | Structure | Name |
|---|---|---|
| 51 | 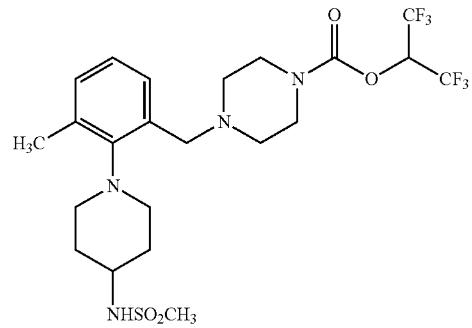 | 1,1,1,3,3,3-hexafluoropropan-2-yl 4-(3-methyl-2-(4-(methylsulfonamido)piperidin-1-yl)benzyl)piperazine-1-carboxylate |
| 52 | 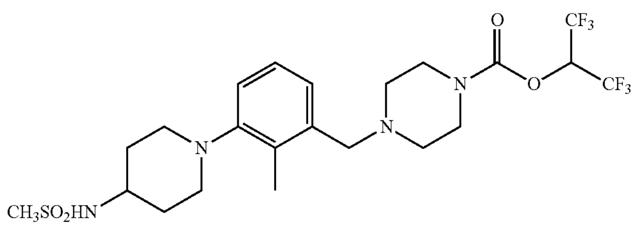 | 1,1,1,3,3,3-hexafluoropropan-2-yl 4-(2-methyl-3-(4-(methylsulfonamido)piperidin-1-yl)benzyl)piperazine-1-carboxylate |
| 53 | 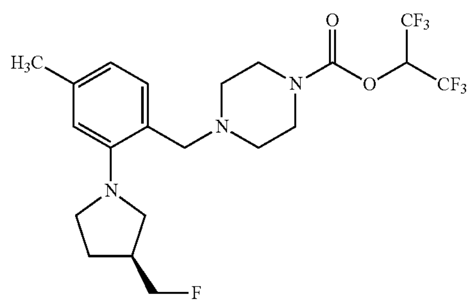 [SMILES: Cc1ccc(CN2CCN(C(=O)OC(C(F)(F)F)C(F)(F)F)CC2)c(N2CC[C@H](CF)C2)c1] | 1,1,1,3,3,3-hexafluoropropan-2-yl (S)-4-(2-(3-(fluoromethyl)pyrrolidin-1-yl)-4-methylbenzyl)piperazine-1-carboxylate |
| 54 | 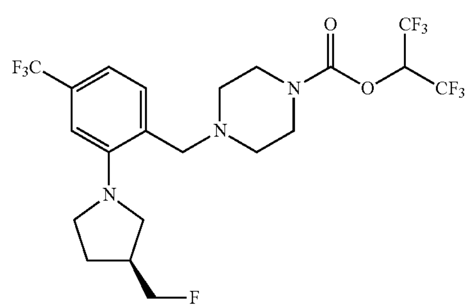 [SMILES: O=C(OC(C(F)(F)F)C(F)(F)F)N1CCN(Cc2ccc(C(F)(F)F)cc2N2CC[C@H](CF)C2)CC1] | 1,1,1,3,3,3-hexafluoropropan-2-yl (S)-4-(2-(3-(fluoromethyl)pyrrolidin-1-yl)-4-(trifluoromethyl)benzyl)piperazine-1-carboxylate |
| 55 | 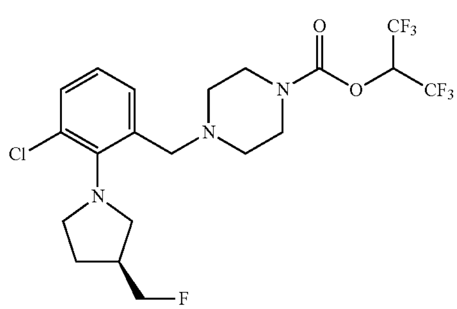 [SMILES: O=C(OC(C(F)(F)F)C(F)(F)F)N1CCN(Cc2cccc(Cl)c2N2CC[C@H](CF)C2)CC1] | 1,1,1,3,3,3-hexafluoropropan-2-yl (S)-4-(3-chloro-2-(3-(fluoromethyl)pyrrolidin-1-yl)benzyl)piperazine-1-carboxylate |

TABLE 1-continued

| Chemical Synthesis Example | Structure | Name |
| --- | --- | --- |
| 56 | 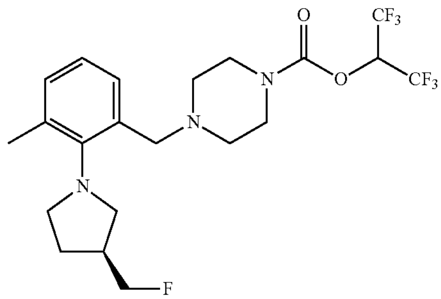 [SMILES: Cc1cccc(CN2CCN(C(=O)OC(C(F)(F)F)C(F)(F)F)CC2)c1N1CC[C@H](CF)C1] | 1,1,1,3,3,3-hexafluoropropan-2-yl (S)-4-(2-(3-(fluoromethyl)pyrrolidin-1-yl)-3-methylbenzyl)piperazine-1-carboxylate |
| 57 | 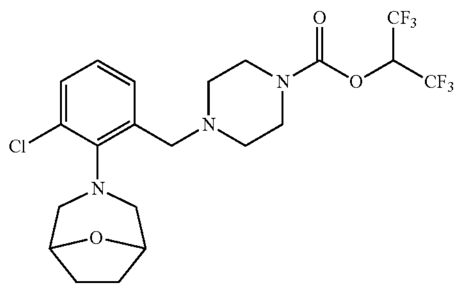 [SMILES: O=C(OC(C(F)(F)F)C(F)(F)F)N1CCN(Cc2cccc(Cl)c2N2CC3CCC(C2)O3)CC1] | 1,1,1,3,3,3-hexafluoropropan-2-yl 4-(2-(8-oxa-3-azabicyclo[3.2.1]octan-3-yl)-3-chlorobenzyl)piperazine-1-carboxylate |
| 58 | 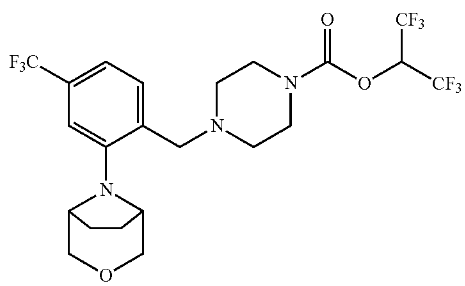 [SMILES: O=C(OC(C(F)(F)F)C(F)(F)F)N1CCN(Cc2ccc(C(F)(F)F)cc2N2C3CCC2COC3)CC1] | 1,1,1,3,3,3-hexafluoropropan-2-yl 4-(2-(3-oxa-8-azabicyclo[3.2.1]octan-8-yl)-4-(trifluoromethyl)benzyl)piperazine-1-carboxylate |
| 59 | 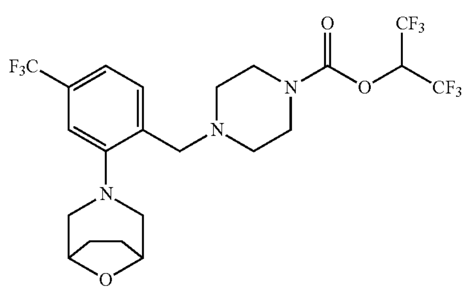 [SMILES: O=C(OC(C(F)(F)F)C(F)(F)F)N1CCN(Cc2ccc(C(F)(F)F)cc2N2CC3CCC(C2)O3)CC1] | 1,1,1,3,3,3-hexafluoropropan-2-yl 4-(2-(8-oxa-3-azabicyclo[3.2.1]octan-3-yl)-4-(trifluoromethyl)benzyl)piperazine-1-carboxylate |
| 60 | 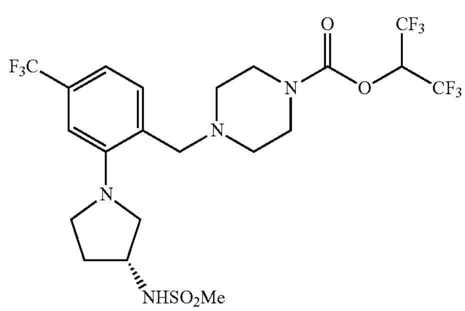 | 1,1,1,3,3,3-hexafluoropropan-2-yl (R)-4-(2-(3-(methylsulfonamido)pyrrolidin-1-yl)-4-(trifluoromethyl)benzyl)piperazine-1-carboxylate |

TABLE 1-continued

| Chemical Synthesis Example | Structure | Name |
|---|---|---|
| 61 | 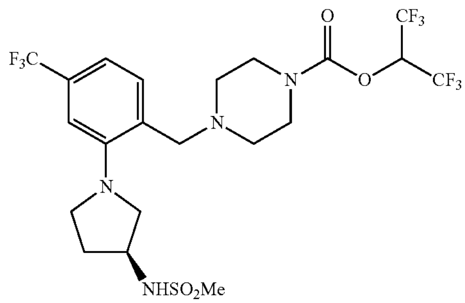 | 1,1,1,3,3,3-hexafluoropropan-2-yl (S)-4-(2-(3-(methylsulfonamido)pyrrolidin-1-yl)-4-(trifluoromethyl)benzyl)piperazine-1-carboxylate |
| 62 | 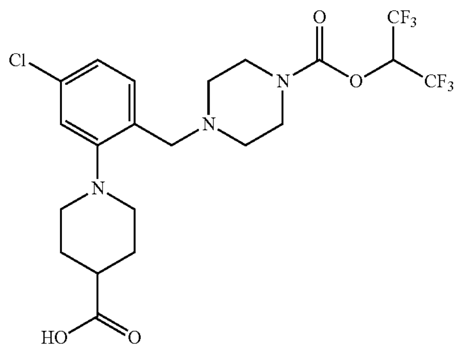 [SMILES: O=C(O)C1CCN(c2cc(Cl)ccc2CN2CCN(C(=O)OC(C(F)(F)F)C(F)(F)F)CC2)CC1] | 1-(5-chloro-2-((4-(((1,1,1,3,3,3-hexafluoropropan-2-yl)oxy)carbonyl)piperazin-1-yl)methyl)phenyl)piperidine-4-carboxylic acid |
| 63 | 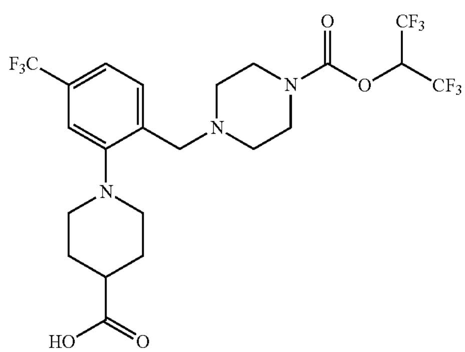 [SMILES: O=C(O)C1CCN(c2cc(C(F)(F)F)ccc2CN2CCN(C(=O)OC(C(F)(F)F)C(F)(F)F)CC2)CC1] | 1-(2-((4-(((1,1,1,3,3,3-hexafluoropropan-2-yl)oxy)carbonyl)piperazin-1-yl)methyl)-5-(trifluoromethyl)phenyl)piperidine-4-carboxylic acid |
| 64 | 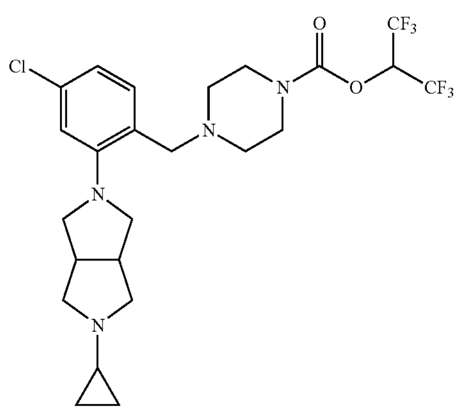 [SMILES: O=C(OC(C(F)(F)F)C(F)(F)F)N1CCN(Cc2ccc(Cl)cc2N2CC3CN(C4CC4)CC3C2)CC1] | 1,1,1,3,3,3-hexafluoropropan-2-yl 4-(4-chloro-2-(5-cyclopropylhexahydropyrrolo[3,4-c]pyrrol-2(1H)-yl)benzyl)piperazine-1-carboxylate |

TABLE 1-continued

| Chemical Synthesis Example | Structure | Name |
|---|---|---|
| 65 | 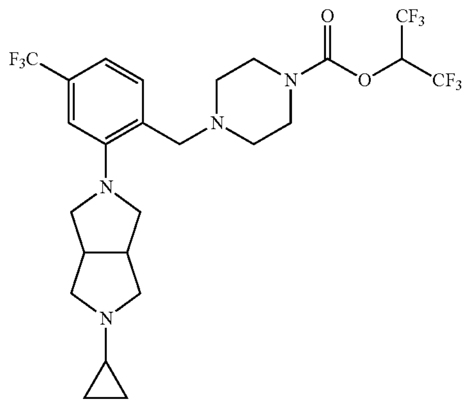 [SMILES: O=C(OC(C(F)(F)F)C(F)(F)F)N1CCN(Cc2ccc(C(F)(F)F)cc2N2CC3CN(C4CC4)CC3C2)CC1] | 1,1,1,3,3,3-hexafluoropropan-2-yl 4-(2-(5-cyclopropylhexahydropyrrolo[3,4-c]pyrrol-2(1H)-yl)-4-(trifluoromethyl)benzyl)piperazine-1-carboxylate |
| 66 | 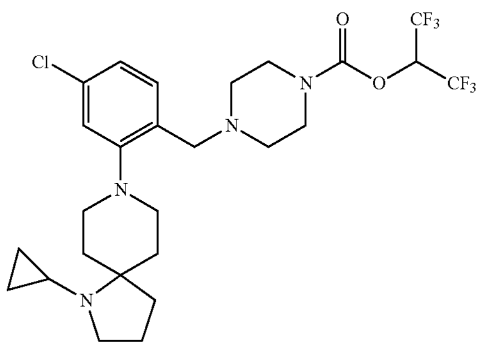 [SMILES: O=C(OC(C(F)(F)F)C(F)(F)F)N1CCN(Cc2ccc(Cl)cc2N2CCC3(CCCN3C3CC3)CC2)CC1] | 1,1,1,3,3,3-hexafluoropropan-2-yl 4-(4-chloro-2-(1-cyclopropyl-1,8-diazaspiro[4.5]decan-8-yl)benzyl)piperazine-1-carboxylate |
| 67 | 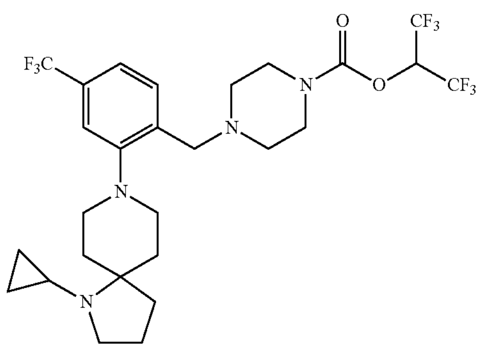 [SMILES: O=C(OC(C(F)(F)F)C(F)(F)F)N1CCN(Cc2ccc(C(F)(F)F)cc2N2CCC3(CCCN3C3CC3)CC2)CC1] | 1,1,1,3,3,3-hexafluoropropan-2-yl 4-(2-(1-cyclopropyl-1,8-diazaspiro[4.5]decan-8-yl)-4-(trifluoromethyl)benzyl)piperazine-1-carboxylate |
| 68 | 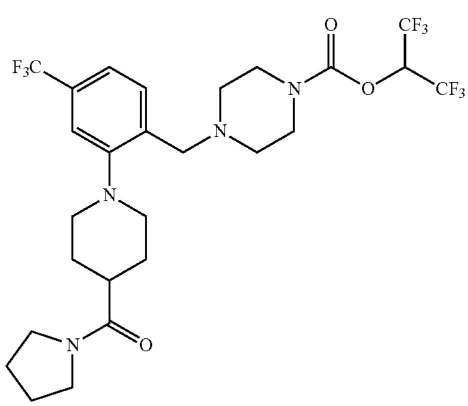 [SMILES: O=C(OC(C(F)(F)F)C(F)(F)F)N1CCN(Cc2ccc(C(F)(F)F)cc2N2CCC(C(=O)N3CCCC3)CC2)CC1] | 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate |

TABLE 1-continued

| Chemical Synthesis Example | Structure | Name |
|---|---|---|
| 69 | 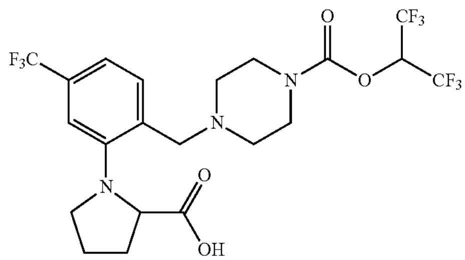 [SMILES: O=C(O)C1CCCN1c1cc(C(F)(F)F)ccc1CN1CCN(C(=O)OC(C(F)(F)F)C(F)(F)F)CC1] | 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate |
| 70 | 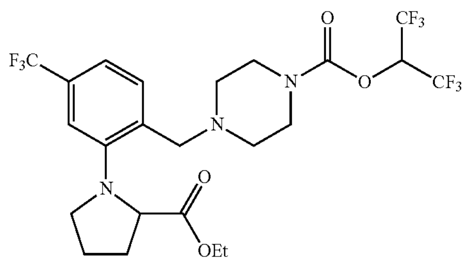 [SMILES: CCOC(=O)C1CCCN1c1cc(C(F)(F)F)ccc1CN1CCN(C(=O)OC(C(F)(F)F)C(F)(F)F)CC1] | 1,1,1,3,3,3-hexafluoropropan-2-yl 4-(2-(2-(ethoxycarbonyl)pyrrolidin-1-yl)-4-(trifluoromethyl)benzyl)piperazine-1-carboxylate |
| 71 | 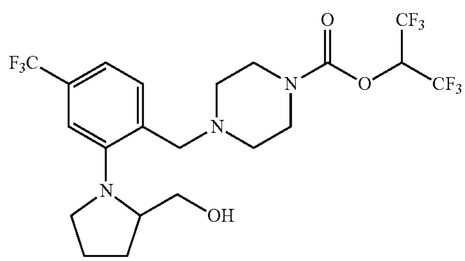 [SMILES: O=C(OC(C(F)(F)F)C(F)(F)F)N1CCN(Cc2ccc(C(F)(F)F)cc2N2CCCC2CO)CC1] | 1,1,1,3,3,3-hexafluoropropan-2-yl 4-(2-(2-(hydroxymethyl)pyrrolidin-1-yl)-4-(trifluoromethyl)benzyl)piperazine-1-carboxylate |
| 72 | 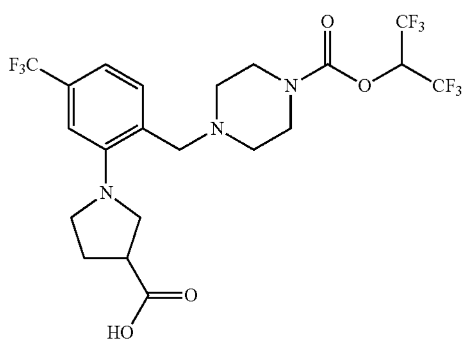 [SMILES: O=C(O)C1CCN(c2cc(C(F)(F)F)ccc2CN2CCN(C(=O)OC(C(F)(F)F)C(F)(F)F)CC2)C1] | 1-(2-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid |
| 73 | 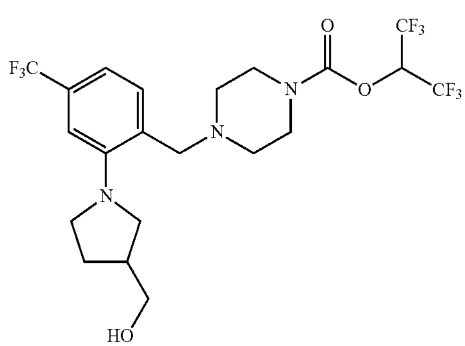 [SMILES: O=C(OC(C(F)(F)F)C(F)(F)F)N1CCN(Cc2ccc(C(F)(F)F)cc2N2CCC(CO)C2)CC1] | 1,1,1,3,3,3-hexafluoropropan-2-yl 4-(2-(3-(hydroxymethyl)pyrrolidin-1-yl)-4-(trifluoromethyl)benzyl)piperazine-1-carboxylate |

TABLE 1-continued

| Chemical Synthesis Example | Structure | Name |
|---|---|---|
| 74 | 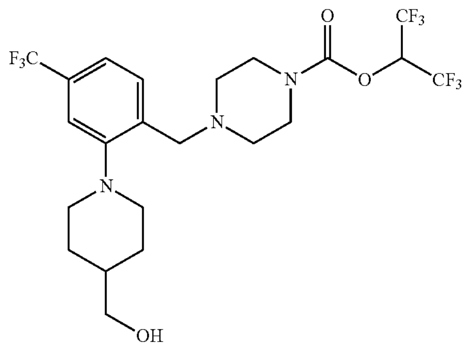 [SMILES: O=C(OC(C(F)(F)F)C(F)(F)F)N1CCN(Cc2ccc(C(F)(F)F)cc2N2CCC(CO)CC2)CC1] | 1,1,1,3,3,3-hexafluoropropan-2-yl 4-(2-(4-(hydroxymethyl)piperidin-1-yl)-4-(trifluoromethyl)benzyl)piperazine-1-carboxylate |
| 75 | 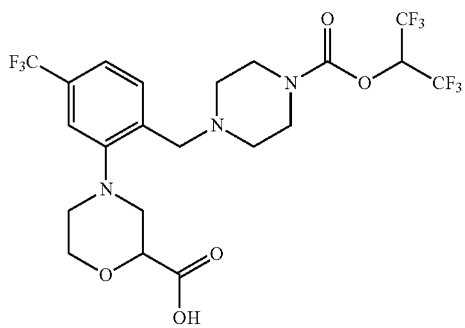 [SMILES: O=C(O)C1CN(c2cc(C(F)(F)F)ccc2CN2CCN(C(=O)OC(C(F)(F)F)C(F)(F)F)CC2)CCO1] | 4-(2-((4-(((1,1,1,3,3,3-hexafluoropropan-2-yl)oxy)carbonyl)piperazin-1-yl)methyl)-5-(trifluoromethyl)phenyl)morpholine-2-carboxylic acid |
| 76 | 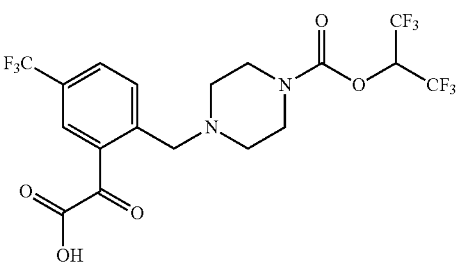 [SMILES: O=C(O)C(=O)c1cc(C(F)(F)F)ccc1CN1CCN(C(=O)OC(C(F)(F)F)C(F)(F)F)CC1] | 2-(2-((4-(((1,1,1,3,3,3-hexafluoropropan-2-yl)oxy)carbonyl)piperazin-1-yl)methyl)-5-(trifluoromethyl)phenyl)-2-oxoacetic acid |
| 77 | 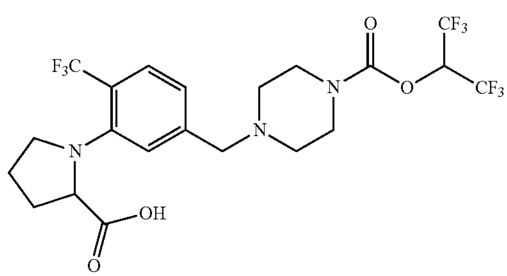 [SMILES: CCOC(=O)C1CCCN1c1cc(CN2CCN(C(=O)OC(C(F)(F)F)C(F)(F)F)CC2)ccc1C(F)(F)F] | (5-((4-(((1,1,1,3,3,3-hexafluoropropan-2-yl)oxy)carbonyl)piperazin-1-yl)methyl)-2-(trifluoromethyl)phenyl)proline |
| 78 | 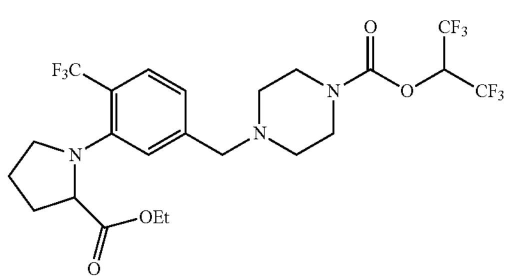 | 1,1,1,3,3,3-hexafluoropropan-2-yl 4-(3-(2-(ethoxycarbonyl)pyrrolidin-1-yl)-4-(trifluoromethyl)benzyl)piperazine-1-carboxylate |

TABLE 1-continued

| Chemical Synthesis Example | Structure | Name |
|---|---|---|
| 79 | 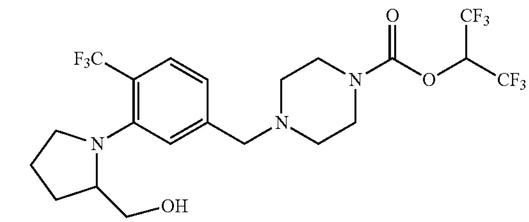 [SMILES: O=C(OC(C(F)(F)F)C(F)(F)F)N1CCN(Cc2ccc(C(F)(F)F)c(N3CCCC3CO)c2)CC1] | 1,1,1,3,3,3-hexafluoropropan-2-yl 4-(3-(2-(hydroxymethyl)pyrrolidin-1-yl)-4-(trifluoromethyl)benzyl)piperazine-1-carboxylate |
| 80 | 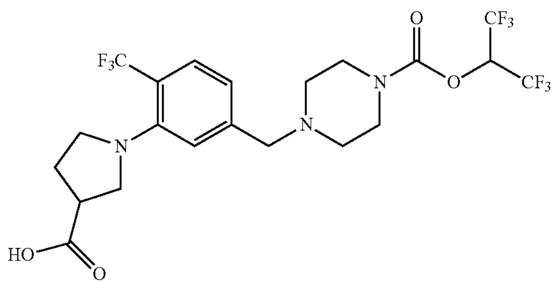 [SMILES: O=C(O)C1CCN(c2cc(CN3CCN(C(=O)OC(C(F)(F)F)C(F)(F)F)CC3)ccc2C(F)(F)F)C1] | 1-(5-((4-(((1,1,1,3,3,3-hexafluoropropan-2-yl)oxy)carbonyl)piperazin-1-yl)methyl)-2-(trifluoromethyl)phenyl)pyrrolidine-3-carboxylic acid |
| 81 | 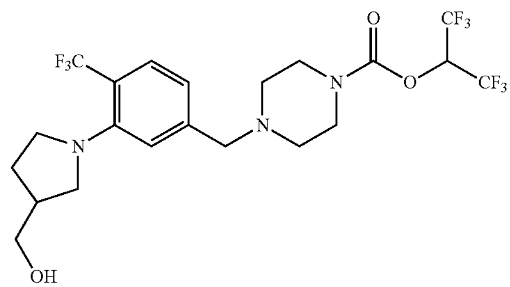 [SMILES: O=C(OC(C(F)(F)F)C(F)(F)F)N1CCN(Cc2ccc(C(F)(F)F)c(N3CCC(CO)C3)c2)CC1] | 1,1,1,3,3,3-hexafluoropropan-2-yl 4-(3-(3-(hydroxymethyl)pyrrolidin-1-yl)-4-(trifluoromethyl)benzyl)piperazine-1-carboxylate |
| 82 | 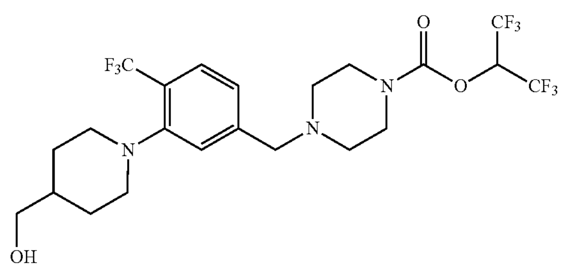 [SMILES: O=C(OC(C(F)(F)F)C(F)(F)F)N1CCN(Cc2ccc(C(F)(F)F)c(N3CCC(CO)CC3)c2)CC1] | 1,1,1,3,3,3-hexafluoropropan-2-yl 4-(3-(4-(hydroxymethyl)piperidin-1-yl)-4-(trifluoromethyl)benzyl)piperazine-1-carboxylate |
| 83 | 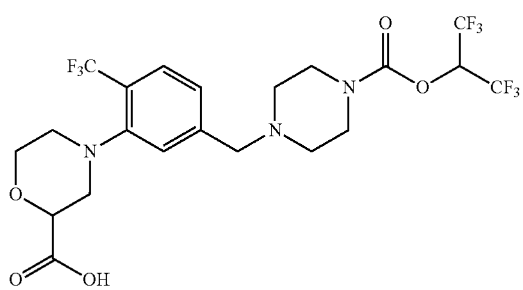 [SMILES: O=C(O)C1CN(c2cc(CN3CCN(C(=O)OC(C(F)(F)F)C(F)(F)F)CC3)ccc2C(F)(F)F)CCO1] | 4-(5-((4-(((1,1,1,3,3,3-hexafluoropropan-2-yl)oxy)carbonyl)piperazin-1-yl)methyl)-2-(trifluoromethyl)phenyl)morpholine-2-carboxylic acid |
| 84 | 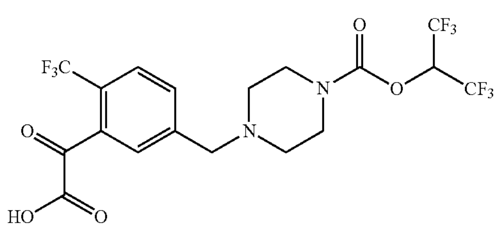 [SMILES: O=C(O)C(=O)c1cc(CN2CCN(C(=O)OC(C(F)(F)F)C(F)(F)F)CC2)ccc1C(F)(F)F] | 2-(5-((4-(((1,1,1,3,3,3-hexafluoropropan-2-yl)oxy)carbonyl)piperazin-1-yl)methyl)-2-(trifluoromethyl)phenyl)-2-oxoacetic acid |

TABLE 1-continued

| Chemical Synthesis Example | Structure | Name |
|---|---|---|
| 85 | 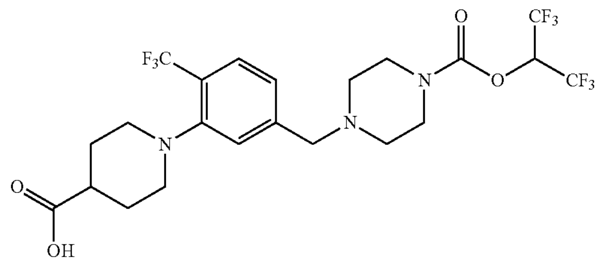 [SMILES: O=C(O)C1CCN(c2cc(CN3CCN(C(=O)OC(C(F)(F)F)C(F)(F)F)CC3)ccc2C(F)(F)F)CC1] | 1-(5-((4-(((1,1,1,3,3,3-hexafluoropropan-2-yl)oxy)carbonyl)piperazin-1-yl)methyl)-2-(trifluoromethyl)phenyl)piperidine-4-carboxylic acid |
| 86 | 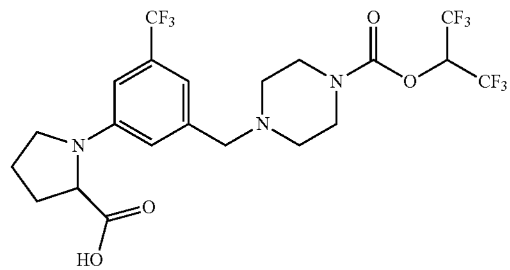 | (3-((4-(((1,1,1,3,3,3-hexafluoropropan-2-yl)oxy)carbonyl)piperazin-1-yl)methyl)-5-(trifluoromethyl)phenyl)proline |
| 87 | 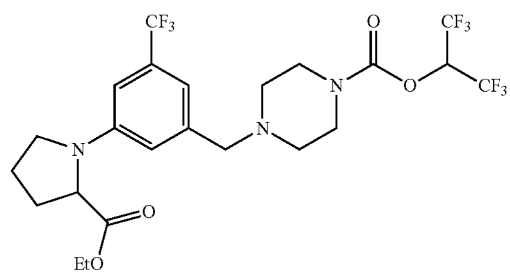 [SMILES: O=C(O)C1CCCN1c1cc(CN2CCN(C(=O)OC(C(F)(F)F)C(F)(F)F)CC2)cc(C(F)(F)F)c1] | 1,1,1,3,3,3-hexafluoropropan-2-yl 4-(3-(2-(ethoxycarbonyl)pyrrolidin-1-yl)-5-(trifluoromethyl)benzyl)piperazine-1-carboxylate |
| 88 | 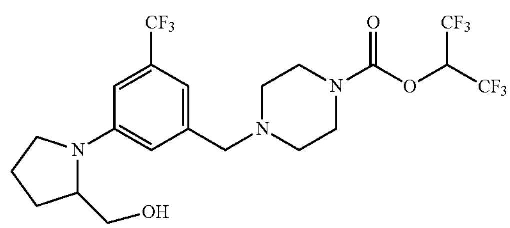 [SMILES: O=C(OC(C(F)(F)F)C(F)(F)F)N1CCN(Cc2cc(N3CCCC3CO)cc(C(F)(F)F)c2)CC1] | 1,1,1,3,3,3-hexafluoropropan-2-yl 4-(3-(2-(hydroxymethyl)pyrrolidin-1-yl)-5-(trifluoromethyl)benzyl)piperazine-1-carboxylate |
| 89 | 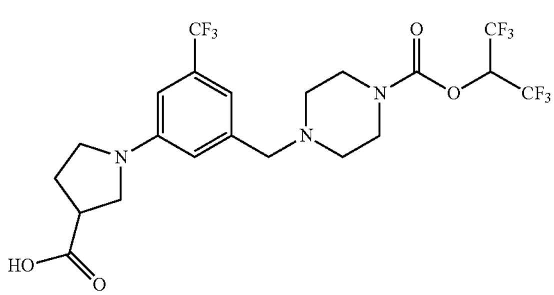 [SMILES: O=C(O)C1CCN(c2cc(CN3CCN(C(=O)OC(C(F)(F)F)C(F)(F)F)CC3)cc(C(F)(F)F)c2)C1] | 1-(3-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid |

TABLE 1-continued

| Chemical Synthesis Example | Structure | Name |
|---|---|---|
| 90 | 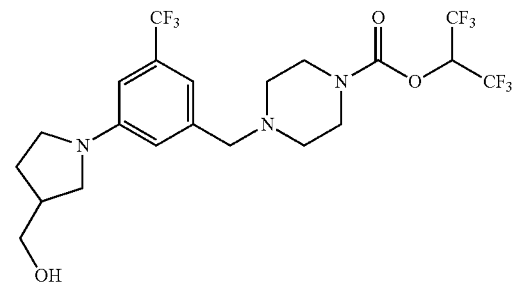 [SMILES: O=C(OC(C(F)(F)F)C(F)(F)F)N1CCN(Cc2cc(N3CCC(CO)C3)cc(C(F)(F)F)c2)CC1] | 1,1,1,3,3,3-hexafluoropropan-2-yl 4-(3-(3-(hydroxymethyl)pyrrolidin-1-yl)-5-(trifluoromethyl)benzyl)piperazine-1-carboxylate |
| 91 | 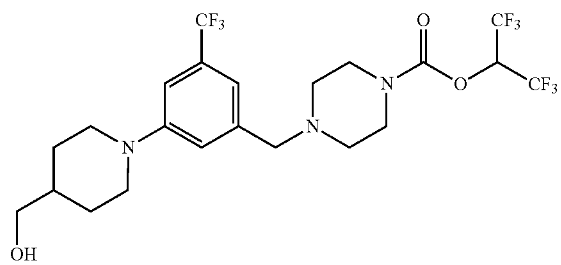 [SMILES: O=C(OC(C(F)(F)F)C(F)(F)F)N1CCN(Cc2cc(N3CCC(CO)CC3)cc(C(F)(F)F)c2)CC1] | 1,1,1,3,3,3-hexafluoropropan-2-yl 4-(3-(4-(hydroxymethyl)piperidin-1-yl)-5-(trifluoromethyl)benzyl)piperazine-1-carboxylate |
| 92 | 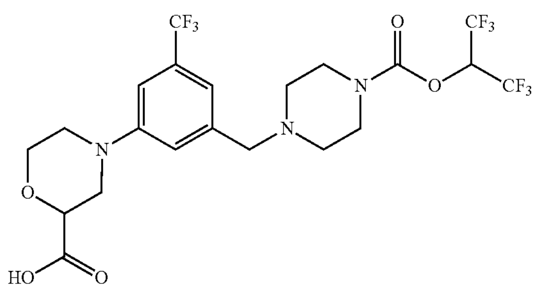 [SMILES: O=C(O)C1CN(c2cc(CN3CCN(C(=O)OC(C(F)(F)F)C(F)(F)F)CC3)cc(C(F)(F)F)c2)CCO1] | 4-(3-((4-(((1,1,1,3,3,3-hexafluoropropan-2-yl)oxy)carbonyl)piperazin-1-yl)methyl)-5-(trifluoromethyl)phenyl)morpholine-2-carboxylic acid |
| 93 | 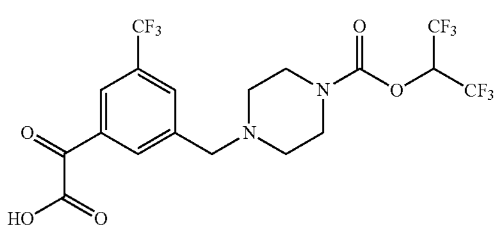 [SMILES: O=C(O)C(=O)c1cc(CN2CCN(C(=O)OC(C(F)(F)F)C(F)(F)F)CC2)cc(C(F)(F)F)c1] | 2-(3-((4-(((1,1,1,3,3,3-hexafluoropropan-2-yl)oxy)carbonyl)piperazin-1-yl)methyl)-5-(trifluoromethyl)phenyl)-2-oxoacetic acid |
| 94 | 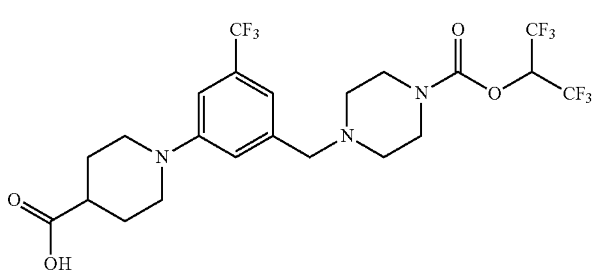 [SMILES: O=C(O)C1CCN(c2cc(CN3CCN(C(=O)OC(C(F)(F)F)C(F)(F)F)CC3)cc(C(F)(F)F)c2)CC1] | 1-(3-((4-(((1,1,1,3,3,3-hexafluoropropan-2-yl)oxy)carbonyl)piperazin-1-yl)methyl)-5-(trifluoromethyl)phenyl)piperidine-4-carboxylic acid |

TABLE 1-continued

| Chemical Synthesis Example | Structure | Name |
|---|---|---|
| 95 | 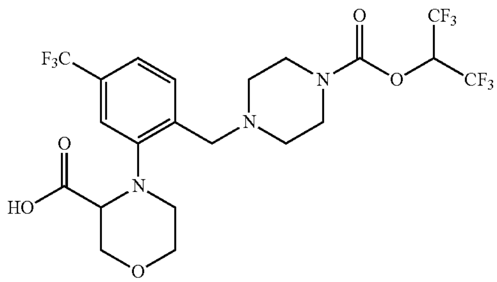 [SMILES: O=C(O)C1COCCN1c1cc(C(F)(F)F)ccc1CN1CCN(C(=O)OC(C(F)(F)F)C(F)(F)F)CC1] | 4-(2-((4-(((1,1,1,3,3,3-hexafluoropropan-2-yl)oxy)carbonyl)piperazin-1-yl)methyl)-5-(trifluoromethyl)phenyl)morpholine-3-carboxylic acid |

In some embodiments, the compound disclosed herein has the structure provided in Table 1A.

TABLE 1A

| Chemical Synthesis Example | Structure | Name |
|---|---|---|
| 96 | 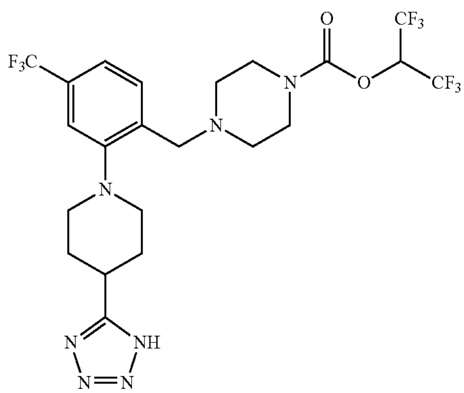 [SMILES: O=C(OC(C(F)(F)F)C(F)(F)F)N1CCN(Cc2ccc(C(F)(F)F)cc2N2CCC(c3nnn[nH]3)CC2)CC1] | 1,1,1,3,3,3-hexafluoropropan-2-yl 4-(2-(4-(1H-tetrazol-5-yl)piperidin-1-yl)-4-(trifluoromethyl)benzyl)piperazine-1-carboxylate |
| 97 | 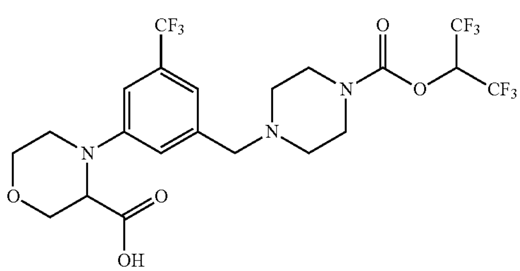 [SMILES: O=C(O)C1COCCN1c1cc(CN2CCN(C(=O)OC(C(F)(F)F)C(F)(F)F)CC2)cc(C(F)(F)F)c1] | 4-(3-((4-(((1,1,1,3,3,3-hexafluoropropan-2-yl)oxy)carbonyl)piperazin-1-yl)methyl)-5-(trifluoromethyl)phenyl)morpholine-3-carboxylic acid |
| 98 | 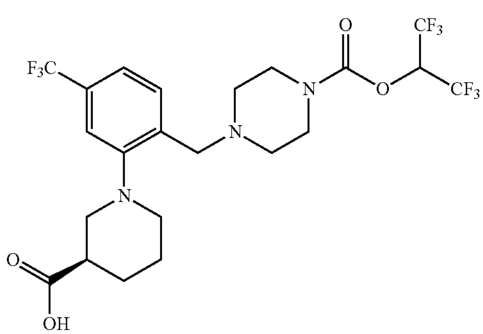 [SMILES: O=C(O)[C@@H]1CCCN(c2cc(C(F)(F)F)ccc2CN2CCN(C(=O)OC(C(F)(F)F)C(F)(F)F)CC2)C1] | (R)-1-(2-((4-(((1,1,1,3,3,3-hexafluoropropan-2-yl)oxy)carbonyl)piperazin-1-yl)methyl)-5-(trifluoromethyl)phenyl)piperidine-3-carboxylic acid |

TABLE 1A-continued

| Chemical Synthesis Example | Structure | Name |
|---|---|---|
| 99 | 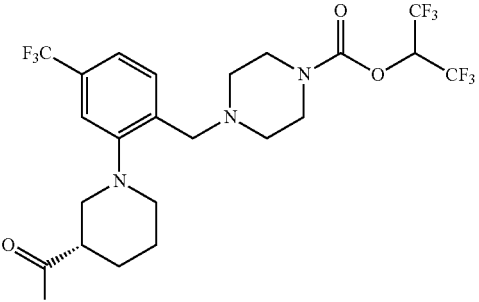 | (S)-1-(2-((4-(((1,1,1,3,3,3-hexafluoropropan-2-yl)oxy)carbonyl)piperazin-1-yl)methyl)-5-(trifluoromethyl)phenyl)piperidine-3-carboxylic acid |
| 100 | 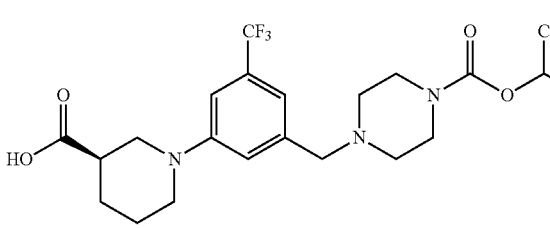 | (R)-1-(3-((4-(((1,1,1,3,3,3-hexafluoropropan-2-yl)oxy)carbonyl)piperazin-1-yl)methyl)-5-(trifluoromethyl)phenyl)piperidine-3-carboxylic acid |
| 101 | 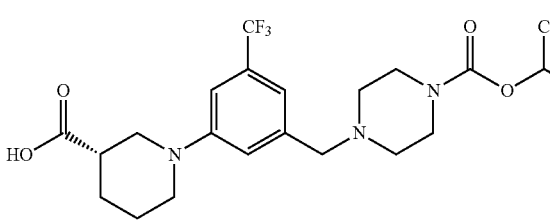 | (S)-1-(3-((4-(((1,1,1,3,3,3-hexafluoropropan-2-yl)oxy)carbonyl)piperazin-1-yl)methyl)-5-(trifluoromethyl)phenyl)piperidine-3-carboxylic acid |

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the piperazine carbamates described herein is P. H. Stahl & C. G. Wermuth "Handbook of Pharmaceutical Salts", Verlag Helvetica Chimica Acta, Zurich, 2002.

The piperazine carbamates are prepared by the general synthetic routes described below in Schemes 1-3.

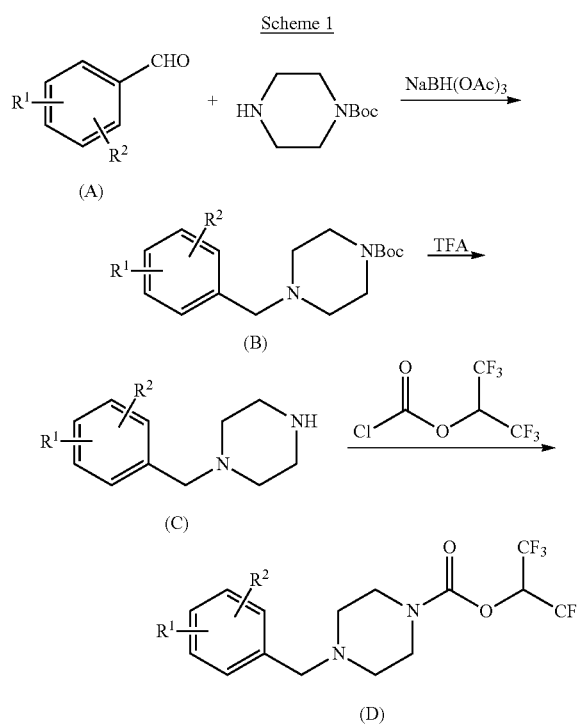

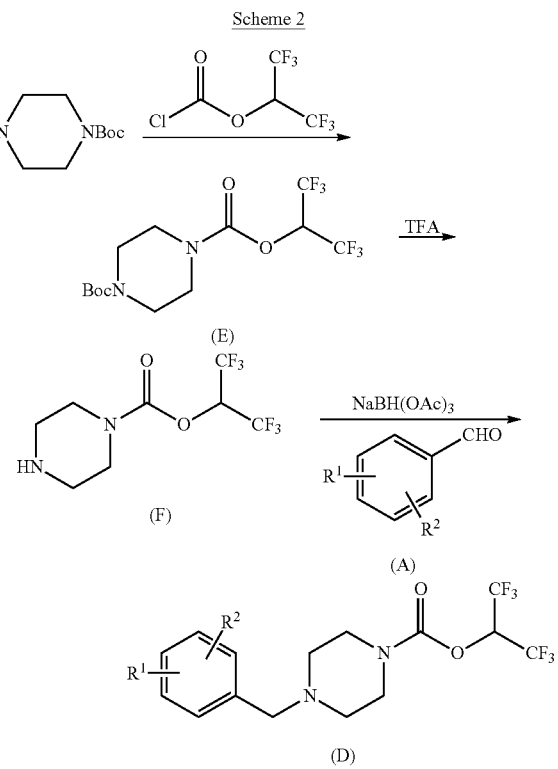

Another method for preparing compounds of formula D is provided in Scheme 2. Boc-protected piperazine is coupled with hexafluoropropan-2-yl chloroformate to provide carbamate intermediate E. Removal of the Boc group with an acid, such as trifluoroacetic acid or HCl, affords intermediate F, which subsequently undergoes a reductive amination, using an agent such as sodium triacetoxyborohydride, with an aldehyde of formula A to lead to a piperazine carbamate of formula D.

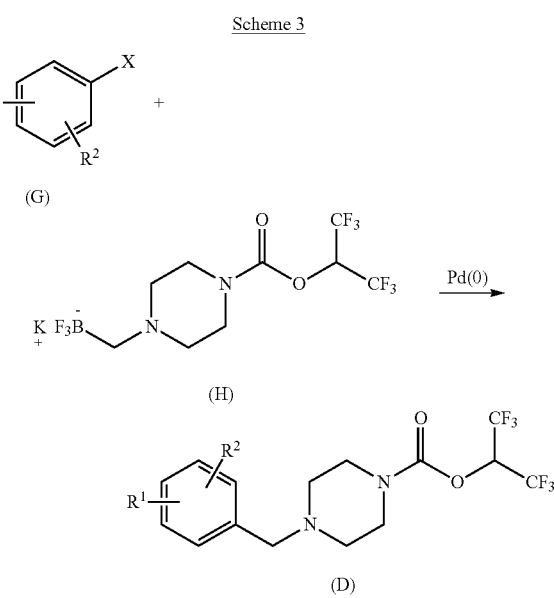

A method for preparing compounds of formula D is provided in Scheme 1. Reductive amination of an aldehyde of formula A with Boc-protected piperazine, using an agent such as sodium triacetoxyborohydride, affords intermediate B. Following Boc-group removal with an acid such as trifluoroacetic acid or HCl, intermediate C is coupled with hexafluoropropan-2-yl chloroformate to provide a piperazine carbamate of formula D. In some embodiments, intermediate B undergoes one or more additional reactions to alter $R^1$ and/or $R^2$ prior to Boc-group removal.

Another method of preparing compounds of formula D is provided in Scheme 3. A compound of formula G, where X is a halogen, is coupled with compound H under palladium-mediated conditions to provide a piperazine carbamate of formula D.

Further Forms of Piperazine Carbamates Disclosed Herein
Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$ $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the piperazine carbamate as described herein is administered as a pure chemical. In other embodiments, the piperazine carbamate described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one piperazine carbamate described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (Ia), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (IIa), or a pharmaceutically acceptable salt thereof.

One embodiment provides a pharmaceutical composition comprising a pharmaceutically acceptable carrier and a compound of Formula (III), or a pharmaceutically acceptable salt thereof.

One embodiment provides a pharmaceutical composition comprising a pharmaceutically acceptable carrier and a compound of Formula (IV), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (Ia), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (IIa), or a pharmaceutically acceptable salt thereof. Another embodiment provides a pharmaceutical composition consisting essentially of a pharmaceutically acceptable carrier and a compound of Formula (III), or a pharmaceutically acceptable salt thereof. Another embodiment provides a pharmaceutical composition consisting essentially of a pharmaceutically acceptable carrier and a compound of Formula (IV), or a pharmaceutically acceptable salt thereof.

In certain embodiments, the piperazine carbamate as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous) rectal, vaginal, or aerosol administration.

Methods

Disclosed herein are methods of modulating the activity of MAGL and/or ABHD6. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (II), (III), or (IV). In some embodiments, the compound utilized by one or more of the foregoing methods is one of the generic, subgeneric, or specific compounds described herein, such as a compound of Formula (I), (Ia), (II), (IIa), (III), or (IV). The ability of compounds described herein to modulate or inhibit MAGL and/or ABHD6 is evaluated by procedures known in the art and/or described herein. Another aspect of this disclosure provides methods of treating a disease associated with expression or activity of MAGL and/or ABHD6 in a patient. For example, provided herein are compounds that are selective in inhibiting MAGL or ABHD6, or both, as compared to inhibition of other serine hydrolases e.g., FAAH, e.g., 10, 100, 1000 or more fold inhibition of MAGL over FAAH. In other embodiments, disclosed compounds are more selective in inhibition of MAGL as compared to ABHD6.

Also disclosed herein are methods of treating and/or preventing in a patient in need thereof a disorder such as one or more of acute or chronic pain and neuropathy. Disclosed methods include administering a pharmaceutically effective amount of a compound described herein.

In certain embodiments, a disclosed compound utilized by one or more of the foregoing methods is one of the generic, subgeneric, or specific compounds described herein, such as a compound of Formula (I), (II), (III), or (IV). In certain embodiments, a disclosed compound utilized by one or more of the foregoing methods is one of the generic, subgeneric, or specific compounds described herein, such as a compound of Formula (I), (Ia), (II), (IIa), (III), or (IV).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:
ACN or MeCN acetonitrile
Bn benzyl
BOC or Boc tert-butyl carbamate
t-Bu tert-butyl
Cy cyclohexyl
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
Et$_2$O diethyl ether
EtOH ethanol
EtOAc ethyl acetate
HPLC high performance liquid chromatography
Me methyl
MeOH methanol
MS mass spectroscopy
NMR nuclear magnetic resonance
RP-HPLC reverse phase-high pressure liquid chromatography
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 1,1,1,3,3,3-hexafluoropropan-2-yl (S)-4-(2-(3-(prop-2-yn-1-yloxy)pyrrolidin-1-yl)-6-(trifluoromethyl)benzyl)piperazine-1-carboxylate

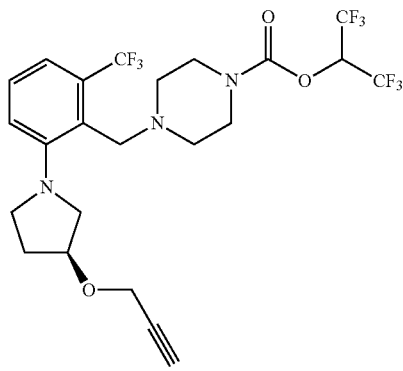 [SMILES: C#CCO[C@H]1CCN(c2cccc(C(F)(F)F)c2CN2CCN(C(=O)OC(C(F)(F)F)C(F)(F)F)CC2)C1]

Step 1: Preparation of (S)-2-(3-hydroxypyrrolidin-1-yl)-6-(trifluoromethyl)benzaldehyde

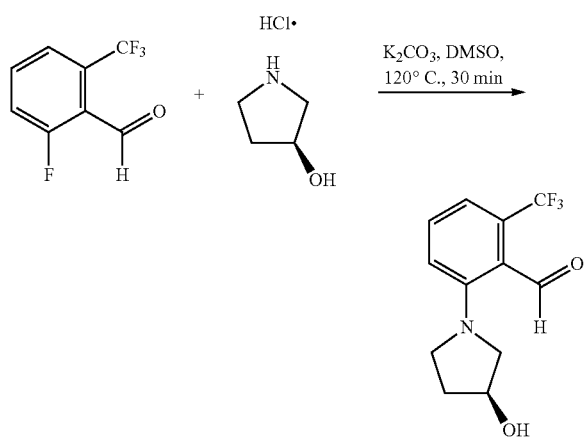

A thick walled flask was charged with (3S)-pyrrolidin-3-ol hydrochloride (900 mg, 7.28 mmol) and K$_2$CO$_3$ (1839 mg, 13.33 mmol) and DMSO (10 mL). The contents were stirred for 5 min. 2-Fluoro-6-(trifluoromethyl)benzaldehyde (1280 mg, 6.66 mmol) was added and the reaction flask was sealed and heated to 125° C. for 30 min. The reaction was diluted in EtOAc (200 mL) and washed with 1N NaOH (2×100 mL) and brine (1×100 mL). The organics were dried over anhydrous Na$_2$SO$_4$ and concentrated. The resulting oil was chromatographed on a silica column (30% EtOAc in hexanes) yielding 2-[(3S)-3-hydroxyl)yrrolidin-1-yl]-6-(trifluoromethyl)benzaldehyde (660 mg, 2.54 mmol, 38% yield) as an orange oil. $^1$H NMR (400 MHz, Chloroform-d) δ 10.37-10.20 (m, 1H), 7.42-7.28 (m, 1H), 7.05 (dd, J=25.7, 8.1 Hz, 2H), 4.59-4.40 (m, 1H), 3.67-3.28 (m, 3H), 3.17-2.98 (m, 1H), 2.69 (d, J=11.7 Hz, 1H), 2.14-1.92 (m, 2H). LCMS 260.0 [M+H]$^+$.

Step 2: Preparation of tert-butyl (S)-4-(2-(3-hydroxypyrrolidin-1-yl)-6-(trifluoromethyl)benzyl) piperazine-1-carboxylate

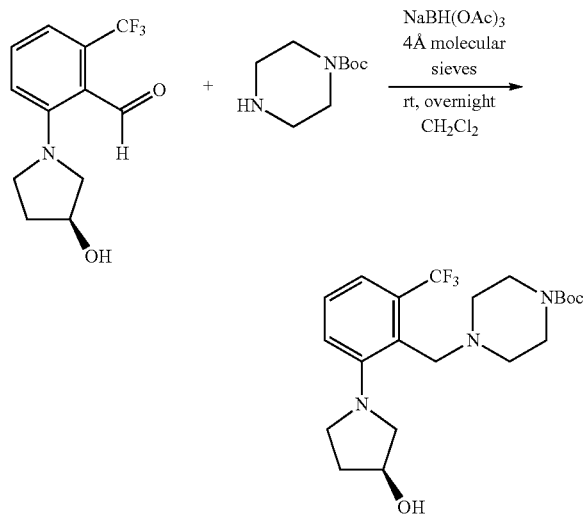

A flask was charged with (S)-2-(3-hydroxypyrrolidin-1-yl)-6-(trifluoromethyl)benzaldehyde (630 mg, 2.43 mmol) and dissolved in DCM (50 mL). 4 Å Molecular sieves (630 mg) and tert-butyl piperazine-1-carboxylate (498 mg, 2.67 mmol) were added. After stirring 30 min at rt, NaBH(OAc)$_3$ (669 mg, 3.16 mmol) was added and the reaction was stirred at rt for 18 h. The reaction was poured into DCM (150 mL) and washed with sat Na$_2$CO$_3$ (2×100 mL). The organics were dried over anhydrous Na$_2$SO$_4$, filtered and concentrated. The resulting oil was chromatographed on a silica column (0 to 50% EtOAc in hexane) and yielded tert-butyl (S)-4-(2-(3-hydroxypyrrolidin-1-yl)-6-(trifluoromethyl) benzyl)piperazine-1-carboxylate (724 mg, 69%) as a white solid. $^1$H NMR (400 MHz, Chloroform-d) δ 7.32-7.15 (m, 3H), 4.42-4.37 (m, 1H), 3.91 (br s, 1H), 3.72 (s, 2H), 3.43-3.29 (m, 5H), 3.26-3.11 (m, 2H), 3.01 (td, J=8.9, 4.6 Hz, 1H), 2.32-2.20 (m, 4H), 2.21-2.05 (m, 1H), 1.99-1.89 (m, 1H), 1.40 (s, 9H). LCMS (ESI, m/z): 430.2 [M+H]$^+$.

Step 3: Preparation of tert-butyl (S)-4-(2-(3-(prop-2-yn-1-yloxy)pyrrolidin-1-yl)-6-(trifluoromethyl) benzyl)piperazine-1-carboxylate

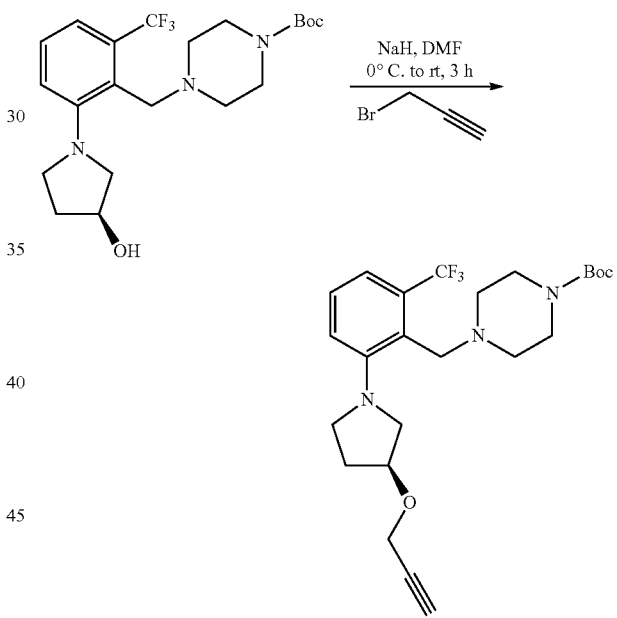

A flask was charged with tert-butyl 4-[[2-[(3S)-3-hydroxypyrrolidin-1-yl]-6-(trifluoromethyl)phenyl]methyl] piperazine-1-carboxylate (724 mg, 1.69 mmol, azeotroped from toluene) and DMF (15 mL) and cooled to 0° C. Sodium hydride was added and the mixture was stirred for 30 min. Propargyl bromide (80% weight solution in toluene, 501 mg, 3.37 mmol) was added dropwise and the reaction was stirred at 0° C. for 1 h and rt for 2 h. The reaction was quenched with brine (50 mL) and diluted in EtOAc (150 mL). The organic phase was washed with brine (2×100 mL). The organics were dried over anhydrous Na$_2$SO$_4$, filtered, and concentrated. The resulting oil was chromatographed on a silica column with a gradient (0 to 25% EtOAc in hexane) and yielded tert-butyl 4-[[2-[(3 S)-3-prop-2-ynoxypyrrolidin-1-yl]-6-(trifluoromethyl)phenyl]methyl]piperazine-1-carboxylate (220 mg, 0.470 mmol, 28% yield) as an orange oil. $^1$H NMR (400 MHz, Chloroform-d) δ 7.35-7.21 (m, 3H), 4.38 (tt, J=5.9, 3.3 Hz, 1H), 4.29-4.12 (m, 2H), 3.70 (s, 2H), 3.44 (dd, J=10.1, 5.7 Hz, 1H), 3.33 (s, 4H), 3.30-3.23 (m, 1H), 3.19-3.06 (m, 2H), 2.45 (td, J=2.4, 1.0 Hz, 1H), 2.30 (s, 4H), 2.17 (dq, J=14.3, 7.2 Hz, 1H), 2.09-1.97 (m, 1H), 1.44 (s, 9H). LCMS (ESI, m/z): 468.2 [M+H]$^+$.

Step 4: Preparation of 1,1,1,3,3,3-hexafluoropropan-2-yl (S)-4-(2-(3-(prop-2-yn-1-yloxy)pyrrolidin-1-yl)-6-(trifluoromethyl)benzyl)piperazine-1-carboxylate

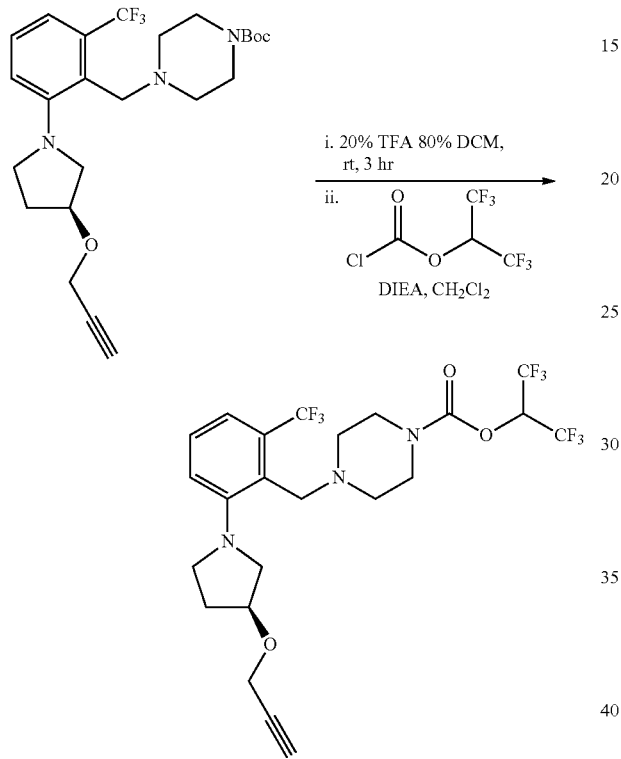

A flask was charged with tert-butyl 4-[[2-[(3S)-3-prop-2-ynoxypyrrolidin-1-yl]-6-(trifluoromethyl)phenyl]methyl]piperazine-1-carboxylate (220 mg, 0.470 mmol) and dissolved in DCM (4 mL). TFA (1 mL) was added and the reaction was stirred at rt for 3 h. The reaction was concentrated and dissolved in DCM (75 mL) and washed with 1N NaOH (50 mL). The aqueous was extracted with DCM (2×50 mL). The organics were dried over anhydrous Na$_2$SO$_4$, filtered, and concentrated and yielded 1-[[2-(3S)-3-prop-2-ynoxypyrrolidin-1-yl)-6-(trifluoromethyl)phenyl]methyl]piperazine (170 mg, 0.463 mmol, 98% yield) which was carried on without further purification. A hexafluoropropan-2-yl chloroformate solution was prepared in situ by treating triphosgene (20 mg, 0.068 mmol) in DCM (3 mL) with hexafluoroisopropanol (21 lit, 0.204 mmol) and DIEA (95 μL, 0.544 mmol) for 2 h at rt. The chloroformate solution was added dropwise to the crude (S)-1-(2-(3-(prop-2-yn-1-yloxy)pyrrolidin-1-yl)-6-(trifluoromethyl)benzyl)piperazine (50 mg, 0.136 mmol) in DCM (3 mL). The reaction was stirred at rt for 18 h. The reaction was diluted in DCM (150 mL) and washed with sat Na$_2$CO$_3$ (2×50 mL). The organics were dried over anhydrous Na$_2$SO$_4$, filtered, and concentrated. The resulting oil was chromatographed on a silica column with a gradient (0 to 20% EtOAc in hexane) and yielded 1,1,1,3,3,3-hexafluoropropan-2-yl (S)-4-(2-(3-(prop-2-yn-1-yloxy)pyrrolidin-1-yl)-6-(trifluoromethyl)benzyl)piperazine-1-carboxylate (63 mg, 82%) as an orange oil. $^1$H NMR (400 MHz, Chloroform-d) δ 7.40-7.26 (m, 3H), 5.76 (hept, J=6.1 Hz, 1H), 4.40 (tt, J=5.9, 3.1 Hz, 1H), 4.23-4.17 (m, 2H), 3.76 (s, 2H), 3.44 (dd, J=30.4, 5.1 Hz, 5H), 3.29 (q, J=7.6 Hz, 1H), 3.21-3.04 (m, 2H), 2.45 (dt, J=2.3, 1.2 Hz, 1H), 2.40 (dt, J=13.0, 4.6 Hz, 4H), 2.20 (dq, J=14.2, 7.2 Hz, 1H), 2.06 (ddt, J=12.6, 7.4, 4.2 Hz, 1H). LCMS (ESI, m/z): 562.2 [M+H]$^+$.

Example 2: 1,1,1,3,3,3-hexafluoropropan-2-yl (R)-4-(2-(3-(prop-2-yn-1-yloxy)pyrrolidin-1-yl)-4-(trifluoromethyl)benzyl)piperazine-1-carboxylate

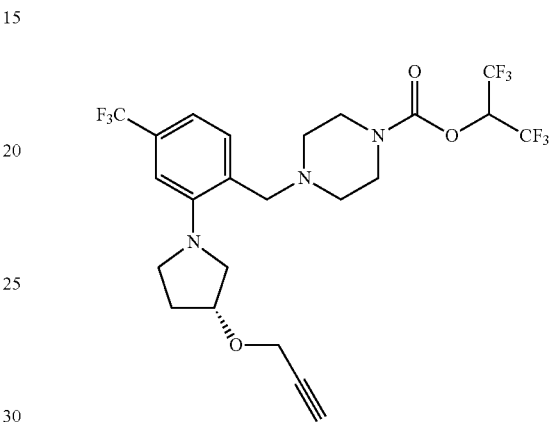

The title compound was prepared from (R)-pyrrolidin-3-ol and 2-fluoro-4-(trifluoromethyl)benzaldehyde according to the representative procedure of Example 1 Steps 1-4 to provide 1,1,1,3,3,3-hexafluoropropan-2-yl (R)-4-(2-(3-(prop-2-yn-1-yloxy)pyrrolidin-1-yl)-4-(trifluoromethyl)benzyl)piperazine-1-carboxylate as an orange oil. $^1$H NMR (400 MHz, Chloroform-d) δ 7.50 (d, J=7.8 Hz, 1H), 7.17-7.07 (m, 2H), 5.74 (hept, 1H), 4.39 (d, J=2.3 Hz, 1H), 4.19 (t, J=2.1 Hz, 2H), 3.64-3.52 (m, 5H), 3.51-3.45 (m, 2H), 3.41 (q, J=8.1, 7.6 Hz, 1H), 3.34 (d, J=10.3 Hz, 1H), 3.27-3.16 (m, 1H), 2.50-2.41 (m, 5H), 2.24-2.06 (m, 2H). LCMS (ESI, m/z): 562.2 [M+H]$^+$.

Example 3: 1,1,1,3,3,3-hexafluoropropan-2-yl (S)-4-(4-chloro-2-(3-(prop-2-yn-1-yloxy)pyrrolidin-1-yl)benzyl)piperazine-1-carboxylate

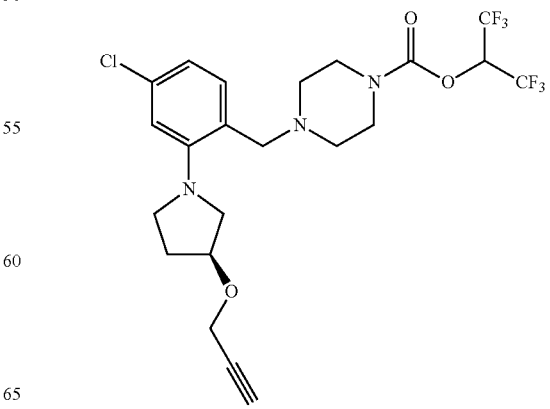

The title compound was prepared from (S)-pyrrolidin-3-ol and 2-fluoro-4-chlorobenzaldehyde according to the representative procedure of Example 1 Steps 1-4 to provide 1,1,1,3,3,3-hexafluoropropan-2-yl (S)-4-(4-chloro-2-(3-(prop-2-yn-1-yloxy)pyrrolidin-1-yl)benzyl)piperazine-1-carboxylate as an orange oil. $^1$H NMR (400 MHz, Chloroform-d) δ 7.20 (d, J=8.7 Hz, 1H), 6.83-6.71 (m, 2H), 5.68 (hept, J=6.2 Hz, 1H), 4.30 (tt, J=5.9, 3.2 Hz, 1H), 4.11 (d, J=2.4 Hz, 2H), 3.54-3.35 (m, 7H), 3.34-3.22 (m, 2H), 3.11 (ddd, J=8.9, 7.7, 4.9 Hz, 1H), 2.44-2.29 (m, 5H), 2.07 (dt, J=13.6, 6.7 Hz, 1H), 2.02-1.89 (m, 1H). LCMS (ESI, m/z): 528.1 [M+H]$^+$.

Example 4: 1,1,1,3,3,3-hexafluoropropan-2-yl (S)-4-(4-chloro-2-(3-(fluoromethyl)pyrrolidin-1-yl)benzyl)piperazine-1-carboxylate

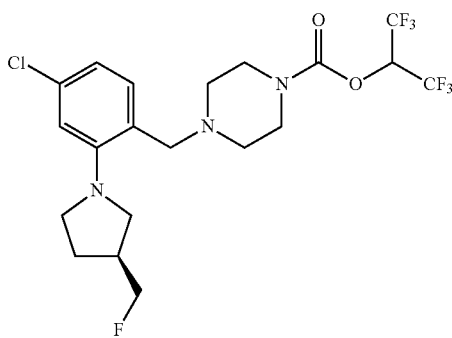 [SMILES: O=C(OC(C(F)(F)F)C(F)(F)F)N1CCN(Cc2ccc(Cl)cc2N2CC[C@H](CF)C2)CC1]

Step 1: Preparation of tert-butyl (S)-4-(4-chloro-2-(3-((tosyloxy)methyl)pyrrolidin-1-yl)benzyl)piperazine-1-carboxylate

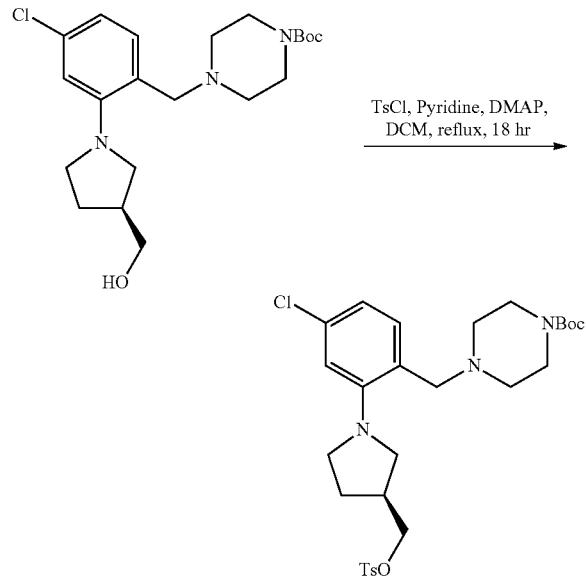

A flask was charged with tert-butyl 4-[[4-chloro-2-[(3S)-3-(hydroxymethyl)pyrrolidin-1-yl]phenyl]methyl]piperazine-1-carboxylate (2.8 g, 6.83 mmol) [prepared from (S)-pyrrolidin-3-ylmethanol and tert-butyl piperazine-1-carboxylate according to the representative procedure of Example 1 Steps 1-2], DCM (100 mL), and pyridine (1.7 mL, 20.5 mmol). DMAP (83 mg, 0.680 mmol) was added and the mixture was cooled to 0° C. 4-methylbenzenesulfonyl chloride (1.56 g, 8.2 mmol) was added and the reaction was refluxed for 18 h. The reaction was diluted in DCM (150 mL) and washed with brine (3×100 mL). The organics were dried over anhydrous Na$_2$SO$_4$ and concentrated. The resulting oil was chromatographed on a silica column with a gradient (0 to 20% EtOAc in hexane) and yielded tert-butyl (S)-4-(4-chloro-2-(3-((tosyloxy)methyl)pyrrolidin-1-yl)benzyl)piperazine-1-carboxylate (1.89 g, 3.35 mmol, 49% yield) as an orange oil. $^1$H NMR (400 MHz, Chloroform-d) δ 7.81 (d, J=8.3 Hz, 2H), 7.36 (d, J=8.0 Hz, 2H), 7.31 (s, 1H), 6.88 (dd, J=8.2, 2.0 Hz, 1H), 6.79 (d, J=2.0 Hz, 1H), 4.11-3.98 (m, 2H), 3.41 (q, J=13.6 Hz, 6H), 3.27-3.08 (m, 3H), 3.07-2.93 (m, 1H), 2.63 (hept, J=7.0 Hz, 1H), 2.46 (s, 3H), 2.35 (t, J=4.5 Hz, 4H), 2.06 (dtd, J=12.8, 7.9, 5.0 Hz, 1H), 1.73 (s, OH), 1.62 (dq, J=14.1, 7.3 Hz, 1H), 1.48 (s, 9H). LCMS (ESI, m/z): 564.3 [M+H]$^+$.

Step 2: Preparation of 1,1,1,3,3,3-hexafluoropropan-2-yl (S)-4-(4-chloro-2-(3-((tosyloxy)methyl)pyrrolidin-1-yl)benzyl)piperazine-1-carboxylate

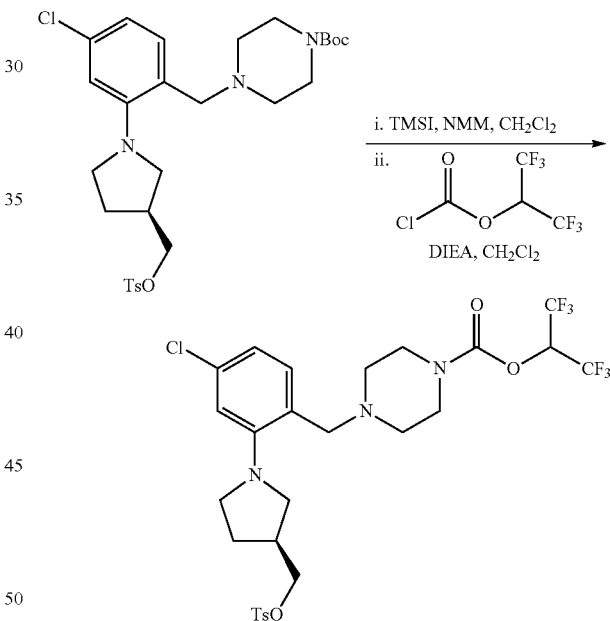

A flask was charged with tert-butyl 4-[[4-chloro-2-[(3S)-3-(p-tolylsulfonyloxymethyl)pyrrolidin-1-yl]phenyl]methyl]piperazine-1-carboxylate (945 mg, 1.68 mmol), DCM (50 mL), and 4-methylmorpholine (0.64 mL, 5.03 mmol). The reaction was cooled to 0° C. and iodo(trimethyl)silane (0.29 mL, 2.01 mmol) was added dropwise. After stirring 30 min at 0° C., the reaction was diluted in DCM and washed with brine (3×). The organics were dried over anhydrous Na$_2$SO$_4$ and concentrated. Crude [(3S)-1-[5-chloro-2-(piperazin-1-ylmethyl)phenyl]pyrrolidin-3-yl]methyl 4-methylbenzenesulfonate (774 mg, 1.67 mmol, 99% yield) was carried on without further purification. A hexafluoropropan-2-yl chloroformate solution was formed in situ by treating triphosgene (165 mg, 0.560 mmol) in DCM (50 mL) with hexafluoroisopropanol (210 μL, 2.04 mmol) and DIEA (870 μL, 5.01 mmol) for 2 h at rt and added dropwise to the crude tosylate solution in DCM (50 mL). The reaction was stirred at rt for 18 h. The reaction was diluted in DCM (150 mL) and washed with sat Na₂CO₃ (2×100 mL). The organics were dried over anhydrous Na₂SO₄, filtered, and concentrated. The resulting oil was chromatographed on a silica column with a gradient (0 to 20% EtOAc in hexanes) and yielded [2,2,2-trifluoro-1-(trifluoromethyl)ethyl]4-[[4-chloro-2-[(3S)-3-(p-tolylsulfonyloxymethyl)pyrrolidin-1-yl]phenyl]methyl]piperazine-1-carboxylate (580 mg, 0.881 mmol, 52% yield) as a yellow oil. ¹H NMR (400 MHz, Chloroform-d) δ 7.82 (d, J=8.3 Hz, 2H), 7.37 (d, J=8.0 Hz, 2H), 7.30 (d, J=8.1 Hz, 1H), 6.90 (dd, J=8.2, 2.0 Hz, 1H), 6.82 (d, J=2.1 Hz, 1H), 5.77 (hept, J=6.3 Hz, 1H), 4.10-4.00 (m, 2H), 3.59-3.39 (m, 6H), 3.27-3.04 (m, 4H), 2.64 (dq, J=13.6, 6.3 Hz, 1H), 2.50-2.40 (m, 7H), 2.15-2.02 (m, 1H), 1.64 (dd, J=12.8, 6.6 Hz, 1H). LCMS (ESI, m/z): 658.1 [M+H]⁺.

Step 3: Preparation of 1,1,1,3,3,3-hexafluoropropan-2-yl (S)-4-(4-chloro-2-(3-(fluoromethyl)pyrrolidin-1-yl)benzyl)piperazine-1-carboxylate

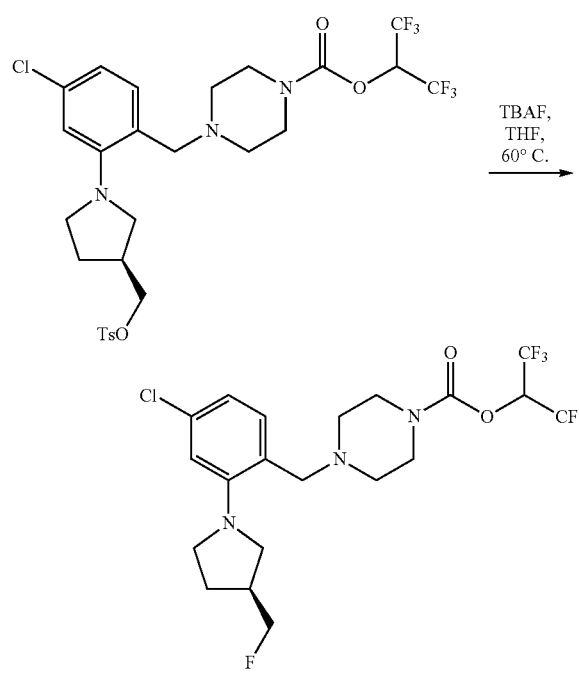

A vial was charged with 1,1,1,3,3,3-hexafluoropropan-2-yl (S)-4-(4-chloro-2-(3-((tosyloxy)methyl)pyrrolidin-1-yl)benzyl)piperazine-1-carboxylate (52 mg, 0.079 mmol) and dissolved in THF (1 mL). A TBAF solution (1M in THF, 158 μL, 0.158 mmol) was added and the reaction was stirred at rt for 18 h. Additional TBAF (200 μL, 0.200 mmol) was added and the reaction was stirred at 60° C. for 2 h. The reaction was concentrated and purified by silica chromatography (0 to 30% EtOAc in hexane) yielding [2,2,2-trifluoro-1-(trifluoromethyl)ethyl] 4-[[4-chloro-2-[(3S)-3-(fluoromethyl)pyrrolidin-1-yl]phenyl]methyl]piperazine-1-carboxylate (12 mg, 30%) as a clear oil. ¹H NMR (400 MHz, Chloroform-d) δ 7.37-7.28 (m, 1H), 6.96-6.88 (m, 2H), 5.85-5.72 (m, 1H), 4.59-4.47 (m, 1H), 4.47-4.34 (m, 1H), 3.61-3.53 (m, 5H), 3.53-3.44 (m, 1H), 3.33-3.16 (m, 4H), 2.71 (tt, J=13.9, 6.7 Hz, 1H), 2.51-2.45 (m, 4H), 2.17-2.07 (m, 1H), 1.78-1.68 (m, 1H). LCMS (ESI, m/z): 506.1 [M+H]⁺.

Example 5: 1,1,1,3,3,3-hexafluoropropan-2-yl 4-(3-(methoxycarbonyl)-4-morpholinobenzyl)piperazine-1-carboxylate

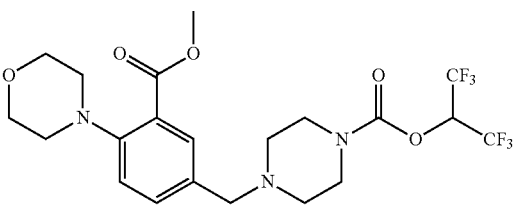 [SMILES: COC(=O)c1cc(CN2CCN(C(=O)OC(C(F)(F)F)C(F)(F)F)CC2)ccc1N1CCOCC1]

The title compound was synthesized directly from commercially available methyl 5-formyl-2-morpholinobenzoate and tert-butyl piperazine-1-carboxylate according to the representative procedure of Example 1, Steps 2 and 4 to provide 1,1,1,3,3,3-hexafluoropropan-2-yl 4-(3-(methoxycarbonyl)-4-morpholinobenzyl)piperazine-1-carboxylate as a clear oil: ¹H NMR (400 MHz, Chloroform-d) δ 7.56 (s, 1H), 7.26 (dd, J=8.3, 2.2 Hz, 1H), 6.83 (d, J=7.7 Hz, 1H), 5.62 (p, J=6.2 Hz, 1H), 3.77 (s, 3H), 3.76-3.70 (m, 4H), 3.43 (dq, J=5.7, 3.4 Hz, 4H), 3.35 (s, 2H), 2.95-2.88 (m, 4H), 2.31 (dt, J=11.5, 5.0 Hz, 4H). LCMS (ESI, m/z): 514.0 [M+H]⁺.

Example 6: 1,1,1,3,3,3-hexafluoropropan-2-yl 4-((3-(prop-2-yn-1-yloxy)-[1,1'-biphenyl]-4-yl)methyl)piperazine-1-carboxylate

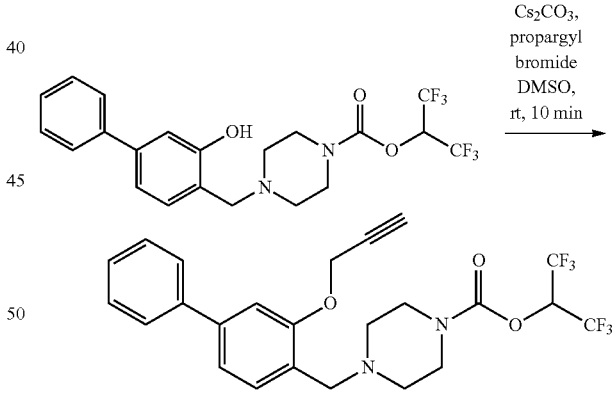

A vial was charged with [2,2,2-trifluoro-1-(trifluoromethyl)ethyl] 4-[(2-hydroxy-4-phenyl-phenyl)methyl]piperazine-1-carboxylate (23 mg, 0.050 mmol), cesium carbonate (32 mg, 0.100 mmol) and dissolved in DMSO (2 mL). The reaction was stirred at rt for 2 min and then a propargyl bromide solution (80% in toluene, 0.02 mL, 0.130 mmol) was added dropwise. After 10 min the reaction was diluted in EtOAc (100 mL) and washed with brine (2×50 mL). The organics were dried over anhydrous Na₂SO₄, filtered, and concentrated. The resulting oil was chromatographed on a silica column with a gradient (0 to 35% EtOAc in hexane) and yielded [2,2,2-trifluoro-1-(trifluoromethyl)ethyl] 4-[(4-phenyl-2-prop-2-ynoxy-phenyl)methyl]piperazine-1-carboxylate (23 mg, 0.045 mmol, 90% yield) as a clear oil. ¹H NMR (400 MHz, Chloroform-d) δ 7.62 (d, J=7.8 Hz, 2H), 7.52-7.35 (m, 4H), 7.27-7.22 (m, 2H), 5.78 (hept, J=6.2 Hz, 1H), 4.82 (d, J=2.3 Hz, 2H), 3.68 (s, 2H), 3.65-3.56 (m, 4H), 2.59-2.53 (m, 5H). LCMS (ESI, m/z): 501.1 [M+H]⁺.

Example 7: 1,1,1,3,3,3-hexafluoropropan-2-yl 4-(3-((4-acetylpiperazin-1-yl)methyl)-2-methoxybenzyl)piperazine-1-carboxylate

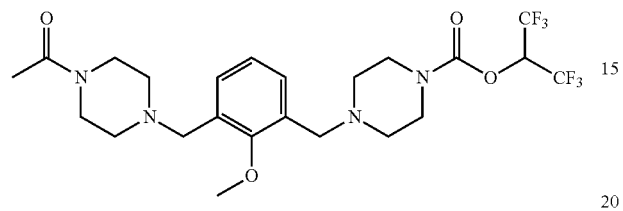

Step 1: Preparation of 1-(4-(3-chloro-2-methoxybenzyl)piperazin-1-yl)ethan-1-one

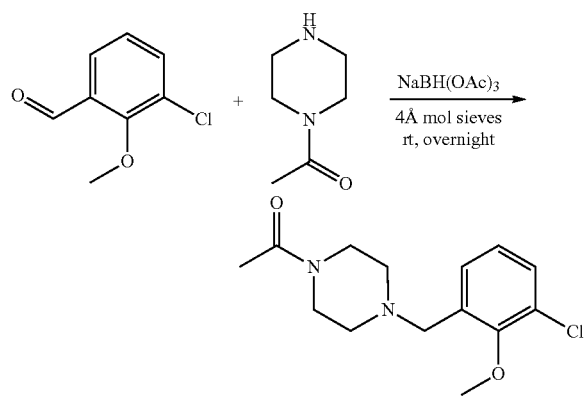

A vial was charged with 3-chloro-2-methoxybenzaldehyde (350 mg, 2.05 mmol), 1-(piperazin-1-yl)ethan-1-one (289 mg, 2.26 mmol), and DCM (3 mL). 4 Å molecular sieves (300 mg) were added and the vial was purged with N₂ and stirred at rt for 2 h. At that point, NaBH(OAc)₃ (506 mg, 2.39 mmol) was added. The reaction was allowed to stir at rt overnight. The reaction was filtered over Celite, rinsed with MeOH, concentrated and taken up in EtOAc. The organic layer was washed 3 times with saturated NaHCO₃, dried over Na₂SO₄ and concentrated to yield an oil. The oil was purified on silica gel by flash column chromatography to afford 1-(4-(3-chloro-2-methoxybenzyl)piperazin-1-yl)ethan-1-one (419 mg, 72% yield). ¹H NMR (400 MHz, Chloroform-d) δ 7.32-7.29 (m, 1H), 7.29-7.26 (m, 1H), 7.12-6.99 (m, 1H), 3.92-3.86 (m, 3H), 3.68-3.60 (m, 2H), 3.60-3.54 (m, 2H), 3.49-3.41 (m, 2H), 2.53-2.43 (m, 4H), 2.13-2.05 (m, 3H).

Step 2: Preparation of potassium trifluoro((4-(((1,1,1,3,3,3-hexafluoropropan-2-yl)oxy)carbonyl)piperazin-1-yl)methyl)borate

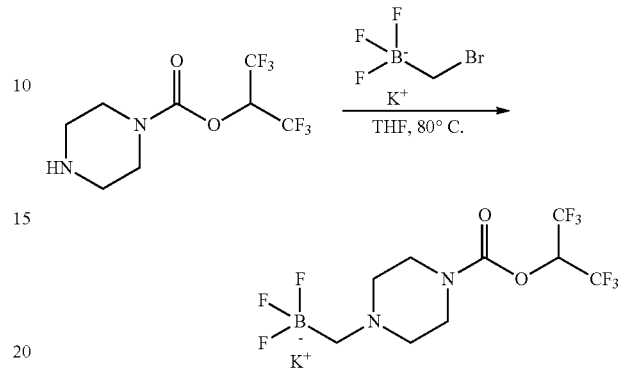

A flask was charged with THF (40 mL) and 1,1,1,3,3,3-hexafluoropropan-2-yl piperazine-1-carboxylate (11.5 g, 41.1 mmol) and potassium (bromomethyl)trifluoroborate (7.89 g, 39.6 mmol) was added. The solution was heated at 80° C. for 3 h and concentrated. The residue was dissolved in acetone (300 mL) and MeOH (500 mL). Potassium carbonate (5.67 g, 41.1 mmol) was added and the solution was stirred at rt for 30 min. The reaction was filtered and the filtrate was concentrated. The resulting residue was re-suspended in a mixture of MeOH (150 mL), hexane (20 mL), and EtOAc (30 mL) resulting in a cloudy solution that partitioned into 2 layers. The top clear yellow layer was decanted and discarded. The remaining solids were dried under reduced pressure yielding trifluoro((4-(((1,1,1,3,3,3-hexafluoropropan-2-yl)oxy)carbonyl)piperazin-1-yl)methyl)borate (4.5 g, 12.5 mmol, 32% yield) as a white amorphous solid. ¹H NMR (400 MHz, DMSO-d6) δ 6.57 (hept, J=6.4 Hz, 1H), 3.40-3.43 (m, 4H), 2.33-2.37 (m, 4H), 1.32-1.36 (m, 2H).

Step 3: Preparation of 1,1,1,3,3,3-hexafluoropropan-2-yl 4-(3-((4-acetylpiperazin-1-yl)methyl)-2-methoxybenzyl)piperazine-1-carboxylate

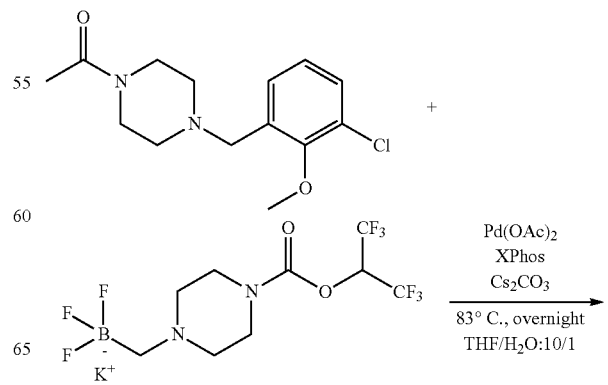

-continued

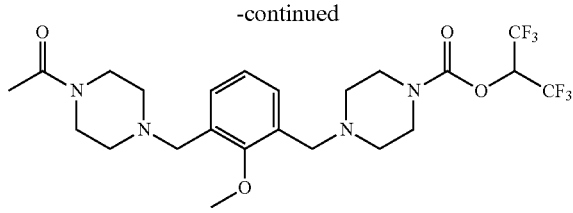

A vial was charged with 1-(4-(3-chloro-2-methoxybenzyl)piperazin-1-yl)ethan-1-one (53.9 mg, 0.191 mmol) and potassium trifluoro((4-(((1,1,1,3,3,3-hexafluoropropan-2-yl)oxy)carbonyl)piperazin-1-yl)methyl)borate (91 mg, 0.229 mmol). To this vial was added Pd(OAc)$_2$ (1.7 mg, 0.04 mmol), XPhos (7.3 mg, 0.08 mmol), and Cs$_2$CO$_3$ (186 mg, 0.572 mmol). The vial was flushed with nitrogen and evacuated 3 times. A 10:1 mixture of THF:H$_2$O (5 mL) was then added by syringe. The resulting mixture was heated at 83° C. for 20 h. The reaction was then cooled to rt whereupon 5 mL H$_2$O was added. The reaction was extracted with EtOAc (3×10 mL) and the combined organic layers were dried over Na$_2$SO$_4$, filtered and concentrated to yield an oil. The oil was purified on silica gel by flash column chromatography to afford 1,1,1,3,3,3-hexafluoropropan-2-yl 4-(3-((4-acetylpiperazin-1-yl)methyl)-2-methoxybenzyl)piperazine-1-carboxylate (35 mg, 34% yield) as an oil: $^1$H NMR (400 MHz, Chloroform-d) δ 7.38-7.31 (m, 2H), 7.16-7.07 (m, 1H), 5.85-5.68 (m, 1H), 3.83 (s, 3H), 3.73-3.51 (m, 9H), 3.53-3.41 (m, 2H), 2.61-2.41 (m, 8H), 2.17-2.03 (m, 3H), 1.60 (s, 2H). LCMS (ESI, m/z): 541.3 [M+H]$^+$.

Example 8: 1,1,1,3,3,3-hexafluoropropan-2-yl 4-(2-methyl-3-((4-(methylsulfonyl)piperazin-1-yl)methyl)benzyl)piperazine-1-carboxylate

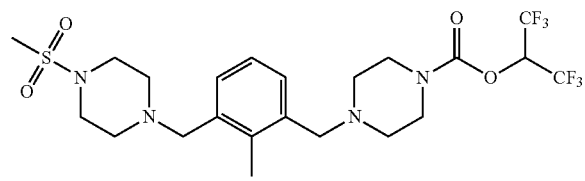 [SMILES: Cc1c(CN2CCN(C(=O)OC(C(F)(F)F)C(F)(F)F)CC2)cccc1CN1CCN(S(C)(=O)=O)CC1]

The title compound was synthesized directly from commercially available 3-chloro-2-methylbenzaldehyde and 1-(methylsulfonyl)piperazine according to the representative procedure of Example 7, Steps 1-3 to provide 1,1,1,3,3,3-hexafluoropropan-2-yl 4-(2-methyl-3-((4-(methylsulfonyl)piperazin-1-yl)methyl)benzyl)piperazine-1-carboxylate as a clear oil: $^1$H NMR (400 MHz, Chloroform-d) δ 7.20-7.13 (m, 2H), 7.13-7.03 (m, 1H), 5.81-5.66 (m, 1H), 3.55-3.46 (m, 7H), 3.27-3.15 (m, 4H), 2.76 (s, 3H), 2.62-2.50 (m, 5H), 2.50-2.40 (m, 3H), 2.39 (s, 1H), 2.33 (s, 3H). LCMS (ESI, m/z): 561.2 [M+H]$^+$.

Example 9: 1,1,1,3,3,3-hexafluoropropan-2-yl 4-(3-((4-fluoropiperidin-1-yl)methyl)-2-methoxybenzyl)piperazine-1-carboxylate

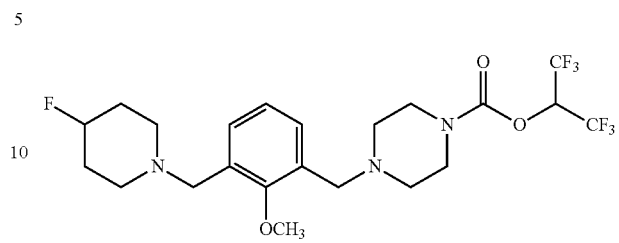

The title compound was synthesized directly from commercially available 3-chloro-2-methoxybenzaldehyde and 4-fluoropiperidine according to the representative procedure of Example 7, Steps 1-3 to provide 1,1,1,3,3,3-hexafluoropropan-2-yl 4-(3-((4-fluoropiperidin-1-yl)methyl)-2-methoxybenzyl)piperazine-1-carboxylate as a clear oil: $^1$H NMR (400 MHz, Chloroform-d) δ 7.30-7.24 (m, 1H), 7.25-7.20 (m, 1H), 7.04-6.98 (m, 1H), 5.75-5.60 (m, 1H), 4.74-4.47 (m, 1H), 3.80-3.69 (m, 3H), 3.57-3.38 (m, 8H), 2.57 (s, 2H), 2.52-2.37 (m, 4H), 2.32 (s, 2H), 1.94-1.70 (m, 4H). LCMS (ESI, m/z): 516.2 [M+H]$^+$.

Example 10: 1,1,1,3,3,3-hexafluoropropan-2-yl 4-(2-methyl-3-((4-(methylsulfonamido)piperidin-1-yl)methyl)benzyl)piperazine-1-carboxylate

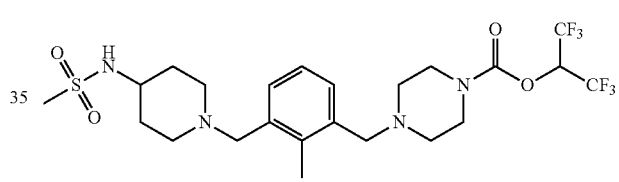

The title compound was synthesized directly from commercially available 3-chloro-2-methylbenzaldehyde and N-piperidin-yl-methansulfonamide according to the representative procedure of Example 7, Steps 1-3 to provide 1,1,1,3,3,3-hexafluoropropan-2-yl 4-(2-methyl-3-((4-(methylsulfonamido)piperidin-1-yl)methyl)benzyl)piperazine-1-carboxylate as a clear oil: $^1$H NMR (400 MHz, Chloroform-d) δ 7.22-7.14 (m, 2H), 7.14-7.07 (m, 1H), 5.85-5.72 (m, 1H), 4.20-4.14 (m, 1H), 3.59-3.49 (m, 5H), 3.49-3.43 (m, 2H), 3.43-3.32 (m, 1H), 3.01 (s, 3H), 2.88-2.74 (m, 2H), 2.54-2.41 (m, 4H), 2.38-2.31 (m, 3H), 2.21-2.09 (m, 2H), 2.01-1.94 (m, 2H), 1.63-1.47 (m, 3H). LCMS (ESI, m/z): 575.2 [M+H]$^+$.

Example 11: 1,1,1,3,3,3-hexafluoropropan-2-yl 4-(3-((4-acetamidopiperidin-1-yl)methyl)-2-methylbenzyl)piperazine-1-carboxylate

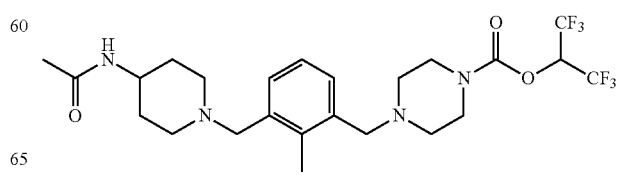

The title compound was synthesized directly from commercially available 3-chloro-2-methylbenzaldehyde and 4-acetomidopiperidine according to the representative procedure of Example 7, Steps 1-3 to provide 1,1,1,3,3,3-hexafluoropropan-2-yl 4-(3-((4-acetamidopiperidin-1-yl)methyl)-2-methylbenzyl)piperazine-1-carboxylate as a clear oil: $^1$H NMR (400 MHz, Chloroform-d) δ 7.24-7.20 (m, 1H), 7.16-6.98 (m, 2H), 5.75-5.63 (m, 1H), 5.40 (s, 1H), 3.79 (s, 1H), 3.69-3.26 (m, 8H), 2.87 (s, 2H), 2.49-2.33 (m, 4H), 2.33-2.07 (m, 5H), 1.95-1.79 (m, 5H), 1.52 (s, 2H). LCMS (ESI, m/z): 539.2 [M+H]$^+$.

Example 12: 1,1,1,3,3,3-hexafluoropropan-2-yl 4-(3-((4,4-difluoropiperidin-1-yl)methyl)-2-methylbenzyl)piperazine-1-carboxylate

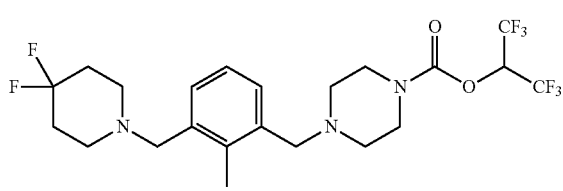 [SMILES: Cc1c(CN2CCN(C(=O)OC(C(F)(F)F)C(F)(F)F)CC2)cccc1CN1CCC(F)(F)CC1]

The title compound was synthesized directly from commercially available 3-chloro-2-methylbenzaldehyde and 4,4-difluoropiperidine according to the representative procedure of Example 7, Steps 1-3 to provide 1,1,1,3,3,3-hexafluoropropan-2-yl 4-(3-((4,4-difluoropiperidin-1-yl)methyl)-2-methylbenzyl)piperazine-1-carboxylate as a clear oil: $^1$H NMR (400 MHz, Chloroform-d) δ 7.20-7.13 (m, 2H), 7.11-7.06 (m, 1H), 5.80-5.64 (m, 1H), 3.55-3.49 (m, 6H), 3.49 (s, 2H), 2.57-2.50 (m, 4H), 2.49-2.40 (m, 4H), 2.33 (s, 3H), 2.03-1.87 (m, 4H). LCMS (ESI, m/z): 518.2 [M+H]$^+$.

Example 13: 1,1,1,3,3,3-hexafluoropropan-2-yl 4-(2-methyl-3-(pyrrolidin-1-ylmethyl)benzyl)piperazine-1-carboxylate

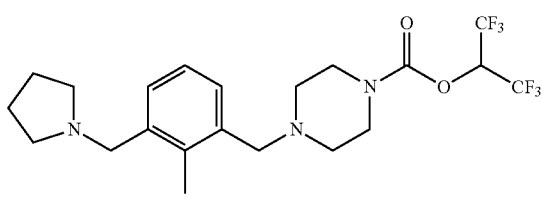 [SMILES: Cc1c(CN2CCCC2)cccc1CN1CCN(C(=O)OC(C(F)(F)F)C(F)(F)F)CC1]

The title compound was synthesized directly from commercially available 3-chloro-2-methylbenzaldehyde and pyrrolidine according to the representative procedure of Example 7, Steps 1-3 to provide 1,1,1,3,3,3-hexafluoropropan-2-yl 4-(2-methyl-3-(pyrrolidin-1-ylmethyl)benzyl)piperazine-1-carboxylate as a clear oil: $^1$H NMR (400 MHz, Chloroform-d) δ 7.24-7.20 (m, 1H), 7.15-7.05 (m, 2H), 5.82-5.66 (m, 1H), 3.63-3.57 (m, 2H), 3.55-3.49 (m, 4H), 3.49-3.44 (m, 2H), 2.57-2.48 (m, 4H), 2.48-2.38 (m, 4H), 2.34 (s, 3H), 1.81-1.72 (m, 4H). LCMS (ESI, m/z): 468.2 [M+H]$^+$.

Example 14: 1,1,1,3,3,3-hexafluoropropan-2-yl 4-(3-((4-acetylpiperazin-1-yl)methyl)-2-methylbenzyl)piperazine-1-carboxylate

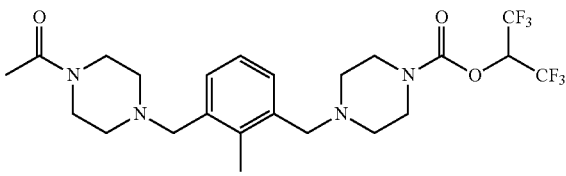 [SMILES: CC(=O)N1CCN(Cc2cccc(CN3CCN(C(=O)OC(C(F)(F)F)C(F)(F)F)CC3)c2C)CC1]

The title compound was synthesized directly from commercially available 3-chloro-2-methylbenzaldehyde and 1-(piperazin-1-yl)ethan-1-one according to the representative procedure of Example 7, Steps 1-3 to provide 1,1,1,3,3,3-hexafluoropropan-2-yl 4-(3-((4-acetylpiperazin-1-yl)methyl)-2-methylbenzyl)piperazine-1-carboxylate as a clear oil: $^1$H NMR (400 MHz, Chloroform-d) δ 7.13-6.93 (m, 3H), 5.69-5.54 (m, 1H), 3.55-3.23 (m, 11H), 2.38-2.28 (m, 7H), 2.24 (s, 3H), 1.96 (s, 3H). LCMS (ESI, m/z): 524.1 [M+H]$^+$.

Example 15: 1,1,1,3,3,3-hexafluoropropan-2-yl 4-(3-((4-fluoropiperidin-1-yl)methyl)-2-methylbenzyl)piperazine-1-carboxylate

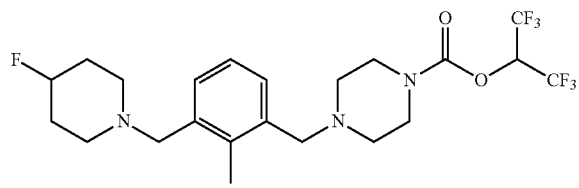 [SMILES: Cc1c(CN2CCC(F)CC2)cccc1CN1CCN(C(=O)OC(C(F)(F)F)C(F)(F)F)CC1]

The title compound was synthesized directly from commercially available 3-chloro-2-methylbenzaldehyde and 4-fluoropiperidine hydrochloride according to the representative procedure of Example 7, Steps 1-3 to provide 1,1,1,3,3,3-hexafluoropropan-2-yl 4-(3-((4-fluoropiperidin-1-yl)methyl)-2-methylbenzyl)piperazine-1-carboxylate as a clear oil: $^1$H NMR (400 MHz, Chloroform-d) δ 7.21-7.16 (m, 1H), 7.15-7.11 (m, 1H), 7.10-7.05 (m, 1H), 5.81-5.67 (m, 1H), 4.80-4.54 (m, 1H), 3.58-3.46 (m, 6H), 3.45 (s, 2H), 2.66-2.51 (m, 2H), 2.51-2.39 (m, 4H), 2.39-2.26 (m, 5H), 1.95-1.74 (m, 4H). LCMS (ESI, m/z): 500.1 [M+H]$^+$.

Example 16: 1,1,1,3,3,3-hexafluoropropan-2-yl 4-(3-((4,4-difluoropiperidin-1-yl)methyl)-2-methoxybenzyl)piperazine-1-carboxylate

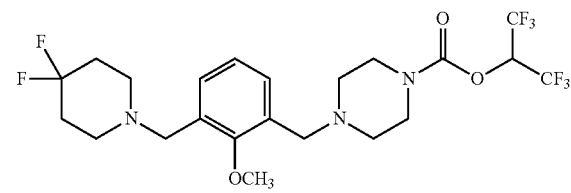 [SMILES: COc1c(CN2CCN(C(=O)OC(C(F)(F)F)C(F)(F)F)CC2)cccc1CN1CCC(F)(F)CC1]

The title compound was synthesized directly from commercially available 3-chloro-2-methoxybenzaldehyde and 4,4-difluoropiperidine according to the representative procedure of Example 7, Steps 1-3 to provide 1,1,1,3,3,3-hexafluoropropan-2-yl 4-(3-((4,4-difluoropiperidin-1-yl)methyl)-2-methoxybenzyl)piperazine-1-carboxylate as a clear oil: $^1$H NMR (400 MHz, Chloroform-d) δ 7.28-7.21 (m, 2H), 7.05-6.99 (m, 1H), 5.77-5.60 (m, 1H), 3.78-3.68 (m, 3H), 3.57-3.40 (m, 8H), 2.57-2.39 (m, 8H), 2.02-1.81 (m, 4H). LCMS (ESI, m/z): 534.2 [M+H]$^+$.

Example 17: 1,1,1,3,3,3-hexafluoropropan-2-yl (R)-4-(3-((3-acetamidopyrrolidin-1-yl)methyl)-2-methylbenzyl)piperazine-1-carboxylate

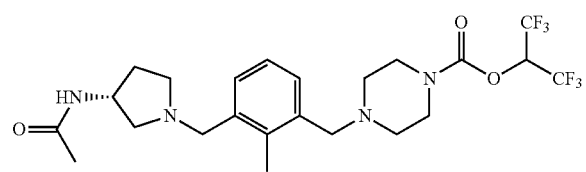 [SMILES: CC(=O)N[C@@H]1CCN(Cc2cccc(CN3CCN(C(=O)OC(C(F)(F)F)C(F)(F)F)CC3)c2C)C1]

The title compound was synthesized directly from commercially available 3-chloro-2-methylbenzaldehyde and (R)—N-(pyrrolidin-3-yl)acetamide according to the representative procedure of Example 7, Steps 1-3 to provide 1,1,1,3,3,3-hexafluoropropan-2-yl (R)-4-(3-((3-acetamidopyrrolidin-1-yl)methyl)-2-methylbenzyl)piperazine-1-carboxylate as a clear oil: $^1$H NMR (400 MHz, Chloroform-d) δ 7.12-7.04 (m, 2H), 7.03-6.97 (m, 1H), 5.76-5.59 (m, 2H), 4.41-4.26 (m, 1H), 3.52 (s, 2H), 3.47-3.38 (m, 6H), 2.83-2.72 (m, 1H), 2.49 (s, 2H), 2.41-2.30 (m, 4H), 2.25 (s, 3H), 2.23-2.14 (m, 2H), 1.88-1.82 (m, 3H), 1.50 (s, 1H). LCMS (ESI, m/z): 524.2 [M+H]$^+$.

Example 18: 1,1,1,3,3,3-hexafluoropropan-2-yl (S)-4-(3-((3-acetamidopyrrolidin-1-yl)methyl)-2-methylbenzyl)piperazine-1-carboxylate

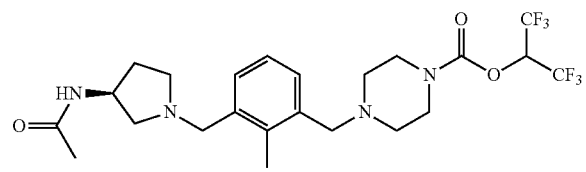 [SMILES: CC(=O)N[C@H]1CCN(Cc2cccc(CN3CCN(C(=O)OC(C(F)(F)F)C(F)(F)F)CC3)c2C)C1]

The title compound was synthesized directly from commercially available 3-chloro-2-methylbenzaldehyde and (S)—N-(pyrrolidin-3-yl)acetamide according to the representative procedure of Example 7, Steps 1-3 to provide 1,1,1,3,3,3-hexafluoropropan-2-yl (S)-4-(3-((3-acetamidopyrrolidin-1-yl)methyl)-2-methylbenzyl)piperazine-1-carboxylate as a clear oil: $^1$H NMR (400 MHz, Chloroform-d) δ 7.15-7.07 (m, 2H), 7.06-7.00 (m, 1H), 5.80-5.59 (m, 2H), 4.44-4.31 (m, 1H), 3.55 (s, 2H), 3.50-3.41 (m, 6H), 2.87-2.75 (m, 1H), 2.52 (s, 2H), 2.44-2.34 (m, 4H), 2.28 (s, 3H), 2.24 (d, J=7.4 Hz, 2H), 1.87 (s, 3H), 1.53 (s, 1H). LCMS (ESI, m/z): 524.2 [M+H]$^+$.

Example 19: 1,1,1,3,3,3-hexafluoropropan-2-yl (R)-4-(2-methyl-3-((2-methylpiperidin-1-yl)methyl)benzyl)piperazine-1-carboxylate

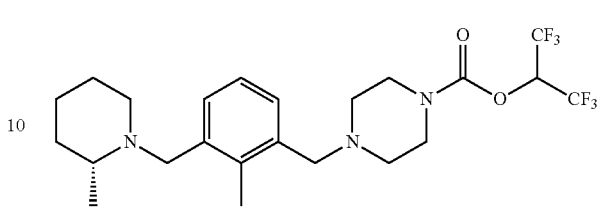

The title compound was synthesized directly from commercially available 3-chloro-2-methylbenzaldehyde and (R)-2-methylpiperidine according to the representative procedure of Example 7, Steps 1-3 to provide 1,1,1,3,3,3-hexafluoropropan-2-yl (R)-4-(2-methyl-3-((2-methylpiperidin-1-yl)methyl)benzyl)piperazine-1-carboxylate as a clear oil: $^1$H NMR (400 MHz, Chloroform-d) δ 7.38 (s, 1H), 7.23-7.08 (m, 2H), 5.84-5.71 (m, 1H), 4.15 (s, 1H), 3.63-3.46 (m, 6H), 3.22 (s, 1H), 2.77 (s, 1H), 2.51-2.43 (m, 4H), 2.40 (s, 3H), 2.05 (s, 1H), 1.79-1.64 (m, 2H), 1.63-1.47 (m, 3H), 1.43-1.12 (m, 5H). LCMS (ESI, m/z): 496.6 [M+H]$^+$.

Example 20: 1,1,1,3,3,3-hexafluoropropan-2-yl (S)-4-(2-methyl-3-((2-methylpiperidin-1-yl)methyl)benzyl)piperazine-1-carboxylate

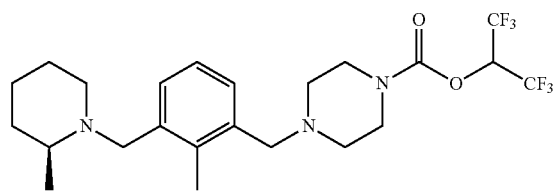 [SMILES: Cc1c(CN2CCN(C(=O)OC(C(F)(F)F)C(F)(F)F)CC2)cccc1CN1CCCC[C@@H]1C]

The title compound was synthesized directly from commercially available 3-chloro-2-methylbenzaldehyde and (S)-2-methylpiperidine according to the representative procedure of Example 7, Steps 1-3 to provide 1,1,1,3,3,3-hexafluoropropan-2-yl (S)-4-(2-methyl-3-((2-methylpiperidin-1-yl)methyl)benzyl)piperazine-1-carboxylate as a clear oil: $^1$H NMR (400 MHz, Chloroform-d) δ 7.12-7.10 (m, 1H), 6.97-6.89 (m, 2H), 5.66-5.52 (m, 1H), 3.87 (d, J=13.4 Hz, 1H), 3.40-3.30 (m, 5H), 2.92-2.82 (m, 1H), 2.54-2.43 (m, 1H), 2.33-2.24 (m, 4H), 2.19 (s, 3H), 1.83-1.70 (m, 1H), 1.52-1.44 (m, 2H), 1.41 (s, 2H), 1.34-1.08 (m, 4H), 1.00 (d, J=6.2 Hz, 3H). LCMS (ESI, m/z): 496.6 [M+H]$^+$.

Example 21: 1,1,1,3,3,3-hexafluoropropan-2-yl 4-(2-methyl-3-(morpholinomethyl)benzyl)piperazine-1-carboxylate

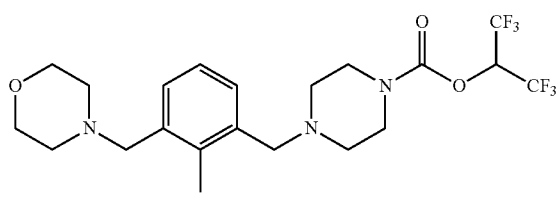 [SMILES: Cc1c(CN2CCOCC2)cccc1CN1CCN(C(=O)OC(C(F)(F)F)C(F)(F)F)CC1]

The title compound was synthesized directly from commercially available 3-chloro-2-methylbenzaldehyde and morpholine according to the representative procedure of Example 7, Steps 1-3 to provide 1,1,1,3,3,3-hexafluoropropan-2-yl 4-(2-methyl-3-(morpholinomethyl)benzyl)piperazine-1-carboxylate: ¹H NMR (400 MHz, Chloroform-d) δ 7.26-7.16 (m, 2H), 7.15-7.06 (m, 1H), 5.79 (hept, J=6.3 Hz, 1H), 3.75-3.65 (m, 4H), 3.60-3.51 (m, 6H), 3.50 (s, 2H), 2.53-2.41 (m, 8H), 2.39 (s, 3H). LCMS (ESI, m/z): 484.2 [M+H]⁺.

Example 22: 1,1,1,3,3,3-hexafluoropropan-2-yl 4-(2-fluoro-3-(morpholinomethyl)benzyl)piperazine-1-carboxylate

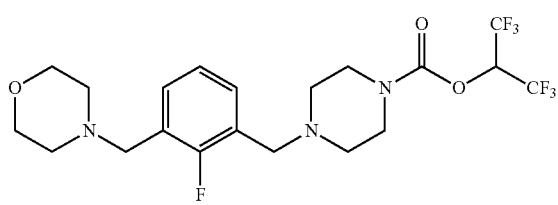 [SMILES: O=C(OC(C(F)(F)F)C(F)(F)F)N1CCN(Cc2cccc(CN3CCOCC3)c2F)CC1]

The title compound was synthesized directly from commercially available 3-chloro-2-fluorobenzaldehyde and morpholine according to the representative procedure of Example 7, Steps 1-3 to provide 1,1,1,3,3,3-hexafluoropropan-2-yl 4-(2-fluoro-3-(morpholinomethyl)benzyl)piperazine-1-carboxylate: ¹H NMR (400 MHz, Chloroform-d) δ 7.37-7.24 (m, 2H), 7.16-7.04 (m, 1H), 5.83-5.68 (m, 1H), 3.76-3.68 (m, 4H), 3.65-3.52 (m, 8H), 2.54-2.42 (m, 8H). LCMS (ESI, m/z): 488.2 [M+H]⁺.

Example 23: 1,1,1,3,3,3-hexafluoropropan-2-yl 4-(4-(morpholinomethyl)-2-(trifluoromethoxy)benzyl)piperazine-1-carboxylate

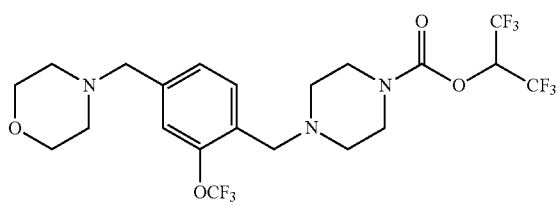 [SMILES: O=C(OC(C(F)(F)F)C(F)(F)F)N1CCN(Cc2ccc(CN3CCOCC3)cc2OC(F)(F)F)CC1]

The title compound was synthesized directly from commercially available 4-chloro-2-(trifluoromethoxy)benzaldehyde and morpholine according to the representative procedure of Example 7, Steps 1-3 to provide 1,1,1,3,3,3-hexafluoropropan-2-yl 4-(4-(morpholinomethyl)-2-(trifluoromethoxy)benzyl)piperazine-1-carboxylate as an oil: ¹H NMR (400 MHz, Chloroform-d) δ 7.46 (s, 1H), 7.32-7.21 (m, 2H), 5.83-5.68 (m, 1H), 3.79-3.67 (m, 4H), 3.62-3.55 (m, 6H), 3.52 (s, 2H), 2.56-2.40 (m, 8H). LCMS (ESI, m/z): 554.0 [M+H]⁺.

Example 24: 1,1,1,3,3,3-hexafluoropropan-2-yl 4-(4-(piperidin-1-ylmethyl)-2-(trifluoromethoxy)benzyl)piperazine-1-carboxylate

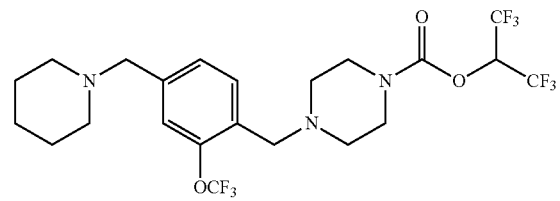

The title compound was synthesized directly from commercially available 4-chloro-2-(trifluoromethoxy)benzaldehyde and piperidine according to the representative procedure of Example 7, Steps 1-3 to provide 1,1,1,3,3,3-hexafluoropropan-2-yl 4-(4-(piperidin-1-ylmethyl)-2-(trifluoromethoxy)benzyl)piperazine-1-carboxylate as an oil: ¹H NMR (400 MHz, Chloroform-d) δ 7.47-7.40 (m, 1H), 7.28-7.23 (m, 2H), 5.83-5.70 (m, 1H), 3.63-3.53 (m, 6H), 3.49 (s, 2H), 2.56-2.44 (m, 4H), 2.44-2.31 (m, 4H), 1.63-1.54 (m, 4H), 1.53-1.35 (m, 2H). LCMS (ESI, m/z): 552.2 [M+H]⁺.

Example 25: 1,1,1,3,3,3-hexafluoropropan-2-yl 4-(4-(pyrrolidin-1-ylmethyl)-2-(trifluoromethoxy)benzyl)piperazine-1-carboxylate

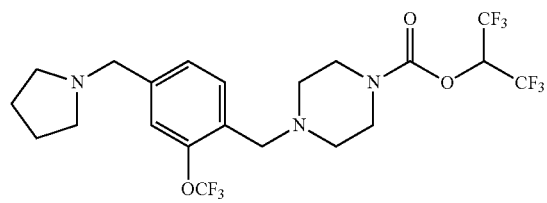 [SMILES: O=C(OC(C(F)(F)F)C(F)(F)F)N1CCN(Cc2ccc(CN3CCCC3)cc2OC(F)(F)F)CC1]

The title compound was synthesized directly from commercially available 4-chloro-2-(trifluoromethoxy)benzaldehyde and pyrrolidine according to the representative procedure of Example 7, Steps 1-3 to provide 1,1,1,3,3,3-hexafluoropropan-2-yl 4-(4-(pyrrolidin-1-ylmethyl)-2-(trifluoromethoxy)benzyl)piperazine-1-carboxylate as an oil: ¹H NMR (400 MHz, Chloroform-d) δ 7.49-7.39 (m, 1H), 7.30-7.22 (m, 2H), 5.83-5.69 (m, 1H), 3.64 (s, 2H), 3.62-3.53 (m, 6H), 2.58-2.45 (m, 8H), 1.85-1.79 (m, 4H).

Example 26: 1,1,1,3,3,3-hexafluoropropan-2-yl 4-(3-(8-oxa-3-azabicyclo[3.2.1]octan-3-yl)-4-(trifluoromethyl)benzyl)piperazine-1-carboxylate

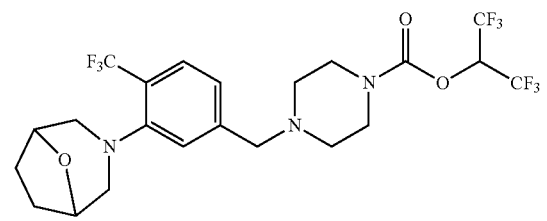 [SMILES: O=C(OC(C(F)(F)F)C(F)(F)F)N1CCN(Cc2ccc(C(F)(F)F)c(N3CC4CCC(C3)O4)c2)CC1]

Step 1: Preparation of tert-butyl 4-(3-bromo-4-(trifluoromethyl)benzyl)piperazine-1-carboxylate

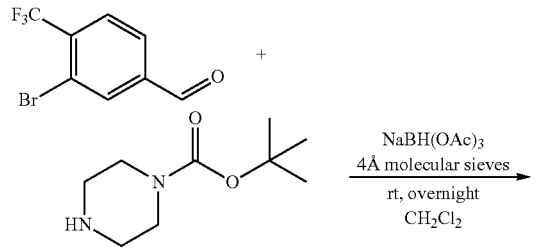

The title compound was synthesized directly from commercially available 3-bromo-4-(trifluoromethyl)benzaldehyde and tert-butyl piperazine-1-carboxylate according to the representative procedure of Example 1, Step 2 to provide tert-butyl 4-(3-bromo-4-(trifluoromethyl)benzyl)piperazine-1-carboxylate as a pale oil: $^1$H NMR (400 MHz, Chloroform-d) δ 7.72 (s, 1H), 7.70-7.57 (m, 1H), 7.43-7.32 (m, 1H), 3.57-3.37 (m, 6H), 2.49-2.30 (m, 4H), 1.47 (s, 9H).

Step 2: Preparation of tert-butyl 4-(3-(8-oxa-3-azabicyclo[3.2.1]octan-3-yl)-4-(trifluoromethly)benzyl)piperazine-1-carboxylate

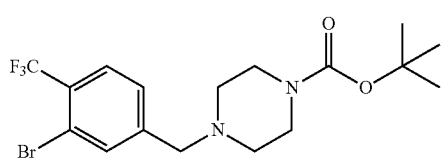

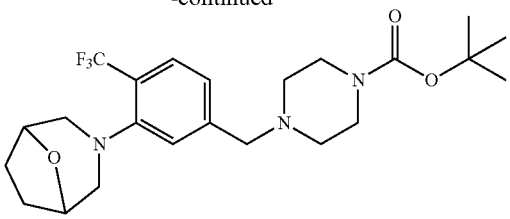

A vial was charged with tert-butyl 4-(3-bromo-4-(trifluoromethyl)benzyl)piperazine-1-carboxylate (296 mg, 0.699 mmol). To this vial was added Pd(OAc)$_2$ (9.4 mg, 0.042 mmol), RuPhos (78.4 mg, 0.168 mmol), and sodium tert-butoxide (201 mg, 2.098 mmol). The vial was flushed with nitrogen and evacuated 3 times. 8-Oxa-3-azabicyclo[3.2.1]octane (271 mg, 2.098 mmol) was added to the vial, followed by anhydrous THF (3 mL). The resulting stirred mixture was heated at 83° C. for 18 h. The reaction was cooled to rt whereupon 5 mL H$_2$O was added. The reaction mixture was extracted with EtOAc (3×10 mL) and the combined organic layers were dried over Na$_2$SO$_4$, filtered and concentrated to yield an oil. The oil was purified on silica gel by flash column chromatography to afford tert-butyl 4-(3-(8-oxa-3-azabicyclo[3.2.1]octan-3-yl)-4-(trifluoromethyl)benzyl)piperazine-1-carboxylate as a clear oil (140 mg, 43% yield). $^1$H NMR (400 MHz, Chloroform-d) δ 7.61-7.55 (m, 1H), 7.48-7.43 (m, 1H), 7.25-7.19 (m, 1H), 4.44-4.36 (m, 2H), 3.56-3.50 (m, 2H), 3.50-3.40 (m, 4H), 3.17-3.11 (m, 2H), 2.75-2.69 (m, 2H), 2.44-2.34 (m, 4H), 2.25-2.16 (m, 2H), 1.98-1.88 (m, 2H), 1.47 (s, 9H). LCMS (ESI, m/z): 456.2 [M+H]$^+$.

Step 3: Preparation of 1,1,1,3,3,3-hexafluoropropan-2-yl 4-(3-(8-oxa-3-azabicyclo[3.2.1]octan-3-yl)-4-(trifluoromethyl)benzyl)piperazine-1-carboxylate

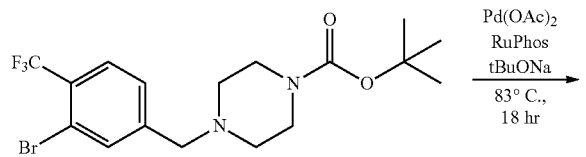

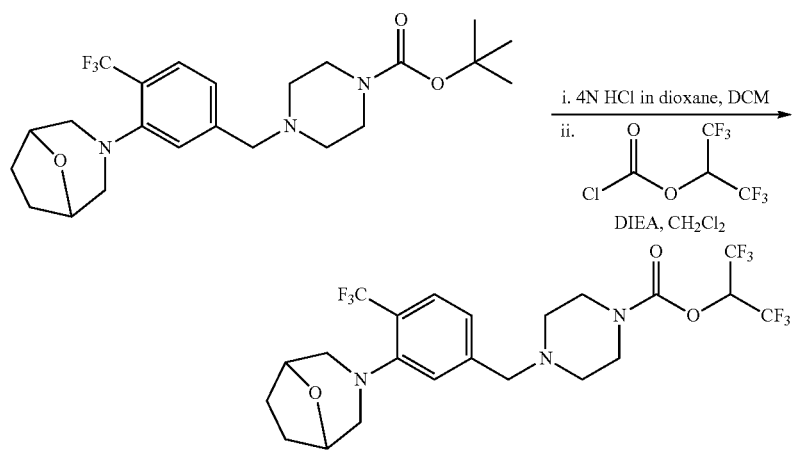

tert-Butyl 4-(3-(8-oxa-3-azabicyclo[3.2.1]octan-3-yl)-4-(trifluoromethyl)benzyl)piperazine-1-carboxylate was added to a vial and stirred with 3 mL DCM. The vial was cooled to 0° C. by ice bath and 4 N HCl in dioxane (0.73 mL, 6.0 eq) was added dropwise. The mixture was stirred at rt overnight. Solvent was removed and the resulting solid was used without further purification according to the representative procedure of Example 1, Step 4 to provide 1,1,1,3,3,3-hexafluoropropan-2-yl 4-(3-(8-oxa-3-azabicyclo[3.2.1]octan-3-yl)-4-(trifluoromethyl)benzyl)piperazine-1-carboxylate as a clear oil (69 mg, 26% yield). $^{1}$H NMR (400 MHz, Chloroform-d) δ 7.64-7.58 (m, 1H), 7.46 (s, 1H), 7.22 (d, J=8.1 Hz, 1H), 5.77 (hept, J=6.2 Hz, 1H), 4.46-4.35 (m, 2H), 3.64-3.53 (m, 6H), 3.18-3.09 (m, 2H), 2.77-2.68 (m, 2H), 2.53-2.40 (m, 4H), 2.25-2.16 (m, 2H), 2.00-1.88 (m, 2H). LCMS (ESI, m/z): 550.2 [M+H]$^{+}$.

Example 27: 1,1,1,3,3,3-hexafluoropropan-2-yl 4-(4-(8-oxa-3-azabicyclo[3.2.1]octan-3-yl)-2-fluorobenzyl)piperazine-1-carboxylate

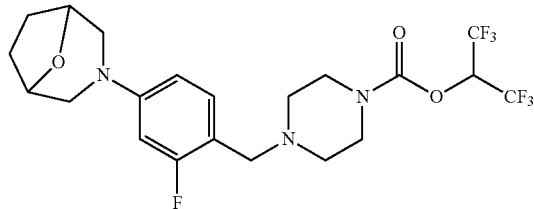 [SMILES: O=C(OC(C(F)(F)F)C(F)(F)F)N1CCN(Cc2ccc(N3CC4CCC(C3)O4)cc2F)CC1]

The title compound was synthesized directly from commercially available 4-chloro-2-fluorobenzaldehyde and 8-oxa-3-azabicylco[3.2.1]octane according to the representative procedure of Example 26, Steps 1-3 to provide 1,1,1,3,3,3-hexafluoropropan-2-yl 4-(4-(8-oxa-3-azabicyclo[3.2.1]octan-3-yl)-2-fluorobenzyl)piperazine-1-carboxylate as an oil: $^{1}$H NMR (400 MHz, Chloroform-d) δ 7.21-7.12 (m, 1H), 6.60-6.54 (m, 1H), 6.52-6.44 (m, 1H), 5.83-5.66 (m, 1H), 4.55-4.45 (m, 2H), 3.64-3.48 (m, 6H), 3.35-3.22 (m, 2H), 3.07-2.97 (m, 2H), 2.54-2.43 (m, 4H), 2.03-1.88 (m, 4H). LCMS (ESI, m/z): 220.1 ($C_{13}H_{15}FNO^{+}$).

Example 28: 1,1,1,3,3,3-hexafluoropropan-2-yl 4-(4-(8-oxa-3-azabicyclo[3.2.1]octan-3-yl)-2-(trifluoromethoxy)benzyl)piperazine-1-carboxylate

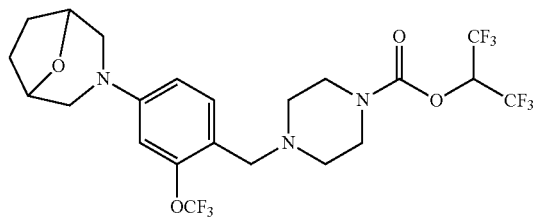 [SMILES: O=C(OC(C(F)(F)F)C(F)(F)F)N1CCN(Cc2ccc(N3CC4CCC(C3)O4)cc2OC(F)(F)F)CC1]

The title compound was synthesized directly from commercially available 4-chloro-2-(trifluoromethoxy)benzaldehyde and 8-oxa-3-azabicylco[3.2.1]octane according to the representative procedure of Example 26, Steps 1-3 to provide 1,1,1,3,3,3-hexafluoropropan-2-yl 4-(4-(8-oxa-3-azabicyclo[3.2.1]octan-3-yl)-2-(trifluoromethoxy)benzyl)piperazine-1-carboxylate as an oil: $^{1}$H NMR (400 MHz, Chloroform-d) δ 7.35-7.23 (m, 1H), 6.77-6.68 (m, 1H), 6.64 (s, 1H), 5.85-5.70 (m, 1H), 4.56-4.48 (m, 2H), 3.63-3.47 (m, 6H), 3.37-3.26 (m, 2H), 3.10-3.00 (m, 2H), 2.53-2.40 (m, 4H), 2.07-1.87 (m, 4H). LCMS (ESI, m/z): 286.0 ($C_{14}H_{15}F_{3}NO_{2}^{+}$).

Example 29: 1,1,1,3,3,3-hexafluoropropan-2-yl 4-(3-chloro-5-(pyrrolidin-1-ylmethyl)benzyl)piperazine-1-carboxylate

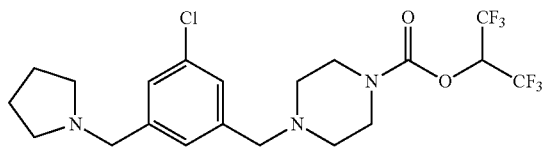 [SMILES: O=C(OC(C(F)(F)F)C(F)(F)F)N1CCN(Cc2cc(Cl)cc(CN3CCCC3)c2)CC1]

The title compound was synthesized directly from commercially available 3-bromo-5-chlorobenzaldehyde and pyrrolidine according to the representative procedure of Example 7, Steps 1-3 to provide 1,1,1,3,3,3-hexafluoropropan-2-yl 4-(3-chloro-5-(pyrrolidin-1-ylmethyl)benzyl)piperazine-1-carboxylate as a clear oil: $^{1}$H NMR (400 MHz, Chloroform-d) δ 7.03-6.98 (m, 2H), 6.95-6.90 (m, 1H), 5.60-5.45 (m, 1H), 3.44-3.29 (m, 6H), 3.26 (s, 2H), 2.32-2.26 (m, 4H), 2.22 (dt, J=10.6, 4.8 Hz, 4H), 1.64-1.50 (m, 4H). LCMS (ESI, m/z): 488.2 [M+H]$^{+}$.

Example 30: 1,1,1,3,3,3-hexafluoropropan-2-yl 4-(2-(8-oxa-3-azabicyclo[3.2.1]octan-3-yl)-4-chlorobenzyl)piperazine-1-carboxylate

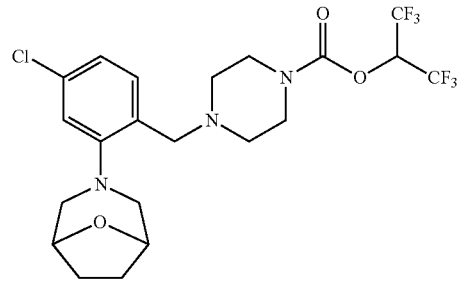 [SMILES: O=C(OC(C(F)(F)F)C(F)(F)F)N1CCN(Cc2ccc(Cl)cc2N2CC3CCC(C2)O3)CC1]

The title compound was prepared from 8-oxa-3-azabicyclo[3.2.1]octane and 4-chloro-2-fluorobenzaldehyde according to the representative procedure of Example 1 Steps 1,2, and 4 and yielded, 1,1,3,3,3-hexafluoropropan-2-yl 4-(2-(8-oxa-3-azabicyclo[3.2.1]octan-3-yl)-4-chlorobenzyl)piperazine-1-carboxylate as a white solid. $^{1}$H NMR (400 MHz, Chloroform-d) δ 7.38 (d, J=8.2 Hz, 1H), 7.14-7.04 (m, 2H), 5.78 (hept, J=6.2 Hz, 1H), 4.44-4.38 (m, 2H), 3.60-3.52 (m, 6H), 3.05 (d, J=10.2 Hz, 2H), 2.83 (d, J=10.9 Hz, 2H), 2.48 (dt, J=9.2, 5.1 Hz, 4H), 2.16-1.95 (m, 4H). LCMS (ESI, m/z): 516.1 [M+H]$^{+}$.

Example 31: 1,1,1,3,3,3-hexafluoropropan-2-yl 4-(2-(8-oxa-3-azabicyclo[3.2.1]octan-3-yl)-3-(trifluoromethoxy)benzyl)piperazine-1-carboxylate

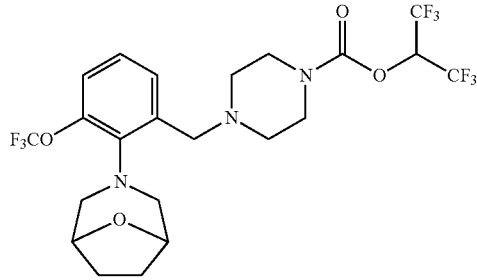 [SMILES: O=C(OC(C(F)(F)F)C(F)(F)F)N1CCN(Cc2cccc(OC(F)(F)F)c2N2CC3CCC(C2)O3)CC1]

The title compound was synthesized directly from commercially available 2-chloro-3-(trifluoromethoxy)benzaldehyde and 8-oxa-3-azabicylco[3.2.1]octane according to the representative procedure of Example 27, Steps 1-3 to provide 1,1,1,3,3,3-hexafluoropropan-2-yl 4-(2-(8-oxa-3-azabicyclo[3.2.1]octan-3-yl)-3-(trifluoromethoxy)benzyl)piperazine-1-carboxylate as an oil: $^1$H NMR (400 MHz, Chloroform-d) δ 7.39-7.31 (m, 1H), 7.26-7.12 (m, 2H), 5.87-5.64 (m, 1H), 4.44-4.28 (m, 2H), 3.71 (s, 2H), 3.66-3.49 (m, 6H), 2.64-2.43 (m, 6H), 2.17-2.06 (m, 2H), 2.05-1.93 (m, 2H). LCMS (ESI, m/z): 566.2 [M+H]$^+$.

Example 32: 1,1,1,3,3,3-hexafluoropropan-2-yl 4-(2-(4-(pyrrolidin-1-yl)piperidin-1-yl)-3-(trifluoromethoxy)benzyl)piperazine-1-carboxylate

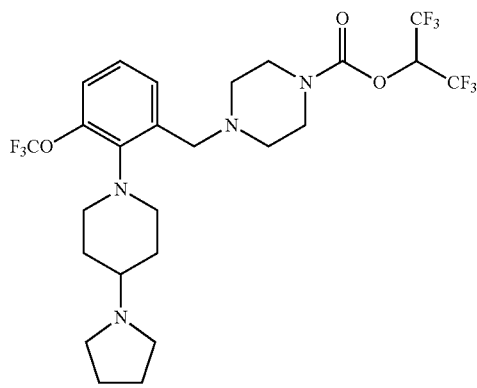 [SMILES: O=C(OC(C(F)(F)F)C(F)(F)F)N1CCN(Cc2cccc(OC(F)(F)F)c2N2CCC(N3CCCC3)CC2)CC1]

The title compound was synthesized directly from commercially available 2-chloro-3-(trifluoromethoxy)benzaldehyde and 4-(pyrrolidin-1-yl)piperidine according to the representative procedure of Example 27, Steps 1-3 to provide 1,1,1,3,3,3-hexafluoropropan-2-yl 4-(2-(4-(pyrrolidin-1-yl)piperidin-1-yl)-3-(trifluoromethoxy)benzyl)piperazine-1-carboxylate as an oil: $^1$H NMR (400 MHz, Chloroform-d) δ 7.36-7.30 (m, 1H), 7.19-7.05 (m, 2H), 5.84-5.65 (m, 1H), 3.63 (s, 2H), 3.59-3.48 (m, 4H), 3.25-2.87 (m, 4H), 2.72-2.53 (m, 4H), 2.53-2.41 (m, 4H), 2.16-2.05 (m, 1H), 2.05-1.94 (m, 2H), 1.91-1.78 (m, J=4.3, 3.8 Hz, 4H), 1.73-1.51 (m, 2H). LCMS (ESI, m/z): 607.3 [M+H]$^+$.

Example 33: 1,1,1,3,3,3-hexafluoropropan-2-yl 4-(2-(4-carbamoylpiperidin-1-yl)-4-chlorobenzyl)piperazine-1-carboxylate

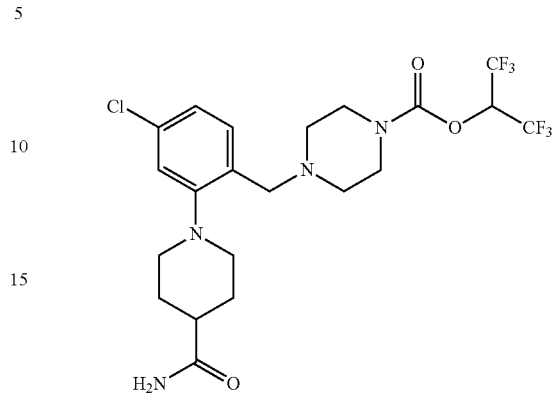

Step 1: Preparation of 1-(5-chloro-2-formylphenyl)piperidine-4-carboxamide

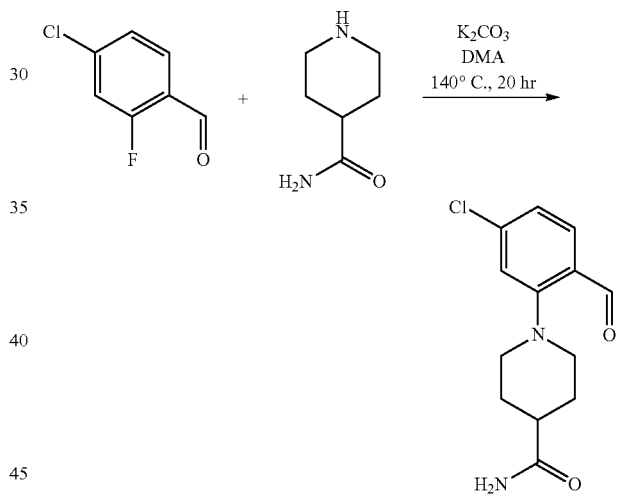

A sealed tube was charged with 4-chloro-2-fluorobenzaldehyde (1 g, 6.30 mmol), piperidine-4-carboxamide (0.970 g, 7.57 mmol), and K$_2$CO$_3$ (2.78 g, 20.2 mmol). DMA (8 mL) was added and the mixture was stirred at 140° C. for 20 h. The reaction was cooled to rt, then diluted with EtOAc (200 mL). The organic layer was washed with brine (3×) and with sat. NH$_4$Cl (1×). The organic layers were dried over Na$_2$SO$_4$, filtered and concentrated to yield a solid. The solid was purified on silica gel by flash column chromatography to afford 1-(5-chloro-2-formylphenyl)piperidine-4-carboxamide as a yellow solid (703 mg, 41% yield). $^1$H NMR (400 MHz, DMSO-d$_6$) δ 10.07 (s, 1H), 7.74-7.62 (m, 1H), 7.40-7.28 (m, 1H), 7.26-7.16 (m, 1H), 7.19-7.10 (m, 1H), 6.85 (s, 1H), 3.33-3.21 (m, 2H), 2.96-2.81 (m, 2H), 2.31-2.20 (m, 1H), 1.89-1.71 (m, 4H).

Step 2: Preparation of 1,1,1,3,3,3-hexafluoropropan-2-yl piperazine-1-carboxylate hydrochloride

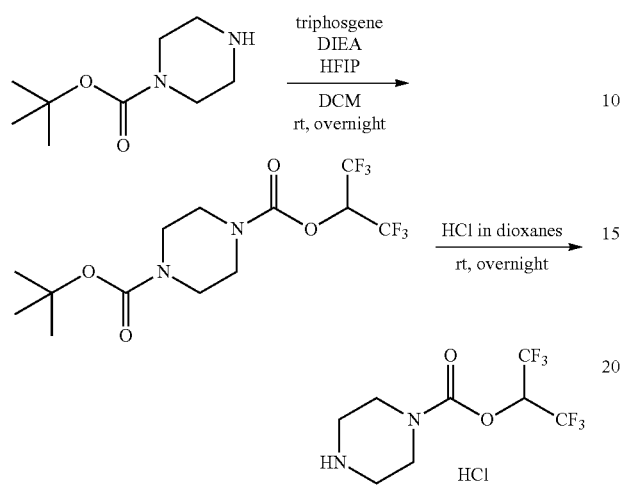

A flask was charged with triphosgene (3.18 g, 10.7 mmol). DCM (60 mL) was added and the mixture was stirred at 0° C. for 10 min while being purged with $N_2$. Hexafluoroisopropanol was added dropwise (5.86 g, 34.8 mmol), followed by DIEA (6.94 g, 53.7 mmol). The reaction stirred at rt for 2 h. At that point, tert-butyl piperazine-1-carboxylate was added (1 g, 5.37 mmol) and the reaction was allowed to stir at rt overnight. The reaction mixture was diluted with DCM, washed with sat. $NaHCO_3$ (3×), dried over $Na_2SO_4$, filtered and concentrated to yield an oil which was purified on silica gel by flash column chromatography to afford 1-(tert-butyl) hexafluoropropan-2-yl) piperazine-1,4-dicarboxylate as a clear oil (1.1 g, 72% yield ($^1$H NMR (400 MHz, Chloroform-d) δ 5.69 (s, 1H), 3.52-3.36 (m, 8H), 1.40 (s, 9H).) The oil was transferred to a 16 mL vial equipped with a magnetic stir bar and stirred in 3 mL DCM at 0° C. 4 N HCl in dioxane was added dropwise (6.82 mL, 27.294 mmol) and the reaction stirred at rt overnight. The reaction was concentrated to afford 1,1,1,3,3,3-hexafluoropropan-2-yl piperazine-1-carboxylate hydrochloride as a white solid (487 mg, 38% yield). $^1$H NMR (400 MHz, Chloroform-d) δ 5.77-5.59 (m, 1H), 3.50-3.33 (m, 4H), 2.85-2.68 (m, 4H), 1.77 (s, 1H).

Step 3: Preparation of 1,1,1,3,3,3-hexafluoropropan-2-yl 4-(2-(4-carbamoylpiperidin-1-yl)-4-chlorobenzyl)piperazine-1-carboxylate

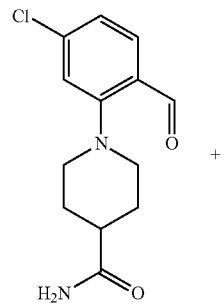 +

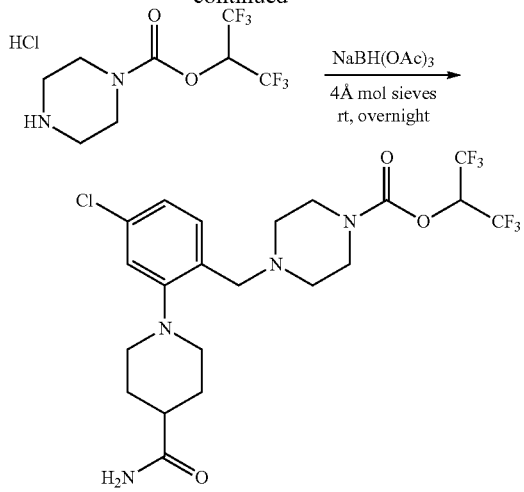

A vial was charged with 1-(5-chloro-2-formylphenyl) piperidine-4-carboxamide (100 mg, 0.375 mmol), 1,1,1,3,3,3-hexafluoropropan-2-yl piperazine-1-carboxylate hydrochloride (130 mg, 0.412 mmol), and 4 Å molecular sieves (100 mg). DMF (4 mL) was added. The vial was purged with $N_2$ and stirred at rt for 2 h. At that point, $NaBH(OAc)_3$ (87 mg, 0.412 mmol) was added. The reaction was stirred at rt overnight, then was diluted with EtOAc and filtered over Celite. The organic layer was washed with sat. $NaHCO_3$ (3×) dried over $Na_2SO_4$, filtered and concentrated to yield an oil. The oil was purified on silica gel by flash column chromatography to afford 1,1,1,3,3,3-hexafluoropropan-2-yl 4-(2-(4-carbamoylpiperidin-1-yl)-4-chlorobenzyl)piperazine-1-carboxylate as a pale oil (58 mg, 29% yield). $^1$H NMR (400 MHz, Chloroform-d) δ 7.41-7.35 (m, 1H), 7.10-7.03 (m, 2H), 5.82-5.73 (m, 1H), 5.57-5.38 (m, 2H), 3.58-3.52 (m, 6H), 3.30-3.21 (m, 2H), 2.73-2.64 (m, 2H), 2.53-2.45 (m, 4H), 2.35-2.25 (m, 1H), 2.01-1.87 (m, 4H). LCMS (ESI, m/z): 531.1 [M+H]$^+$.

Example 34: 1,1,1,3,3,3-hexafluoropropan-2-yl 4-(4-chloro-2-(4-(dimethylcarbamoyl)piperidin-1-yl)benzyl)piperazine-1-carboxylate

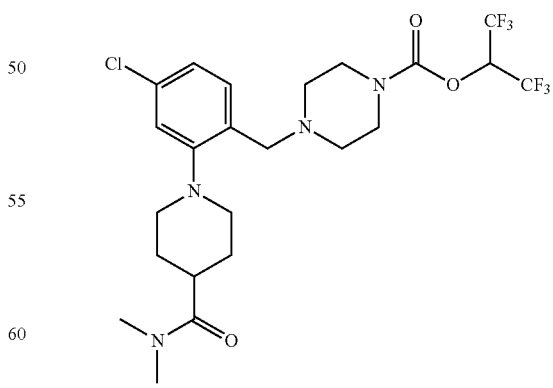

The title compound was synthesized directly from commercially available 4-chloro-2-fluorobenzaldehyde and N,N-dimethylpiperidine-4-carboxamide according to the representative procedure of Example 33, Steps 1-3 to provide 1,1,1,3,3,3-hexafluoropropan-2-yl 4-(4-chloro-2-(4-(dimethylcarbamoyl)piperidin-1-yl)benzyl)piperazine-1-carboxylate as a pale oil: ¹H NMR (400 MHz, Chloroform-d) δ 7.40-7.32 (m, 1H), 7.07-6.99 (m, 2H), 5.82-5.70 (m, 1H), 3.60-3.46 (m, 6H), 3.33-3.21 (m, 2H), 3.10 (s, 3H), 2.99 (s, 3H), 2.75-2.61 (m, 3H), 2.54-2.42 (m, 4H), 2.07-1.93 (m, 2H), 1.87-1.74 (m, 2H). LCMS (ESI, m/z): 559.2 [M+H]⁺.

Example 35: 1,1,1,3,3,3-hexafluoropropan-2-yl 4-(2-(4-(dimethylcarbamoyl)piperidin-1-yl)-4-(trifluoromethyl)benzyl)piperazine-1-carboxylate

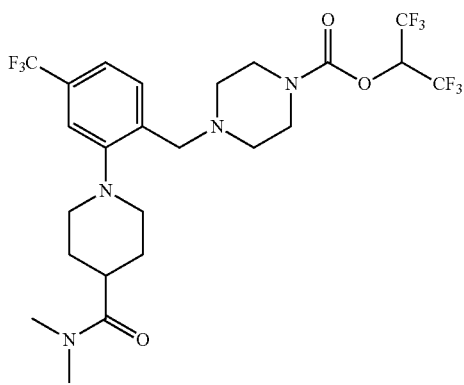 [SMILES: CN(C)C(=O)C1CCN(c2cc(C(F)(F)F)ccc2CN2CCN(C(=O)OC(C(F)(F)F)C(F)(F)F)CC2)CC1]

The title compound was synthesized directly from commercially available 2-fluoro-4-(trifluoromethyl)benzaldehyde and N,N-dimethylpiperidine-4-carboxamide according to the representative procedure of Example 33, Steps 1-3 to provide 1,1,1,3,3,3-hexafluoropropan-2-yl 4-(2-(4-(dimethylcarbamoyl)piperidin-1-yl)-4-(trifluoromethyl)benzyl)piperazine-1-carboxylate as a pale oil: ¹H NMR (400 MHz, Chloroform-d) δ 7.64-7.56 (m, 1H), 7.35-7.30 (m, 2H), 5.84-5.70 (m, 1H), 3.63 (s, 2H), 3.60-3.51 (m, 4H), 3.32-3.22 (m, 2H), 3.12 (s, 3H), 3.00 (s, 3H), 2.81-2.63 (m, 3H), 2.56-2.43 (m, 4H), 2.11-1.97 (m, 2H). LCMS (ESI, m/z): 593.2 [M+H]⁺.

Example 36: 1,1,1,3,3,3-hexafluoropropan-2-yl 4-(2-(4-carbamoylpiperidin-1-yl)-4-(trifluoromethyl)benzyl)piperazine-1-carboxylate

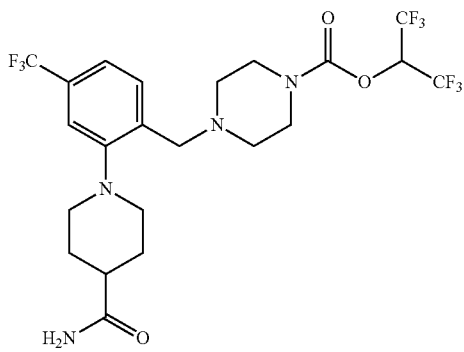 [SMILES: NC(=O)C1CCN(c2cc(C(F)(F)F)ccc2CN2CCN(C(=O)OC(C(F)(F)F)C(F)(F)F)CC2)CC1]

The title compound was synthesized directly from commercially available 2-fluoro-4-(trifluoromethyl)benzaldehyde and piperidine-4-carboxamide according to the representative procedure of Example 33, Steps 1-3 to provide 1,1,1,3,3,3-hexafluoropropan-2-yl 4-(2-(4-carbamoylpiperidin-1-yl)-4-(trifluoromethyl)benzyl)piperazine-1-carboxylate as a clear oil: ¹H NMR (400 MHz, Chloroform-d) δ 7.61 (s, 1H), 7.34 (s, 1H), 7.32-7.29 (m, 1H), 5.84-5.72 (m, 1H), 5.67-5.50 (m, 2H), 3.70-3.50 (m, 6H), 3.32-3.20 (m, 2H), 2.79-2.66 (m, 2H), 2.61-2.44 (m, 4H), 2.39-2.27 (m, 1H), 2.06-1.86 (m, 4H). LCMS (ESI, m/z): 565.2 [M+H]⁺.

Example 37: 1,1,1,3,3,3-hexafluoropropan-2-yl 4-(4-chloro-2-(4-(pyrrolidine-1-carbonyl)piperidin-1-yl)benzyl)piperazine-1-carboxylate

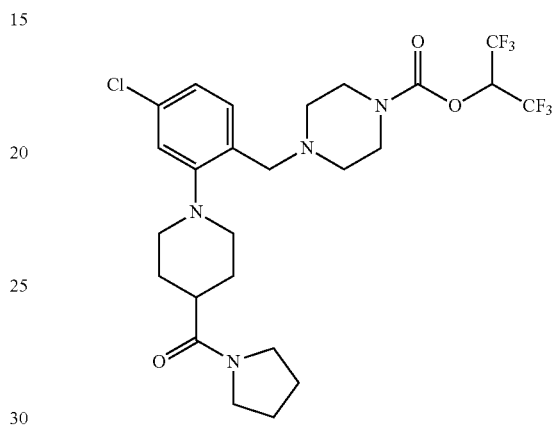

Step 1: Preparation of 4-chloro-2-[4-[(pyrrolidin-1-yl)carbonyl]piperidin-1-yl]benzaldehyde

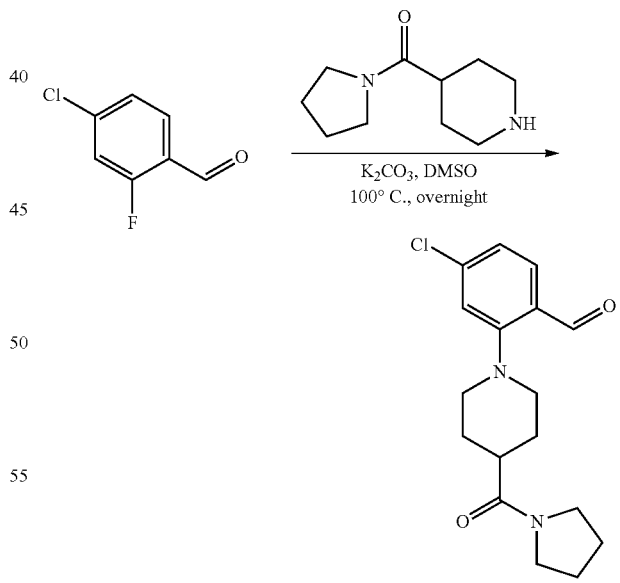

A flask was charged with 4-chloro-2-fluorobenzaldehyde (1.00 g, 6.31 mmol, 1.00 equiv), 4-[(pyrrolidin-1-yl)carbonyl]piperidine hydrochloride (1.65 g, 7.54 mmol, 1.20 equiv), K₂CO₃ (3.47 g, 25.1 mmol, 3.98 equiv), DMSO (10 mL) under nitrogen. The resulting solution was stirred overnight at 100° C. and then diluted with H₂O (10 mL). The resulting solution was extracted with EtOAc (3×20 mL) and the organic layers were combined, washed with H₂O (3×5 mL), dried over anhydrous Na₂SO₄, filtered and concentrated. The residue was chromatographed on a silica gel column (1:3 EtOAc/petroleum ether) to provide of 4-chloro-2-[4-[(pyrrolidin-1-yl)carbonyl]piperidin-1-yl]benzaldehyde (1.50 g, 74% yield) as a yellow solid. ¹H NMR (300 MHz, Chloroform-d) δ 10.26 (s, 1H), 7.70-7.75 (m, 1H), 7.05-7.08 (m, 2H), 3.38-3.53 (m, 6H), 2.90-2.99 (m, 2H), 1.86-2.16 (m, 8H). LCMS (ESI, m/z): 321 [M+H]⁺.

Step 2: Preparation of tert-butyl 4-[(4-chloro-2-[4-[(pyrrolidin-1-yl)carbonyl]piperidin-1-yl]phenyl) methyl]piperazine-1-carboxylate

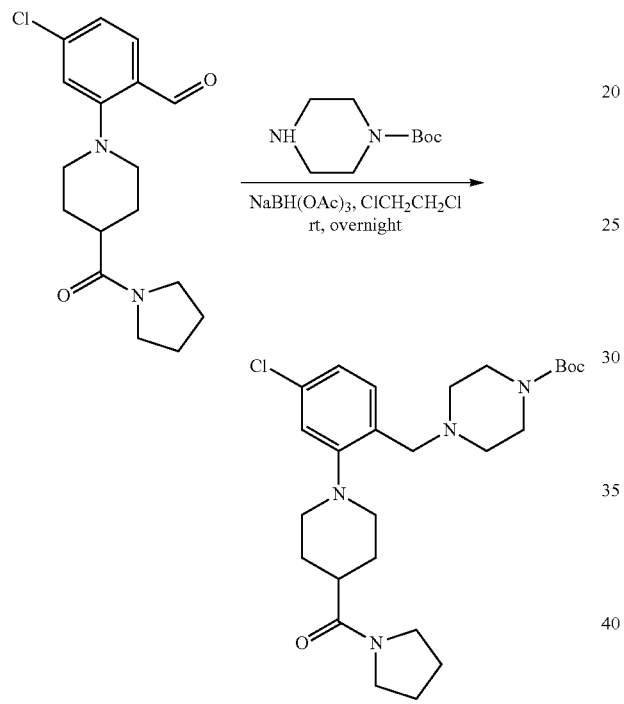

A flask was charged with 4-chloro-2-[4-[(pyrrolidin-1-yl)carbonyl]piperidin-1-yl]benzaldehyde (321 mg, 1.00 mmol, 1.10 equiv), tert-butyl piperazine-1-carboxylate (169 mg, 0.909 mmol, 1.00 equiv), and 1,2-dichloroethane (10 mL). The mixture was stirred at rt for 30 min. NaBH(OAc)₃ (385 mg, 1.82 mmol, 2.00 equiv) was added. The resulting solution was stirred overnight at rt and then diluted with H₂O (10 mL). The resulting solution was extracted with EtOAc (3×20 mL) and the organic layers were combined, washed with H₂O (3×5 mL), dried over anhydrous Na₂SO₄, filtered and concentrated. The residue was chromatographed on a silica gel column (1:4 EtOAc/petroleum ether) to provide of tert-butyl 4-[(4-chloro-2-[4-[(pyrrolidin-1-yl)carbonyl]piperidin-1-yl]phenyl)methyl]piperazine-1-carboxylate (400 mg, 81% yield) as light yellow oil. ¹H NMR (300 MHz, Chloroform-d) δ 7.37 (d, J=8.4 Hz, 1H), 7.01-7.03 (m, 2H), 3.73 (m, 2H), 3.52-3.73 (m, 6H), 3.38-3.49 (m, 4H), 3.26-3.29 (m, 2H), 2.43-2.50 (m, 5H), 1.82-2.04 (m, 8H), 1.45 (s, 9H). LCMS (ESI, m/z): 491 [M+H]⁺.

Step 3: Preparation of 1-[(4-chloro-2-[4-[(pyrrolidin-1-yl)carbonyl]piperidin-1-yl]phenyl)methyl] piperazine

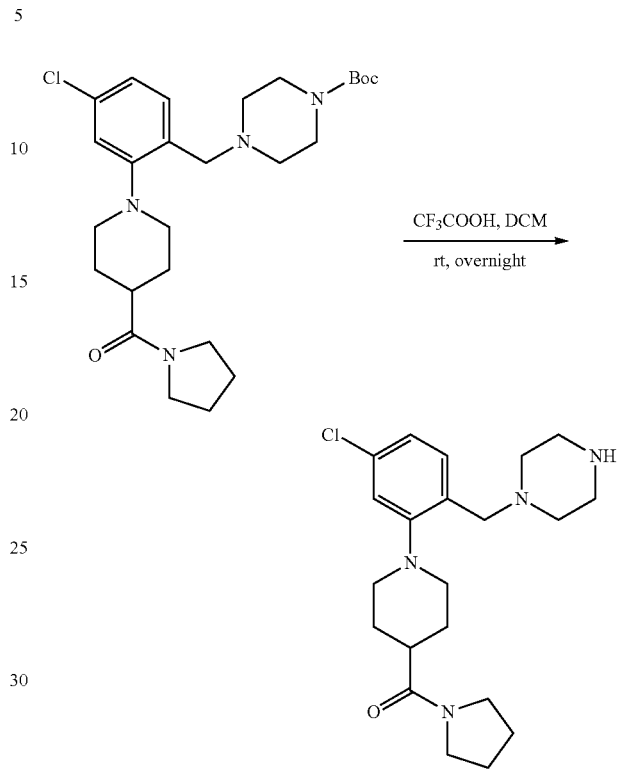

A flask was charged with tert-butyl 4-[(4-chloro-2-[4-[(pyrrolidin-1-yl)carbonyl]piperidin-1-yl]phenyl)methyl] piperazine-1-carboxylate (400 mg, 0.81 mmol, 1.00 equiv) and DCM (5 mL). TFA (1 mL) was added dropwise. The resulting solution was stirred overnight at rt. The resulting solution was concentrated to provide 1-[(4-chloro-2-[4-[(pyrrolidin-1-yl)carbonyl]piperidin-1-yl]phenyl)methyl] piperazine (1000 mg) as yellow oil, which was carried on without further purification. LCMS (ESI, m/z): 391 [M+H]⁺.

Step 4: Preparation of 1,1,1,3,3,3-hexafluoropropan-2-yl 4-(4-chloro-2-(4-(pyrrolidine-1-carbonyl) piperidin-1-yl)benzyl)piperazine-1-carboxylate

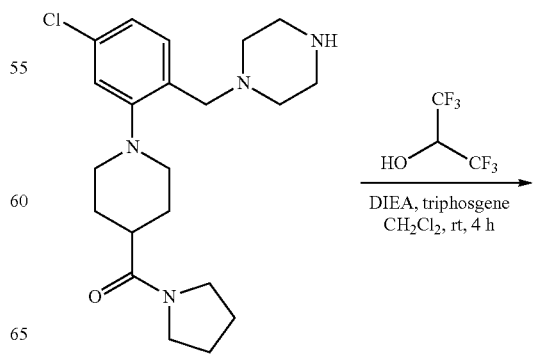

117
-continued

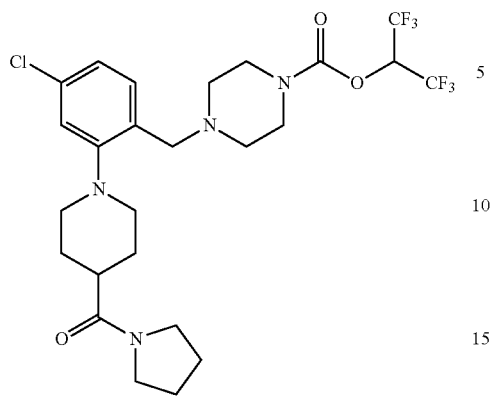

A flask was charged with 1,1,1,3,3,3-hexafluoropropan-2-ol (215 mg, 1.28 mmol, 1.00 equiv), triphosgene (127 mg, 0.428 mmol, 0.33 equiv), and DCM (10 mL). DIEA (495 mg, 3.83 mmol, 2.99 equiv) was added dropwise. The mixture was stirred at rt for 2 h. 1-[(4-Chloro-2-[4-[(pyrrolidin-1-yl)carbonyl]piperidin-1-yl]phenyl)methyl]piperazine (500 mg, 1.28 mmol, 1.00 equiv) was added. The resulting solution was stirred for 2 h at rt and diluted with H$_2$O (20 mL). The mixture was extracted with DCM (3×30 mL) and the organic layers were combined, washed with H$_2$O (3×10 mL), dried over anhydrous Na$_2$SO$_4$, filtered and concentrated. The residue was chromatographed on a silica gel column (9:1 EtOAc/petroleum ether). The crude product (305 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in yielding 1,1,1,3,3,3-hexafluoropropan-2-yl 4-(4-chloro-2-(4-(pyrrolidine-1-carbonyl)piperidin-1-yl)benzyl)piperazine-1-carboxylate (131.3 mg, 17% yield) as an orange semi-solid. $^1$H NMR (300 MHz, Chloroform-d) δ 7.31-7.36 (m, 1H), 7.01-7.04 (m, 2H), 5.73-5.81 (m, 1H), 3.50-3.54 (m, 10H), 3.24-3.28 (m, 2H), 2.63-2.70 (m, 2H), 2.50 (br, 5H), 1.97-2.07 (m, 4H), 1.79-1.92 (m, 4H). LCMS (ESI, m/z): 585 [M+H]$^+$.

118

Example 38: 1,1,1,3,3,3-hexafluoropropan-2-yl 4-(4-chloro-2-(3-(3,5-dimethyl-1H-pyrazol-1-yl)azetidin-1-yl)benzyl)piperazine-1-carboxylate

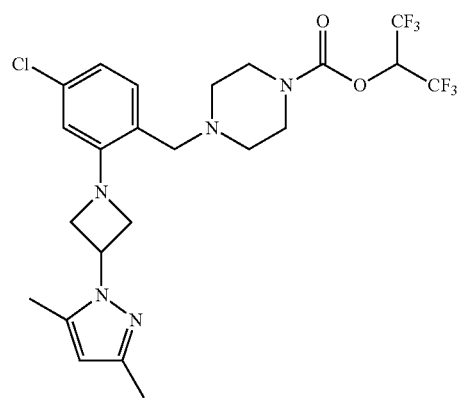 [SMILES: Cc1cc(C)n(C2CN(c3cc(Cl)ccc3CN3CCN(C(=O)OC(C(F)(F)F)C(F)(F)F)CC3)C2)n1]

The title compound was synthesized directly from commercially available 4-chloro-2-fluorobenzaldehyde and 1-(azetidin-3-yl)-3,5-dimethyl-1H-pyrazole according to the representative procedure of Example 37, Steps 1-3, substituting DIEA for K$_2$CO$_3$ in Step 1, to provide 1,1,1,3,3,3-hexafluoropropan-2-yl 4-(4-chloro-2-(3-(3,5-dimethyl-1H-pyrazol-1-yl)azetidin-1-yl)benzyl)piperazine-1-carboxylate as colorless oil. $^1$H NMR (300 MHz, Chloroform-d): δ 7.09 (d, J=8.1 Hz, 1H), 6.75 (d, J=7.5 Hz, 1H), 6.52 (s, 1H), 5.70-5.82 (m, 2H), 5.02-5.11 (m, 1H), 4.33-4.47 (m, 4H), 3.55 (br, 4H), 3.40 (br, 2H), 2.43 (br, 4H), 2.26 (s, 3H), 2.22 (s, 3H). LCMS (ESI, m/z): 554 [M+H]$^+$.

Example 39: 1,1,1,3,3,3-hexafluoropropan-2-yl (R)-4-(4-chloro-2-(3-(methylsulfonamido)pyrrolidin-1-yl)benzyl)piperazine-1-carboxylate

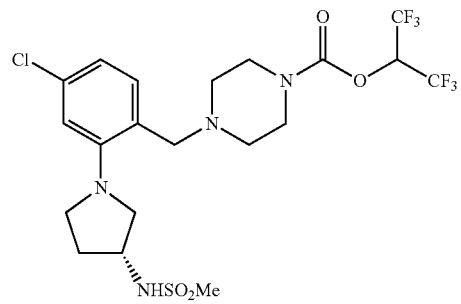

Step 1: Preparation of tert-butyl N-[(3R)-1-(5-chloro-2-formylphenyl)pyrrolidin-3-yl]carbamate

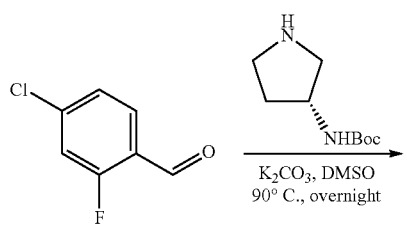

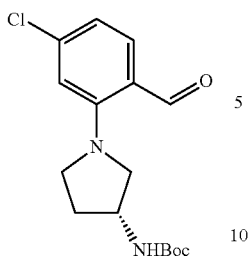

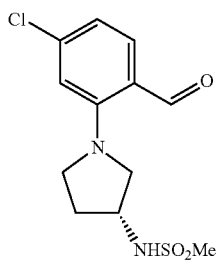

A flask was charged with 4-chloro-2-fluorobenzaldehyde (2.00 g, 12.6 mmol, 1.00 equiv), tert-butyl N-[(3R)-pyrrolidin-3-yl]carbamate (2.10 g, 11.3 mmol, 0.89 equiv), $K_2CO_3$ (4.00 g, 28.9 mmol, 2.29 equiv), and DMSO (20 mL). The resulting solution was stirred overnight at 90° C. and then diluted with $H_2O$ (30 mL). The resulting solution was extracted with DCM (3×20 mL) and the organic layers were combined, dried over anhydrous $Na_2SO_4$, filtered and concentrated. The residue was chromatographed on a silica gel column (17:83 EtOAc/petroleum ether) to provide tert-butyl N-[(3R)-1-(5-chloro-2-formylphenyl)pyrrolidin-3-yl]carbamate (3.00 g, 73% yield) as a yellow solid. LCMS (ESI, m/z): 325 [M+H]$^+$.

A vial was charged with 2-[(3R)-3-aminopyrrolidin-1-yl]-4-chlorobenzaldehyde (150 mg, 0.670 mmol, 1.00 equiv), methanesulfonyl chloride (100 mg, 0.880 mmol, 1.30 equiv), DCM (10 mL), and triethylamine (134 mg, 1.32 mmol, 1.98 equiv). The resulting solution was stirred for 30 min at rt then diluted with $H_2O$ (10 mL). The resulting solution was extracted with DCM (3×10 mL) and the organic layers were combined, dried over anhydrous $Na_2SO_4$, filtered and concentrated. The residue was chromatographed on a silica gel column (55:45 EtOAc/petroleum ether) to provide N-[(3R)-1-(5-chloro-2-formylphenyl)pyrrolidin-3-yl]methanesulfonamide (180 mg, 89% yield) as a yellow solid. LCMS (ESI, m/z): 303 [M+H]$^+$.

Step 2: Preparation of 2-[(3R)-3-aminopyrrolidin-1-yl]-5-chlorobenzaldehyde

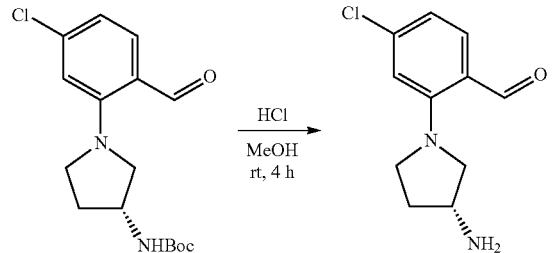 [SMILES: CC(C)(C)OC(=O)N[C@@H]1CCN(c2cc(Cl)ccc2C=O)C1 ; Cl ; N[C@@H]1CCN(c2cc(Cl)ccc2C=O)C1]

A flask was charged with tert-butyl N-[(3R)-1-(4-chloro-2-formylphenyl)pyrrolidin-3-yl]carbamate (1.40 g, 4.31 mmol, 1.00 equiv), HCl (5 mL), and MeOH (20 mL). The resulting solution was stirred for 4 h at rt. The resulting mixture was concentrated to provide 2-[(3R)-3-aminopyrrolidin-1-yl]-5-chlorobenzaldehyde (960 mg, 99% yield) as yellow oil, which was carried on without further purification. LCMS (ESI, m/z): 225 [M+H]$^+$.

Step 3: Preparation of N-[(3R)-1-(5-chloro-2-formylphenyl)pyrrolidin-3-yl]methanesulfonamide

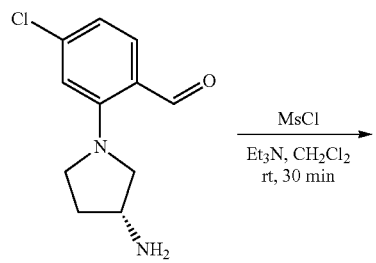

Step 4: Preparation of tert-butyl 4-([4-chloro-2-[(3R)-3-methanesulfonamidopyrrolidin-1-yl]phenyl]methyl)piperazine-1-carboxylate

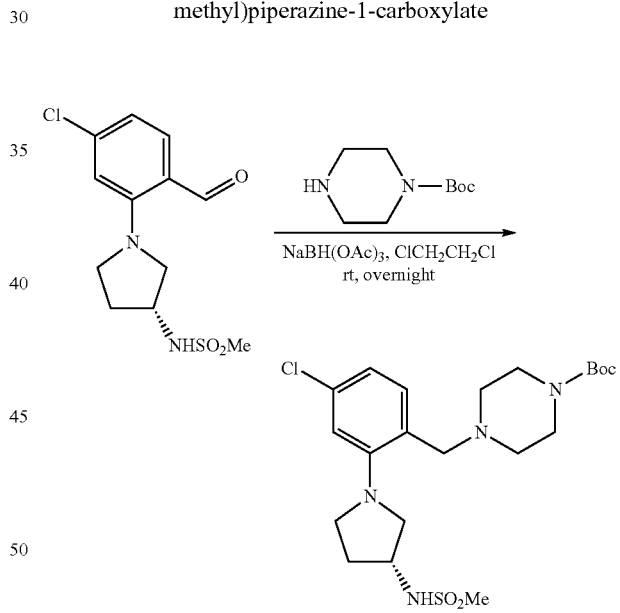

A flask was charged with N-[(3R)-1-(5-chloro-2-formylphenyl)pyrrolidin-3-yl]methanesulfonamide (180 mg, 0.590 mmol, 1.00 equiv), tert-butyl piperazine-1-carboxylate (133 mg, 0.710 mmol, 1.20 equiv), and 1,2-dichloroethane (10 mL). The resulting solution was stirred for 30 min at rt. $NaBH(OAc)_3$ (375 mg, 1.77 mmol, 2.98 equiv) was added. The resulting solution was stirred overnight at rt and diluted with $H_2O$ (10 mL). The resulting solution was extracted with DCM (2×10 mL) and the organic layers were combined, dried over anhydrous $Na_2SO_4$, filtered and concentrated. The residue was chromatographed on a silica gel column (70:30 EtOAc/petroleum ether) to provide tert-butyl 4-([4-chloro-2-[(3R)-3-methanesulfonamidopyrrolidin-1-yl]phenyl]methyl)piperazine-1-carboxylate (250 mg, 89% yield) as yellow oil. LCMS (ESI, m/z): 473 [M+H]⁺.

Step 5: Preparation of N-[(3R)-1-[5-chloro-2-(piperazin-1-ylmethyl)phenyl]pyrrolidin-3-yl]methanesulfonamide

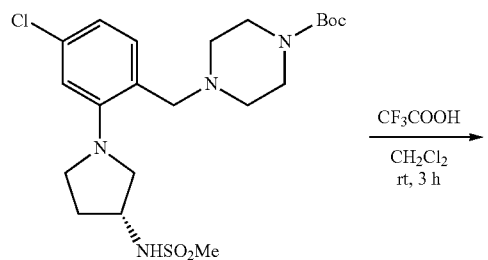

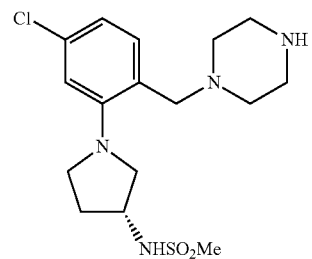

A flask was charged with tert-butyl 4-([4-chloro-6-[(3R)-3-methanesulfonamidopyrrolidin-1-yl]cyclohexa-1,5-dien-1-yl]methyl)piperazine-1-carboxylate (250 mg, 0.530 mmol, 1.00 equiv), TFA (2 mL), and DCM (10 mL). The resulting solution was stirred for 3 h at rt. The resulting mixture was concentrated to provide N-[(3R)-1-[5-chloro-2-(piperazin-1-ylmethyl)phenyl]pyrrolidin-3-yl]methanesulfonamide (180 mg, 91% yield) as yellow oil, which was carried on without further purification. LCMS (ESI, m/z): 373 [M+H]⁺.

Step 6: Preparation of 1,1,1,3,3,3-hexafluoropropan-2-yl (R)-4-(4-chloro-2-(3-(methylsulfonamido)pyrrolidin-1-yl)benzyl)piperazine-1-carboxylate

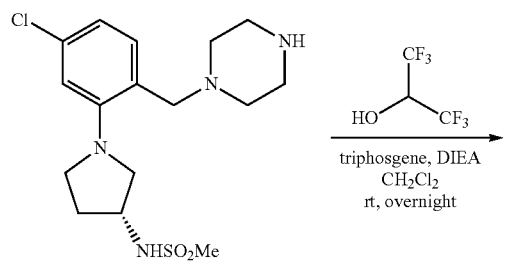

-continued

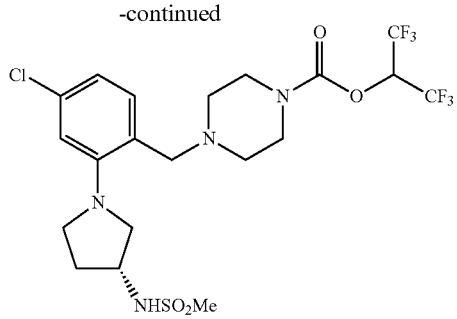

A flask was charged with triphosgene (21.0 mg, 0.0710 mmol, 0.30 equiv), DCM (10 mL), 1,1,1,3,3,3-hexafluoropropan-2-ol (50.0 mg, 0.300 mmol, 1.00 equiv), and DIEA (62.0 mg, 0.480 mmol, 1.61 equiv). The resulting solution was stirred for 2 h at rt. N-[(3R)-1-[4-Chloro-2-(piperazin-1-ylmethyl)phenyl]pyrrolidin-3-yl]methanesulfonamide (90.0 mg, 0.240 mmol, 0.81 equiv) was added dropwise. The resulting solution was stirred overnight at rt and concentrated. The crude product (300 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 um; Mobile phase: Phase A: aqueous NH₄HCO₃ (0.05%); Phase B: CH₃CN; Detector, UV220 & 254 nm. Purification resulted in 1,1,1,3,3,3-hexafluoropropan-2-yl (R)-4-(4-chloro-2-(3-(methylsulfonamido)pyrrolidin-1-yl)benzyl)piperazine-1-carboxylate (67.9 mg, 40% yield) as a white solid. ¹H NMR (300 MHz, Chloroform-d) δ 7.26 (d, J=7.8 Hz, 1H), 6.90 (t, J=8.7 Hz, 2H), 5.70-5.79 (m, 1H), 4.80 (br, 1H), 4.06-4.14 (m, 1H), 3.31-3.56 (m, 9H), 3.07-3.15 (m, 1H), 3.01 (s, 3H), 2.31-2.45 (m, 5H), 1.95-1.97 (m, 1H). LCMS (ESI, m/z): 567 [M+H]⁺.

Example 40: 1,1,1,3,3,3-hexafluoropropan-2-yl (S)-4-(4-chloro-2-(3-(methylsulfonamido)pyrrolidin-1-yl)benzyl)piperazine-1-carboxylate

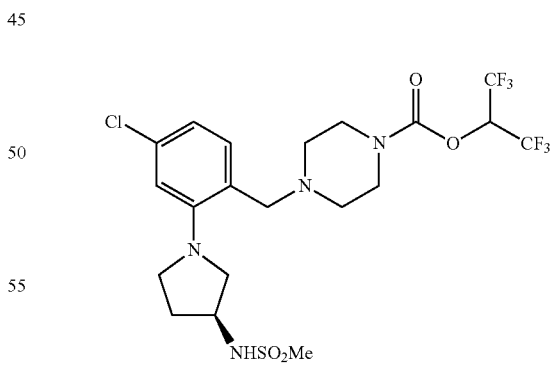

The title compound was synthesized directly from commercially available 4-chloro-2-fluorobenzaldehyde and tert-butyl N-[(3S)-pyrrolidin-3-yl]carbamate according to the representative procedure of Example 39, Steps 1-6, to provide 1,1,1,3,3,3-hexafluoropropan-2-yl (S)-4-(4-chloro-2-(3-(methylsulfonamido)pyrrolidin-1-yl)benzyl)piperazine-1-carboxylate (60.4 mg, 57% yield) as a white solid. ¹H NMR (300 MHz, Chloroform-d) δ 7.26 (d, J=8.1 Hz, 1H), 6.90 (t, J=8.6 Hz, 2H), 5.70-5.79 (m, 1H), 4.80 (br, 1H), 4.06-4.14 (m, 1H), 3.30-3.56 (m, 9H), 3.07-3.15 (m, 1H), 3.01 (s, 3H), 2.31-2.45 (m, 5H), 1.95-1.97 (m, 1H). LCMS (ESI, m/z): 567 [M+H]$^+$.

Example 41: 1,1,1,3,3,3-hexafluoropropan-2-yl (R)-4-(4-chloro-2-(2-oxo-[1,3'-bipyrrolidin]-1'-yl)benzyl)piperazine-1-carboxylate

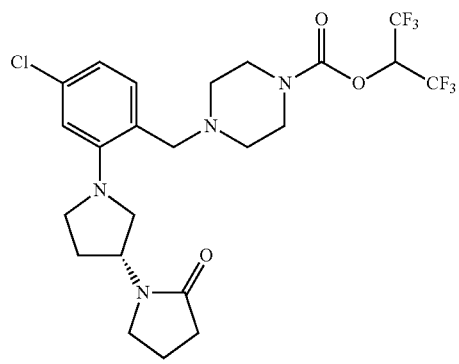 [SMILES: O=C(OC(C(F)(F)F)C(F)(F)F)N1CCN(Cc2ccc(Cl)cc2N2CC[C@@H](N3CCCC3=O)C2)CC1]

Step 1: Preparation of 4-chloro-N-[(3R)-1-(5-chloro-2-formylphenyl)pyrrolidin-3-yl]butanamide

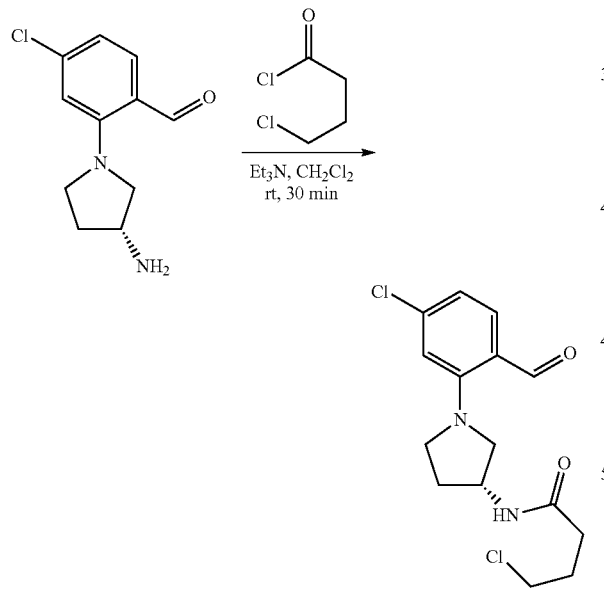

A vial was charged with 2-[(3R)-3-aminopyrrolidin-1-yl]-4-chlorobenzaldehyde (50.0 mg, 0.220 mmol, 1.00 equiv) [synthesized from Example 39, Steps 1-2], 4-chlorobutanoyl chloride (39.0 mg, 0.280 mmol, 1.24 equiv), DCM (5 mL), and triethylamine (45.0 mg, 0.446 mmol, 2.00 equiv). The resulting solution was stirred for 30 min at rt and then diluted with H$_2$O (10 mL). The mixture was extracted with DCM (3×10 mL) and the organic layers were combined, dried over anhydrous Na$_2$SO$_4$, filtered and concentrated. The residue was chromatographed on a silica gel column (70:30 EtOAc/petroleum ether) to provide 4-chloro-N-[(3R)-1-(5-chloro-2-formylphenyl)pyrrolidin-3-yl]butanamide (60.0 mg, 82% yield) as yellow oil. LCMS (ESI, m/z): 329 [M+H]$^+$.

Step 2: Preparation of tert-butyl 4-([4-chloro-2-[(3R)-3-(4-chlorobutanamido)pyrrolidin-1-yl]phenyl]methyl)piperazine-1-carboxylate

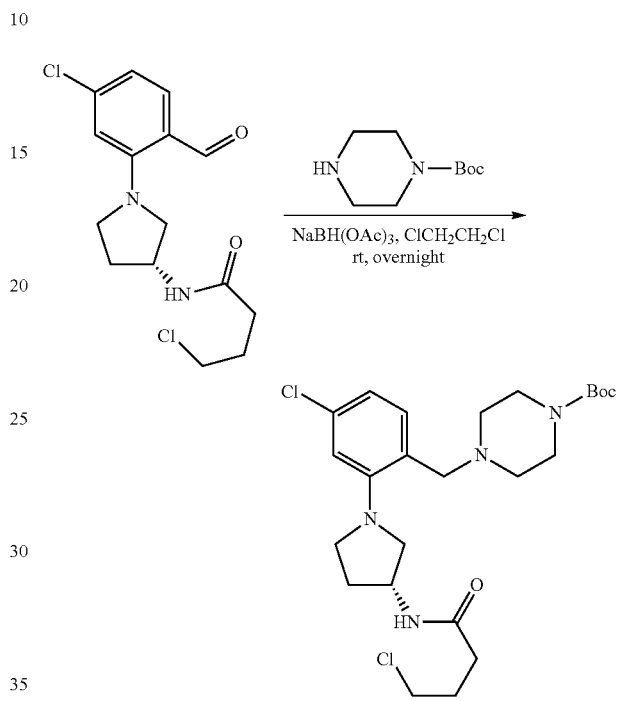

The title compound was synthesized from 4-chloro-N-[(3R)-1-(5-chloro-2-formylphenyl)pyrrolidin-3-yl]butanamide according to the representative procedure of Example 39, Step 4, to provide tert-butyl 4-([4-chloro-2-[(3R)-3-(4-chlorobutanamido)pyrrolidin-1-yl]phenyl]methyl)piperazine-1-carboxylate (90.0 mg, 56% yield) as yellow oil. LCMS (ESI, m/z): 499 [M+H]$^+$.

Step 3: Preparation of tert-butyl 4-([4-chloro-2-[(3R)-3-(2-oxopyrrolidin-1-yl)pyrrolidin-1-yl]phenyl]methyl)piperazine-1-carboxylate

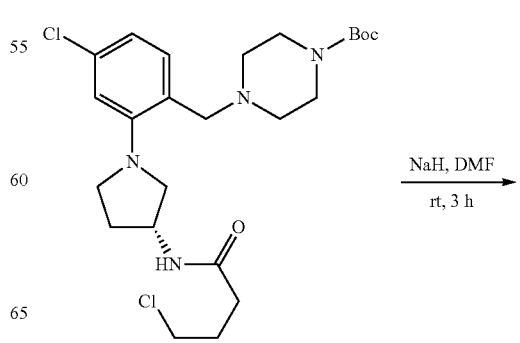

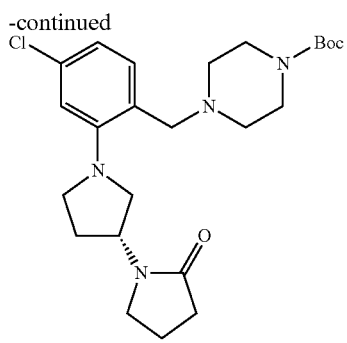

A vial was charged with tert-butyl 4-([4-chloro-2-[(3R)-3-(4-chlorobutanamido)pyrrolidin-1-yl]phenyl]methyl)piperazine-1-carboxylate (90.0 mg, 0.180 mmol, 1.00 equiv), NaH (5.30 mg, 0.220 mmol, 1.23 equiv), and DMF (2 mL). The resulting solution was stirred for 3 h at rt and diluted with H₂O (5 mL). The resulting solution was extracted with DCM (3×15 mL) and the organic layers were combined, dried over anhydrous Na₂SO₄, filtered and concentrated. The residue was chromatographed on a silica gel column (80:20 DCM/MeOH) to provide tert-butyl 4-([4-chloro-2-[(3R)-3-(2-oxopyrrolidin-1-yl)pyrrolidin-1-yl]phenyl]methyl)piperazine-1-carboxylate (80.0 mg, 96% yield) as yellow oil. LCMS (ESI, m/z): 463 [M+H]⁺.

Step 4: Preparation of 1-[(3R)-1-[5-chloro-2-(piperazin-1-ylmethyl)phenyl]pyrrolidin-3-yl]pyrrolidin-2-one

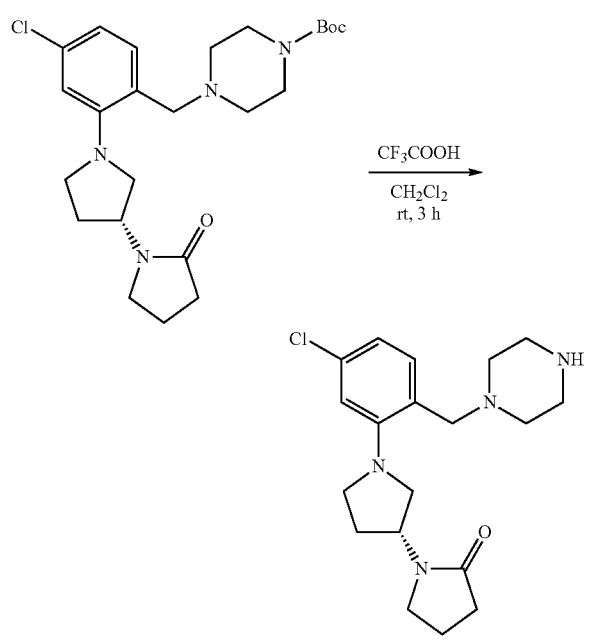

The title compound was synthesized from tert-butyl 4-([4-chloro-2-[(3R)-3-(2-oxopyrrolidin-1-yl)pyrrolidin-1-yl]phenyl]methyl)piperazine-1-carboxylate according to the representative procedure of Example 39, Step 5, to provide 1-[(3R)-1-[5-chloro-2-(piperazin-1-ylmethyl)phenyl]pyrrolidin-3-yl]pyrrolidin-2-one (70.0 mg) as yellow oil, which was carried on without further purification. LCMS (ESI, m/z): 363 [M+H]⁺.

Step 5: Preparation of 1,1,1,3,3,3-hexafluoropropan-2-yl (R)-4-(4-chloro-2-(2-oxo-[1,3'-bipyrrolidin]-1'-yl)benzyl)piperazine-1-carboxylate

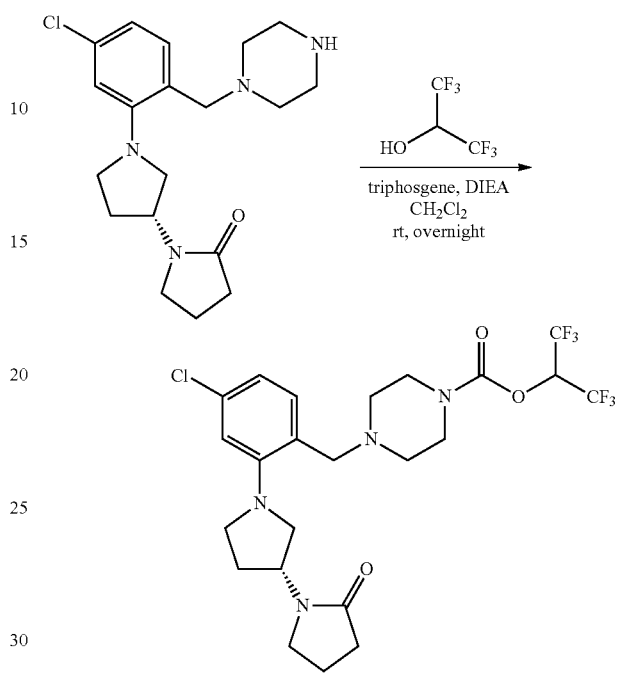

The title compound was synthesized from 1-[(3R)-1-[5-chloro-2-(piperazin-1-ylmethyl)phenyl]pyrrolidin-3-yl]pyrrolidin-2-one according to the representative procedure of Example 39, Step 6, to provide 1,1,1,3,3,3-hexafluoropropan-2-yl (R)-4-(4-chloro-2-(2-oxo-[1,3'-bipyrrolidin]-1'-yl)benzyl)piperazine-1-carboxylate as a white solid. ¹H NMR (300 MHz, Chloroform-d) δ 7.31 (d, J=7.8 Hz, 1H), 6.88-6.92 (m, 2H), 5.70-5.79 (m, 1H), 4.85-4.86 (m, 1H), 3.44-3.55 (m, 8H), 3.21-3.37 (m, 2H), 3.10-3.19 (m, 2H), 2.35-2.51 (m, 6H), 2.19-2.28 (m, 1H), 1.93-2.09 (m, 3H). LCMS (ESI, m/z): 557 [M+H]⁺.

Example 42: 1,1,1,3,3,3-hexafluoropropan-2-yl (S)-4-(4-chloro-2-(2-oxo-[1,3'-bipyrrolidin]-1'-yl)benzyl)piperazine-1-carboxylate

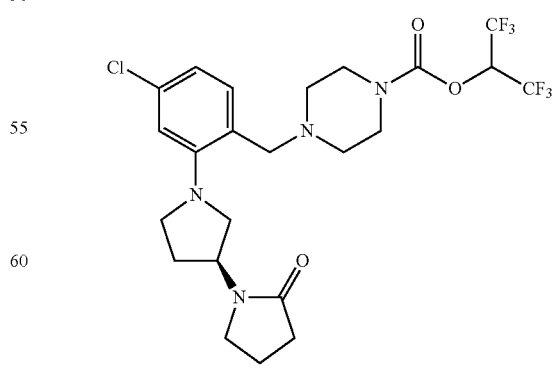

The title compound was synthesized directly from commercially available 2-[(3S)-3-aminopyrrolidin-1-yl]-4-chlorobenzaldehyde according to the representative procedure of Example 41 to provide 1,1,1,3,3,3-hexafluoropropan-2-yl (S)-4-(4-chloro-2-(2-oxo-[1,3'-bipyrrolidin]-1'-yl)benzyl)piperazine-1-carboxylate as yellow oil. $^1$H NMR (300 MHz, Chloroform-d) δ 7.27-7.29 (m, 1H), 6.87-6.92 (m, 2H), 5.71-5.79 (m, 1H), 4.85-4.89 (m, 1H), 3.49-3.54 (m, 8H), 3.35-3.47 (m, 2H), 3.11-3.32 (m, 2H), 2.27-2.44 (m, 6H), 2.19-2.26 (m, 1H), 1.95-2.09 (m, 3H). LCMS (ESI, m/z): 579 [M+H]$^+$.

Example 43: 1,1,1,3,3,3-hexafluoropropan-2-yl (R)-4-(4-chloro-2-(3-(2-oxopiperidin-1-yl)pyrrolidin-1-yl)benzyl)piperazine-1-carboxylate

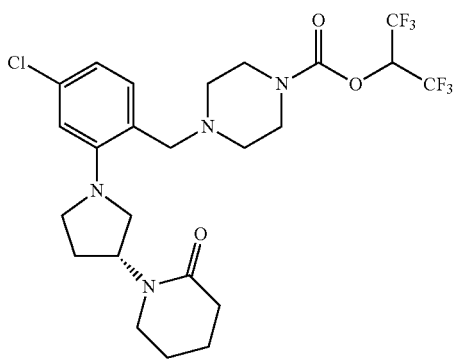 [SMILES: O=C(OC(C(F)(F)F)C(F)(F)F)N1CCN(Cc2ccc(Cl)cc2N2CC[C@@H](N3CCCCC3=O)C2)CC1]

The title compound was synthesized directly from commercially available 5-bromopentanoyl chloride according to the representative procedure of Example 41, Steps 1-5, to provide 1,1,1,3,3,3-hexafluoropropan-2-yl (R)-4-(4-chloro-2-(3-(2-oxopiperidin-1-yl)pyrrolidin-1-yl)benzyl)piperazine-1-carboxylate as yellow oil. $^1$H NMR (300 MHz, Chloroform-d) δ 7.26-7.29 (m, 1H), 6.88-6.92 (m, 2H), 5.71-5.79 (m, 1H), 5.36-5.41 (m, 1H), 3.44-3.54 (m, 6H), 3.19-3.37 (m, 4H), 3.09-3.18 (m, 2H), 2.42-2.44 (m, 6H), 2.17-2.28 (m, 1H), 1.98-2.05 (m, 1H), 1.80-1.95 (m, 4H). LCMS (ESI, m/z): 593 [M+H]$^+$.

Example 44: 1,1,1,3,3,3-hexafluoropropan-2-yl (S)-4-(4-chloro-2-(3-(2-oxopiperidin-1-yl)pyrrolidin-1-yl)benzyl)piperazine-1-carboxylate

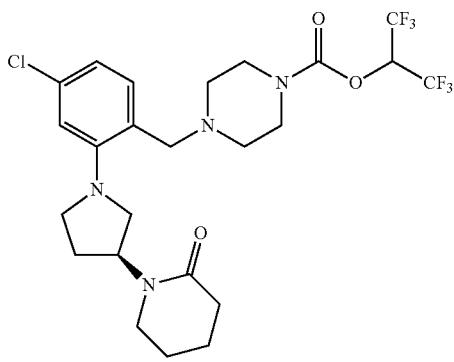 [SMILES: O=C(OC(C(F)(F)F)C(F)(F)F)N1CCN(Cc2ccc(Cl)cc2N2CC[C@H](N3CCCCC3=O)C2)CC1]

The title compound was synthesized according to the representative procedure of Example 43 to provide 1,1,1,3,3-hexafluoropropan-2-yl (S)-4-(4-chloro-2-(3-(2-oxopiperidin-1-yl)pyrrolidin-1-yl)benzyl)piperazine-1-carboxylate as yellow oil. $^1$H NMR (300 MHz, Chloroform-d) δ 7.26-7.29 (m, 1H), 6.89-6.92 (m, 2H), 5.71-5.81 (m, 1H), 5.37-5.41 (m, 1H), 3.44-3.54 (m, 6H), 3.21-3.37 (m, 4H), 3.09-3.19 (m, 2H), 2.44 (br, 6H), 2.20-2.28 (m, 1H), 1.93-2.18 (m, 1H), 1.75-1.88 (m, 4H). LCMS (ESI, m/z): 593 [M+H]$^+$.

Example 45: 1,1,1,3,3,3-hexafluoropropan-2-yl (R)-4-(4-chloro-2-(3-(1,1-dioxidoisothiazolidin-2-yl)pyrrolidin-1-yl)benzyl)piperazine-1-carboxylate

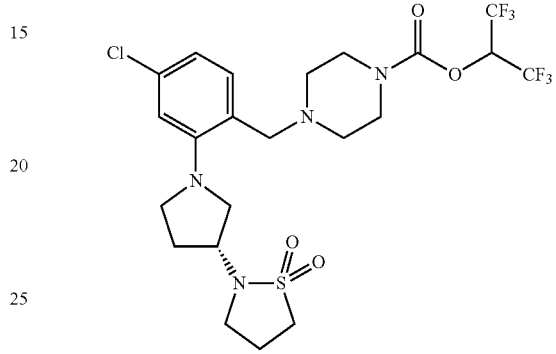

The title compound was synthesized directly from commercially available 3-chloropropane-1-sulfonyl chloride according to the representative procedure of Example 41, Steps 1-5, to provide 1,1,1,3,3,3-hexafluoropropan-2-yl (R)-4-(4-chloro-2-(3-(1,1-dioxidoisothiazolidin-2-yl)pyrrolidin-1-yl)benzyl)piperazine-1-carboxylate as yellow oil. $^1$H NMR (300 MHz, Chloroform-d) δ 7.21-7.25 (m, 1H), 6.84-6.88 (m 2H), 5.70-5.79 (m, 1H), 4.02-4.11 (m, 1H), 3.42-3.64 (m, 8H), 3.24-3.40 (m, 3H), 3.17-3.22 (m, 3H), 2.26-2.45 (m, 7H), 2.08-2.18 (m, 1H). LCMS (ESI, m/z): 593 [M+H]$^+$.

Example 46: 1,1,1,3,3,3-hexafluoropropan-2-yl (S)-4-(4-chloro-2-(3-(1,1-dioxidoisothiazolidin-2-yl)pyrrolidin-1-yl)benzyl)piperazine-1-carboxylate

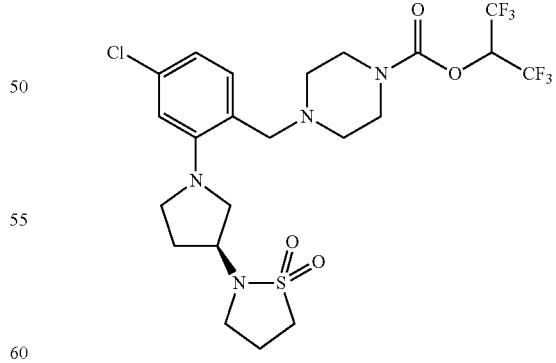

The title compound was synthesizes according to the representative procedure of Example 45 to provide 1,1,1,3,3,3-hexafluoropropan-2-yl (S)-4-(4-chloro-2-(3-(1,1-dioxidoisothiazolidin-2-yl)pyrrolidin-1-yl)benzyl)piperazine-1-carboxylate as yellow oil. $^1$H NMR (300 MHz, Chloroform-d) δ 7.22-7.26 (m, 1H), 6.84-6.91 (m, 2H), 5.70-5.78 (m, 1H), 4.02-4.09 (m, 1H), 3.41-3.64 (m, 8H), 3.22-3.39 (m, 3H), 3.12-3.19 (m, 3H), 2.26-2.44 (m, 7H), 2.06-2.18 (m, 1H). LCMS (ESI, m/z): 593 [M+H]⁺.

Example 47: 1,1,1,3,3,3-hexafluoropropan-2-yl (R)-4-(2-(3-(methylsulfonamido)pyrrolidin-1-yl)-6-(trifluoromethyl)benzyl)piperazine-1-carboxylate

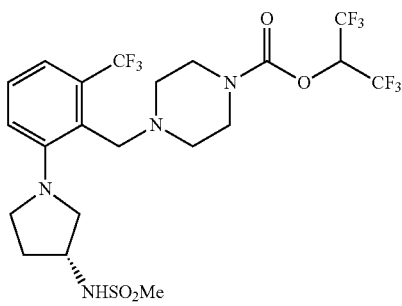

The title compound was synthesized directly from commercially available 2-fluoro-6-(trifluoromethyl)benzaldehyde according to the representative procedure of Example 39 to provide 1,1,1,3,3,3-hexafluoropropan-2-yl (R)-4-(2-(3-(methylsulfonamido)pyrrolidin-1-yl)-6-(trifluoromethyl)benzyl)piperazine-1-carboxylate as a white solid. ¹H NMR (300 MHz, Chloroform-d) δ 7.31-7.41 (m, 2H), 7.22-7.25 (m, 1H), 5.70-5.78 (m, 1H), 4.94-4.96 (m, 1H), 4.15 (br, 1H), 3.71-3.82 (m, 2H), 3.40-3.42 (m, 4H), 3.32-3.38 (m, 2H), 3.13-3.17 (m, 1H), 3.00-3.10 (m, 4H), 2.37-2.46 (m, 5H), 1.98-2.05 (m, 1H). LCMS (ESI, m/z): 601 [M+H]⁺.

Example 48: 1,1,1,3,3,3-hexafluoropropan-2-yl (S)-4-(2-(3-(methylsulfonamido)pyrrolidin-1-yl)-6-(trifluoromethyl)benzyl)piperazine-1-carboxylate

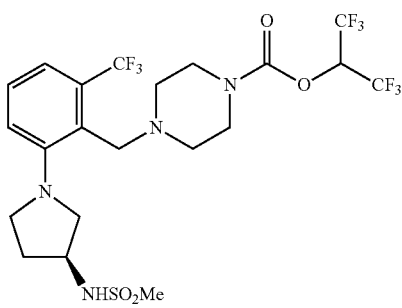

The title compound was synthesized directly from commercially available N-[(3S)-pyrrolidin-3-yl]carbamate according to the representative procedure of Example 47 to provide 1,1,1,3,3,3-hexafluoropropan-2-yl (S)-4-(2-(3-(methylsulfonamido)pyrrolidin-1-yl)-6-(trifluoromethyl)benzyl)piperazine-1-carboxylate as yellow oil. ¹H NMR (300 MHz, Chloroform-d) δ 7.30-7.40 (m, 2H), 7.21-7.24 (m, 1H), 5.69-5.77 (m, 1H), 4.90-4.92 (m, 1H), 4.13-4.14 (m, 1H), 3.70-3.81 (m, 2H), 3.49-3.50 (m, 4H), 3.31-3.40 (m, 2H), 3.01-3.16 (m, 5H), 2.36-2.45 (m, 5H), 2.00 (br, 1H). LCMS (ESI, m/z): 601 [M+H]⁺.

Example 49: 1,1,1,3,3,3-hexafluoropropan-2-yl 4-(2-(3-oxa-8-azabicyclo[3.2.1]octan-8-yl)-6-(trifluoromethyl)benzyl)piperazine-1-carboxylate

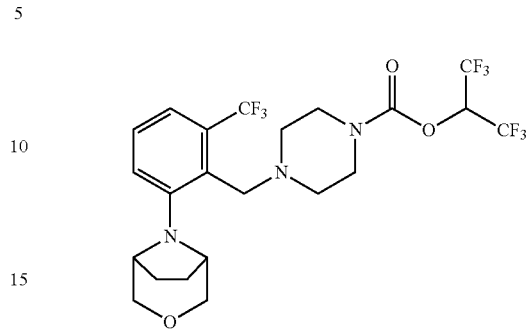

The title compound was synthesized directly from commercially available 2-fluoro-6-trifluoromethylbenzaldehyde and 3-oxa-8-azabicyclo[3.2.1]octane according to the representative procedure of Example 37 to provide 1,1,1,3,3,3-hexafluoropropan-2-yl 4-(2-(3-oxa-8-azabicyclo[3.2.1]octan-8-yl)-6-(trifluoromethyl)benzyl)piperazine-1-carboxylate as yellow oil. ¹H NMR (300 MHz, Chloroform-d) δ 7.35 (d, J=7.2 Hz, 1H), 7.24-7.29 (m, 1H), 7.05 (d, J=7.8 Hz, 1H), 5.69-5.82 (m, 1H), 3.96 (d, J=10.2 Hz, 2H), 3.87 (s, 2H), 3.67 (d, J=10.2 Hz, 2H), 3.45-3.51 (m, 6H), 2.42-2.46 (m, 4H), 1.93-2.09 (m, 4H). LCMS (ESI, m/z): 550 [M+H]⁺.

Example 50: 1,1,1,3,3,3-hexafluoropropan-2-yl 4-(2-(8-oxa-3-azabicyclo[3.2.1]octan-3-yl)-6-(trifluoromethyl)benzyl)piperazine-1-carboxylate

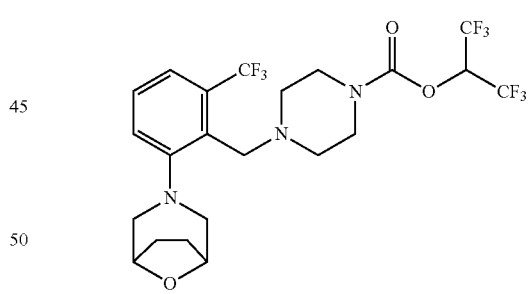

The title compound was synthesized directly from commercially available 2-fluoro-6-(trifluoromethyl)benzaldehyde and 8-oxa-3-azabicyclo[3.2.1]octane according to the representative procedure of Example 37 to provide 1,1,1,3,3,3-hexafluoropropan-2-yl 4-(2-(8-oxa-3-azabicyclo[3.2.1]octan-3-yl)-6-(trifluoromethyl)benzyl)piperazine-1-carboxylate as a white solid. ¹H NMR (300 MHz, Chloroform-d) δ 7.35-7.51 (m, 3H), 5.68-5.81 (m, 1H), 4.41 (s, 2H), 3.86 (s, 2H), 3.47-3.48 (m, 4H), 3.09-3.13 (m, 2H), 2.65 (d, J=11.1 Hz, 2H), 2.39-2.40 (m, 4H), 1.96-2.18 (m, 4H). LCMS (ESI, m/z): 550 [M+H]⁺.

Example 51: 1,1,1,3,3,3-hexafluoropropan-2-yl 4-(3-methyl-2-(4-(methylsulfonamido)piperidin-1-yl)benzyl)piperazine-1-carboxylate

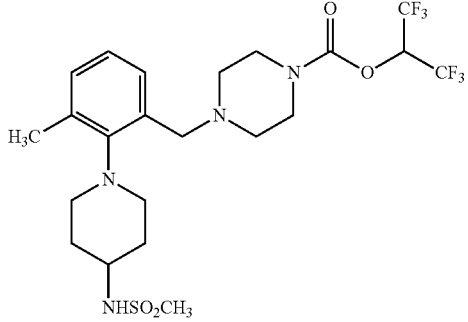

Step 1: Preparation of (2-bromo-3-methylphenyl)methanol

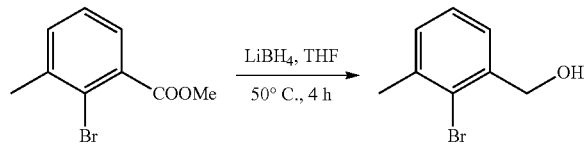

A flask was charged with methyl 2-bromo-3-methylbenzoate (10.0 g, 43.6 mmol, 1.00 equiv), lithium borohydride (4.80 g, 231 mmol, 5.00 equiv), and THF (100 mL). The resulting solution was stirred for 4 h at 50° C. and then diluted with H₂O (30 mL). The resulting mixture was extracted with EtOAc (3×50 mL) and the organic layers were combined, washed with brine (1×200 mL), dried over anhydrous Na₂SO₄, filtered and concentrated. The residue was chromatographed on a silica gel column (30:70 EtOAc/petroleum ether) to provide (2-bromo-3-methylphenyl)methanol (7.50 g, 85% yield) as a white solid. GCMS (EI, m/z): 200 [M]⁺.

Step 2: Preparation of 2-bromo-3-methylbenzaldehyde

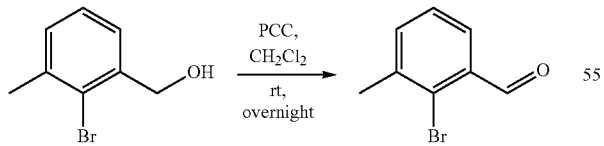

A flask was charged with (2-bromo-3-methylphenyl)methanol (5.00 g, 24.9 mmol, 1.00 equiv), pyridinium chlorochromate (16.2 g, 75.0 mmol, 3.00 equiv), and DCM (70 mL). The resulting solution was stirred overnight at rt and concentrated. The residue was chromatographed on a silica gel column (20:80 EtOAc/petroleum ether) to provide 2-bromo-3-methylbenzaldehyde (4.40 g, 89% yield) as a white solid. GCMS (EI, m/z): 198 [M]⁺.

Step 3: Preparation of tert-butyl 4-[(2-bromo-3-methylphenyl)methyl]piperazine-1-carboxylate

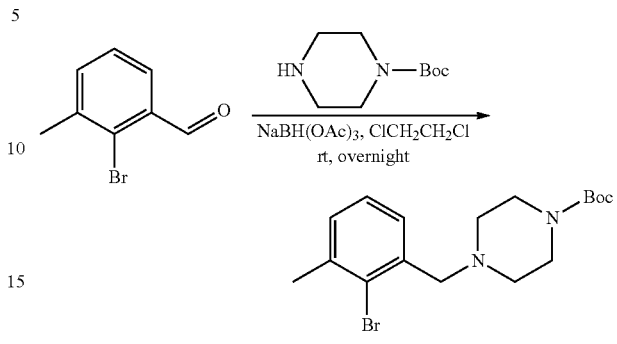

A flask was charged with 2-bromo-3-methylbenzaldehyde (3.00 g, 15.1 mmol, 1.00 equiv), tert-butyl piperazine-1-carboxylate (3.40 g, 18.2 mmol, 1.20 equiv), and 1,2-dichloroethane (50 mL). The mixture was stirred for 30 min at rt. NaBH(OAc)₃ (9.60 g, 45.3 mmol, 3.00 equiv) was added. The resulting solution was stirred overnight at rt and then diluted with H₂O (20 mL). The resulting mixture was extracted with DCM (3×20 mL) and the organic layers were combined, washed with brine (1×100 mL), dried over anhydrous Na₂SO₄, filtered and concentrated. The residue was chromatographed on a silica gel column (20:80 EtOAc/petroleum ether) to provide tert-butyl 4-[(2-bromo-3-methylphenyl)methyl]piperazine-1-carboxylate (4.80 g, 86% yield) as colorless oil. LCMS (ESI, m/z): 369 [M+H]⁺.

Step 4: Preparation of tert-butyl 4-[[2-(4-methanesulfonamidopiperidin-1-yl)-3-methylphenyl]methyl]piperazine-1-carboxylate

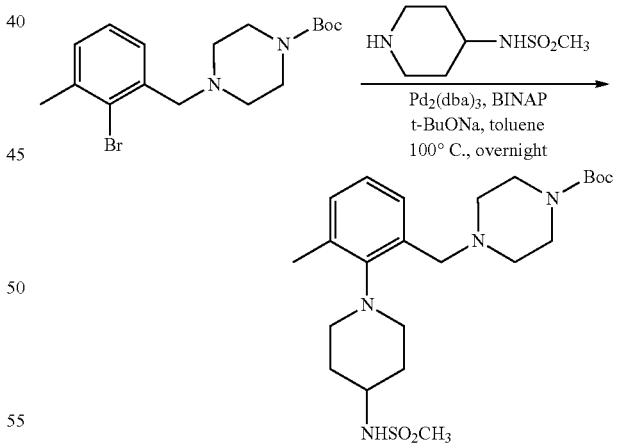

A flask was charged with tert-butyl 4-[(2-bromo-3-methylphenyl)methyl]piperazine-1-carboxylate (500 mg, 1.35 mmol, 1.00 equiv), N-(piperidin-4-yl)methanesulfonamide (363 mg, 2.04 mmol, 1.50 equiv), tris(dibenzylideneacetone)dipalladium (62.0 mg, 0.0700 mmol, 0.05 equiv), 2-(diphenylphosphino)-1-(2-(diphenylphosphino)naphthalen-1-yl)naphthalene (127 mg, 0.200 mmol, 0.15 equiv), sodium tert-butoxide (196 mg, 2.04 mmol, 1.50 equiv), and toluene (20 mL) under nitrogen. The resulting solution was stirred overnight at 100° C. and concentrated. The residue was chromatographed on a silica gel column (30:70 EtOAc/petroleum ether) to provide tert-butyl 4-[[2-(4-methanesulfonamidopiperidin-1-yl)-3-methylphenyl]methyl]piperazine-1-carboxylate (210 mg, 33% yield) as yellow oil. LCMS (ESI, m/z): 467 [M+H]+.

Step 5: Preparation of N-[1-[2-methyl-6-(piperazin-1-ylmethyl)phenyl]piperidin-4-yl]methanesulfonamide

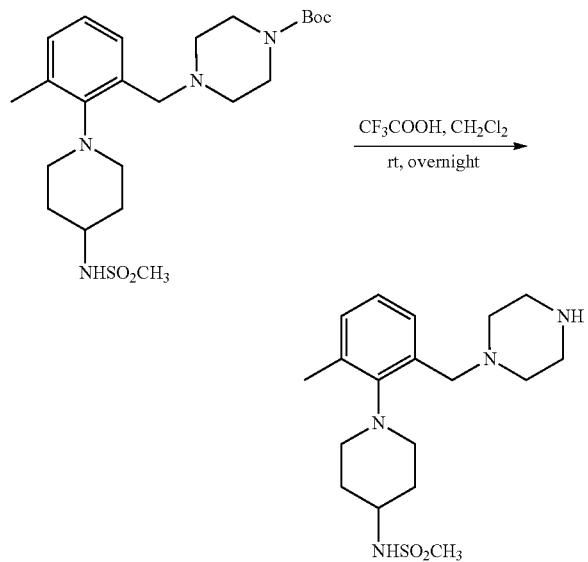

A flask was charged with tert-butyl 4-[[2-(4-methanesulfonamidopiperidin-1-yl)-3-methylphenyl]methyl]piperazine-1-carboxylate (210 mg, 0.450 mmol, 1.00 equiv), TFA (2 mL), and DCM (10 mL). The resulting solution was stirred overnight at rt and concentrated to yield N-[1-[2-methyl-6-(piperazin-1-ylmethyl)phenyl]piperidin-4-yl]methanesulfonamide (150 mg, 91% yield) as yellow oil, which was carried on without further purification. LCMS (ESI, m/z): 367 [M+H]+.

Step 6: Preparation of 1,1,1,3,3,3-hexafluoropropan-2-yl 4-(3-methyl-2-(4-(methylsulfonamido)piperidin-1-yl)benzyl)piperazine-1-carboxylate

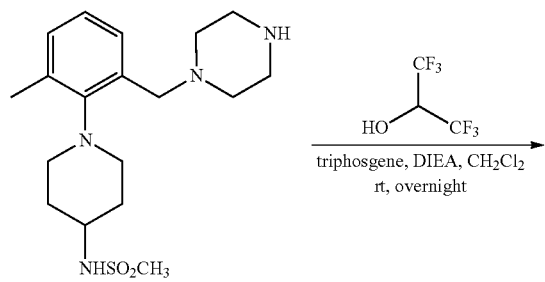

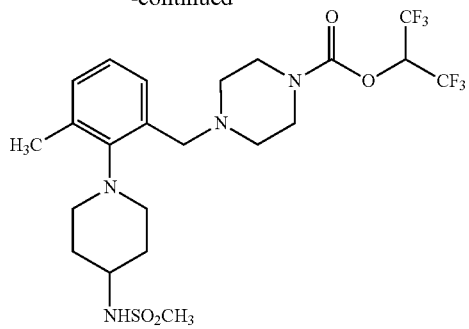

A flask was charged with triphosgene (91.0 mg, 0.310 mmol, 0.70 equiv) and DCM (15 mL). 1,1,1,3,3,3-hexafluoropropan-2-ol (147 mg, 0.870 mmol, 2.00 equiv) and DIEA (451 mg, 3.49 mmol, 8.00 equiv) were added at 0° C. The mixture was stirred for 2 h at rt. N-[1-[2-methyl-6-(piperazin-1-ylmethyl)phenyl]piperidin-4-yl]methanesulfonamide (160 mg, 0.440 mmol, 1.00 equiv) was added. The resulting solution was stirred overnight at rt and concentrated. The crude product (700 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: aqueous NH$_4$HCO$_3$ (0.05%); Phase B: CH$_3$CN; Detector, UV220 & 254 nm. Purification resulted in 1,1,1,3,3,3-hexafluoropropan-2-yl 4-(3-methyl-2-(4-(methylsulfonamido)piperidin-1-yl)benzyl)piperazine-1-carboxylate (105.8 mg, 43% yield) as a yellow solid. $^1$H NMR (300 MHz, Chloroform-d) δ 6.97-7.18 (m, 3H), 5.71-5.79 (m, 1H), 4.31-4.36 (m, 1H), 3.42-3.54 (m, 7H), 3.13-3.39 (m, 2H), 2.99-3.07 (m, 5H), 2.44-2.47 (m, 4H), 2.31-2.33 (m, 3H), 2.03-2.06 (m, 2H), 1.62-1.74 (m, 2H). LCMS (ESI, m/z): 561 [M+H]+.

Example 52: 1,1,1,3,3,3-hexafluoropropan-2-yl 4-(2-methyl-3-(4-(methylsulfonamido)piperidin-1-yl)benzyl)piperazine-1-carboxylate

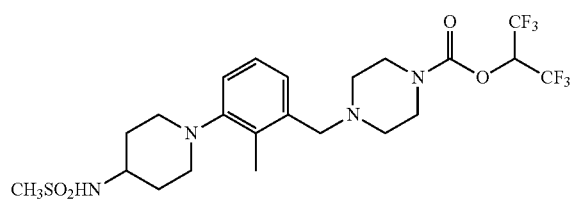

Step 1: Preparation of tert-butyl 4-[(3-bromo-2-methylphenyl)methyl]piperazine-1-carboxylate

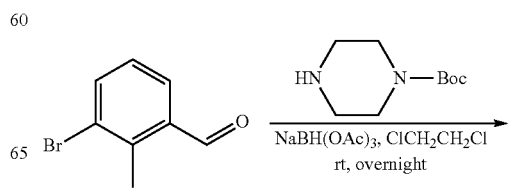

-continued

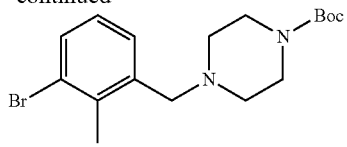

The title compound was synthesized directly from commercially available 3-bromo-2-methylbenzaldehyde according to the representative procedure of Example 51, Step 3, to provide tert-butyl 4-[(3-bromo-2-methylphenyl)methyl]piperazine-1-carboxylate (5.10 g, 92% yield) as colorless oil. LCMS (ESI, m/z): 369 [M+H]⁺.

Step 2: Preparation of tert-butyl 4-[[3-(4-methanesulfonamidopiperidin-1-yl)-2-methylphenyl]methyl]piperazine-1-carboxylate

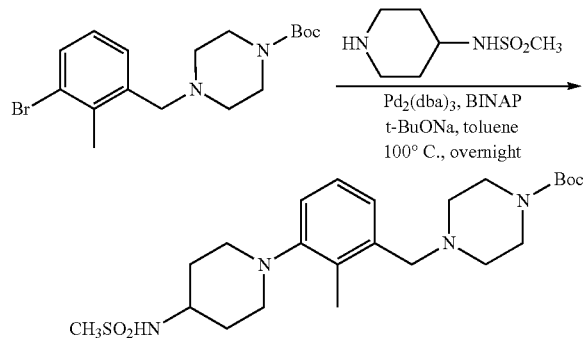

The title compound was synthesized according to the representative procedure of Example 51, Step 4, to provide tert-butyl 4-[[3-(4-methanesulfonamidopiperidin-1-yl)-2-methylphenyl]methyl]piperazine-1-carboxylate as yellow oil. LCMS (ESI, m/z): 467 [M+H]⁺.

Step 3: Preparation of N-[1-[2-methyl-3-(piperazin-1-ylmethyl)phenyl]piperidin-4-yl]methanesulfonamide

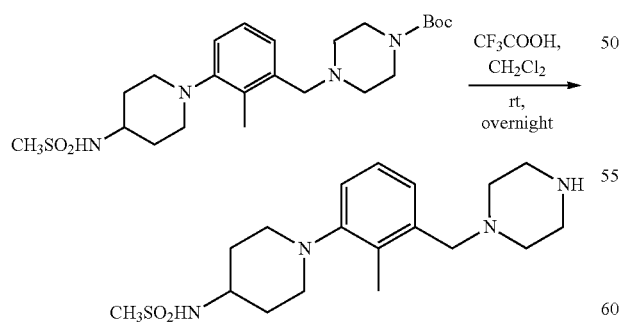

The title compound was synthesized according to the representative procedure of Example 51, Step 5, to provide N-[1-[2-methyl-3-(piperazin-1-ylmethyl)phenyl]piperidin-4-yl]methanesulfonamide as yellow oil. LCMS (ESI, m/z): 367 [M+H]⁺.

Step 4: Preparation of 1,1,1,3,3,3-hexafluoropropan-2-yl 4-(2-methyl-3-(4-(methylsulfonamido)piperidin-1-yl)benzyl)piperazine-1-carboxylate

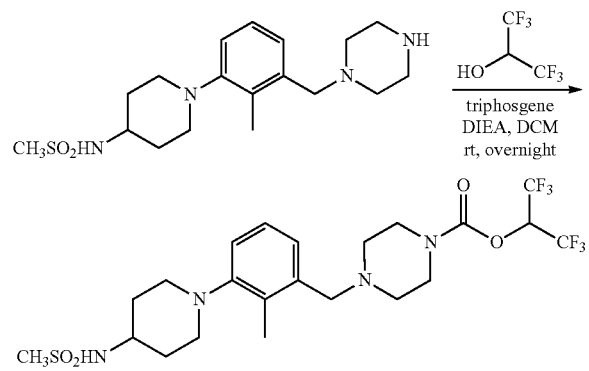

The title compound was synthesized according to the representative procedure of Example 51, Step 6, to provide 1,1,1,3,3,3-hexafluoropropan-2-yl 4-(2-methyl-3-(4-(methylsulfonamido)piperidin-1-yl)benzyl)piperazine-1-carboxylate as a white solid. ¹H NMR (300 MHz, Chloroform-d) δ 7.09-7.14 (m, 1H), 6.96-7.00 (m, 2H), 5.71-5.79 (m, 1H), 4.27-4.30 (m, 1H), 3.47-3.52 (m, 7H), 3.03-3.09 (m, 5H), 2.70-2.78 (m, 2H), 2.45 (br, 4H), 2.30 (s, 3H), 2.10-2.14 (m, 2H), 1.67-1.80 (m, 2H). LCMS (ESI, m/z): 561 [M+H]⁺.

Example 53: 1,1,1,3,3,3-hexafluoropropan-2-yl (S)-4-(2-(3-(fluoromethyl)pyrrolidin-1-yl)-4-methylbenzyl)piperazine-1-carboxylate

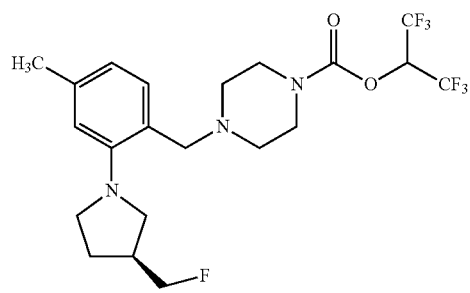 [SMILES: Cc1ccc(CN2CCN(C(=O)OC(C(F)(F)F)C(F)(F)F)CC2)c(N2CC[C@H](CF)C2)c1]

Step 1: Preparation of 2-[(3S)-3-(hydroxymethyl)pyrrolidin-1-yl]-4-methylbenzaldehyde

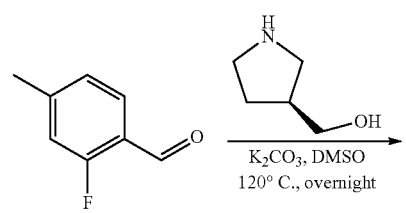

-continued

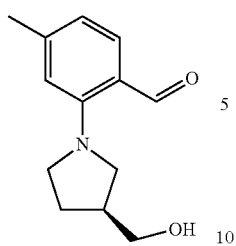

A flask was charged with 2-fluoro-4-methylbenzaldehyde (1.00 g, 7.24 mmol, 1.00 equiv), (3S)-pyrrolidin-3-ylmethanol (1.10 g, 10.9 mmol, 1.50 equiv), $K_2CO_3$ (2.00 g, 14.5 mmol, 2.00 equiv), and DMSO (10 mL). The resulting solution was stirred overnight at 120° C. and then diluted with $H_2O$ (10 mL). The resulting mixture was extracted with EtOAc (3×10 mL). The organic layers were combined, washed with brine (1×50 mL), dried over anhydrous $Na_2SO_4$, filtered and concentrated. The residue was chromatographed on a silica gel column (50:50 EtOAc/petroleum ether) to provide 2-[(3S)-3-(hydroxymethyl)pyrrolidin-1-yl]-4-methylbenzaldehyde (1.20 g, 76% yield) as yellow oil. LCMS (ESI, m/z): 220 [M+H]+.

Step 2: Preparation of tert-butyl 4-([2-[(3S)-3-(hydroxymethyl)pyrrolidin-1-yl]-4-methylphenyl]methyl)piperazine-1-carboxylate

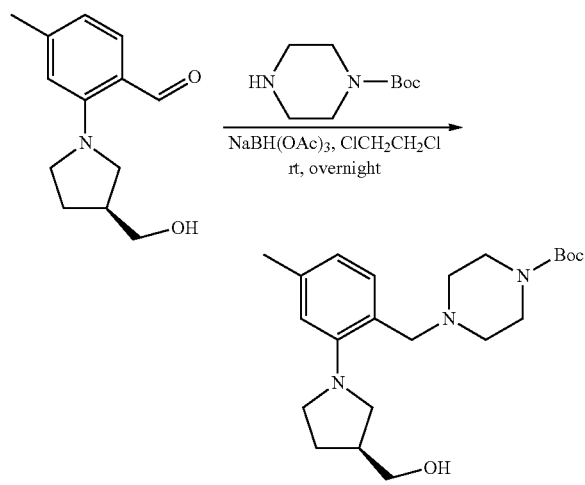

A flask was charged with 2-[(3S)-3-(hydroxymethyl)pyrrolidin-1-yl]-4-methylbenzaldehyde (0.700 g, 3.19 mmol, 1.00 equiv), tert-butyl piperazine-1-carboxylate (0.713 g, 3.83 mmol, 1.20 equiv), and 1,2-dichloroethane (10 mL). The mixture was stirred for 1 h at rt. $NaBH(OAc)_3$ (2.00 g, 9.44 mmol, 3.00 equiv) was added. The resulting solution was stirred overnight at rt and then diluted with $H_2O$ (10 mL). The resulting mixture was extracted with DCM (3×10 mL). The organic layers were combined, washed with brine (1×50 mL), dried over anhydrous $Na_2SO_4$, filtered and concentrated. The residue was chromatographed on a silica gel column (30:70 EtOAc/petroleum ether) to provide tert-butyl 4-([2-[(3S)-3-(hydroxymethyl)pyrrolidin-1-yl]-4-methylphenyl]methyl)piperazine-1-carboxylate (1.10 g, 88% yield) as yellow oil. LCMS (ESI, m/z): 390 [M+H]+.

Step 3: Preparation of tert-butyl 4-([4-methyl-2-[(3S)-3-([[(4-methylbenzene)sulfonyl]oxy]methyl)pyrrolidin-1-yl]phenyl]methyl)piperazine-1-carboxylate A flask was charged with tert-butyl 4-([2-[(3S)-3-(hydroxymethyl)pyrrolidin-1-yl]-4-methylphenyl]methyl)piperazine-1-carboxylate (1.10 g, 2.82 mmol, 1.00 equiv), 4-methylbenzene-1-sulfonyl chloride (0.808 g, 4.24 mmol, 1.50 equiv), pyridine (0.446 g, 5.64 mmol, 2.00 equiv), 4-dimethylaminopyridine (0.0340 g, 0.280 mmol, 0.10 equiv), and DCM (15 mL). The resulting solution was stirred overnight at 40° C. and then diluted with $H_2O$ (10 mL). The resulting mixture was extracted with DCM (3×10 mL). The organic layers were combined and washed with brine (1×50 mL), dried over anhydrous $Na_2SO_4$, filtered and concentrated. The residue was chromatographed on a silica gel column (90:10 DCM/MeOH) to provide tert-butyl 4-([4-methyl-2-[(3 S)-3-([[(4-methylbenzene)sulfonyl]oxy]methyl)pyrrolidin-1-yl]phenyl]methyl)piperazine-1-carboxylate (1.00 g, 65% yield) as yellow oil. LCMS (ESI, m/z): 544 [M+H]+.

Step 4: Preparation of tert-butyl 4-([2-[(3S)-3-(fluoromethyl)pyrrolidin-1-yl]-4-methylphenyl]methyl)piperazine-1-carboxylate

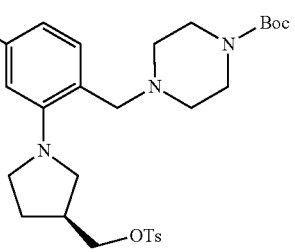

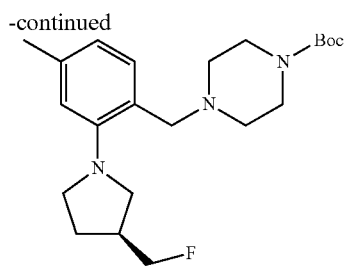

A flask was charged with tert-butyl 4-([4-methyl-2-[(3S)-3-([[(4-methylbenzene)sulfonyl]oxy]methyl)pyrrolidin-1-yl]phenyl]methyl)piperazine-1-carboxylate (1.00 g, 1.84 mmol, 1.00 equiv), tetrabutylammonium fluoride (1.90 g, 7.27 mmol, 4.00 equiv), and THF (10 mL). The resulting solution was stirred overnight at 60° C. and concentrated. The residue was chromatographed on a silica gel column (15:85 EtOAc/petroleum ether) to provide tert-butyl 4-([2-[(3 S)-3-(fluoro methyl)pyrrolidin-1-yl]-4-methylphenyl]methyl)piperazine-1-carboxylate (0.290 g, 40% yield) as colorless oil. LCMS (ESI, m/z): 392 [M+H]$^+$.

Step 5: Preparation of 1-([2-[(3S)-3-(fluoromethyl)pyrrolidin-1-yl]-4-methylphenyl]methyl)piperazine

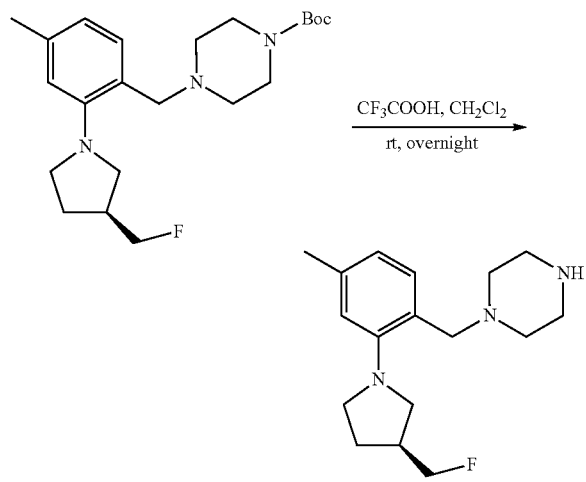

The title compound was synthesized according to the representative procedure of Example 37, Step 3, to provide 1-([2-[(3S)-3-(fluoromethyl)pyrrolidin-1-yl]-4-methylphenyl]methyl)piperazine as yellow oil. LCMS (ESI, m/z): 292 [M+H]$^+$.

Step 6: Preparation of 1,1,1,3,3,3-hexafluoropropan-2-yl (S)-4-(2-(3-(fluoromethyl)pyrrolidin-1-yl)-4-methylbenzyl)piperazine-1-carboxylate

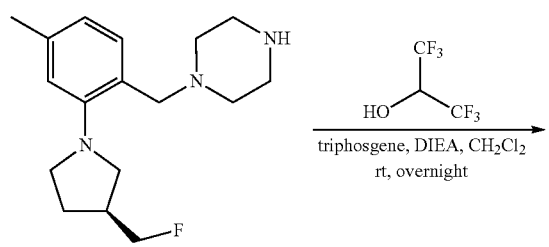

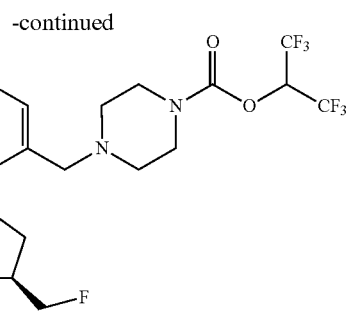

The title compound was synthesized according to the representative procedure of Example 37, Step 4, to provide 1,1,1,3,3,3-hexafluoropropan-2-yl (S)-4-(2-(3-(fluoromethyl)pyrrolidin-1-yl)-4-methylbenzyl)piperazine-1-carboxylate as yellow oil. $^1$H NMR (300 MHz, Chloroform-d) δ 7.22-7.25 (m, 1H), 6.76-6.80 (m, 2H), 5.71-5.79 (m, 1H), 4.50 (d, J=7.2 Hz, 1H), 4.34 (d, J=6.9 Hz, 1H), 3.44-3.59 (m, 6H), 3.10-3.26 (m, 4H), 2.59-2.72 (m, 1H), 2.47 (br, 4H), 2.32 (s, 3H), 2.01-2.12 (m, 1H), 1.57-1.70 (m, 1H). LCMS (ESI, m/z): 486 [M+H]$^+$.

Example 54: 1,1,1,3,3,3-hexafluoropropan-2-yl (S)-4-(2-(3-(fluoromethyl)pyrrolidin-1-yl)-4-(trifluoromethyl)benzyl)piperazine-1-carboxylate The title compound was synthesized directly from commercially available 2-fluoro-4-(trifluoromethyl)benzaldehyde according to the representative procedure of Example 53 to provide 1,1,1,3,3,3-hexafluoropropan-2-yl (S)-4-(2-(3-(fluoromethyl)pyrrolidin-1-yl)-4-(trifluoromethyl)benzyl)piperazine-1-carboxylate as colorless oil. $^1$H NMR (300 MHz, Chloroform-d) δ 7.51-7.55 (m, 1H), 7.14-7.18 (m, 2H), 5.71-5.80 (m, 1H), 4.50-4.54 (m, 1H), 4.31-4.47 (m, 1H), 3.50-3.63 (m, 6H), 3.18-3.29 (m, 4H), 2.65-2.74 (m, 1H), 2.44-2.47 (m, 4H), 2.06-2.16 (m, 1H), 1.65-1.76 (m, 1H). LCMS (ESI, m/z): 540 [M+H]$^+$.

Example 55: 1,1,1,3,3,3-hexafluoropropan-2-yl (S)-4-(3-chloro-2-(3-(fluoromethyl)pyrrolidin-1-yl)benzyl)piperazine-1-carboxylate

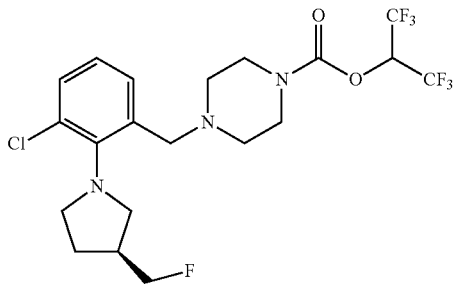 [SMILES: O=C(OC(C(F)(F)F)C(F)(F)F)N1CCN(Cc2cccc(Cl)c2N2CC[C@H](CF)C2)CC1]

The title compound was synthesized directly from commercially available 3-chloro-2-fluorobenzaldehyde according to the representative procedure of Example 53 to provide 1,1,1,3,3,3-hexafluoropropan-2-yl (S)-4-(3-chloro-2-(3-(fluoromethyl)pyrrolidin-1-yl)benzyl)piperazine-1-carboxylate as orange oil. $^1$H NMR (300 MHz, Chloroform-d) δ 7.28-7.30 (m, 2H), 7.07-7.12 (m, 1H), 5.71-5.80 (m, 1H), 4.54-4.57 (m, 1H), 4.38-4.41 (m, 1H), 3.52-3.63 (m, 6H), 3.26-3.46 (m, 3H), 3.08-3.12 (m, 1H), 2.74-2.79 (m, 1H), 2.44-2.46 (m, 4H), 2.10-2.16 (m, 1H), 1.76-1.83 (m, 1H). LCMS (ESI, m/z): 506 [M+H]$^+$.

Example 56: 1,1,1,3,3,3-hexafluoropropan-2-yl (S)-4-(2-(3-(fluoromethyl)pyrrolidin-1-yl)-3-methylbenzyl)piperazine-1-carboxylate

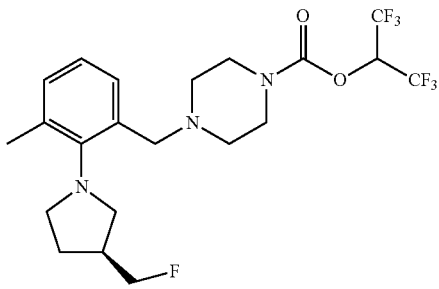 [SMILES: Cc1cccc(CN2CCN(C(=O)OC(C(F)(F)F)C(F)(F)F)CC2)c1N1CC[C@H](CF)C1]

Step 1: Preparation of tert-butyl 4-([2-[(3S)-3-(hydroxymethyl)pyrrolidin-1-yl]-3-methylphenyl]methyl)piperazine-1-carboxylate

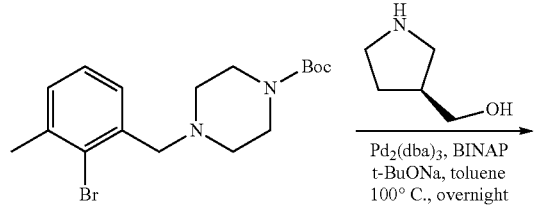

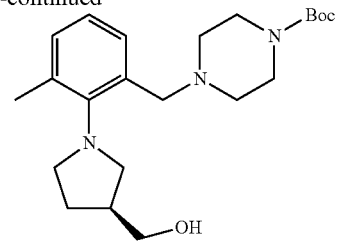

The title compound was synthesized directly from commercially available (3S)-pyrrolidin-3-ylmethanol according to the representative procedure of Example 51, Step 4, to provide tert-butyl 4-([2-[(3S)-3-(hydroxymethyl)pyrrolidin-1-yl]-3-methylphenyl]methyl)piperazine-1-carboxylate as yellow oil. LCMS (ESI, m/z): 390 [M+H]$^+$.

Step 2: Preparation of tert-butyl 4-([3-methyl-2-[(3S)-3-([[(4-methylbenzene)sulfonyl]oxy]methyl)pyrrolidin-1-yl]phenyl]methyl)piperazine-1-carboxylate

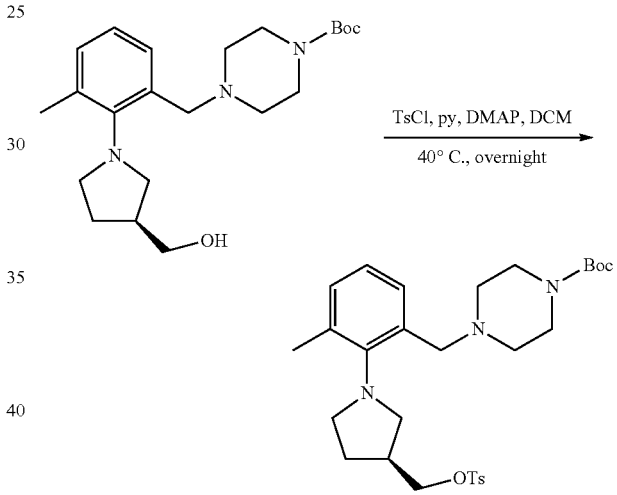

The title compound was synthesized according to the representative procedure of Example 53, Step 3, to provide tert-butyl 4-([3-methyl-2-[(3S)-3-([[(4-methylbenzene)sulfonyl]oxy]methyl)pyrrolidin-1-yl]phenyl]methyl)piperazine-1-carboxylate (320 mg, 82% yield) as yellow oil. LCMS (ESI, m/z): 544 [M+H]$^+$.

Step 3: Preparation of tert-butyl 4-([2-[(3S)-3-(fluoromethyl)pyrrolidin-1-yl]-3-methylphenyl]methyl)piperazine-1-carboxylate

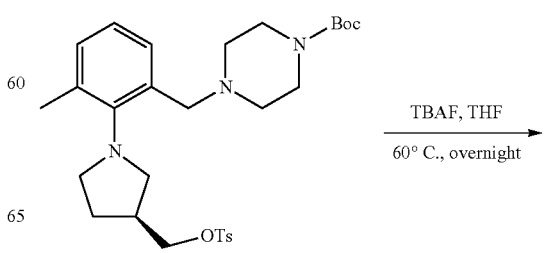

-continued

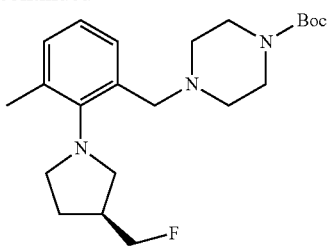

The title compound was synthesized according to the representative procedure of Example 53, Step 4, to provide tert-butyl 4-([2-[(3S)-3-(fluoromethyl)pyrrolidin-1-yl]-3-methylphenyl]methyl)piperazine-1-carboxylate (80.0 mg, 35% yield) as colorless oil. LCMS (ESI, m/z): 392 [M+H]+.

Step 4: Preparation of 1-([2-[(3S)-3-(fluoromethyl)pyrrolidin-1-yl]-3-methylphenyl]methyl)piperazine

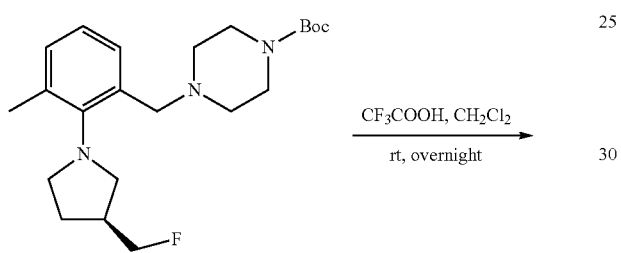

The title compound was synthesized according to the representative procedure of Example 37, Step 3, to provide 1-([2-[(3S)-3-(fluoromethyl)pyrrolidin-1-yl]-3-methylphenyl]methyl)piperazine as yellow oil. LCMS (ESI, m/z): 292 [M+H]+.

Step 5: Preparation of 1,1,1,3,3,3-hexafluoropropan-2-yl (S)-4-(2-(3-(fluoromethyl)pyrrolidin-1-yl)-3-methylbenzyl)piperazine-1-carboxylate

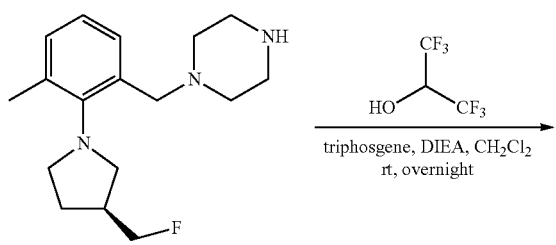

-continued

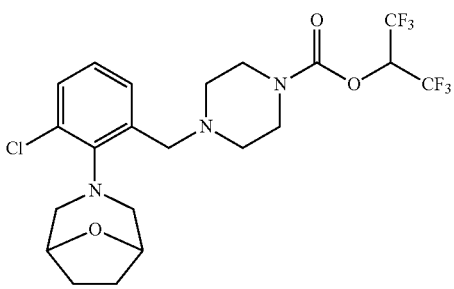 [SMILES: O=C(OC(C(F)(F)F)C(F)(F)F)N1CCN(Cc2cccc(Cl)c2N2CC3CCC(C2)O3)CC1]

The title compound was synthesized according to the representative procedure of Example 37, Step 4, to provide 1,1,1,3,3,3-hexafluoropropan-2-yl (S)-4-(2-(3-(fluoromethyl)pyrrolidin-1-yl)-3-methylbenzyl)piperazine-1-carboxylate as yellow oil. ¹H NMR (300 MHz, Chloroform-d) δ 7.24 (s, 1H), 7.04-7.12 (m, 2H), 5.71-5.80 (m, 1H), 4.54-4.56 (m, 1H), 4.38-4.41 (m, 1H), 3.52-3.55 (m, 6H), 3.22-3.37 (m, 3H), 3.06-3.10 (m, 1H), 2.68-2.80 (m, 1H), 2.44-2.46 (m, 4H), 2.27 (s, 3H), 2.06-2.16 (m, 1H), 1.72-1.83 (m, 1H). LCMS (ESI, m/z): 486 [M+H]+.

Example 57: 1,1,1,3,3,3-hexafluoropropan-2-yl 4-(2-(8-oxa-3-azabicyclo[3.2.1]octan-3-yl)-3-chlorobenzyl)piperazine-1-carboxylate The title compound was synthesized directly from commercially available 3-chloro-2-fluorobenzaldehyde and 8-oxa-3-azabicyclo[3.2.1]octane according to the representative procedure of Example 37 to provide 1,1,1,3,3,3-hexafluoropropan-2-yl 4-(2-(8-oxa-3-azabicyclo[3.2.1]octan-3-yl)-3-chlorobenzyl)piperazine-1-carboxylate as a white solid. ¹H NMR (400 MHz, Chloroform-d) δ 7.32-7.40 (m, 1H), 7.24-7.26 (m, 1H), 7.05-7.14 (m, 1H), 5.71-5.80 (m, 1H), 4.35-4.40 (m, 2H), 3.91-3.94 (m, 2H), 3.51-3.70 (m, 6H), 2.44-2.67 (m, 6H), 2.11-2.34 (m, 2H), 1.93-2.10 (m, 2H). LCMS (ESI, m/z): 516 [M+H]+.

145

Example 58: 1,1,1,3,3,3-hexafluoropropan-2-yl 4-(2-(3-oxa-8-azabicyclo[3.2.1]octan-8-yl)-4-(trifluoromethyl)benzyl)piperazine-1-carboxylate

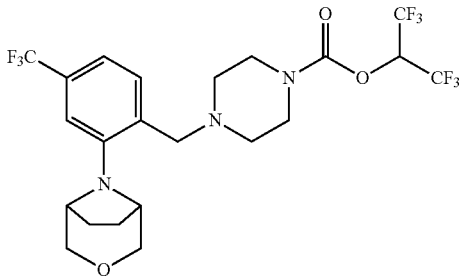 [SMILES: O=C(OC(C(F)(F)F)C(F)(F)F)N1CCN(Cc2ccc(C(F)(F)F)cc2N2C3CCC2COC3)CC1]

The title compound was synthesized directly from commercially available 2-fluoro-4-(trifluoromethyl)benzaldehyde and 3-oxa-8-azabicyclo[3.2.1]octane according to the representative procedure of Example 37 to provide 1,1,1,3,3,3-hexafluoropropan-2-yl 4-(2-(3-oxa-8-azabicyclo[3.2.1]octan-8-yl)-4-(trifluoromethyl)benzyl)piperazine-1-carboxylate as an off-white solid. $^1$H NMR (300 MHz, Chloroform-d) δ 7.57 (d, J=7.8 Hz, 1H), 7.22 (d, J=7.8 Hz, 1H), 7.06 (s, 1H), 5.71-5.79 (m, 1H), 3.91 (d, J=10.2 Hz, 2H), 3.64-3.72 (m, 6H), 3.56 (br, 4H), 2.52 (br, 4H), 1.94-2.07 (m, 4H). LCMS (ESI, m/z): 550 [M+H]$^+$.

Example 59: 1,1,1,3,3,3-hexafluoropropan-2-yl 4-(2-(8-oxa-3-azabicyclo[3.2.1]octan-3-yl)-4-(trifluoromethyl)benzyl)piperazine-1-carboxylate

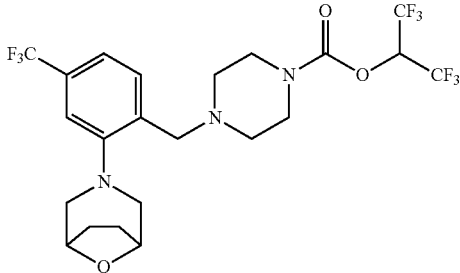 [SMILES: O=C(OC(C(F)(F)F)C(F)(F)F)N1CCN(Cc2ccc(C(F)(F)F)cc2N2CC3CCC(C2)O3)CC1]

The title compound was synthesized directly from commercially available 2-fluoro-4-(trifluoromethyl)benzaldehyde and 8-oxa-3-azabicyclo[3.2.1]octane according to the representative procedure of Example 37 to provide 1,1,1,3,3-hexafluoropropan-2-yl 4-(2-(8-oxa-3-azabicyclo[3.2.1]octan-3-yl)-4-(trifluoromethyl)benzyl)piperazine-1-carboxylate as a yellow solid. $^1$H NMR (300 MHz, Chloroform-d) δ 7.59 (d, J=7.8 Hz, 1H), 7.33-7.36 (m, 2H), 5.69-5.82 (m, 1H), 4.42 (s, 2H), 3.64 (s, 2H), 3.56-3.57 (m, 4H), 3.09 (d, J=10.5 Hz, 2H), 2.80 (d, J=11.1 Hz, 2H), 2.47-2.48 (m, 4H), 1.93-2.12 (m, 4H). LCMS (ESI, m/z): 550 [M+H]$^+$.

146

Example 60: 1,1,1,3,3,3-hexafluoropropan-2-yl (R)-4-(2-(3-(methylsulfonamido)pyrrolidin-1-yl)-4-(trifluoromethyl)benzyl)piperazine-1-carboxylate

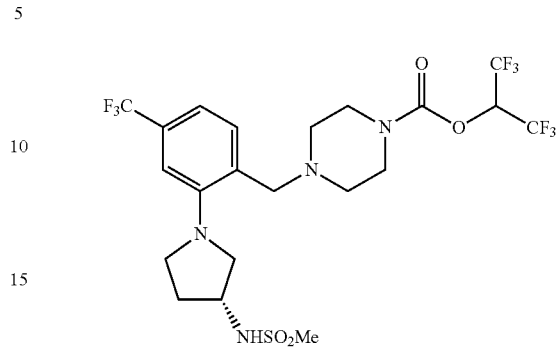

Step 1: Preparation of tert-butyl N-[(3R)-1-[2-formyl-5-(trifluoromethyl)phenyl]pyrrolidin-3-yl]carbamate

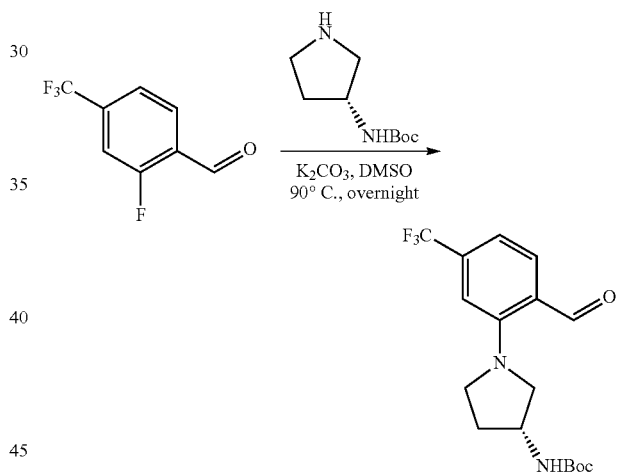

A flask was charged with 2-fluoro-4-(trifluoromethyl)benzaldehyde (1.00 g, 5.21 mmol, 1.00 equiv), tert-butyl N-[(3R)-pyrrolidin-3-yl]carbamate (1.16 g, 6.23 mmol, 1.20 equiv), K$_2$CO$_3$ (2.12 g, 15.3 mmol, 3.00 equiv), and DMSO (10 mL) under nitrogen. The resulting solution was stirred overnight at 90° C. and diluted with H$_2$O (20 mL). The mixture was extracted with DCM (3×30 mL) and the organic layers were combined, washed with H$_2$O (3×10 mL), dried over anhydrous Na$_2$SO$_4$, filtered and concentrated. The residue was chromatographed on a silica gel column (12:88 EtOAc/petroleum ether) to provide tert-butyl N-[(3R)-1-[2-formyl-5-(trifluoromethyl)phenyl]pyrrolidin-3-yl]carbamate (1.30 g, 70% yield) as a yellow solid. LCMS (ESI, m/z): 359 [M+H]$^+$.

Step 2: Preparation of 2-[(3R)-3-aminopyrrolidin-1-yl]-4-(trifluoromethyl)benzaldehyde

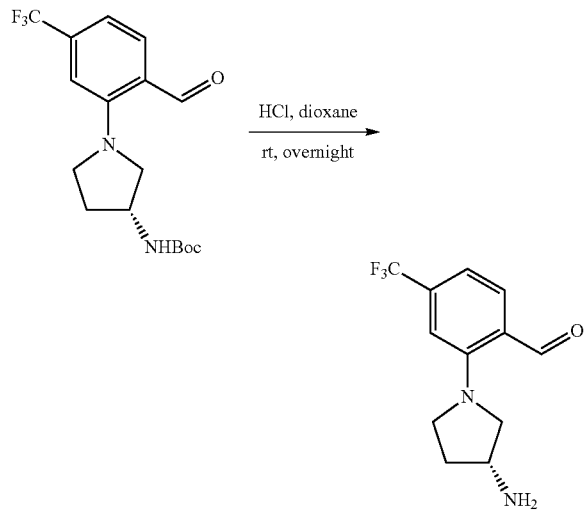

A flask was charged with tert-butyl N-[(3R)-1-[2-formyl-5-(trifluoromethyl)phenyl]pyrrolidin-3-yl]carbamate (1.30 g, 3.63 mmol, 1.00 equiv), dioxane (16 mL), and HCl (4 mL). The resulting solution was stirred overnight at rt. The reaction progress was monitored by LCMS. The resulting mixture was concentrated to provide 2-[(3R)-3-aminopyrrolidin-1-yl]-4-(trifluoromethyl)benzaldehyde (1.20 g) as a yellow solid, which was carried on without further purification. LCMS (ESI, m/z): 259 [M+H]$^+$.

Step 3: Preparation of N-[(3R)-1-[2-formyl-5-(trifluoromethyl)phenyl]pyrrolidin-3-yl]methanesulfonamide

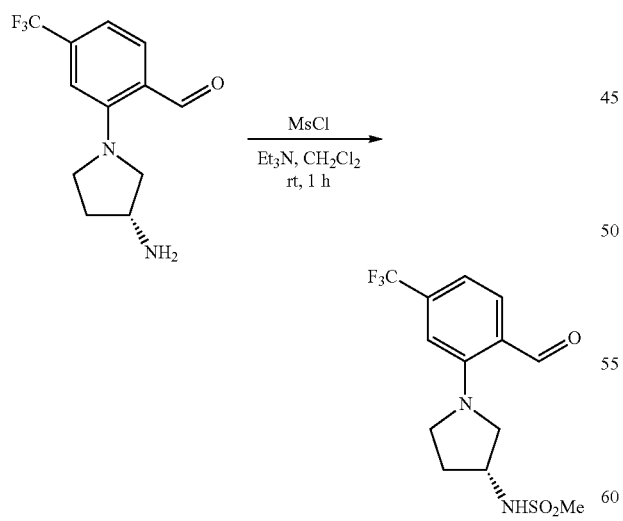

A flask was charged with 2-[(3R)-3-aminopyrrolidin-1-yl]-4-(trifluoromethyl)benzaldehyde (600 mg, 2.32 mmol, 1.00 equiv), and DCM (5 mL). The mixture was cooled to 0° C. Triethylamine (705 mg, 6.97 mmol, 3.00 equiv) was added. Methanesulfonyl chloride (401 mg, 3.49 mmol, 1.50 equiv) was added dropwise. The resulting solution was stirred for 1 h at rt and diluted with H$_2$O (20 mL). The mixture was extracted with DCM (3×30 mL) and the organic layers were combined, washed with H$_2$O (3×10 mL), dried over anhydrous Na$_2$SO$_4$, filtered and concentrated. The residue was chromatographed on a silica gel column (2:3 EtOAc/petroleum ether) to provide N-[(3R)-1-[2-formyl-5-(trifluoromethyl)phenyl]pyrrolidin-3-yl]methanesulfonamide (290 mg, 37% yield) as yellow oil. LCMS (ESI, m/z): 337 [M+H]$^+$.

Step 4: Preparation of tert-butyl 4-([2-[(3R)-3-methanesulfonamidopyrrolidin-1-yl]-4-(trifluoromethyl)phenyl]methyl)piperazine-1-carboxylate

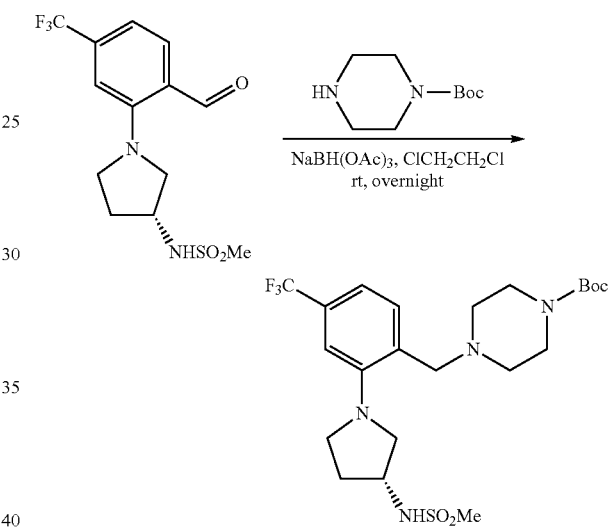

The title compound was synthesized according to the representative procedure of Example 39, Step 4, to provide tert-butyl 4-([2-[(3R)-3-methanesulfonamidopyrrolidin-1-yl]-4-(trifluoromethyl)phenyl]methyl)piperazine-1-carboxylate as a light yellow solid. LCMS (ESI, m/z): 507 [M+H]$^+$.

Step 5: Preparation of N-[(3R)-1-[2-(piperazin-1-ylmethyl)-5-(trifluoromethyl)phenyl]pyrrolidin-3-yl]methanesulfonamide

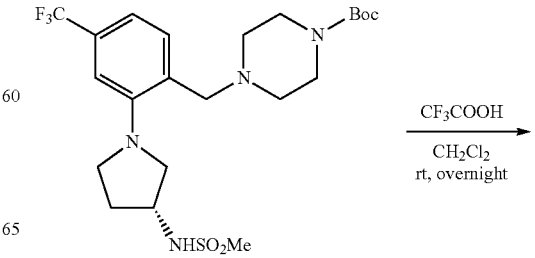

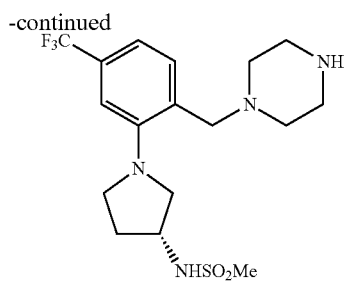

A flask was charged with tert-butyl 4-([2-[(3R)-3-methanesulfonamidopyrrolidin-1-yl]-4-(trifluoromethyl)phenyl]methyl)piperazine-1-carboxylate (300 mg, 0.592 mmol, 1.00 equiv) and DCM (10 mL). TFA (2 mL) was added dropwise. The resulting solution was stirred overnight at rt and concentrated to provide N-[(3R)-1-[2-(piperazin-1-ylmethyl)-5-(trifluoromethyl)phenyl]pyrrolidin-3-yl]methanesulfonamide (230 mg, 96% yield) as yellow oil, which was carried on without further purification. LCMS (ESI, m/z): 407 [M+H]⁺.

Step 6: Preparation of 1,1,1,3,3,3-hexafluoropropan-2-yl (R)-4-(2-(3-(methylsulfonamido)pyrrolidin-1-yl)-4-(trifluoromethyl)benzyl)piperazine-1-carboxylate

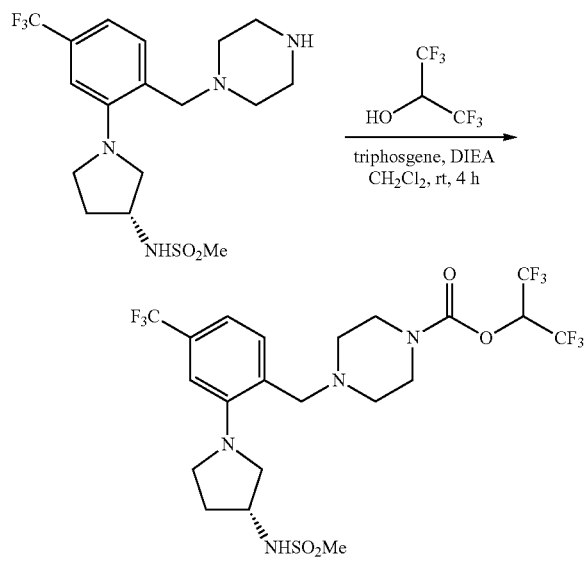

A flask was charged with 1,1,1,3,3,3-hexafluoropropan-2-ol (190 mg, 1.13 mmol, 2.00 equiv), triphosgene (117 mg, 0.394 mmol, 0.70 equiv), and DCM (5 mL). The mixture was cooled to 0° C. DIEA (292 mg, 2.26 mmol, 4.00 equiv) was added dropwise. The mixture was stirred at rt for 2 h. N-[(3R)-1-[2-(Piperazin-1-ylmethyl)-5-(trifluoromethyl)phenyl]pyrrolidin-3-yl]methanesulfonamide (230 mg, 0.565 mmol, 1.00 equiv) was added. The resulting solution was stirred for 2 h at rt and concentrated. The crude product (125 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm 5 um; Mobile phase: Phase A: aqueous NH₄HCO₃ (0.05%); Phase B: CH₃CN; Detector, UV220 & 254 nm. Purification resulted in 1,1,1,3,3,3-hexafluoropropan-2-yl (R)-4-(2-(3-(methylsulfonamido)pyrrolidin-1-yl)-4-(trifluoromethyl)benzyl)piperazine-1-carboxylate (46.0 mg, 14% yield) as a white solid. ¹H NMR (300 MHz, Chloroform-d) δ 7.50 (d, J=8.1 Hz, 1H), 7.20 (d, J=8.4 Hz, 1H), 7.11 (s, 1H), 5.70-5.79 (m, 1H), 4.69 (d, J=6.9 Hz, 1H), 4.12-4.19 (m, 1H), 3.33-3.58 (m, 9H), 3.10-3.18 (m, 1H), 3.02 (s, 3H), 2.34-2.46 (m, 5H), 1.99 (s, 1H). LCMS (ESI, m/z): 601 [M+H]⁺.

Example 61: 1,1,1,3,3,3-hexafluoropropan-2-yl (S)-4-(2-(3-(methylsulfonamido)pyrrolidin-1-yl)-4-(trifluoromethyl)benzyl)piperazine-1-carboxylate

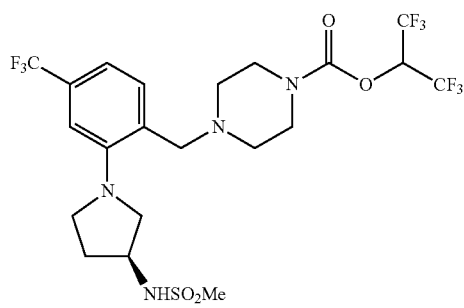

The title compound was synthesized directly from commercially available tert-butyl N-[(3S)-pyrrolidin-3-yl]carbamate according to the representative procedure of Example 60 to provide 1,1,1,3,3,3-hexafluoropropan-2-yl (S)-4-(2-(3-(methylsulfonamido)pyrrolidin-1-yl)-4-(trifluoromethyl)benzyl)piperazine-1-carboxylate as an off-white solid. ¹H NMR (300 MHz, Chloroform-d) δ 7.49 (d, J=7.8 Hz, 1H), 7.20 (d, J=7.2 Hz, 1H), 7.11 (s, 1H), 5.68-5.78 (m, 1H), 4.71 (d, J=7.5 Hz, 1H), 4.15 (s, 1H), 3.25-3.79 (m, 9H), 3.10-3.18 (m, 1H) 3.02 (s, 3H), 2.32-2.47 (m, 5H), 1.99 (s, 1H). LCMS (ESI, m/z): 601 [M+H]⁺.

Example 62: 1-(5-chloro-2-((4-(((1,1,1,3,3,3-hexafluoropropan-2-yl)oxy)carbonyl)piperazin-1-yl)methyl)phenyl)piperidine-4-carboxylic acid

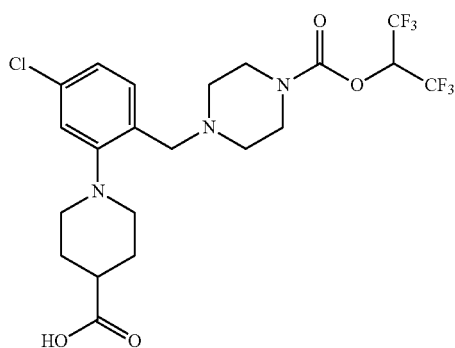 [SMILES: O=C(O)C1CCN(c2cc(Cl)ccc2CN2CCN(C(=O)OC(C(F)(F)F)C(F)(F)F)CC2)CC1]

151

Step 1: Preparation of ethyl 1-(5-chloro-2-formylphenyl)piperidine-4-carboxylate

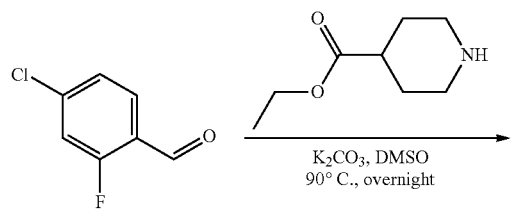

The title compound was synthesized directly from commercially available 2-fluoro-4-chlorobenzaldehyde according to the representative procedure of Example 60, Step 1, to provide ethyl 1-(5-chloro-2-formylphenyl) piperidine-4-carboxylate as yellow oil. LCMS (ESI, m/z): 296 [M+H]$^+$.

Step 2: Preparation of tert-butyl 4-([4-chloro-2-[4-(ethoxycarbonyl)piperidin-1-yl]phenyl]methyl)piperazine-1-carboxylate

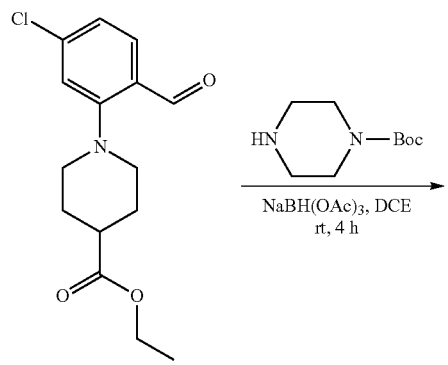

152

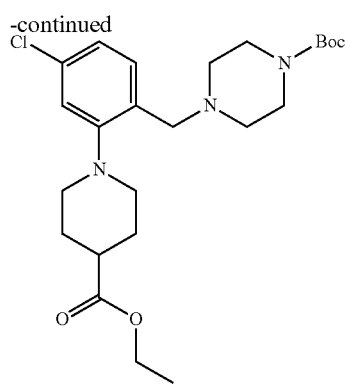

A flask was charged with ethyl 1-(5-chloro-2-formylphenyl)piperidine-4-carboxylate (1.33 g, 4.50 mmol, 1.00 equiv), tert-butyl piperazine-1-carboxylate (0.920 g, 4.94 mmol, 1.10 equiv), and 1,2-dichloroethane (10 mL). The resulting solution was stirred for 1 h at rt. NaBH(OAc)$_3$ (2.86 g, 13.6 mmol, 3.00 equiv) was added at rt. The resulting solution was stirred for 3 h at rt and diluted with H$_2$O (20 mL). The mixture was extracted with DCM (3×50 mL) and the organic layers were combined, washed with brine (3×50 mL), dried over anhydrous Na$_2$SO$_4$, filtered and concentrated. The residue was chromatographed on a silica gel column (3:7 EtOAc/petroleum ether) to provide tert-butyl 4-([4-chloro-2-[4-(ethoxycarbonyl)piperidin-1-yl]phenyl]methyl)piperazine-1-carboxylate (1.82 g, 87% yield) as colorless oil. LCMS (ESI, m/z): 466 [M+H]$^+$.

Step 3: Preparation of 1-[2-([4-[(tert-butoxy)carbonyl]piperazin-1-yl]methyl)-5-chlorophenyl]piperidine-4-carboxylic acid

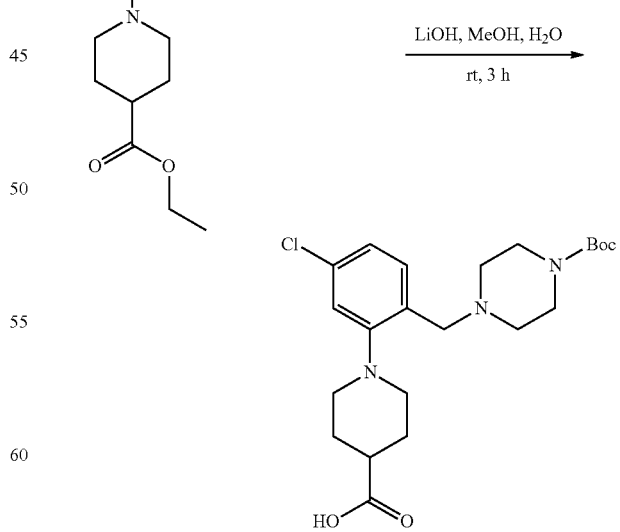

A flask was charged with tert-butyl 4-([4-chloro-2-[4-(ethoxycarbonyl)piperidin-1-yl]phenyl]methyl)piperazine-1-carboxylate (1.82 g, 3.91 mmol, 1.00 equiv), MeOH (10 mL), H₂O (5 mL), and LiOH (0.469 g, 19.6 mmol, 5.00 equiv). The resulting solution was stirred for 3 h at rt. The pH value of the solution was adjusted to 7 with HCl (1 M, 1.5 mL). The mixture was extracted with DCM (3×50 mL) and the organic layers were combined, washed with brine (3×50 mL), dried over anhydrous Na₂SO₄, filtered and concentrated to provide 1-[2-([4-[(tert-butoxy)carbonyl]piperazin-1-yl]methyl)-5-chlorophenyl]piperidine-4-carboxylic acid (1.54 g, 90% yield) as a light yellow solid. LCMS (ESI, m/z): 438 [M+H]⁺.

Step 4: Preparation of 1-[5-chloro-2-(piperazin-1-ylmethyl)phenyl]piperidine-4-carboxylic acid

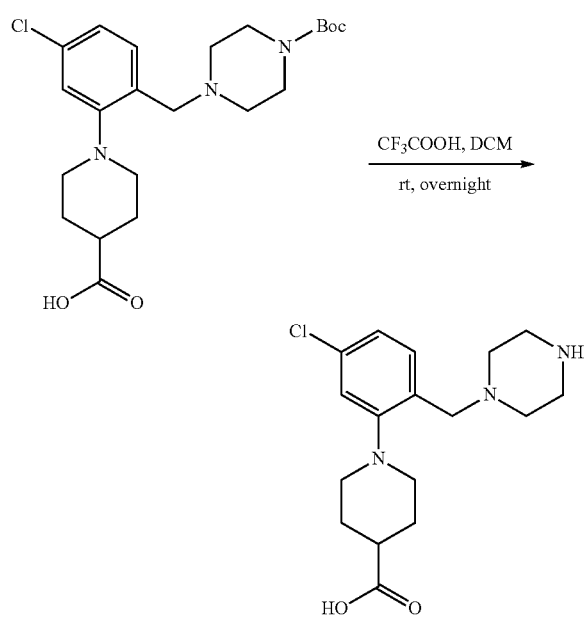

The title compound was synthesized according to the representative procedure of Example 60, Step 5, to provide 1-[5-chloro-2-(piperazin-1-ylmethyl)phenyl]piperidine-4-carboxylic acid as a light yellow solid. LCMS (ESI, m/z): 338 [M+H]⁺.

Step 5: Preparation of 1-(5-chloro-2-((4-(((1,1,1,3,3,3-hexafluoropropan-2-yl)oxy)carbonyl)piperazin-1-yl)methyl)phenyl)piperidine-4-carboxylic acid

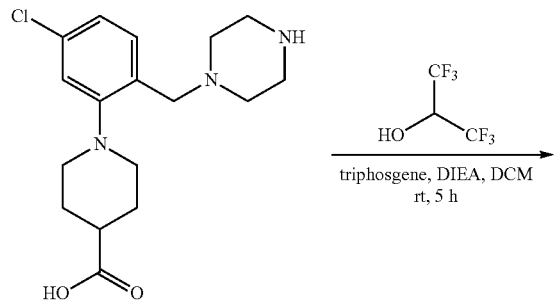

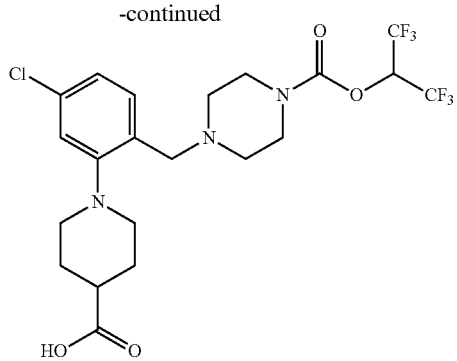

A flask was charged with triphosgene (59.4 mg, 0.200 mmol, 0.40 equiv) and DCM (5 mL). 1,1,1,3,3,3-Hexafluoropropan-2-ol (169 mg, 1.01 mmol, 1.00 equiv) was added dropwise at 0° C. DIEA (194 mg, 1.50 mmol, 3.00 equiv) was added dropwise at 0° C. The resulting solution was stirred for 2 h at rt. 1-[5-Chloro-2-(piperazin-1-ylmethyl)phenyl]piperidine-4-carboxylic acid (100 mg, 0.30 mmol, 1.20 equiv) was added. The resulting solution was stirred for 3 h at rt and diluted with H₂O (20 mL). The mixture was extracted with DCM (3×30 mL) and the organic layers were combined, washed with brine (3×30 mL), dried over anhydrous Na₂SO₄, filtered and concentrated. The crude product (230 mg) was purified by preparative HPLC using the following gradient conditions: 20% CH₃CN/80% NH₄HCO₃ (5%) increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm 5 um; Detector, UV220 & 254 nm. Purification resulted in 1-(5-chloro-2-((4-(((1,1,1,3,3,3-hexafluoropropan-2-yl)oxy)carbonyl)piperazin-1-yl)methyl)phenyl)piperidine-4-carboxylic acid (36.0 mg, 7% yield) as a light yellow solid. ¹H NMR (400 MHz, Chloroform-d) δ 7.28-7.36 (m, 1H), 6.99-7.05 (m, 2H), 5.70-5.79 (m, 1H), 3.53 (br, 6H), 3.18 (d, J=11.6 Hz, 2H), 2.69 (t, J=10.8 Hz, 2H), 2.40 (br, 5H), 2.01-2.06 (m, 2H), 1.85-1.95 (m, 2H). LCMS (ESI, m/z): 532 [M+H]⁺.

Example 63: 1-(2-((4-(((1,1,1,3,3,3-hexafluoropropan-2-yl)oxy)carbonyl)piperazin-1-yl)methyl)-5-(trifluoromethyl)phenyl)piperidine-4-carboxylic acid

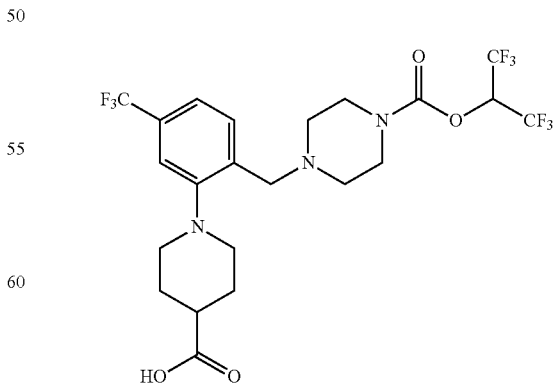

The title compound was synthesized directly from commercially available 2-fluoro-4-(trifluoromethyl)benzaldehyde according to the representative procedure of Example 62 to provide 1-(2-((4-(((1,1,1,3,3,3-hexafluoropropan-2-yl)oxy)carbonyl)piperazin-1-yl)methyl)-5-(trifluoromethyl)phenyl)piperidine-4-carboxylic acid as a white solid. ¹H NMR (300 MHz, Chloroform-d) δ 7.56-7.66 (m, 1H), 7.29-7.44 (m, 2H), 5.68-5.81 (m, 1H), 3.40-3.87 (m, 6H), 3.16-3.30 (m, 2H), 2.72-2.80 (m, 2H), 2.40-2.64 (m, 5H), 2.06-2.19 (m, 2H), 1.87-2.06 (m, 2H). LCMS (ESI, m/z): 566 [M+H]⁺.

Example 64: 1,1,1,3,3,3-hexafluoropropan-2-yl 4-(4-chloro-2-(5-cyclopropylhexahydropyrrolo[3,4-c]pyrrol-2(1H)-yl)benzyl)piperazine-1-carboxylate

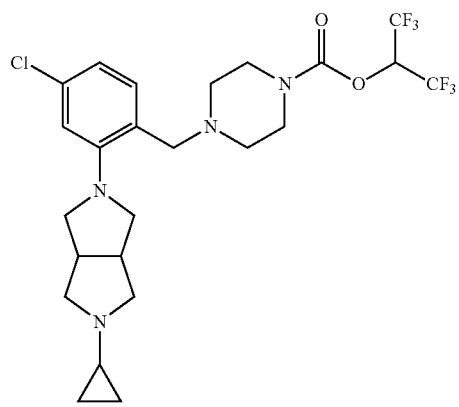 [SMILES: O=C(OC(C(F)(F)F)C(F)(F)F)N1CCN(Cc2ccc(Cl)cc2N2CC3CN(C4CC4)CC3C2)CC1]

Step 1: Preparation of tert-butyl 5-(5-chloro-2-formylphenyl)-octahydropyrrolo[3,4-c]pyrrole-2-carboxylate

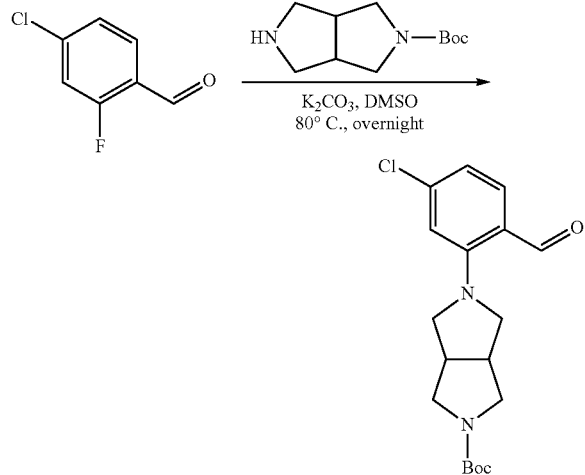

A flask was charged with 4-chloro-2-fluorobenzaldehyde (0.791 g, 4.98 mmol, 1.00 equiv), tert-butyl octahydropyrrolo[3,4-c]pyrrole-2-carboxylate (1.27 g, 5.98 mmol, 1.50 equiv), DMSO (10 mL) and K₂CO₃ (2.00 g, 14.5 mmol, 2.00 equiv). The mixture was stirred overnight at 80° C. and diluted with H₂O (20 mL). The resulting solution was extracted with EtOAc (3×20 mL) and the organic layers were combined, washed with H₂O (3×10 mL), dried over anhydrous Na₂SO₄, filtered and concentrated. The residue was chromatographed on a silica gel column (1:1 EtOAc/petroleum ether) to provide tert-butyl 5-(5-chloro-2-formylphenyl)-octahydropyrrolo[3,4-c]pyrrole-2-carboxylate (1.40 g, 80% yield) as a yellow solid. LCMS (ESI, m/z): 351 [M+H]⁺.

Step 2: Preparation of tert-butyl 5-(5-chloro-2-((4-(((1,1,1,3,3,3-hexafluoropropan-2-yl)oxy)carbonyl)piperazin-1-yl)methyl)phenyl)hexahydropyrrolo[3,4-c]pyrrole-2(1H)-carboxylate

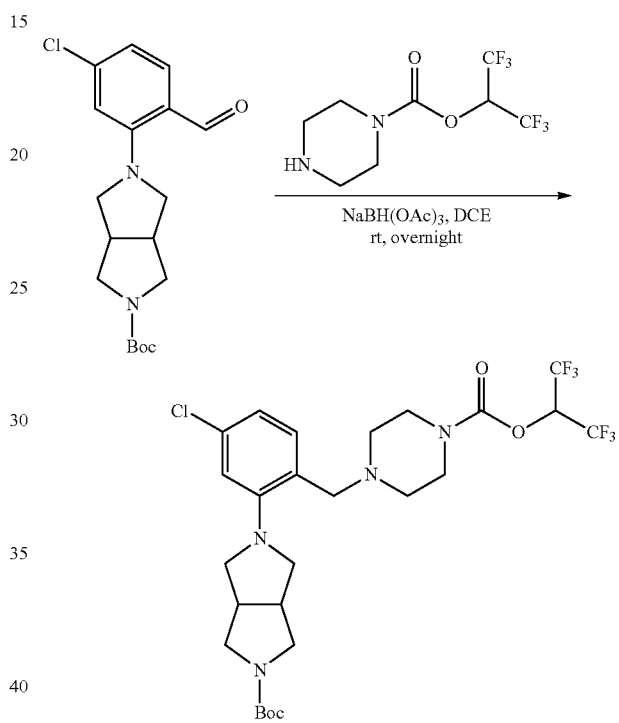

A flask was charged with tert-butyl 5-(5-chloro-2-formylphenyl)-octahydropyrrolo[3,4-c]pyrrole-2-carboxylate (700 mg, 2.00 mmol, 1.00 equiv), 1,1,1,3,3,3-hexafluoropropan-2-yl piperazine-1-carboxylate (840 mg, 3.00 mmol, 1.50 equiv) [as prepared in Example 33, Step 2], 1,2-dichloroethane (20 mL) and NaBH(OAc)₃ (848 mg, 4.00 mmol, 2.00 equiv). The resulting solution was stirred overnight at rt and quenched by H₂O (20 mL). The mixture was extracted with DCM (3×20 mL) and the organic layers were combined, washed with H₂O (3×10 mL), dried over anhydrous Na₂SO₄, filtered and concentrated. The residue was chromatographed on a silica gel column (1:1 EtOAc/petroleum ether) to provide tert-butyl 5-(5-chloro-2-((4-(((1,1,1,3,3,3-hexafluoropropan-2-yl)oxy)carbonyepiperazin-1-yl)methyl)phenyl)hexahydropyrrolo[3,4-c]pyrrole-2(1H)-carboxylate (800 mg, 65% yield) as a yellow oil. LCMS (ESI, m/z): 615 [M+H]⁺.

Step 3: Preparation of 1,1,1,3,3,3-hexafluoropropan-2-yl 4-[(4-chloro-2-[octahydropyrrolo[3,4-c]pyrrol-2-yl]phenyl)methyl]piperazine-1-carboxylate

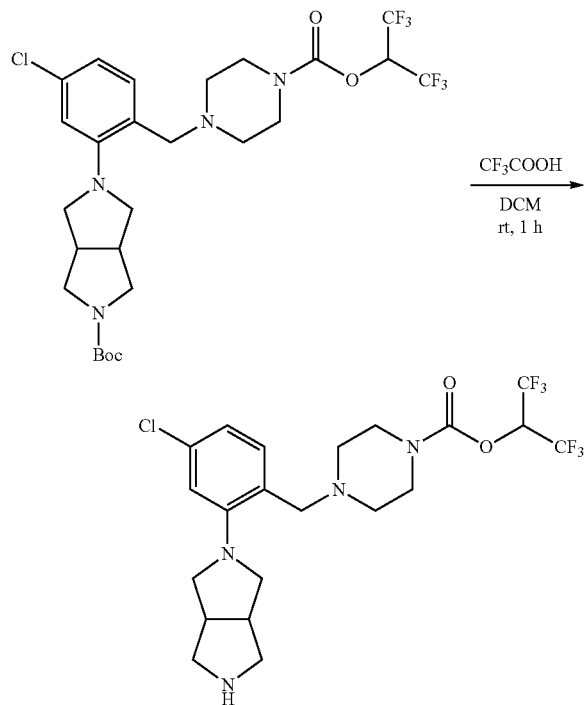

A flask was charged with 1,1,1,3,3,3-hexafluoropropan-2-yl 4-[(2-[5-[(tert-butoxy)carbonyl]-octahydropyrrolo[3,4-c]pyrrol-2-yl]-4-chlorophenyl)methyl]piperazine-1-carboxylate (800 mg, 1.30 mmol, 1.00 equiv), DCM (10 mL) and TFA (5 mL). The resulting solution was stirred for 1 h at rt and concentrated to provide 1,1,1,3,3,3-hexafluoropropan-2-yl 4-[(4-chloro-2-[octahydropyrrolo[3,4-c]pyrrol-2-yl]phenyl)methyl]piperazine-1-carboxylate (800 mg) as a yellow oil, which was carried on without further purification. LCMS (ESI, m/z): 515 [M+H]+.

Step 4: Preparation of 1,1,1,3,3,3-hexafluoropropan-2-yl 4-(4-chloro-2-(5-cyclopropylhexahydropyrrolo[3,4-c]pyrrol-2(1H)-yl)benzyl)piperazine-1-carboxylate

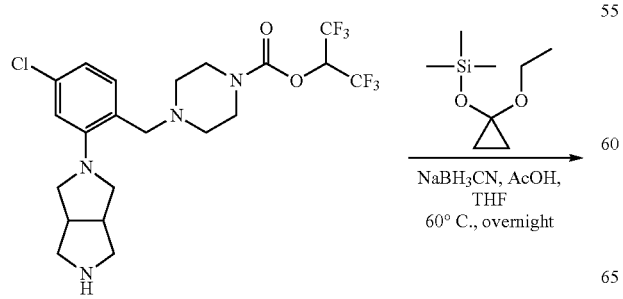

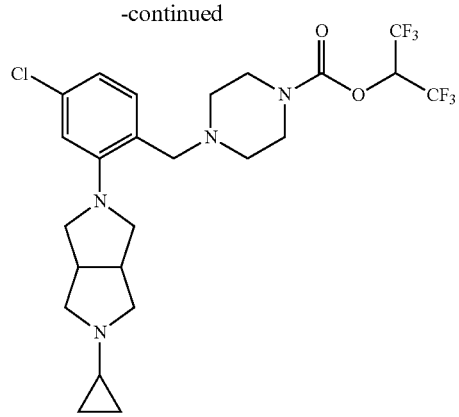

A flask was charged with 1,1,1,3,3,3-hexafluoropropan-2-yl 4-[(4-chloro-2-[octahydropyrrolo[3,4-c]pyrrol-2-yl]phenyl)methyl]piperazine-1-carboxylate (205 mg, 0.401 mmol, 1.00 equiv), (1-ethoxycyclopropoxy)trimethylsilane (208 mg, 1.19 mmol, 3.00 equiv), THF (15 mL), acetic acid (98.0 mg, 1.63 mmol, 4.00 equiv) and sodium cyanoborohydride (80.0 mg, 1.27 mmol, 3.00 equiv). The resulting solution was stirred overnight at 60° C. and diluted with DCM (50 mL). The resulting mixture was washed with H₂O (3×50 mL), dried over anhydrous Na₂SO₄, filtered and concentrated. The residue was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm 5 um; Mobile phase: Phase A: aqueous NH₄HCO₃ (0.05%); Phase B: CH₃CN; Detector, UV220 & 254 nm. Purification resulted in 1,1,1,3,3,3-hexafluoropropan-2-yl 4-(4-chloro-2-(5-cyclopropylhexahydropyrrolo13,4-clpyrrol-2(1H)-yl)benzyl)piperazine-1-carboxylate (119.3 mg, 54% yield) as yellow oil. ¹H NMR (400 MHz, Chloroform-d) δ 7.37 (d, J=6.1 Hz, 1H), 6.99-7.05 (m, 2H), 5.69-5.79 (m, 1H), 3.50-3.65 (m, 6H), 3.05-3.15 (m, 2H), 2.94-3.03 (m, 4H), 2.85 (s, 2H), 2.38-2.42 (m, 6H), 1.58-1.65 (m, 1H), 0.41-0.50 (m, 4H). LCMS (ESI, m/z): 555 [M+H]+.

Example 65: 1,1,1,3,3,3-hexafluoropropan-2-yl 4-(2-(5-cyclopropylhexahydropyrrolo[3,4-c]pyrrol-2(1H)-yl)-4-(trifluoromethyl)benzyl)piperazine-1-carboxylate

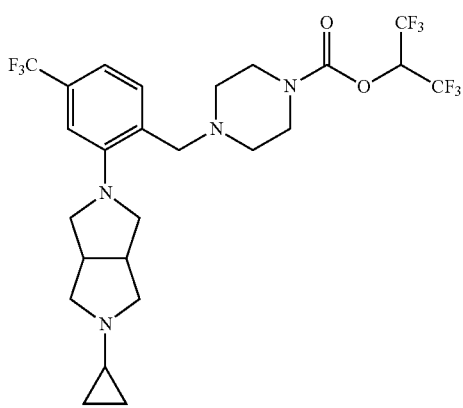 [SMILES: O=C(OC(C(F)(F)F)C(F)(F)F)N1CCN(Cc2ccc(C(F)(F)F)cc2N2CC3CN(C4CC4)CC3C2)CC1]

The title compound was synthesized directly form commercially available 2-fluoro-4-(trifluoromethyl)benzaldehyde according to the representative procedure of Example 64 to provide 1,1,1,3,3,3-hexafluoropropan-2-yl 4-(2-(5-cyclopropylhexahydropyrrolo[3,4-c]pyrrol-2(1H)-yl)-4-(trifluoromethyl)benzyl)piperazine-1-carboxylate as a yellow oil. ¹H NMR (400 MHz, chloroform-d) δ 7.60 (d, J=7.9 Hz, 1H), 7.25-7.29 (m, 2H), 5.72-5.81 (m, 1H), 3.58-3.61 (m, 6H), 3.12-3.16 (m, 2H), 2.99-3.12 (m, 4H), 2.88 (s, 2H), 2.42-3.60 (m, 6H), 1.66 (s, 1H), 0.42-0.58 (m, 4H). LCMS (ESI, m/z): 589 [M+H]⁺.

Example 66: 1,1,1,3,3,3-hexafluoropropan-2-yl 4-(4-chloro-2-(1-cyclopropyl-1,8-diazaspiro[4.5]decan-8-yl)benzyl)piperazine-1-carboxylate

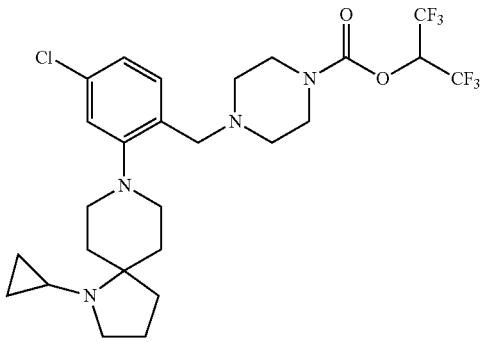 [SMILES: O=C(OC(C(F)(F)F)C(F)(F)F)N1CCN(Cc2ccc(Cl)cc2N2CCC3(CCCN3C3CC3)CC2)CC1]

The title compound was synthesized directly from commercially available tert-butyl 1,8-diazaspiro[4.5]decane-1-carboxylate according to the representative procedure of Example 64 to provide 1,1,1,3,3,3-hexafluoropropan-2-yl 4-(4-chloro-2-(1-cyclopropyl-1,8-diazaspiro[4.5]decan-8-yl)benzyl)piperazine-1-carboxylate as a yellow oil. ¹H NMR (400 MHz, chloroform-d) δ 7.38 (d, J=8.1 Hz, 1H), 7.02-7.08 (m, 2H), 5.69-5.81 (m, 1H), 3.49-3.61 (s, 6H), 3.08-3.18 (m, 2H), 2.93 (s, 2H), 2.72 (t, J=10.7 Hz, 2H), 2.44-2.53 (m, 4H), 2.16 (t, J=11.0 Hz, 2H), 1.70-1.91 (m, 5H), 1.45 (s, 2H), 0.35-0.62 (m, 4H). LCMS (ESI, m/z): 583 [M+H]⁺.

Example 67: 1,1,1,3,3,3-hexafluoropropan-2-yl 4-(2-(1-cyclopropyl-1,8-diazaspiro[4.5]decan-8-yl)-4-(trifluoromethyl)benzyl)piperazine-1-carboxylate

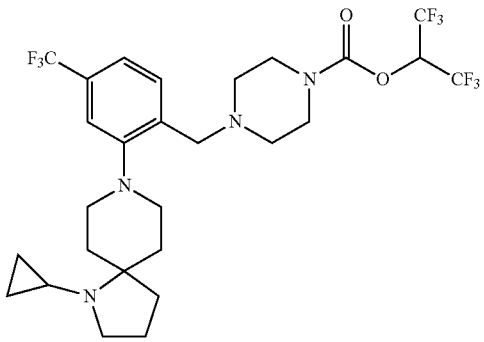 [SMILES: O=C(OC(C(F)(F)F)C(F)(F)F)N1CCN(Cc2ccc(C(F)(F)F)cc2N2CCC3(CCCN3C3CC3)CC2)CC1]

The title compound was synthesized directly from commercially available 2-fluoro-4-(trifluoromethyl)benzaldehyde and tert-butyl 1,8-diazaspiro[4.5]decane-1-carboxylate according to the representative procedure of Example 64 to provide 1,1,1,3,3,3-hexafluoropropan-2-yl 4-(2-(1-cyclopropyl-1,8-diazaspiro[4.5]decan-8-yl)-4-(trifluoromethyl)benzyl)piperazine-1-carboxylate as a white solid. ¹H NMR (300 MHz, chloroform-d) δ 7.55-7.63 (m, 1H), 7.31 (s, 2H), 5.70-5.81 (m, 1H), 3.50-3.65 (m, 6H), 3.02-3.20 (m, 2H), 2.91 (s, 2H), 2.71-2.82 (m, 2H), 3.50 (s, 4H), 2.18 (s, 2H), 1.70-1.95 (m, 4H), 1.56 (s, 2H), 1.36-1.51 (m, 2H), 0.35-0.62 (m, 3H). LCMS (ESI, m/z): 617 [M+H]⁺.

Example 68: 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate

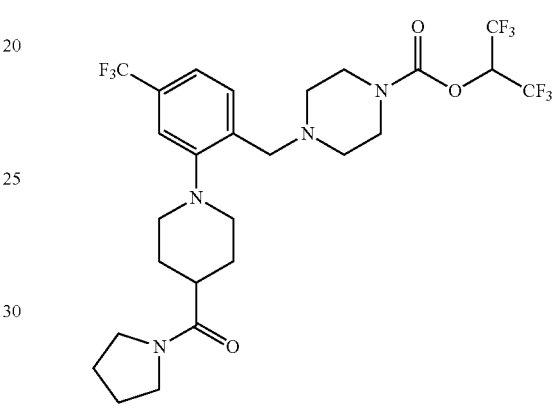

The title compound was synthesized directly from commercially available 2-fluoro-4-(trifluoromethyl)benzaldehyde and piperidin-4-yl(pyrrolidin-1-yl)methanone compound with methane (1:2) according to the representative procedure of Example 33, Steps 1-3 to provide 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate as a pale oil: ¹H NMR (400 MHz, Chloroform-d) δ 7.59 (d, J=7.8 Hz, 1H), 7.35-7.30 (m, 2H), 5.84-5.70 (m, 1H), 3.64 (s, 2H), 3.61-3.48 (m, 8H), 3.32-3.24 (m, 2H), 2.81-2.69 (m, 2H), 2.57-2.45 (m, 5H), 2.13-1.96 (m, 4H), 1.95-1.80 (m, 4H). LCMS (ESI, m/z): 619.2 [M+H]⁺.

Example 69: 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate

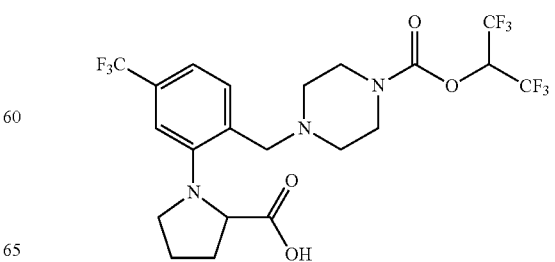

Step 1: Preparation of (2-formyl-5-(trifluoromethyl)phenyl)proline

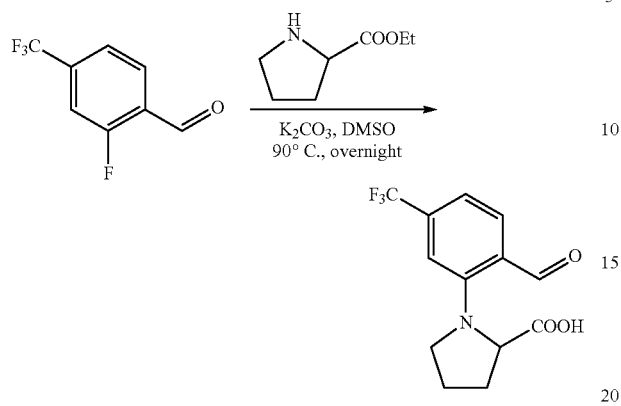

A 50-mL round-bottom flask was charged with 2-fluoro-4-(trifluoromethyl)benzaldehyde (0.600 g, 3.12 mmol, 1.00 equiv), ethyl pyrrolidine-2-carboxylate (0.894 g, 6.24 mmol, 2.00 equiv), dimethyl sulfoxide (15 mL), and potassium carbonate (1.29 g, 9.33 mmol, 3.00 equiv) under nitrogen. The resulting solution was stirred overnight at 90° C. and quenched with water (20 mL). The resulting mixture was extracted with dichloromethane (3×30 mL) and the organic layers were combined, washed with brine (1×100 mL), dried over anhydrous sodium sulfate, filtered, and concentrated under reduced pressure. The residue was chromatographed on a silica gel column with ethyl acetate/petroleum ether (1/4) to provide 0.0800 g (9% yield) of 1-[2-formyl-5-(trifluoromethyl)phenyl]pyrrolidine-2-carboxylic acid as a yellow solid. LCMS (ESI, m/z): 288 [M+H]$^+$.

Step 2: Preparation of 1-(tert-butyl) 4-(1,1,1,3,3,3-hexafluoropropan-2-yl) piperazine-1,4-dicarboxylate

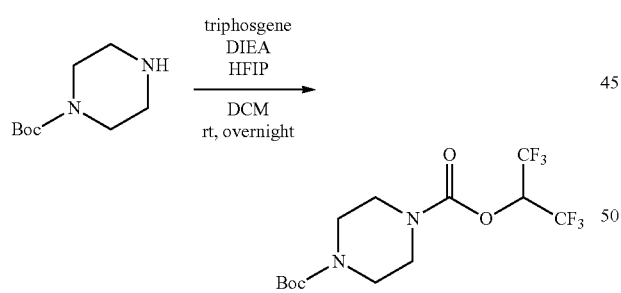

A 500-mL round-bottom flask was charged with triphosgene (7.82 g, 26.3 mmol, 0.70 equiv), and dichloromethane (200 mL). 1,1,1,3,3,3-hexafluoropropan-2-ol (12.7 g, 75.6 mmol, 2.00 equiv) was added at 0° C., followed by N,N-Diisopropylethylamine (19.4 g, 150 mmol, 4.00 equiv). The mixture was stirred for 2 h at room temperature after which tert-butyl piperazine-1-carboxylate (7.00 g, 37.6 mmol, 1.00 equiv) was added. The resulting solution was stirred overnight at room temperature and quenched with water (150 mL). The resulting mixture was extracted with dichloromethane (3×250 mL) and the organic layers were combined, washed with brine (1×300 mL), dried over anhydrous sodium sulfate, filtered and concentrated under reduced pressure. The residue was chromatographed on a silica gel column with ethyl acetate/petroleum ether (1/9) to provide 4.70 g (33% yield) of 1-tert-butyl 4-(1,1,1,3,3,3-hexafluoropropan-2-yl) piperazine-1,4-dicarboxylate as a white solid. LCMS (ESI, m/z): 381 [M+H]$^+$.

Step 3: Preparation of 1,1,1,3,3,3-hexafluoropropan-2-yl piperazine-1-carboxylate

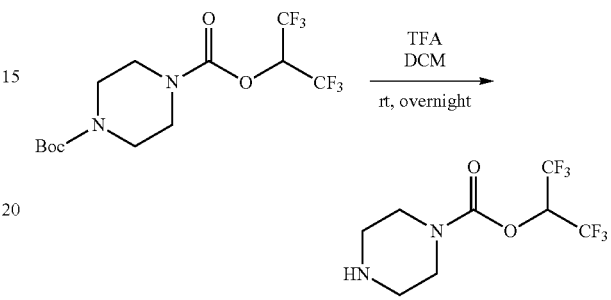

A 50-mL round-bottom flask was charged with 1-tert-butyl 4-(1,1,1,3,3,3-hexafluoropropan-2-yl) piperazine-1,4-dicarboxylate (750 mg, 1.97 mmol, 1.00 equiv), dichloromethane (10 mL), and trifluoroacetic acid (4 mL). The resulting solution was stirred overnight at room temperature and concentrated under reduced pressure to provide 900 mg (crude) of 1,1,1,3,3,3-hexafluoropropan-2-yl piperazine-1-carboxylate as a yellow solid. LCMS (ESI, m/z): 281 [M+H]$^+$.

Step 4: Preparation of 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate

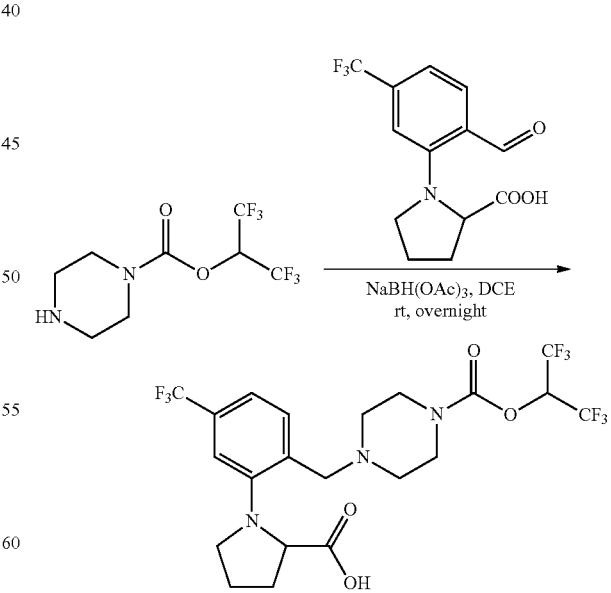

A 50-mL round-bottom flask was charged with 1,1,1,3,3,3-hexafluoropropan-2-yl piperazine-1-carboxylate (85.6 mg, 0.310 mmol, 1.10 equiv), 1-[2-formyl-5-(trifluoromethyl)phenyl]pyrrolidine-2-carboxylic acid (80.0 mg, 0.280 mmol, 1.00 equiv), and 1,2-dichloroethane (10 mL). The mixture was stirred for 1 h at room temperature. Sodium triacetoxyborohydride (177 mg, 0.830 mmol, 3.00 equiv) was added. The resulting solution was stirred overnight at room temperature and quenched with water (10 mL). The resulting mixture was extracted with dichloromethane (3×15 mL) and the organic layers were combined, washed with brine (1×50 mL), dried over anhydrous sodium sulfate, filtered and concentrated under reduced pressure. The crude product (400 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm 5 um; Mobile phase: Phase A: aqueous $NH_4HCO_3$ (0.05%); Phase B: $CH_3CN$; Detector, UV220 & 254 nm. Purification resulted in 45.6 mg (30% yield) of 1,1,1,3,3,3-hexafluoropropan-2-yl 4-(2-(4-(pyrrolidine-1-carbonyl)piperidin-1-yl)-4-(trifluoromethyl)benzyl)piperazine-1-carboxylate as a white solid. $^1$H NMR (300 MHz, Chloroform-d) δ 13.5 (br, 1H), 7.50 (s, 1H), 7.40 (d, J=7.8 Hz, 1H), 7.29 (d, J=7.8 Hz, 1H), 5.69-5.77 (m, 1H), 4.36-4.41 (m, 1H), 4.17-4.21 (m, 1H), 3.56-3.65 (m, 5H), 3.07-3.11 (m, 1H), 2.84-2.92 (m, 1H), 2.50-2.62 (m, 5H), 2.21-2.30 (m, 1H), 1.96-2.10 (m, 2H). LCMS (ESI, m/z): 552 [M+H]$^+$.

Example 70: 1,1,1,3,3,3-hexafluoropropan-2-yl 4-(2-(2-(ethoxycarbonyl)pyrrolidin-1-yl)-4-(trifluoromethyl)benzyl)piperazine-1-carboxylate

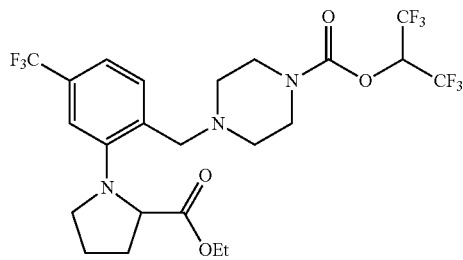 [SMILES: CCOC(=O)C1CCCN1c1cc(C(F)(F)F)ccc1CN1CCN(C(=O)OC(C(F)(F)F)C(F)(F)F)CC1]

Step 1: Preparation of ethyl (2-formyl-5-(trifluoromethyl)phenyl)prolinate

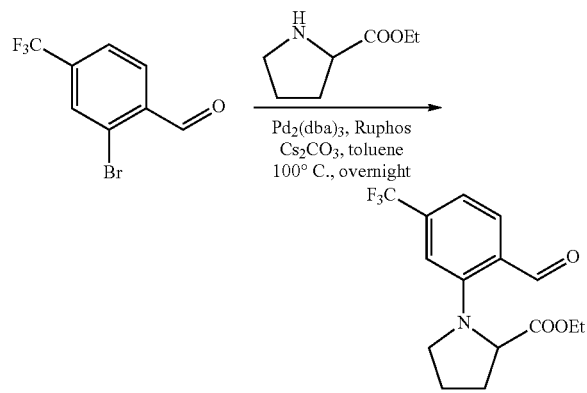

A 50-mL round-bottom flask was charged with 2-bromo-4-(trifluoromethyl)benzaldehyde (0.300 g, 1.19 mmol, 1.00 equiv), ethyl pyrrolidine-2-carboxylate (0.340 g, 2.37 mmol, 2.00 equiv), cesium carbonate (1.16 g, 3.57 mmol, 3.00 equiv), dicyclohexyl(2',6'-diisopropoxybiphenyl-2-yl)phosphine (0.222 g, 0.480 mmol, 0.40 equiv), tris(dibenzylideneacetone)dipalladium (0.109 g, 0.120 mmol, 0.10 equiv), and toluene (10 mL) under nitrogen. The resulting solution was stirred overnight at 100° C. and quenched with water (15 mL). The resulting mixture was extracted with dichloromethane (3×25 mL). The organic layers were combined and washed with brine (1×60 mL), dried over anhydrous sodium sulfate, filtered and concentrated under reduced pressure. The residue was chromatographed on a silica gel column with ethyl acetate/petroleum ether (1/5) to provide 0.0700 g (19% yield) of ethyl 1-[2-formyl-5-(trifluoromethyl)phenyl]pyrrolidine-2-carboxylate as a yellow solid. LCMS (ESI, m/z): 316 [M+H]$^+$.

Step 2: Preparation of 1,1,1,3,3,3-hexafluoropropan-2-yl 4-(2-(2-(ethoxycarbonyl)pyrrolidin-1-yl)-4-(trifluoromethyl)benzyl)piperazine-1-carboxylate The title compound was prepared according to the representative procedure of Example 69, Steps 2-4, using ethyl (2-formyl-5-(trifluoromethyl)phenyl)prolinate in Step 4 to provide 1,1,1,3,3,3-hexafluoropropan-2-yl 4-([2-[2-(ethoxycarbonyl)pyrrolidin-1-yl]-4-(trifluoromethyl)benzyl)piperazine-1-carboxylate as yellow oil. $^1$H NMR (300 MHz, Chloroform-d) δ 7.58-7.61 (m, 1H), 7.20-7.28 (m, 2H), 5.70-5.78 (m, 1H), 4.41-4.43 (m, 1H), 3.98-4.05 (m, 2H), 3.64-3.69 (m, 7H), 3.12 (br, 1H), 2.36-2.56 (m, 5H), 1.95-2.13 (m, 3H), 1.08-1.12 (m, 3H). LCMS (ESI, m/z): 580 [M+H]$^+$.

Example 71: 1,1,1,3,3,3-hexafluoropropan-2-yl 4-(2-(2-(hydroxymethyl)pyrrolidin-1-yl)-4-(trifluoromethyl)benzyl)piperazine-1-carboxylate

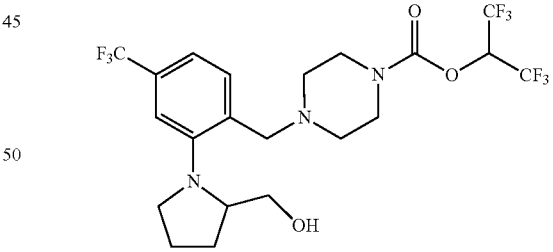

The title compound was synthesized directly from commercially available 2-fluoro-4-(trifluoromethyl)benzaldehyde and pyrrolidin-2-ylmethanol according to the representative procedure of Example 69, Steps 1-4 to provide 1,1,1,3,3,3-hexafluoropropan-2-yl 4-(2-(2-(hydroxymethyl)pyrrolidin-1-yl)-4-(trifluoromethyl)benzyl)piperazine-1-carboxylate as yellow oil. $^1$H NMR (300 MHz, Chloroform-d) δ 7.50 (s, 1H), 7.25-7.31 (m, 2H), 5.68-5.77 (m, 1H), 5.14 (br, 1H), 4.16-4.20 (m, 1H), 3.72-3.74 (m, 1H), 3.58-3.59 (m, 4H), 3.32-3.50 (m, 3H), 2.94-2.98 (m, 1H), 2.80-2.87 (m, 1H), 2.47-2.49 (m, 4H), 1.95-2.12 (m, 4H). LCMS (ESI, m/z): 538 [M+H]$^+$.

Example 72: 1-(2-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid

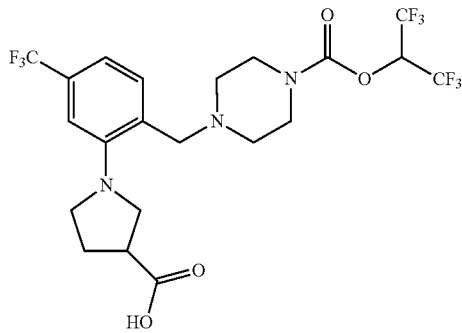 [SMILES: O=C(O)C1CCN(c2cc(C(F)(F)F)ccc2CN2CCN(C(=O)OC(C(F)(F)F)C(F)(F)F)CC2)C1]

Step 1: Preparation of methyl 1-(2-formyl-5-(trifluoromethyl)phenyl)pyrrolidine-3-carboxylate

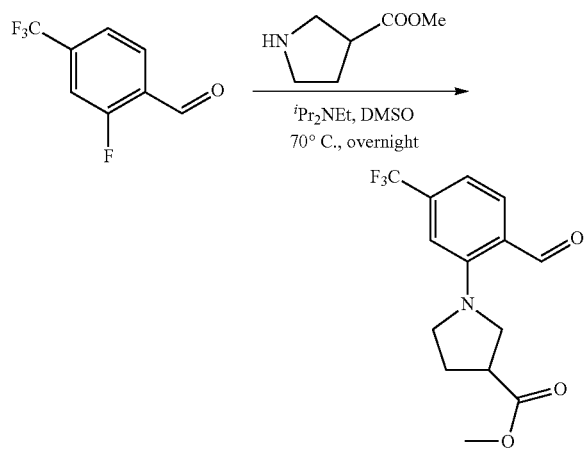

A 50-mL round-bottom flask was charged with 2-fluoro-4-(trifluoromethyl)benzaldehyde (0.600 g, 3.12 mmol, 1.00 equiv), methyl pyrrolidine-3-carboxylate (0.806 g, 6.24 mmol, 2.00 equiv), dimethyl sulfoxide (15 mL), and N,N-Diisopropylethylamine (1.21 g, 9.36 mmol, 3.00 equiv) under nitrogen. The resulting solution was stirred overnight at 70° C. and quenched with water (20 mL). The resulting mixture was extracted with dichloromethane (3×30 mL) and the organic layers were combined, washed with brine (1×100 mL), dried over anhydrous sodium sulfate, filtered and concentrated under reduced pressure. The residue was chromatographed on a silica gel column with ethyl acetate/petroleum ether (1/9) to provide 0.165 g (18% yield) of methyl 1-(2-formyl-5-(trifluoromethyl)phenyl)pyrrolidine-3-carboxylate as a yellow solid. LCMS (ESI, m/z): 302 [M+H]$^+$.

Step 2: Preparation of 1-(2-formyl-5-(trifluoromethyl)phenyl)pyrrolidine-3-carboxylic acid

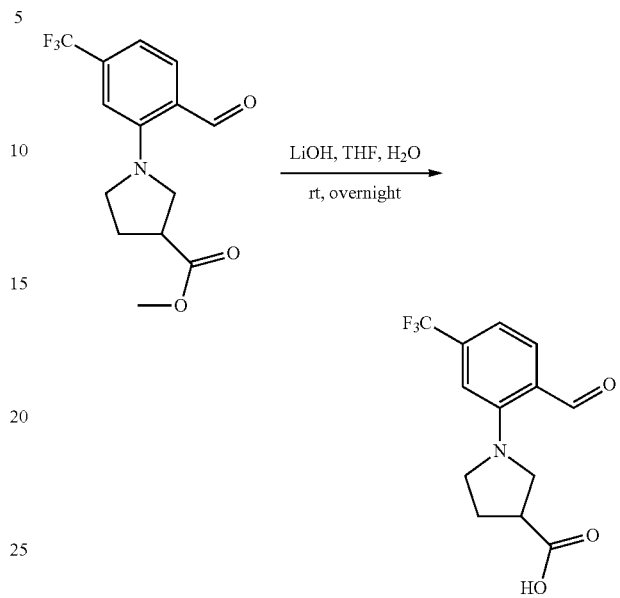

A 50-mL round-bottom flask was charged with methyl 1-[2-formyl-5-(trifluoromethyl)phenyl]pyrrolidine-3-carboxylate (165 mg, 0.550 mmol, 1.00 equiv), tetrahydrofuran (9 mL), lithium hydroxide (39.5 mg, 1.65 mmol, 3.00 equiv), and water (3 mL). The resulting solution was stirred overnight at room temperature and quenched with water (10 mL). The PH of the solution was adjusted to 5 with hydrochloric acid (1M, 3 mL). The resulting solution was extracted with ethyl acetate (3×15 mL) and the organic layers were combined, washed with brine (1×50 mL), dried over anhydrous sodium sulfate, filtered and concentrated under reduced pressure to provide 150 mg (95% yield) of 1-(2-formyl-5-(trifluoromethyl)phenyl)pyrrolidine-3-carboxylic acid as a white solid. LCMS (ESI, m/z): 288 [M+H]$^+$.

Step 3: Preparation of 1-(2-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid The title compound was prepared according to the representative procedure of Example 69, Steps 2-4, using 1-(2-formyl-5-(trifluoromethyl)phenyl)pyrrolidine-3-carboxylic acid in Step 4 to provide 1-(2-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid as a white solid. $^1$H NMR (300 MHz, Chloroform-d) δ 7.50 (d, J=7.8 Hz, 1H), 7.20-7.24 (m, 2H), 5.68-5.81 (m, 1H), 3.52-3.69 (m, 7H), 3.32-3.39 (m, 2H), 3.16-3.26 (m, 2H), 2.46-2.47 (m, 4H), 2.28-2.39 (m, 2H). LCMS (ESI, m/z): 552 [M+H]$^+$.

Example 73: 1,1,1,3,3,3-hexafluoropropan-2-yl 4-(2-(3-(hydroxymethyl)pyrrolidin-1-yl)-4-(trifluoromethyl)benzyl)piperazine-1-carboxylate

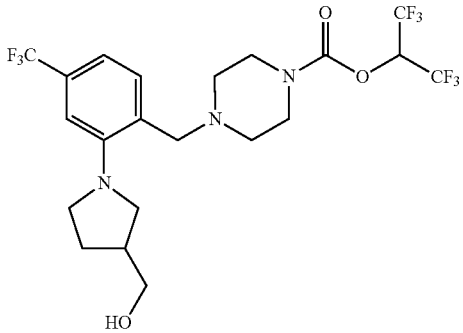 [SMILES: O=C(OC(C(F)(F)F)C(F)(F)F)N1CCN(Cc2ccc(C(F)(F)F)cc2N2CCC(CO)C2)CC1]

The title compound was synthesized directly from commercially available 2-fluoro-4-(trifluoromethyl)benzaldehyde and pyrrolidin-3-ylmethanol according to the representative procedure of Example 69, Steps 1-4 to provide 1,1,1,3,3,3-hexafluoropropan-2-yl 4-(2-(3-(hydroxymethyl)pyrrolidin-1-yl)-4-(trifluoromethyl)benzyl)piperazine-1-carboxylate as yellow oil. $^1$H NMR (300 MHz, Chloroform-d) δ 7.48-7.50 (m, 1H), 7.16-7.18 (m, 2H), 5.71-5.79 (m, 1H), 3.75-3.80 (m, 1H), 3.59-3.70 (m, 7H), 3.11-3.40 (m, 4H), 2.47-2.57 (m, 5H), 2.09-2.20 (m, 2H), 1.80-1.89 (m, 1H). LCMS (ESI, m/z): 538 [M+H]$^+$.

Example 74: 1,1,1,3,3,3-hexafluoropropan-2-yl 4-(2-(4-(hydroxymethyl)piperidin-1-yl)-4-(trifluoromethyl)benzyl)piperazine-1-carboxylate

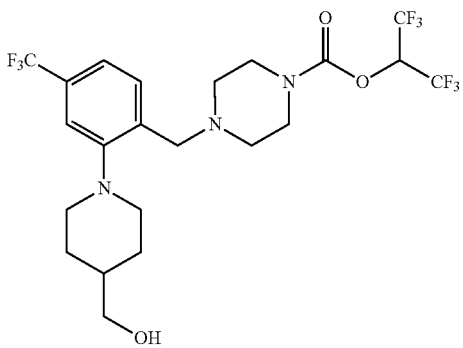 [SMILES: O=C(OC(C(F)(F)F)C(F)(F)F)N1CCN(Cc2ccc(C(F)(F)F)cc2N2CCC(CO)CC2)CC1]

The title compound was synthesized directly from commercially available 2-fluoro-4-(trifluoromethyl)benzaldehyde and piperidin-4-ylmethanol according to the representative procedure of Example 69, Steps 1-4 to provide 1,1,1,3,3,3-hexafluoropropan-2-yl 4-(2-(4-(hydroxymethyl)piperidin-1-yl)-4-(trifluoromethyl)benzyl)piperazine-1-carboxylate as colorless oil. $^1$H NMR (300 MHz, Chloroform-d) δ 7.57-7.60 (m, 1H), 7.30 (br, 2H), 5.69-5.81 (m, 1H), 3.56-3.60 (m, 8H), 3.10-3.18 (m, 2H), 2.61-2.74 (m, 2H), 2.48-2.50 (m, 4H), 1.83-1.87 (m, 2H), 1.60-1.71 (m, 1H), 1.42-1.50 (m, 3H). LCMS (ESI, m/z): 552 [M+H]$^+$.

Example 75: 4-(2-((4-(((1,1,1,3,3,3-hexafluoropropan-2-yl)oxy)carbonyl)piperazin-1-yl)methyl)-5-(trifluoromethyl)phenyl)morpholine-2-carboxylic acid

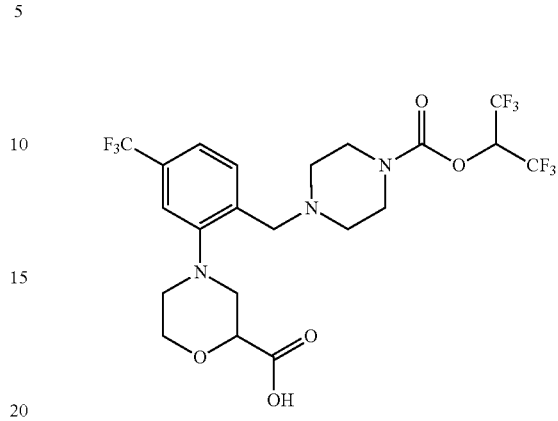

The title compound was synthesized directly from commercially available 2-fluoro-4-(trifluoromethyl)benzaldehyde and methyl morpholine-2-carboxylate according to the representative procedure of Example 70, Steps 1-2 to provide 4-(2-((4-(((1,1,1,3,3,3-hexafluoropropan-2-yl)oxy)carbonyl)piperazin-1-yl)methyl)-5-(trifluoromethyl)phenyl)morpholine-2-carboxylic acid as a white solid. $^1$H NMR (300 MHz, Chloroform-d) δ 7.51-7.54 (m, 1H), 7.37-7.39 (m, 1H), 7.33 (s, 1H), 5.67-5.78 (m, 1H), 4.34-3.38 (m, 1H), 4.16-4.20 (m, 1H), 3.82-3.93 (m, 2H), 3.56-3.67 (m, 6H), 3.00-3.03 (m, 2H), 2.90-2.94 (m, 1H), 2.56 (br, 4H). LCMS (ESI, m/z): 568 [M+H]$^+$.

Example 76: 2-(2-((4-(((1,1,1,3,3,3-hexafluoropropan-2-yl)oxy)carbonyl)piperazin-1-yl)methyl)-5-(trifluoromethyl)phenyl)-2-oxoacetic acid

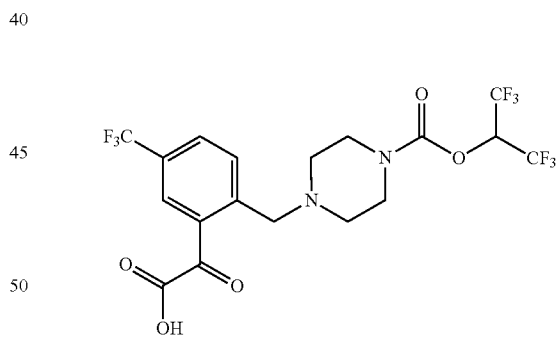

Step 1: Preparation of tert-butyl 4-(2-bromo-4-(trifluoromethyl)benzyl)piperazine-1-carboxylate

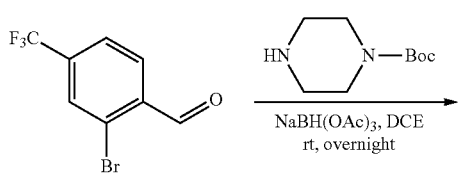

-continued

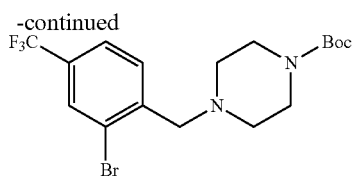

A 100-mL round-bottom flask was charged with 2-bromo-4-(trifluoromethyl)benzaldehyde (1.10 g, 4.35 mmol, 1.00 equiv), tert-butyl piperazine-1-carboxylate (1.06 g, 5.69 mmol, 1.30 equiv), and 1.2-dichloroehane (10 mL). The mixture was stirred for 1 h at room temperature. Sodium triacetoxyborohydride (2.78 g, 13.1 mmol, 3.00 equiv) was added. The resulting solution was stirred overnight at room temperature and quenched with water (15 mL). The mixture was extracted with dichloromethane (3×20 mL) and the organic layers were combined, washed with brine (1×60 mL), dried over anhydrous sodium sulfate, filtered and concentrated under reduced pressure. The residue was chromatographed on a silica gel column with ethyl acetate/petroleum ether (1/4) to provide 1.40 g (76% yield) of tert-butyl 4-(2-bromo-4-(trifluoromethyl)benzyl)piperazine-1-carboxylate as colorless oil. LCMS (ESI, m/z): 423 [M+H]⁺.

Step 2: Preparation of tert-butyl 4-(2-(2-ethoxy-2-oxoacetyl)-4-(trifluoromethyl)benzyl)piperazine-1-carboxylate

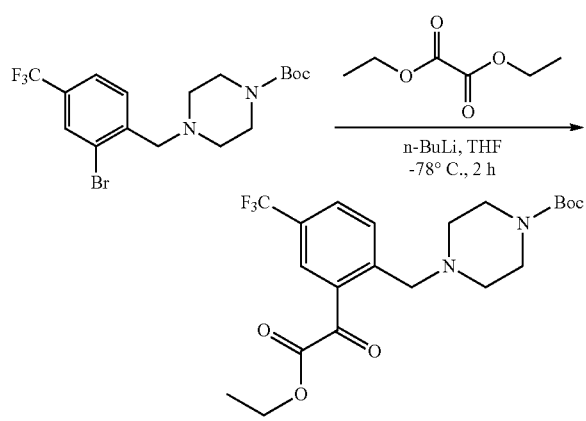

A 50-mL round-bottom flask was charged with tert-butyl 4-[[2-bromo-4-(trifluoromethyl)benzyl]piperazine-1-carboxylate (0.360 g, 0.850 mmol, 1.00 equiv) and tetrahydrofuran (8 mL) under nitrogen. The mixture was cooled to −78° C. n-Butyllithium (2.5 M in hexane, 0.52 mL, 1.28 mmol, 1.50 equiv) was added at −78° C. The mixture was stirred for 1 h at −78° C. and diethyl oxalate (1.99 g, 13.6 mmol, 16.00 equiv) was added. The resulting solution was stirred for 2 h at −78° C. and quenched with saturated ammonium chloride aqueous solution (10 mL). The resulting solution was extracted with dichloromethane (3×15 mL) and the organic layers were combined, washed with brine (1×50 mL), dried over anhydrous sodium sulfate, filtered and concentrated under reduced pressure. The residue was chromatographed on a silica gel column with ethyl acetate/petroleum ether (1/5) to provide 0.0850 g (22% yield) of 4-(2-(2-ethoxy-2-oxoacetyl)-4-(trifluoromethyl)benzyl)piperazine-1-carboxylate as a light yellow solid. LCMS (ESI, m/z): 445 [M+H]⁺.

Step 3: Preparation of 2-(2-((4-(tert-butoxycarbonyl)piperazin-1-yl)methyl)-5-(trifluoromethyl)phenyl)-2-oxoacetic acid

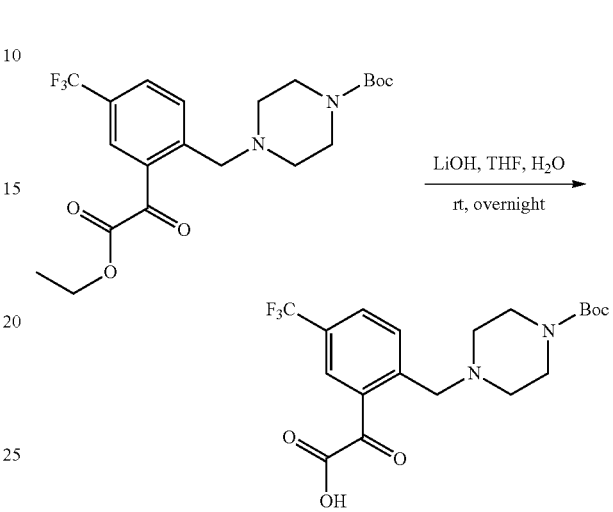

A 50-mL round-bottom flask was charged with tert-butyl 4-[[2-(2-ethoxy-2-oxoacetyl)-4-(trifluoromethyl)phenyl]methyl]piperazine-1-carboxylate (70.0 mg, 0.160 mmol, 1.00 equiv), tetrahydrofuran (4 mL), lithium hydroxide (37.8 mg, 1.58 mmol, 10.00 equiv), and water (1 mL). The resulting solution was stirred overnight at room temperature and quenched with water (5 mL). The pH of the solution was adjusted to 5 with hydrochloric acid (1M). The resulting solution was extracted with ethyl acetate (3×10 mL) and the organic layers were combined, washed with brine (1×20 mL), dried over anhydrous sodium sulfate, filtered and concentrated under reduced pressure to provide 65.0 mg (99% yield) of 2-(2-((4-(tert-butoxycarbonyl)piperazin-1-yl)methyl)-5-(trifluoromethyl)phenyl)-2-oxoacetic acid as colorless oil. LCMS (ESI, m/z): 417 [M+H]⁺.

Step 4: Preparation of 2-oxo-2-(2-(piperazin-1-ylmethyl)-5-(trifluoromethyl)phenyl)acetic acid

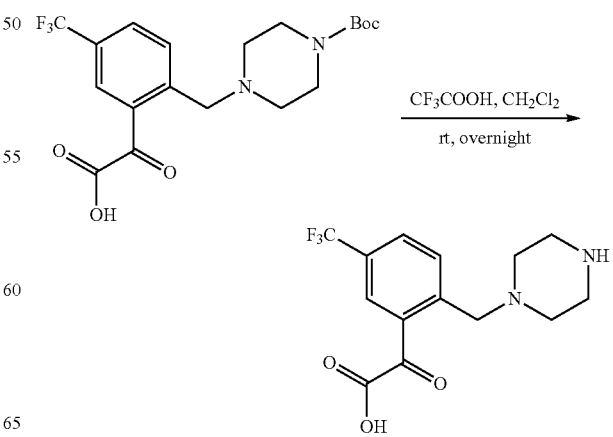

A 50-mL round-bottom flask was charged with 2-[2-([4-[(tert-butoxy)carbonyl]piperazin-1-yl]methyl)-5-(trifluoromethyl)phenyl]-2-oxoacetic acid (65.0 mg, 0.160 mmol, 1.00 equiv), dichloromethane (8 mL), and trifluoroacetic acid (2 mL). The resulting solution was stirred overnight at room temperature and concentrated under reduced pressure to provide 100 mg (crude) of 2-oxo-2-(2-(piperazin-1-ylmethyl)-5-(trifluoromethyl)phenyl)acetic acid as colorless oil. LCMS (ESI, m/z): 317 [M+H]+.

Step 5: Preparation of 2-(2-((4-(((1,1,1,3,3,3-hexafluoropropan-2-yl)oxy)carbonyl)piperazin-1-yl)methyl)-5-(trifluoromethyl)phenyl)-2-oxoacetic acid

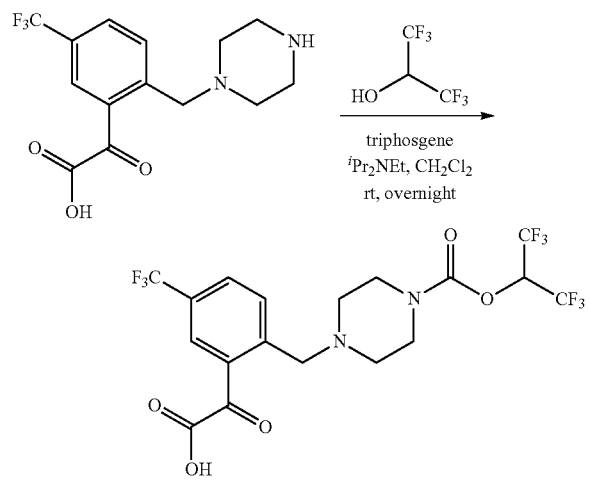

A 50-mL round-bottom flask was charged with triphosgene (31.6 mg, 0.110 mmol, 0.70 equiv), and dichloromethane (8 mL). 1,1,1,3,3,3-hexafluoropropan-2-ol (51.0 mg, 0.300 mmol, 2.00 equiv) was added at 0° C. N,N-Diisopropylethylamine (78.4 mg, 0.610 mmol, 4.00 equiv) was added at 0° C. The mixture was stirred for 2 h at room temperature. 2-oxo-2-(2-(piperazin-1-ylmethyl)-5-(trifluoromethyl)phenyl)acetic acid (48.0 mg, 0.150 mmol, 1.00 equiv) was added. The resulting solution was stirred overnight at room temperature and quenched with water (10 mL). The resulting mixture was extracted with dichloromethane (3×15 mL) and the organic layers were combined, washed with brine (1×50 mL), dried over anhydrous sodium sulfate, filtered and concentrated under reduced pressure. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm 5 um; Mobile phase: Phase A: aqueous NH$_4$HCO$_3$ (0.05%); Phase B: CH$_3$CN; Detector, UV220 & 254 nm. Purification resulted in 21.1 mg (27% yield) of 2-(2-((4-(((1,1,1,3,3,3-hexafluoropropan-2-yl)oxy)carbonyl)piperazin-1-yl)methyl)-5-(trifluoromethyl)phenyl)-2-oxoacetic acid as a white solid. $^1$H NMR (300 MHz, Chloroform-d) δ 8.18 (br, 2H), 7.66 (br, 1H), 5.62-5.75 (m, 1H), 3.47 (br, 6H), 2.36 (br, 4H). LCMS (ESI, m/z): 511 [M+H]+.

Example 77: (5-((4-(((1,1,1,3,3,3-hexafluoropropan-2-yl)oxy)carbonyl)piperazin-1-yl)methyl)-2-(trifluoromethyl)phenyl)proline

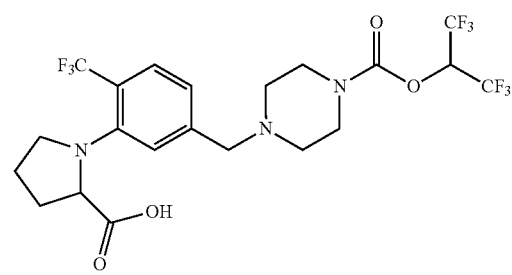

Step 1: Preparation of tert-butyl 4-(3-(2-(ethoxycarbonyl)pyrrolidin-1-yl)-4-(trifluoromethyl)benzyl)piperazine-1-carboxylate

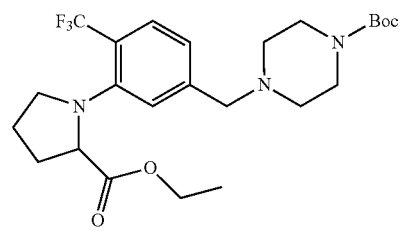 [SMILES: CCOC(=O)C1CCCN1c1cc(CN2CCN(C(=O)OC(C)(C)C)CC2)ccc1C(F)(F)F]

The listed intermediate was prepared according to the representative procedure of Example 52, Steps 1-2, using ethyl prolinate in Step 2 to provide tert-butyl 4-(3-(2-(ethoxycarbonyl)pyrrolidin-1-yl)-4-(trifluoromethyl)benzyl)piperazine-1-carboxylate as yellow oil. LCMS (ESI, m/z): 486 [M+H]+.

Step 2: Preparation of (5-((4-(tert-butoxycarbonyl)piperazin-1-yl)methyl)-2-(trifluoromethyl)phenyl)proline

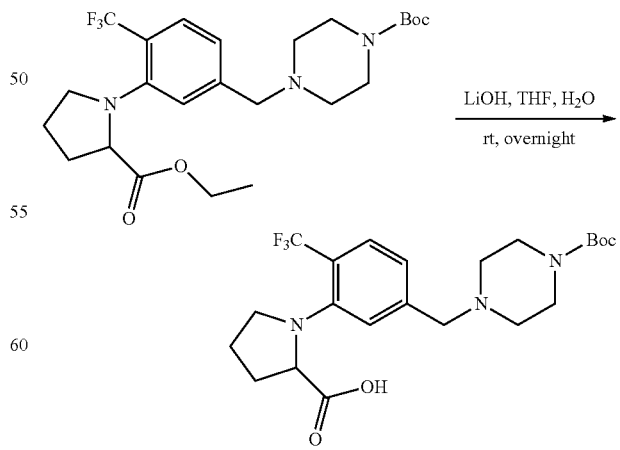

A 100-mL round-bottom flask was charged with tert-butyl tert-butyl 4-(3-(2-(ethoxycarbonyl)pyrrolidin-1-yl)-4-(trifluoromethyl)benzyl)piperazine-1-carboxylate (200 mg, 0.410 mmol, 1.00 equiv), tetrahydrofuran (10 mL), water (2 mL), and lithium hydroxide (98.4 mg, 4.11 mmol, 10.0 equiv). The resulting solution was stirred overnight at room temperature and quenched with water (10 mL). The pH of the solution was adjusted to 5 with hydrochloric acid (1M, 3 mL). The resulting solution was extracted with ethyl acetate (3×15 mL) and the organic layers were combined, washed with brine (1×50 mL), dried over anhydrous sodium sulfate, filtered and concentrated under reduced pressure to provide 180 mg (96% yield) of (5-((4-(tert-butoxycarbonyl) piperazin-1-yl)methyl)-2-(trifluoromethyl)phenyl)proline as yellow oil. LCMS (ESI, m/z): 458 [M+H]$^+$.

Step 3: Preparation of (5-((4-(((1,1,1,3,3,3-hexafluoropropan-2-yl)oxy)carbonyl)piperazin-1-yl) methyl)-2-(trifluoromethyl)phenyl)proline The title compound was prepared from (5-((4-(tert-butoxycarbonyl)piperazin-1-yl)methyl)-2-(trifluoromethyl) phenyl)proline according to the representative procedure of Example 52, Steps 3-4 to provide (5-((4-(((1,1,1,3,3,3-hexafluoropropan-2-yl)oxy)carbonyl)piperazin-1-yl) methyl)-2-(trifluoromethyl)phenyl)proline as a white solid. $^1$H NMR (300 MHz, Methanol-d$_4$) δ 7.50 (s, 1H), δ 7.18 (s, 1H), 6.93-6.96 (m, 1H), 6.08-6.21 (m, 1H), 4.38 (t, J=6.3 Hz, 1H), 3.71-3.79 (m, 1H), 3.55-3.62 (m, 6H), 3.23-3.27 (m, 1H), 2.37-2.50 (m, 5H), 1.91-2.13 (m, 3H). LCMS (ESI, m/z): 552 [M+H]$^+$.

Example 78: 1,1,1,3,3,3-hexafluoropropan-2-yl 4-(3-(2-(ethoxycarbonyl)pyrrolidin-1-yl)-4-(trifluoromethyl)benzyl)piperazine-1-carboxylate

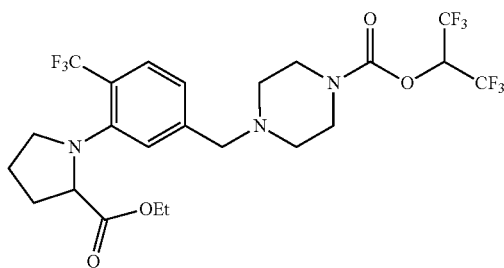 [SMILES: CCOC(=O)C1CCCN1c1cc(CN2CCN(C(=O)OC(C(F)(F)F)C(F)(F)F)CC2)ccc1C(F)(F)F]

The title compound was prepared from 3-bromo-4-(trifluoromethyl)benzaldehyde according to the representative procedure of Example 52, Steps 1-4, using ethyl prolinate in Step 2 to provide 1,1,1,3,3,3-hexafluoropropan-2-yl 4-(3-(2-(ethoxycarbonyl)pyrrolidin-1-yl)-4-(trifluoromethyl)benzyl)piperazine-1-carboxylate as a light yellow oil. $^1$H NMR (300 MHz, Chloroform-d) δ 7.51 (s, 1H), δ 7.09 (s, 1H), 6.93 (d, J=6.0 Hz, 1H), 5.71-5.79 (m, 1H), 4.42-4.46 (m, 1H), 4.01-4.08 (m, 2H), 3.68-3.76 (m, 1H), 3.46-3.57 (m, 6H), 3.22-3.29 (m, 1H), 2.35-2.45 (m, 5H), 1.89-2.14 (m, 3H), 1.12 (t, J=6.9 Hz, 3H). LCMS (ESI, m/z): 580 [M+H]$^+$.

Example 79: 1,1,1,3,3,3-hexafluoropropan-2-yl 4-(3-(2-(hydroxymethyl)pyrrolidin-1-yl)-4-(trifluoromethyl)benzyl)piperazine-1-carboxylate

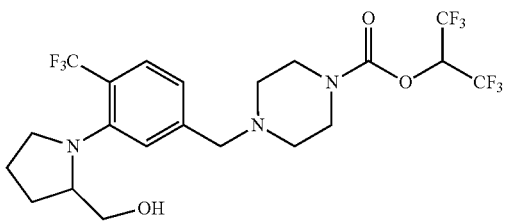 [SMILES: O=C(OC(C(F)(F)F)C(F)(F)F)N1CCN(Cc2ccc(C(F)(F)F)c(N3CCCC3CO)c2)CC1]

The title compound was prepared from 3-bromo-4-(trifluoromethyl)benzaldehyde according to the representative procedure of Example 52, Steps 1-4, using pyrrolidin-2-ylmethanol in Step 2 to provide 1,1,1,3,3,3-hexafluoropropan-2-yl 4-(3-(2-(hydroxymethyl)pyrrolidin-1-yl)-4-(trifluoromethyl)benzyl)piperazine-1-carboxylate as a yellow oil. $^1$H NMR (300 MHz, Chloroform-d) δ 7.57 (s, 1H), δ 7.32 (s, 1H), 7.12 (d, J=8.1 Hz, 1H), 5.69-5.81 (m, 1H), 3.77 (br, 1H), 3.50-3.58 (m, 8H), 3.40-3.50 (m, 1H), 2.87-2.95 (m, 1H), 2.46 (br, 4H), 1.81-2.24 (m, 5H). LCMS (ESI, m/z): 538 [M+H]$^+$.

Example 80: 1-(5-((4-(((1,1,3,3,3-hexafluoropropan-2-yl)oxy)carbonyl)piperazin-1-yl)methyl)-2-(trifluoromethyl)phenyl)pyrrolidine-3-carboxylic acid

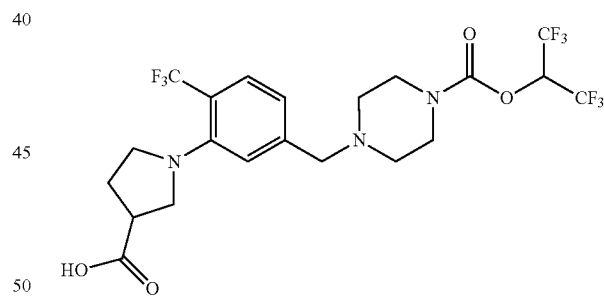

The title compound was prepared according to the representative procedure of Example 77, using methyl pyrrolidine-3-carboxylate in Step 1, to provide 1-(5-((4-(((1,1,1,3,3,3-hexafluoropropan-2-yl)oxy)carbonyl)piperazin-1-yl) methyl)-2-(trifluoromethyl)phenyl)pyrrolidine-3-carboxylic acid as a white solid. $^1$H NMR (300 MHz, Methanol-d$_4$) δ 7.59 (d, J=8.1 Hz, 1H), δ 7.23 (s, 1H), 7.02 (d, J=8.1 Hz, 1H), 6.12-6.25 (m, 1H), δ 3.84 (s, 2H), 3.78 (br, 4H), 3.58-3.68 (m, 2H), 3.31-3.42 (m, 2H), 3.14-3.24 (m, 1H), 2.79 (br, 4H), 2.20-2.28 (m, 2H). LCMS (ESI, m/z): 552 [M+H]$^+$.

Example 81: 1,1,1,3,3,3-hexafluoropropan-2-yl 4-(3-(3-(hydroxymethyl)pyrrolidin-1-yl)-4-(trifluoromethyl)benzyl)piperazine-1-carboxylate

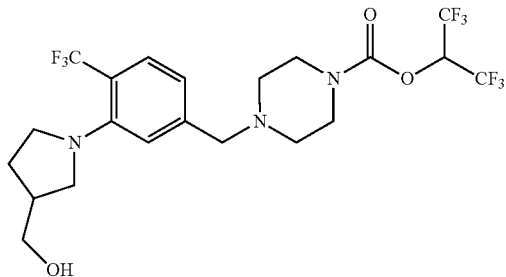 [SMILES: O=C(OC(C(F)(F)F)C(F)(F)F)N1CCN(Cc2ccc(C(F)(F)F)c(N3CCC(CO)C3)c2)CC1]

The title compound was prepared according to the representative procedure of Example 52, Steps 1-4 using 3-bromo-4-(trifluoromethyl)benzaldehyde in Step 1 and pyrrolidin-3-ylmethanol in Step 2 to provide 1,1,1,3,3,3-hexafluoropropan-2-yl 4-(3-(3-(hydroxymethyl)pyrrolidin-1-yl)-4-(trifluoromethyl)benzyl)piperazine-1-carboxylate as a yellow oil. $^1$H NMR (300 MHz, Chloroform-d) δ 7.52 (s, 1H), δ 7.02 (s, 1H), 6.90 (d, J=8.1 Hz, 1H), 5.71-5.79 (m, 1H), 3.67-3.76 (m, 2H), 3.51-3.64 (m, 6H), 3.18-3.43 (m, 4H), 2.47-2.56 (m, 5H), 2.01-2.17 (m, 1H), 1.73-1.85 (m, 2H). LCMS (ESI, m/z): 538 [M+H]$^+$.

Example 82: 1,1,1,3,3,3-hexafluoropropan-2-yl 4-(3-(4-(hydroxymethyl)piperidin-1-yl)-4-(trifluoromethyl)benzyl)piperazine-1-carboxylate

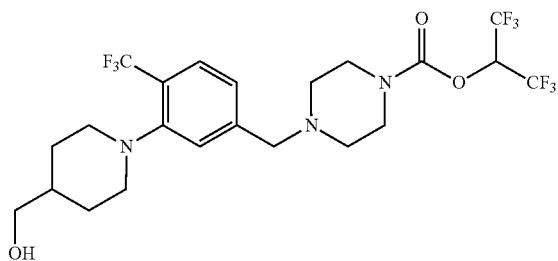 [SMILES: O=C(OC(C(F)(F)F)C(F)(F)F)N1CCN(Cc2ccc(C(F)(F)F)c(N3CCC(CO)CC3)c2)CC1]

The title compound was prepared according to the representative procedure of Example 52, Steps 1-4 using 3-bromo-4-(trifluoromethyl)benzaldehyde in Step 1 and piperidin-4-ylmethanol in Step 2 to provide 1,1,1,3,3,3-hexafluoropropan-2-yl 4-(3-(4-(hydroxymethyl)piperidin-1-yl)-4-(trifluoromethyl)benzyl)piperazine-1-carboxylate as a yellow oil. $^1$H NMR (300 MHz, Chloroform-d) δ 7.56 (d, J=8.1 Hz, 1H), 7.36 (s, 1H), 7.15 (d, J=7.8 Hz, 1H), 5.68-5.81 (m, 1H), 3.33-3.80 (m, 8H), 3.09-3.13 (m, 2H), 2.69-2.76 (m, 2H), 2.47 (br, 4H), 1.78-1.82 (m, 2H), 1.58-1.69 (m, 1H), 1.43-1.51 (m, 3H). LCMS (ESI, m/z): 552 [M+H]$^+$.

Example 83: 4-(5-((4-(((1,1,1,3,3,3-hexafluoropropan-2-yl)oxy)carbonyl)piperazin-1-yl)methyl)-2-(trifluoromethyl)phenyl)morpholine-2-carboxylic acid

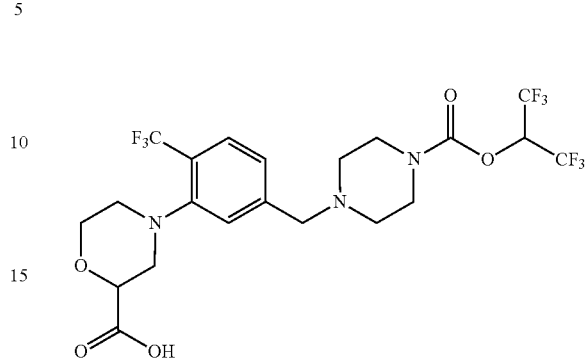

The title compound was prepared according to the representative procedure of Example 77, using 3-bromo-4-(trifluoromethyl)benzaldehyde and methyl morpholine-2-carboxylate in Step 1 to provide 4-(5-((4-(((1,1,1,3,3,3-hexafluoropropan-2-yl)oxy)carbonyl)piperazin-1-yl)methyl)-2-(trifluoromethyl)phenyl)morpholine-2-carboxylic acid as a white solid. $^1$H NMR (300 MHz, Methanol-d$_4$) δ 7.62 (d, J=8.1 Hz, 1H), 7.50 (s, 1H), 7.32 (d, J=8.1 Hz, 1H), 6.09-6.18 (m, 1H), 4.16-4.19 (m, 1H), 4.05-4.08 (m, 1H), 3.77-3.84 (m, 1H), 3.58-3.62 (m, 6H), 3.26-3.32 (m, 1H), 2.83-2.95 (m, 3H), 2.50 (br, 4H). LCMS (ESI, m/z): 568 [M+H]$^+$.

Example 84: 2-(5-((4-(((1,1,1,3,3,3-hexafluoropropan-2-yl)oxy)carbonyl)piperazin-1-yl)methyl)-2-(trifluoromethyl)phenyl)-2-oxoacetic acid

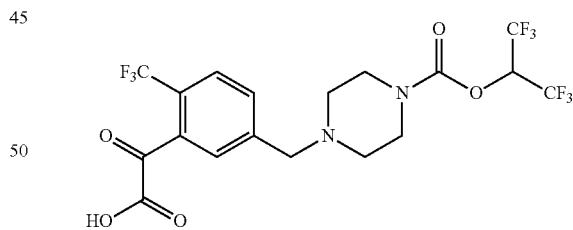

The title compound was prepared according to the representative procedure of Example 76, using 3-bromo-4-(trifluoromethyl) benzaldehyde in Step 1 to provide 2-(5-((4-(((1,1,1,3,3,3-hexafluoropropan-2-yl)oxy)carbonyl) piperazin-1-yl)methyl)-2-(trifluoromethyl)phenyl)-2-oxoacetic acid as a white solid. $^1$H NMR (300 MHz, Methanol-d$_4$) δ 7.75-7.79 (m, 2H), 7.65-7.68 (m, 1H), 6.08-6.21 (m, 1H), 3.66 (s, 2H), 3.56-3.61 (m, 4H), 2.47-2.53 (m, 4H). LCMS (ESI, m/z): 511 [M+H]$^+$.

Example 85: 1-(5-((4-(((1,1,1,3,3,3-hexafluoropropan-2-yl)oxy)carbonyl)piperazin-1-yl)methyl)-2-(trifluoromethyl)phenyl)piperidine-4-carboxylic acid

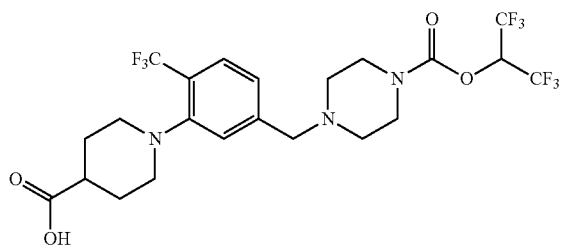 [SMILES: O=C(O)C1CCN(c2cc(CN3CCN(C(=O)OC(C(F)(F)F)C(F)(F)F)CC3)ccc2C(F)(F)F)CC1]

The title compound was prepared according to the representative procedure of Example 77, using 3-bromo-4-(trifluoromethyl)benzaldehyde and ethyl piperidine-4-carboxylate in Step 1 to provide 1-(5-((4-(((1,1,1,3,3,3-hexafluoropropan-2-yl)oxy)carbonyl)piperazin-1-yl)methyl)-2-(trifluoromethyl)phenyl)piperidine-4-carboxylic acid as a white solid. $^1$H NMR (300 MHz, Methanol-$d_4$) δ 7.58 (d, J=7.8 Hz, 1H), 7.46 (s, 1H), 7.26 (d, J=8.1 Hz, 1H), 6.12-6.16 (m, 1H), 3.60 (s, 6H), 3.03-3.07 (m, 2H), 2.77-2.84 (m, 2H), 2.38-2.49 (m, 5H), 1.83-1.99 (m, 4H). LCMS (ESI, m/z): 566 [M+H]$^+$.

Example 86: (3-((4-(((1,1,1,3,3,3-hexafluoropropan-2-yl)oxy)carbonyl)piperazin-1-yl)methyl)-5-(trifluoromethyl)phenyl)proline

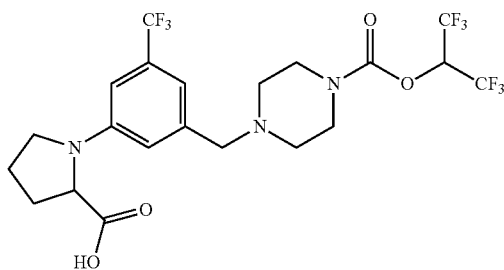 [SMILES: O=C(O)C1CCCN1c1cc(CN2CCN(C(=O)OC(C(F)(F)F)C(F)(F)F)CC2)cc(C(F)(F)F)c1]

Step 1: Preparation of 1-(tert-butyl) 4-(1,1,1,3,3,3-hexafluoropropan-2-yl) piperazine-1,4-dicarboxylate

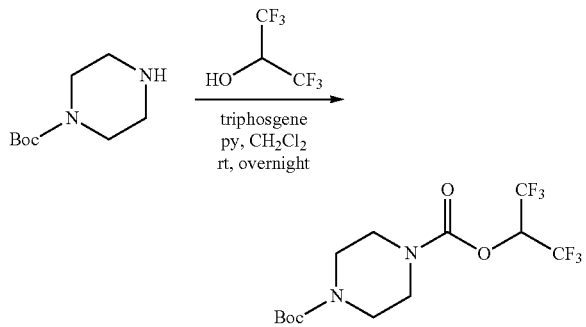

A 250-mL round-bottom flask was charged with triphosgene (5.60 g, 18.9 mmol, 0.70 equiv), and dichloromethane (50 mL). 1,1,1,3,3,3-hexafluoropropan-2-ol (9.00 g, 53.6 mmol, 2.00 equiv) was added at 0° C. Pyridine (12.7 g, 161 mmol, 6.00 equiv) was added at 0° C. The mixture was stirred for 2 h at room temperature. tert-Butyl piperazine-1-carboxylate (5.00 g, 26.9 mmol, 1.00 equiv) was added. The resulting solution was stirred overnight at room temperature and then quenched with water (30 mL). The resulting mixture was extracted with dichloromethane (3×30 mL) and the organic layers were combined, washed with brine (1×100 mL), dried over anhydrous sodium sulfate, filtered and concentrated under reduced pressure. The residue was chromatographed on a silica gel column with ethyl acetate/petroleum ether (15/85) to provide 9.20 g (90% yield) of 1-tert-butyl 4-(1,1,1,3,3,3-hexafluoropropan-2-yl) piperazine-1,4-dicarboxylate as a yellow solid. LCMS (ESI, m/z): 381 [M+H]$^+$.

Step 2: Preparation of 1,1,1,3,3,3-hexafluoropropan-2-yl piperazine-1-carboxylate

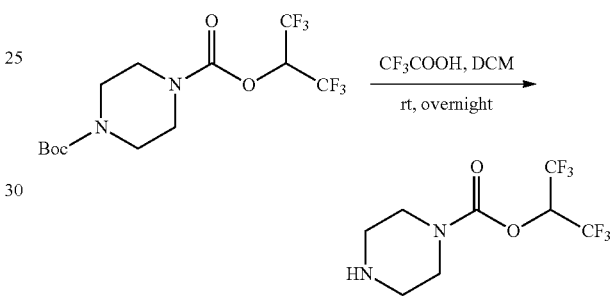

A 40-mL round-bottom flask was charged with 1-tert-butyl 4-(1,1,1,3,3,3-hexafluoropropan-2-yl) piperazine-1,4-dicarboxylate (433 mg, 1.14 mmol, 1.00 equiv), dichloromethane (5 mL), and trifluoroacetic acid (2 mL). The resulting solution was stirred overnight at room temperature and concentrated under reduced pressure to afford 500 mg (crude) of 1,1,1,3,3,3-hexafluoropropan-2-yl piperazine-1-carboxylate as colorless oil. LCMS (ESI, m/z): 281 [M+H]$^+$.

Step 3: Preparation of ethyl (3-formyl-5-(trifluoromethyl)phenyl)prolinate

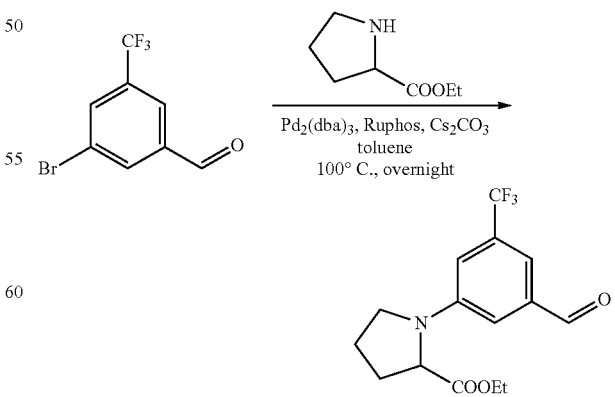

A 100-mL round-bottom flask was charged with 3-bromo-5-(trifluoromethyl)benzaldehyde (1.01 g, 3.99 mmol, 1.00 equiv), ethyl pyrrolidine-2-carboxylate (0.686 g, 4.79 mmol, 1.20 equiv), tris(dibenzylideneacetone)dipalladium (0.182 g, 0.199 mmol, 0.05 equiv), dicyclohexyl(2',6'-diisopropoxybiphenyl-2-yl)phosphine (0.372 g, 0.798 mmol, 0.20 equiv), cesium carbonate (3.91 g, 12.0 mmol, 3.00 equiv), and toluene (10 mL) under nitrogen. The resulting solution was stirred overnight at 100° C. and quenched with water (20 mL). The mixture was extracted with ethyl acetate (3×30 mL) and the organic layers were combined, washed with brine (3×30 mL), dried over anhydrous sodium sulfate, filtered and concentrated under reduced pressure. The residue was chromatographed on a silica gel column with ethyl acetate/petroleum ether (1/9) to provide 0.480 g (38% yield) of ethyl 1-[3-formyl-5-(trifluoromethyl)phenyl]pyrrolidine-2-carboxylate as yellow oil. LCMS (ESI, m/z): 316 [M+H]$^+$.

Step 4: Preparation of (3-formyl-5-(trifluoromethyl)phenyl)proline

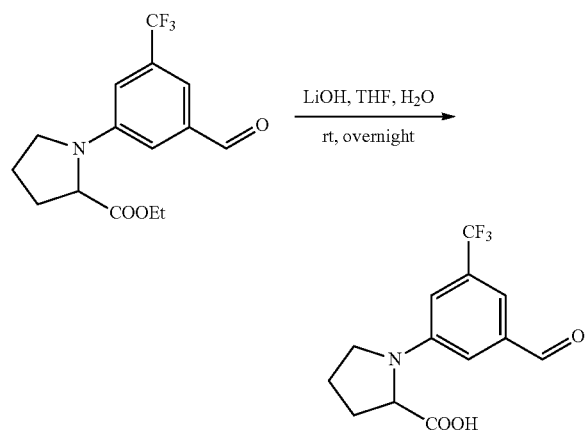

A 40-mL round-bottom flask was charged with ethyl 1-[3-formyl-5-(trifluoromethyl)phenyl]pyrrolidine-2-carboxylate (300 mg, 0.952 mmol, 1.00 equiv), lithium hydroxide (114 mg, 4.76 mmol, 5.00 equiv), tetrahydrofuran (3 mL), and water (1 mL). The resulting solution was stirred overnight at room temperature. The pH of the solution was adjusted to 5 with hydrochloric acid (1M, 5 mL). The mixture was extracted with dichloromethane (3×30 mL) and the organic layers were combined, washed with brine (3×30 mL), dried over anhydrous sodium sulfate, filtered and concentrated under reduced pressure to provide 250 mg (91% yield) of 1-[3-formyl-5-(trifluoromethyl)phenyl]pyrrolidine-2-carboxylic acid as yellow oil. LCMS (ESI, m/z): 288 [M+H]$^+$.

Step 5: Preparation of (3-((4-(((1,1,1,3,3,3-hexafluoropropan-2-yl)oxy)carbonyl)piperazin-1-yl)methyl)-5-(trifluoromethyl)phenyl)proline

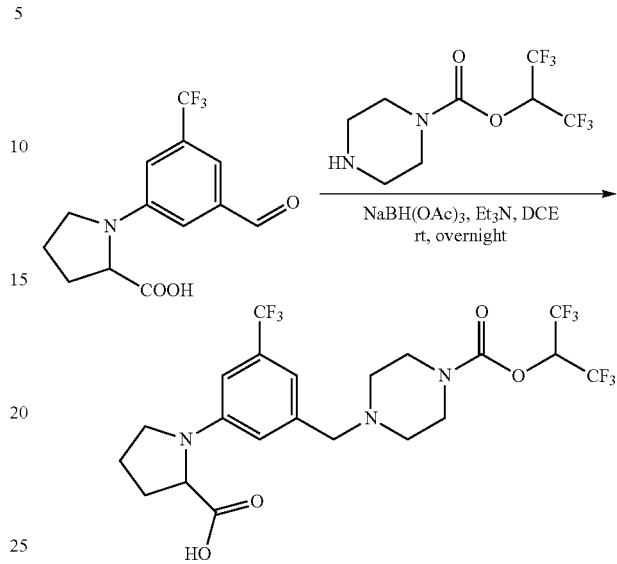

A 40-mL round-bottom flask was charged with 1-[3-formyl-5-(trifluoromethyl)phenyl]pyrrolidine-2-carboxylic acid (155 mg, 0.540 mmol, 1.00 equiv), 1,1,1,3,3,3-hexafluoropropan-2-yl piperazine-1-carboxylate (179 mg, 0.648 mmol, 1.20 equiv), and 1,2-dichloroethane (5 mL), triethylamine (164 mg, 1.62 mmol, 3.00 equiv). The resulting solution was stirred for 2 h at room temperature. Sodium triacetoxyborohydride (343 mg, 1.62 mmol, 3.00 equiv) was added. The resulting solution was stirred overnight at room temperature and quenched with water (20 mL). The mixture was extracted with dichloromethane (3×30 mL) and the organic layers were combined, washed with brine (3×30 mL), dried over anhydrous sodium sulfate, filtered and concentrated under reduced pressure. The crude product (300 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm 5 um; Mobile phase: Phase A: aqueous NH$_4$HCO$_3$ (0.05%); Phase B: CH$_3$CN; Detector, UV220 & 254 nm. Purification resulted in 52.1 mg (18% yield) of (3-((4-(((1,1,1,3,3,3-hexafluoropropan-2-yl)oxy)carbonyl)piperazin-1-yl)methyl)-5-(trifluoromethyl)phenyl)proline as a white solid. $^1$H NMR (300 MHz, Methanol-d$_4$) δ 6.89 (s, 1H), 6.77 (s, 1H), 6.67 (s, 1H), 6.09-6.18 (m, 1H), 4.18-4.22 (m, 1H), 3.57 (br, 7H), 3.31-3.57 (m, 1H), 2.51-2.52 (m, 4H), 2.33-2.40 (m, 1H), 2.07-2.22 (m, 3H). LCMS (ESI, m/z): 552 [M+H]$^+$.

Example 87: 1,1,1,3,3,3-hexafluoropropan-2-yl 4-(3-(2-(ethoxycarbonyl)pyrrolidin-1-yl)-5-(trifluoromethyl)benzyl)piperazine-1-carboxylate

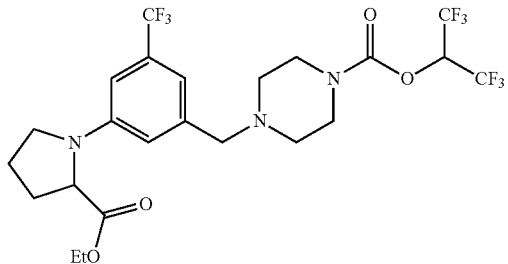

The title compound was prepared according to the representative procedure of Example 86, Steps 1, 2, 4 and 5, using ethyl prolinate in Step 3 to provide 1,1,1,3,3,3-hexafluoropropan-2-yl 4-(3-(2-(ethoxycarbonyl)pyrrolidin-1-yl)-5-(trifluoromethyl)benzyl)piperazine-1-carboxylate as a light yellow oil. $^1$H NMR (300 MHz, Chloroform-d) δ 6.91 (s, 1H), 6.66 (s, 2H), 5.72-5.78 (m, 1H), 4.10-4.29 (m, 3H), 3.52-3.63 (m, 7H), 3.37-3.45 (m, 1H), 2.48 (br, 4H), 2.07-2.35 (m, 4H), 1.26 (t, J=7.2 Hz, 3H). LCMS (ESI, m/z): 580 [M+H]$^+$.

Example 88: 1,1,1,3,3,3-hexafluoropropan-2-yl 4-(3-(2-(hydroxymethyl)pyrrolidin-1-yl)-5-(trifluoromethyl)benzyl)piperazine-1-carboxylate

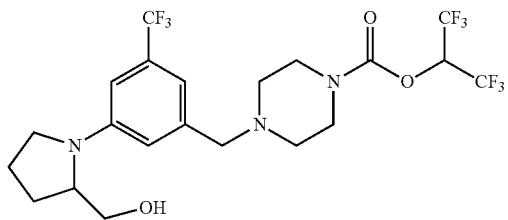 [SMILES: O=C(OC(C(F)(F)F)C(F)(F)F)N1CCN(Cc2cc(N3CCCC3CO)cc(C(F)(F)F)c2)CC1]

The title compound was prepared according to the representative procedure of Example 86, Steps 1, 2, 4 and 5, using pyrrolidin-2-ylmethanol in Step 3 to provide 1,1,1,3,3,3-hexafluoropropan-2-yl 4-(3-(2-(hydroxymethyl)pyrrolidin-1-yl)-5-(trifluoromethyl)benzyl)piperazine-1-carboxylate as a light yellow oil. $^1$H NMR (400 MHz, Chloroform-d) δ 6.88 (s, 1H), 6.83 (br, 1H), 6.77 (s, 1H), 5.70-5.79 (m, 1H), 3.91 (br, 1H), 3.50-3.91 (m, 9H), 3.15-3.21 (m, 1H), 2.61 (br, 4H), 1.98-2.17 (m, 4H). LCMS (ESI, m/z): 538 [M+H]$^+$.

Example 89: 1-(3-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid

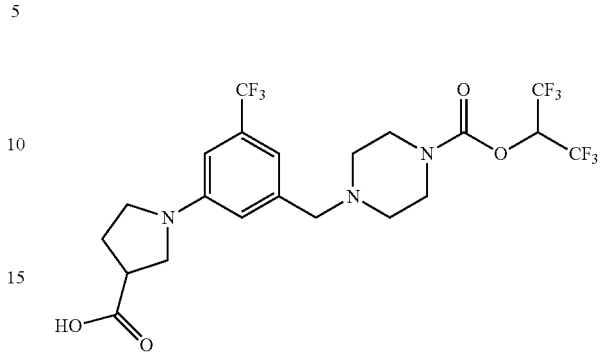

The title compound was prepared according to the representative procedure of Example 77, Steps 1-5, using 3-bromo-5-(trifluoromethyl)benzaldehyde in Step 1, and using methyl pyrrolidine-3-carboxylate in Step 2 as well as replacing the palladium coupling conditions of Step 2 with those used in Step 3 of Example 86 to provide 1-(3-((4-(((1,1,1,3,3,3-hexafluoropropan-2-yl)oxy)carbonyl)piperazin-1-yl)methyl)-5-(trifluoromethyl)phenyl)pyrrolidine-3-carboxylic acid as a light yellow solid. $^1$H NMR (400 MHz, Chloroform-d) δ 6.81 (s, 1H), 6.77 (s, 1H), 6.70 (s, 1H), 5.70-5.79 (m, 1H), 3.46-3.62 (m, 9H), 3.36-3.42 (m, 1H), 3.21-3.29 (m, 1H), 2.59 (br, 4H), 2.31-2.38 (m, 2H). LCMS (ESI, m/z): 552 [M+H]$^+$.

Example 90: 1,1,1,3,3,3-hexafluoropropan-2-yl 4-(3-(3-(hydroxymethyl)pyrrolidin-1-yl)-5-(trifluoromethyl)benzyl)piperazine-1-carboxylate

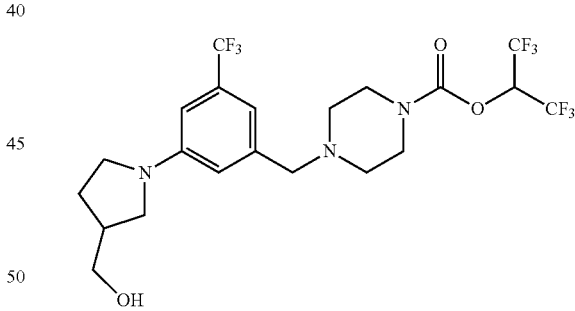

The title compound was prepared according to the representative procedure of Example 52, using 3-bromo-5-(trifluoromethyl)benzaldehyde in Step 1, and pyrrolidin-3-ylmethanol and Ruphos in Step 2 to provide 1,1,1,3,3,3-hexafluoropropan-2-yl 4-(3-(3-(hydroxymethyl)pyrrolidin-1-yl)-5-(trifluoromethyl)benzyl)piperazine-1-carboxylate as a yellow oil. $^1$H NMR (400 MHz, Chloroform-d) δ 6.86 (s, 1H), 6.65 (s, 2H), 5.71-5.76 (m, 1H), 3.72-3.76 (m, 2H), 3.69 (br, 4H), 3.67 (s, 2H), 3.31-3.47 (m, 3H), 3.15-3.19 (m, 1H), 2.58-2.64 (m, 1H), 2.45-2.48 (m, 4H), 2.15-2.19 (m, 1H), 1.83-1.88 (m, 1H). LCMS (ESI, m/z): 538 [M+H]$^+$.

Example 91: 1,1,1,3,3,3-hexafluoropropan-2-yl 4-(3-(4-(hydroxymethyl)piperidin-1-yl)-5-(trifluoromethyl)benzyl)piperazine-1-carboxylate

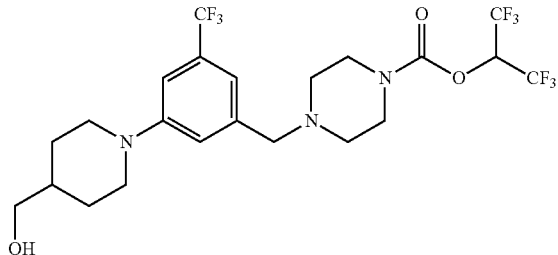 [SMILES: O=C(OC(C(F)(F)F)C(F)(F)F)N1CCN(Cc2cc(N3CCC(CO)CC3)cc(C(F)(F)F)c2)CC1]

The title compound was prepared according to the representative procedure of Example 52, using 3-bromo-5-(trifluoromethyl)benzaldehyde in Step 1, and piperidin-4-yl-methanol and Ruphos in Step 2 to provide 1,1,1,3,3,3-hexafluoropropan-2-yl 4-(3-(4-(hydroxymethyl)piperidin-1-yl)-5-(trifluoromethyl)benzyl)piperazine-1-carboxylate as a yellow oil. $^1$H NMR (400 MHz, Chloroform-d) δ 6.98-7.06 (m, 3H), 5.68-5.80 (m, 1H), 3.56-3.81 (m, 10H), 2.76-2.84 (m, 2H), 2.50 (br, 3H), 1.86-1.91 (m, 2H), 2.69-2.76 (m, 1H), 1.33-1.46 (m, 3H). LCMS (ESI, m/z): 552 [M+H]$^+$.

Example 92: 4-(3-((4-(((1,1,1,3,3,3-hexafluoropropan-2-yl)oxy)carbonyl)piperazin-1-yl)methyl)-5-(trifluoromethyl)phenyl)morpholine-2-carboxylic acid

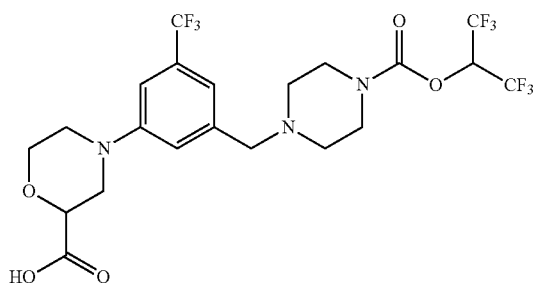 [SMILES: O=C(O)C1CN(c2cc(CN3CCN(C(=O)OC(C(F)(F)F)C(F)(F)F)CC3)cc(C(F)(F)F)c2)CCO1]

The title compound was prepared according to the representative procedure of Example 77, using 3-bromo-5-(trifluoromethyl)benzaldehyde in Step 1, and methyl morpholine-2-carboxylate and Ruphos in Step 2 to provide 4-(3-((4-(((1,1,1,3,3,3-hexafluoropropan-2-yl)oxy)carbonyl)piperazin-1-yl)methyl)-5-(trifluoromethyl)phenyl)morpholine-2-carboxylic acid as a white solid. $^1$H NMR (400 MHz, Chloroform-d) δ 7.12 (s, 1H), 7.00-7.06 (m, 2H), 5.69-5.78 (m, 1H), 4.22-4.24 (m, 2H), 3.82-3.89 (m, 2H), 3.60 (br, 5H), 3.41-3.44 (m, 2H), 2.93-2.95 (m, 2H), 2.56 (br, 4H). LCMS (ESI, m/z): 568 [M+H]$^+$.

Example 93: 2-(3-((4-(((1,1,1,3,3,3-hexafluoropropan-2-yl)oxy)carbonyl)piperazin-1-yl)methyl)-5-(trifluoromethyl)phenyl)-2-oxoacetic acid

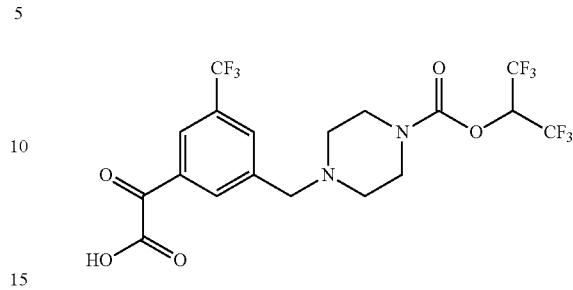

The title compound was prepared according to the representative procedure of Example 76, using 3-bromo-5-(trifluoromethyl)benzaldehyde in Step 1 to provide 2-(3-((4-(((1,1,1,3,3,3-hexafluoropropan-2-yl)oxy)carbonyl)piperazin-1-yl)methyl)-5-(trifluoromethyl)phenyl)-2-oxoacetic acid as a white solid. $^1$H NMR (300 MHz, Methanol-d$_4$) δ 8.20-8.26 (m, 2H), 7.97 (s, 1H), 6.15-6.19 (m, 1H), 3.74-3.79 (m, 2H), 3.63 (br, 4H), 2.59-2.66 (m, 4H). LCMS (ESI, m/z): 511 [M+H]$^+$.

Example 94: 1-(3-((4-(((1,1,1,3,3,3-hexafluoropropan-2-yl)oxy)carbonyl)piperazin-1-yl)methyl)-5-(trifluoromethyl)phenyl)piperidine-4-carboxylic acid

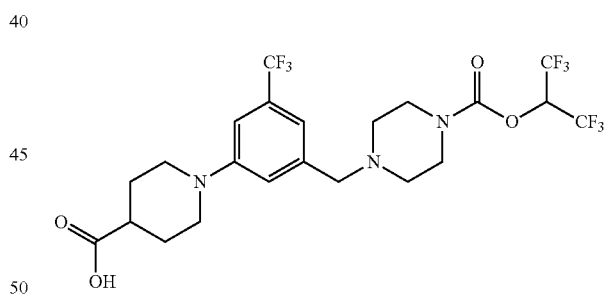

The title compound was prepared according to the representative procedure of Example 77, using 3-bromo-5-(trifluoromethyl)benzaldehyde in Step 1, and ethyl piperidine-4-carboxylate and Ruphos in Step 2 to provide 1-(3-((4-(((1,1,1,3,3,3-hexafluoropropan-2-yl)oxy)carbonyl)piperazin-1-yl)methyl)-5-(trifluoromethyl)phenyl)piperidine-4-carboxylic acid as a white solid. $^1$H NMR (300 MHz, Chloroform-d) δ 7.01-7.08 (m, 3H), 5.68-5.79 (m, 1H), 3.45-3.70 (m, 8H), 2.82-2.90 (m, 2H), 2.51 (br, 5H), 2.08-2.13 (m, 2H), 1.83-1.94 (m, 2H). LCMS (ESI, m/z): 566 [M+H]$^+$.

Example 95: 4-(2-((4-(((1,1,1,3,3,3-hexafluoropropan-2-yl)oxy)carbonyl)piperazin-1-yl)methyl)-5-(trifluoromethyl)phenyl)morpholine-3-carboxylic acid

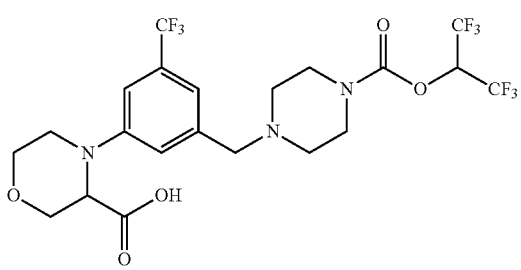 [SMILES: O=C(O)C1COCCN1c1cc(CN2CCN(C(=O)OC(C(F)(F)F)C(F)(F)F)CC2)cc(C(F)(F)F)c1]

Step 1: Preparation of methyl 4-(3-formyl-5-(trifluoromethyl)phenyl)morpholine-3-carboxylate

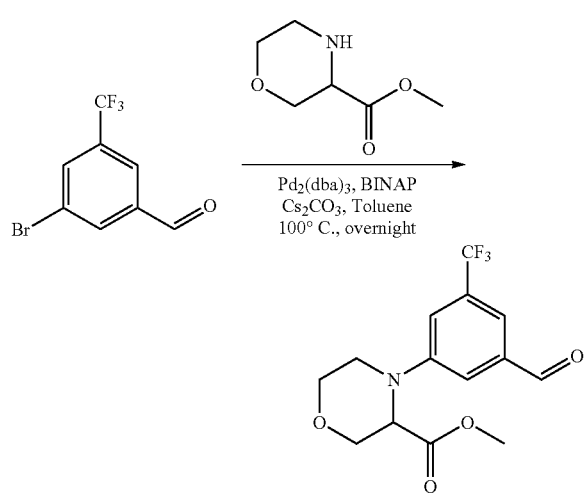

The listed intermediate was prepared directly from commercially available 3-bromo-5-(trifluoromethyl)benzaldehyde according to the representative procedure of Example 51, Step 4, using cesium carbonate to afford 4-(3-formyl-5-(trifluoromethyl)phenyl)morpholine-3-carboxylate. LCMS (ESI, m/z): 318 [M+H]+.

Step 2: Preparation of methyl 4-(3-((4-(tert-butoxycarbonyl)piperazin-1-yl)methyl)-5-(trifluoromethyl)phenyl)morpholine-3-carboxylate

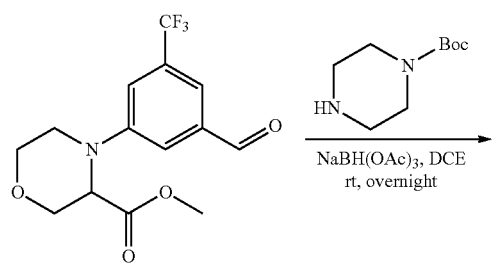

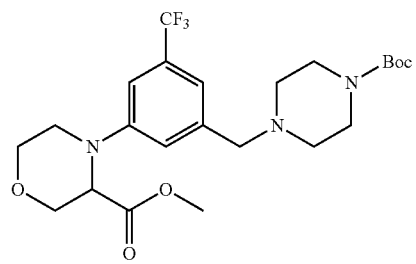

The listed intermediate was prepared from 4-(3-formyl-5-(trifluoromethyl)phenyl)morpholine-3-carboxylate according to the representative procedure of Example 39, Step 4 to afford methyl 4-(3-((4-(tert-butoxycarbonyl)piperazin-1-yl)methyl)-5-(trifluoromethyl)phenyl)morpholine-3-carboxylate as yellow oil. LCMS (ESI, m/z): 488 [M+H]+.

Step 3: Preparation of 4-(3-((4-(tert-butoxycarbonyl)piperazin-1-yl)methyl)-5-(trifluoromethyl)phenyl)morpholine-3-carboxylic acid

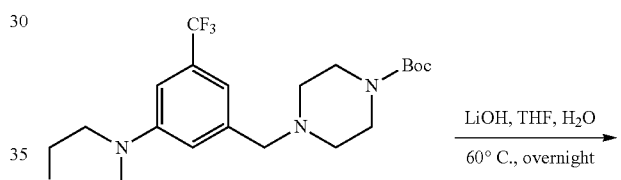

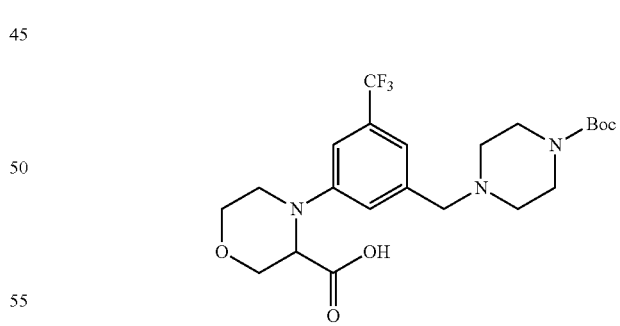

The title compound was prepared from 4-(3-((4-(tert-butoxycarbonyl)piperazin-1-yl)methyl)-5-(trifluoromethyl)phenyl)morpholine-3-carboxylate according to the representative procedure of Example 77, Step 2 to afford 4-(3-((4-(tert-butoxycarbonyl)piperazin-1-yl)methyl)-5-(trifluoromethyl)phenyl)morpholine-3-carboxylic acid as yellow oil. LCMS (ESI, m/z): 474 [M+H]+.

Step 4: Preparation of 4-(3-(piperazin-1-ylmethyl)-5-(trifluoromethyl)phenyl)morpholine-3-carboxylic acid

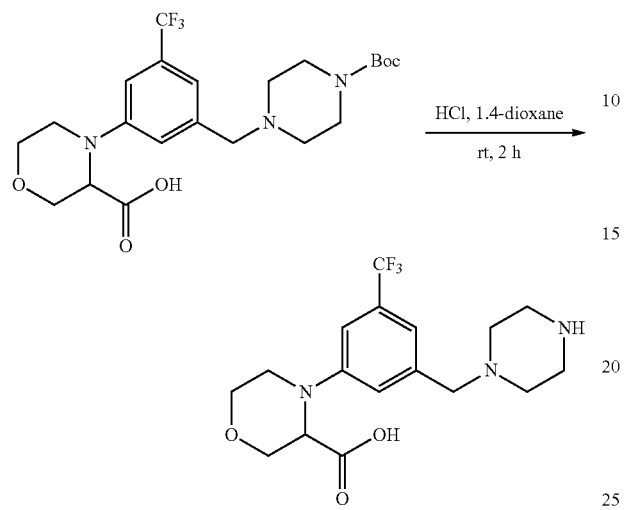

The title compound was prepared from 4-(3-((4-(tert-butoxycarbonyl)piperazin-1-yl)methyl)-5-(trifluoromethyl)phenyl)morpholine-3-carboxylic acid according to the representative procedure of Example 60, Step 2 to afford 4-(3-(piperazin-1-ylmethyl)-5-(trifluoromethyl)phenyl)morpholine-3-carboxylic acid as yellow oil. LCMS (ESI, m/z): 374 [M+H]⁺.

Step 5: Preparation of 4-(3-((4-(((1,1,1,3,3,3-hexafluoropropan-2-yl)oxy)carbonyl)piperazin-1-yl)methyl)-5-(trifluoromethyl)phenyl)morpholine-3-carboxylic acid

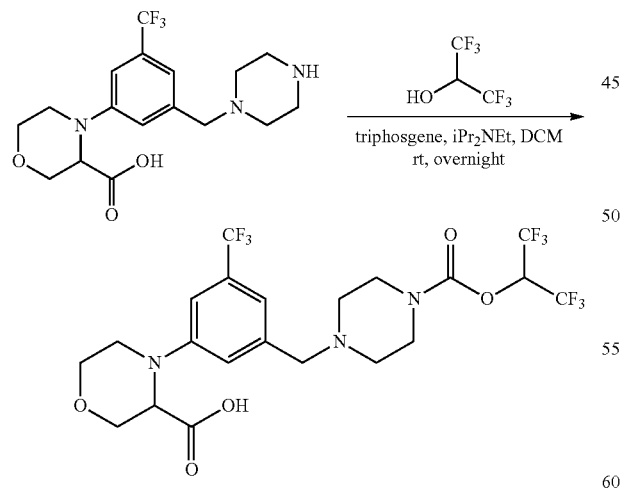

The title compound was prepared from 4-(3-(piperazin-1-ylmethyl)-5-(trifluoromethyl)phenyl)morpholine-3-carboxylic acid according to the representative procedure of Example 39, Step 6 to afford 4-(3-((4-(((1,1,1,3,3,3-hexafluoropropan-2-yl)oxy)carbonyl)piperazin-1-yl)methyl)-5-(trifluoromethyl)phenyl)morpholine-3-carbox-ylic acid as a white solid. ¹H NMR (300 MHz, Chloroform-d) δ 7.14 (s, 1H), 7.06 (s, 2H), 6.10-6.18 (m, 1H), 4.39-4.43 (m, 1H), 4.34 (s, 1H), 3.89-4.04 (m, 1H), 3.85-3.88 (m, 1H), 3.48-3.75 (m, 8H), 3.39-3.43 (m, 1H), 2.38-2.50 (m, 4H). LCMS (ESI, m/z): 568 [M+H]⁺.

Examples 96-101 are prepared using similar procedures as outlined in the preceding examples.

Example 96: 1,1,1,3,3,3-hexafluoropropan-2-yl 4-(2-(4-(1H-tetrazol-5-yl)piperidin-1-yl)-4-(trifluoromethyl)benzyl)piperazine-1-carboxylate

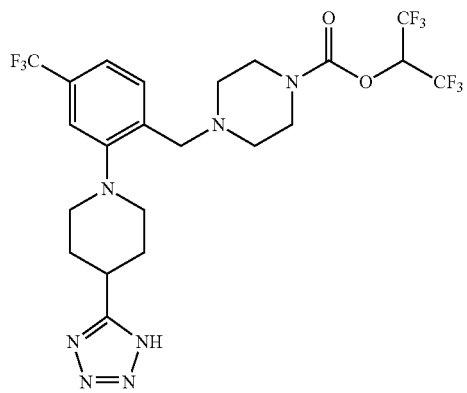 [SMILES: O=C(OC(C(F)(F)F)C(F)(F)F)N1CCN(Cc2ccc(C(F)(F)F)cc2N2CCC(c3nnn[nH]3)CC2)CC1]

Example 97: 4-(3-((4-(((1,1,1,3,3,3-hexafluoropropan-2-yl)oxy)carbonyl)piperazin-1-yl)methyl)-5-(trifluoromethyl)phenyl)morpholine-3-carboxylic acid

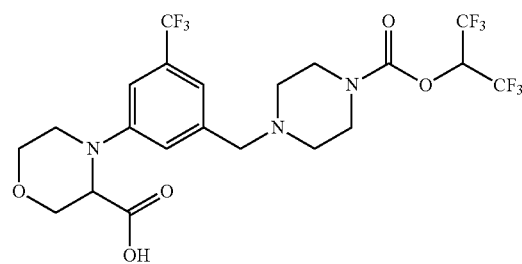 [SMILES: O=C(O)C1COCCN1c1cc(CN2CCN(C(=O)OC(C(F)(F)F)C(F)(F)F)CC2)cc(C(F)(F)F)c1]

Example 98: (R)-1-(2-((4-(((1,1,1,3,3,3-hexafluoropropan-2-yl)oxy)carbonyl)piperazin-1-yl)methyl)-5-(trifluoromethyl)phenyl)piperidine-3-carboxylic acid

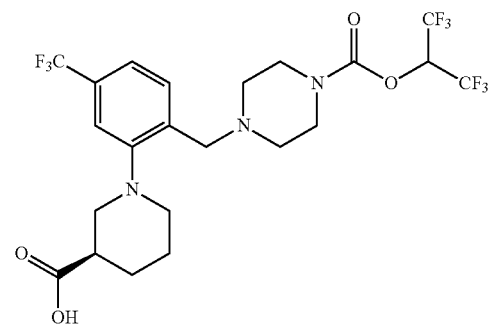 [SMILES: O=C(O)[C@@H]1CCCN(c2cc(C(F)(F)F)ccc2CN2CCN(C(=O)OC(C(F)(F)F)C(F)(F)F)CC2)C1]

Example 99: (S)-1-(2-((4-(((1,1,1,3,3,3-hexafluoropropan-2-yl)oxy)carbonyl)piperazin-1-yl)methyl)-5-(trifluoromethyl)phenyl)piperidine-3-carboxylic acid

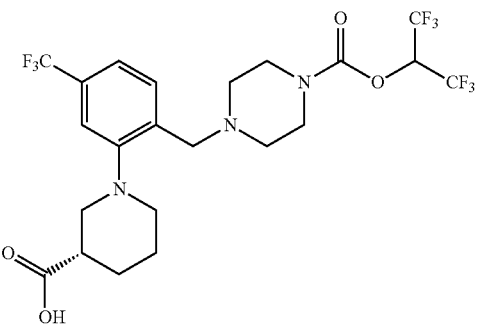 [SMILES: O=C(O)[C@H]1CCCN(c2cc(C(F)(F)F)ccc2CN2CCN(C(=O)OC(C(F)(F)F)C(F)(F)F)CC2)C1]

Example 100: (R)-1-(3-((4-(((1,1,1,3,3,3-hexafluoropropan-2-yl)oxy)carbonyl)piperazin-1-yl)methyl)-5-(trifluoromethyl)phenyl)piperidine-3-carboxylic acid

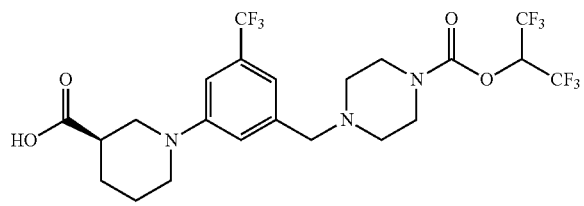 [SMILES: O=C(O)[C@@H]1CCCN(c2cc(CN3CCN(C(=O)OC(C(F)(F)F)C(F)(F)F)CC3)cc(C(F)(F)F)c2)C1]

Example 101: (S)-1-(3-((4-(((1,1,1,3,3,3-hexafluoropropan-2-yl)oxy)carbonyl)piperazin-1-yl)methyl)-5-(trifluoromethyl)phenyl)piperidine-3-carboxylic acid

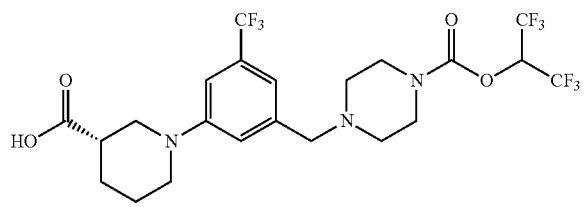 [SMILES: O=C(O)[C@H]1CCCN(c2cc(CN3CCN(C(=O)OC(C(F)(F)F)C(F)(F)F)CC3)cc(C(F)(F)F)c2)C1]

II. Biological Evaluation

Compounds are tested to assess their MAGL and serine hydrolase activity using the following in vitro and in vivo assays.

In Vitro Competitive Activity-Based Protein Profiling (Mouse).

Proteomes (mouse brain membrane fraction or cell lysates) (50 µL, 1.0 mg/mL total protein concentration) were preincubated with varying concentrations of inhibitors at 37° C. After 30 min, FP—Rh (1.0 µL, 50 µM in DMSO) was added and the mixture was incubated for another 30 min at 37° C. Reactions were quenched with SDS loading buffer (50 µL-4×) and run on SDS-PAGE. Following gel imaging, serine hydrolase activity was determined by measuring fluorescent intensity of gel bands corresponding to MAGL, ABHD6 and FAAH using ImageJ 1.43u software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44)

Compounds demonstrated activity in the assays described herein as indicated in the following tables (Tables 2 and 3).

TABLE 2

| Compd | Mouse ($IC_{50}$ value, nM) | | |
|---|---|---|---|
| | MAGL | FAAH | ABHD6 |
| 2 | *** | * | * |
| 3 | *** | * | * |
| 4 | *** | * | * |
| 5 | *** | * | ** |
| 7 | ** | * | ** |
| 8 | *** | * | *** |
| 9 | *** | * | ** |
| 10 | *** | * | ** |
| 11 | ** | * | ** |
| 12 | *** | * | ** |
| 13 | ** | * | ** |
| 14 | *** | * | *** |
| 15 | *** | * | ** |
| 16 | *** | * | ** |
| 17 | ** | * | ** |
| 18 | ** | * | ** |
| 19 | ** | * | ** |
| 20 | ** | * | ** |
| 21 | ** | * | ** |
| 22 | *** | * | ** |
| 23 | *** | * | * |
| 24 | ** | * | * |
| 25 | ** | * | * |
| 26 | *** | * | ** |
| 27 | *** | * | ** |
| 28 | ** | * | * |
| 29 | ** | * | * |
| 30 | *** | * | * |
| 31 | *** | * | * |
| 32 | *** | * | * |
| 33 | *** | * | ** |
| 34 | ** | * | * |
| 35 | *** | * | * |
| 36 | *** | * | ** |
| 37 | ** | * | * |
| 38 | *** | * | ** |
| 39 | *** | * | * |
| 40 | *** | * | * |
| 41 | *** | * | * |
| 42 | *** | * | ** |
| 43 | *** | * | * |
| 44 | *** | * | * |
| 45 | *** | * | ** |
| 46 | *** | * | * |
| 51 | *** | * | * |
| 52 | *** | * | ** |
| 53 | *** | * | * |
| 54 | *** | * | * |
| 55 | *** | * | * |
| 56 | *** | * | * |
| 57 | *** | * | * |
| 58 | *** | * | * |
| 59 | *** | * | * |
| 60 | *** | * | * |
| 61 | *** | * | * |
| 62 | ** | * | * |
| 63 | *** | * | ** |
| 64 | ** | * | * |

TABLE 2-continued

| Compd | Mouse (IC$_{50}$ value, nM) | | |
|---|---|---|---|
| | MAGL | FAAH | ABHD6 |
| 65 | *** | * | * |
| 66 | ** | * | * |
| 67 | ** | * | * |
| 68 | ** | * | * |
| 69 | *** | * | * |
| 70 | *** | * | ** |
| 71 | *** | * | * |
| 72 | *** | * | ** |
| 73 | *** | * | ** |
| 74 | *** | * | * |
| 75 | *** | * | * |
| 76 | *** | * | * |
| 77 | ** | * | * |
| 78 | *** | * | ** |
| 79 | *** | * | *** |
| 80 | *** | * | ** |
| 81 | ** | * | ** |
| 82 | *** | * | ** |
| 83 | *** | * | ** |
| 84 | *** | * | *** |
| 85 | ** | * | ** |
| 86 | ** | * | ** |
| 87 | *** | * | ** |
| 88 | ** | * | ** |
| 89 | ** | * | *** |
| 90 | *** | * | ** |
| 91 | ** | * | ** |
| 92 | *** | * | * |
| 93 | *** | * | ** |
| 94 | ** | * | *** |

*** is less than 100 nM;
** is between 1000 and 100 nM;
* is greater than 1000 nM

TABLE 3

| Compd | % Inhibition at 1 µM | | | % Inhibition at 5 mg/kg | | |
|---|---|---|---|---|---|---|
| | MAGL | FAAH | ABHD6 | MAGL | FAAH | ABHD6 |
| 3 | | | | ### | # | # |
| 4 | ### | # | # | ### | # | # |
| 7 | ### | # | ### | | | |
| 8 | ### | # | ### | | | |
| 9 | ### | # | ### | | | |
| 10 | ### | # | ### | | | |
| 11 | ### | # | ## | | | |
| 12 | ### | # | ### | | | |
| 13 | ### | # | ### | | | |
| 14 | ### | # | ### | | | |
| 15 | ### | # | ### | | | |
| 16 | ### | # | ### | ### | # | ## |
| 17 | ### | # | ### | | | |
| 18 | ### | # | ### | | | |
| 19 | ### | # | ### | | | |
| 20 | ### | # | ### | | | |
| 21 | ### | # | ### | | | |
| 22 | ### | # | ### | | | |
| 23 | ### | # | # | ### | # | # |
| 24 | ### | # | # | | | |
| 25 | ### | # | # | | | |
| 26 | ### | # | ### | ### | # | ### |
| 27 | ### | # | ## | | | |
| 28 | ### | # | # | | | |
| 29 | ### | # | # | | | |
| 30 | | | | ### | # | # |
| 31 | ### | # | # | ## | # | # |
| 32 | ### | # | # | # | # | # |
| 33 | ### | # | ### | ### | # | ### |
| 34 | ### | # | # | | | |
| 35 | ### | # | # | ### | # | # |
| 36 | ### | # | ### | | | |
| 37 | ### | # | # | | | |
| 38 | ### | # | # | | | |
| 39 | ### | # | ## | ### | # | ## |
| 40 | ### | # | # | ### | # | # |
| 41 | ### | # | ## | ### | # | # |
| 42 | ### | # | ## | ### | # | # |
| 43 | ### | # | # | ## | # | # |
| 44 | ### | # | # | # | # | # |
| 45 | ### | # | ### | ## | # | # |
| 46 | ### | ## | ## | | | |
| 47 | ### | # | # | | | |
| 48 | ## | # | # | | | |
| 49 | ## | # | # | | | |
| 50 | # | # | # | | | |
| 51 | ### | # | # | ### | # | # |
| 52 | ### | # | ### | | | |
| 53 | ### | # | # | ### | # | # |
| 54 | ### | # | # | ### | # | # |
| 55 | ### | # | # | ### | # | # |
| 56 | ### | # | # | ### | # | # |
| 57 | ### | # | # | ### | # | # |
| 58 | ### | # | # | ### | # | # |
| 59 | ### | # | # | ### | # | # |
| 60 | ### | # | # | ### | # | # |
| 61 | ### | # | # | ### | # | # |
| 62 | ### | # | # | | | |
| 63 | ### | # | ### | | | |
| 64 | ### | # | # | | | |
| 65 | ### | # | ## | # | # | # |
| 66 | ### | # | ## | | | |
| 67 | ### | # | # | | | |
| 68 | ### | # | # | | | |
| 69 | ### | # | # | | | |
| 70 | ### | # | ### | | | |
| 71 | ### | # | # | ### | # | # |
| 72 | ### | # | ### | | | |
| 73 | ### | # | ### | | | |
| 74 | ### | # | # | ## | # | # |
| 75 | ### | # | # | # | # | # |
| 76 | ### | # | ### | | | |
| 77 | ### | # | ### | | | |
| 78 | ### | # | ### | | | |
| 79 | ### | # | ### | | | |
| 80 | ### | # | ## | | | |
| 81 | ### | # | ### | | | |
| 82 | ### | # | ### | | | |
| 83 | ### | # | # | | | |
| 84 | ### | # | ### | | | |
| 85 | ## | # | ### | | | |
| 86 | ### | # | ## | ### | # | ### |
| 87 | ### | # | ### | | | |
| 88 | ### | # | ## | | | |
| 89 | ### | # | ### | | | |
| 90 | ### | # | ### | | | |
| 91 | ### | # | ### | | | |
| 92 | ### | # | # | | | |
| 93 | ### | # | ### | | | |
| 94 | ## | # | ### | | | | is ≥75%;
## is between 25 and 75%;
is ≤25

We claim:

1. A method of treating pain in a patient in need thereof, comprising administering to the patient a therapeutically effective amount of a compound of Formula (I), or a solvate, hydrate, N-oxide, stereoisomer, or pharmaceutically acceptable salt thereof:

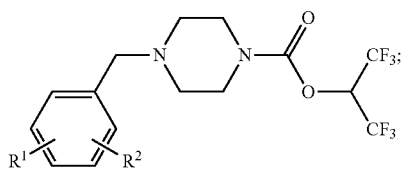

Formula (I)

wherein:
R¹ is halogen, —OR³, —CN, C$_{1-6}$ alkyl optionally substituted by halogen, or —C(O)OR⁹;
R² is —NR⁵R⁶;
R³ is selected from H, C$_{1-6}$alkyl, C$_{1-6}$ haloalkyl, and C$_{1-6}$ aminoalkyl;
R⁵ and R⁶, together with the nitrogen to which they are attached, form
  (i) a 4-6 membered saturated monocyclic heterocycle; or
  (ii) a 7-8 membered bridged heterocyclic ring optionally containing an additional O, N, or S;
  wherein the 4-6 membered saturated monocyclic heterocycle is substituted with one or two substituents independently selected from —C(O)OR⁹; and the 4-6 membered saturated monocyclic heterocycle optionally contains an additional O, N, or S; and
  the 7-8 membered bridged heterocyclic ring is optionally substituted with one or two substituents independently selected from halogen, oxo, and C$_{1-6}$ alkyl; and
each R⁹ is independently selected from H and C$_{1-6}$ alkyl.

2. The method of claim 1, wherein R¹ is halogen, OR³, or C$_{1-6}$ alkyl optionally substituted by halogen.

3. The method of claim 2, wherein R⁵ and R⁶, together with the nitrogen to which they are attached, form a 4-6 membered saturated monocyclic heterocycle, wherein:
  the 4-6 membered saturated monocyclic heterocycle is substituted with one —C(O)OR⁹; and the 4-6 membered saturated monocyclic heterocycle optionally contains an additional O, N, or S.

4. The method of claim 3, wherein R⁵ and R⁶, together with the nitrogen to which they are attached, form a 4-6 membered saturated monocyclic heterocycle wherein:
  the 4-6 membered saturated monocyclic heterocycle is substituted with one —C(O)OR⁹; and the 4-6 membered saturated monocyclic heterocycle is selected from azetidine, pyrrolidine, piperidine, and morpholine.

5. The method of claim 4, wherein R⁵ and R⁶, together with the nitrogen to which they are attached, form a 4-6 membered saturated monocyclic heterocycle substituted with one —C(O)OR⁹, wherein the 4-6 membered saturated monocyclic heterocycle is selected from pyrrolidine, piperidine, and morpholine.

6. The method of claim 5, wherein R⁵ and R⁶, together with the nitrogen to which they are attached, form a 4-6 membered saturated monocyclic heterocycle substituted with one —C(O)OR⁹, wherein the 4-6 membered saturated monocyclic heterocycle is pyrrolidine.

7. The method of claim 5, wherein R⁵ and R⁶, together with the nitrogen to which they are attached, form a 4-6 membered saturated monocyclic heterocycle substituted with one —C(O)OR⁹, wherein the 4-6 membered saturated monocyclic heterocycle is piperidine.

8. The method of claim 5, wherein R⁵ and R⁶, together with the nitrogen to which they are attached, form a 4-6 membered saturated monocyclic heterocycle substituted with one —C(O)OR⁹, wherein the 4-6 membered saturated monocyclic heterocycle is morpholine.

9. The method of claim 5, wherein R¹ is halogen, —CH₃, —CF₃, —OCH₃, or —OCF₃.

10. The method of claim 1, wherein the compound is

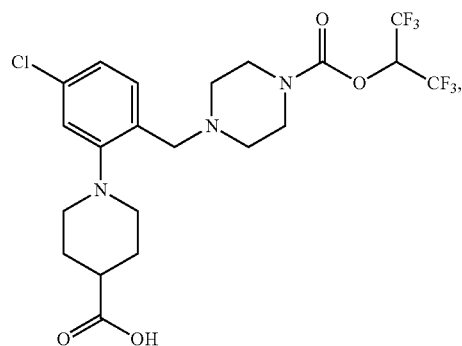 [SMILES: O=C(O)C1CCN(c2cc(Cl)ccc2CN2CCN(C(=O)OC(C(F)(F)F)C(F)(F)F)CC2)CC1]

or a solvate, hydrate, N-oxide, or pharmaceutically acceptable salt thereof.

11. The method of claim 1, wherein the compound is

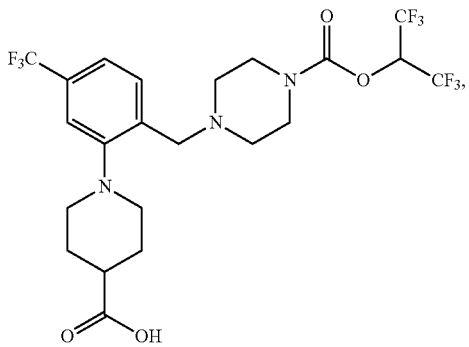 [SMILES: O=C(O)C1CCN(c2cc(C(F)(F)F)ccc2CN2CCN(C(=O)OC(C(F)(F)F)C(F)(F)F)CC2)CC1]

or a solvate, hydrate, N-oxide, or pharmaceutically acceptable salt thereof.

12. The method of claim 1, wherein the compound is

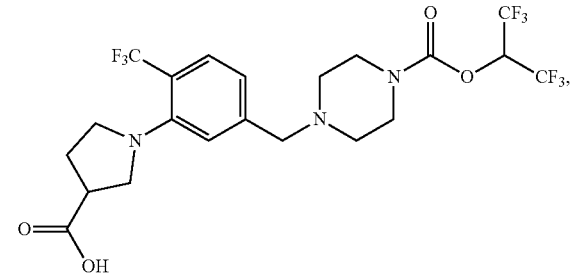 [SMILES: O=C(O)C1CCN(c2cc(CN3CCN(C(=O)OC(C(F)(F)F)C(F)(F)F)CC3)ccc2C(F)(F)F)C1]

or a solvate, hydrate, N-oxide, stereoisomer, or pharmaceutically acceptable salt thereof.

13. The method of claim 1, wherein the compound is
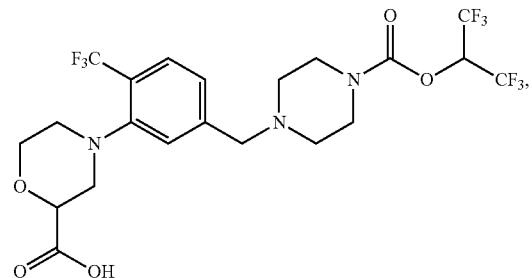 [SMILES: O=C(O)C1CN(c2cc(CN3CCN(C(=O)OC(C(F)(F)F)C(F)(F)F)CC3)ccc2C(F)(F)F)CCO1]
or a solvate, hydrate, N-oxide, stereoisomer, or pharmaceutically acceptable salt thereof.
14. A method of treating pain in a patient in need thereof, comprising administering to the patient a therapeutically effective amount of a compound selected from:
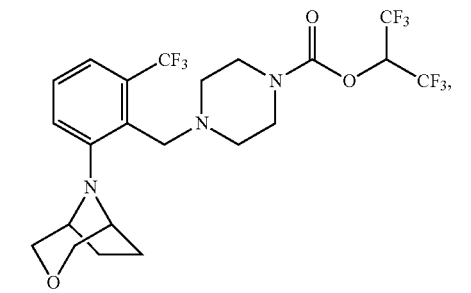
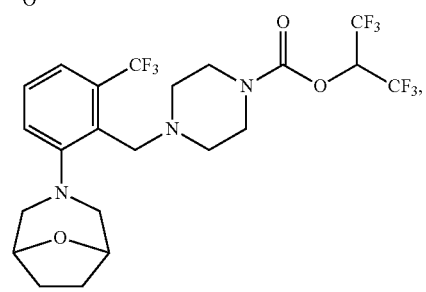
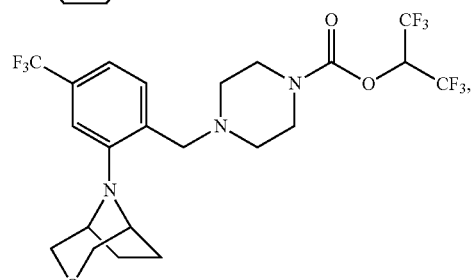
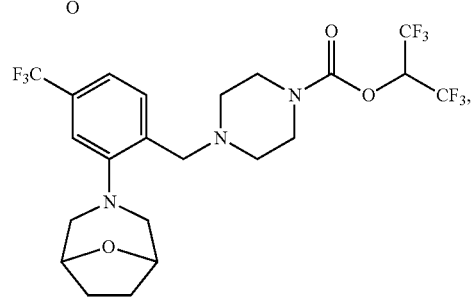
-continued
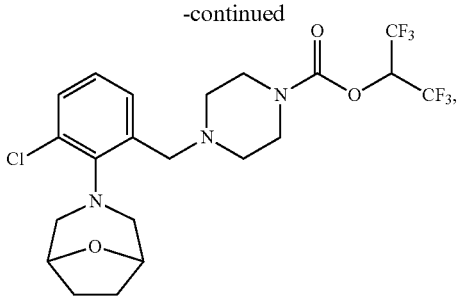
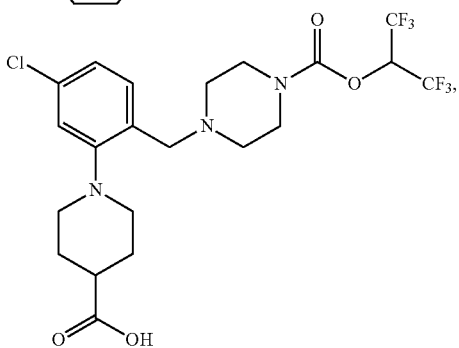
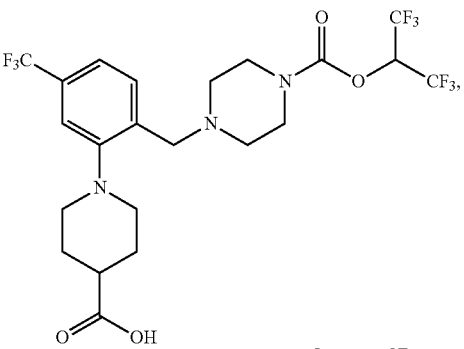
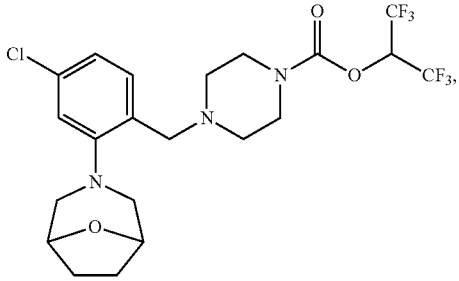
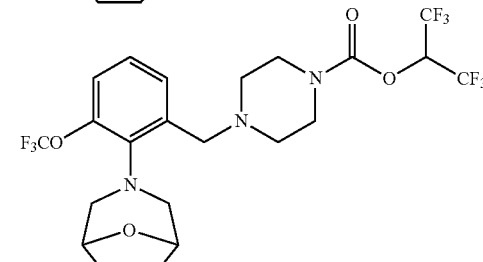
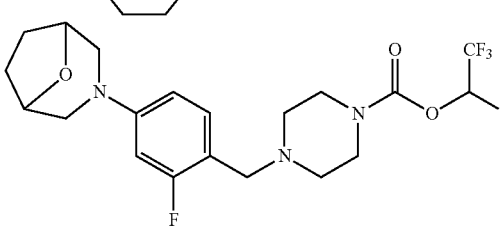

197
-continued
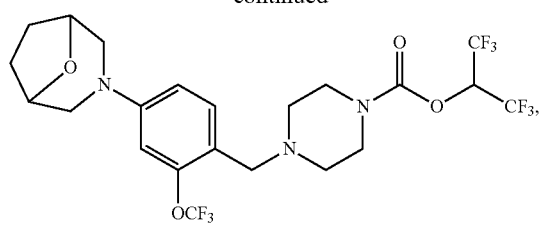
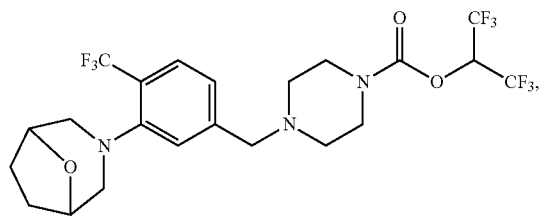
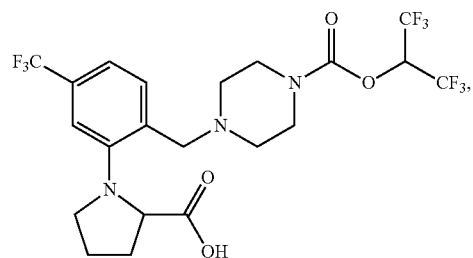
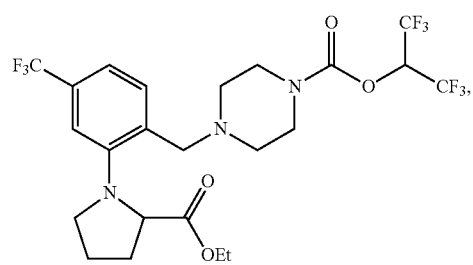
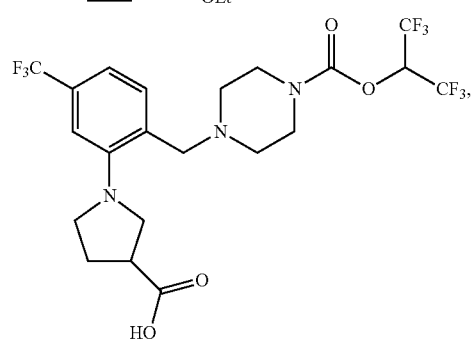
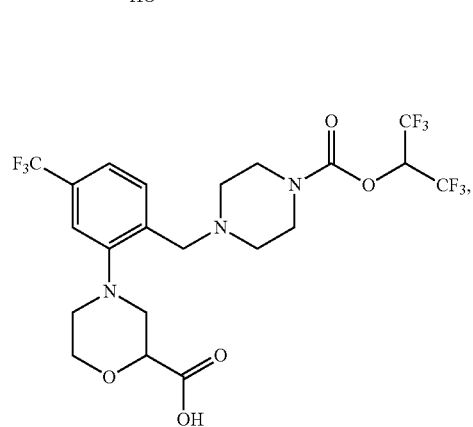
198
-continued
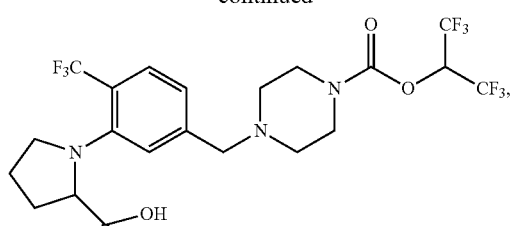
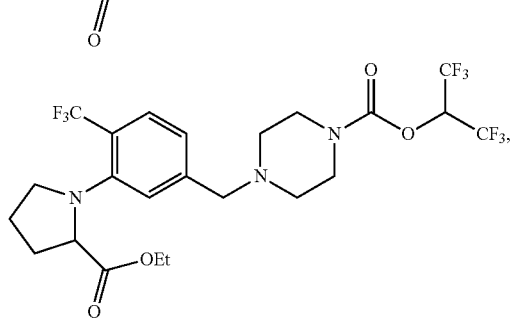
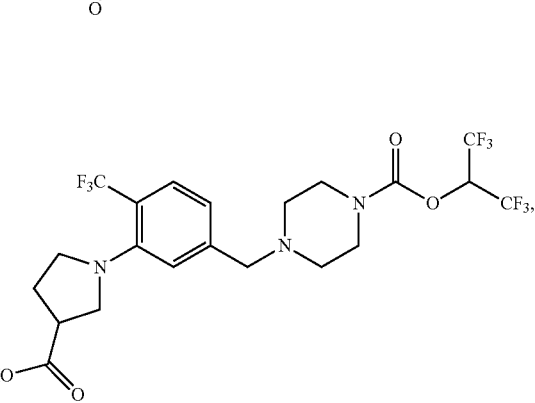
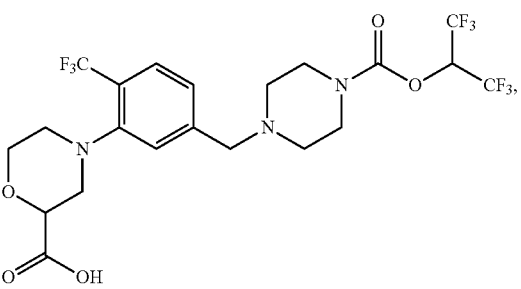
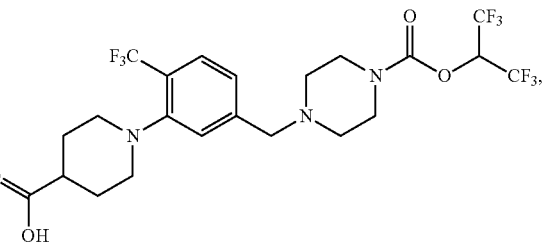
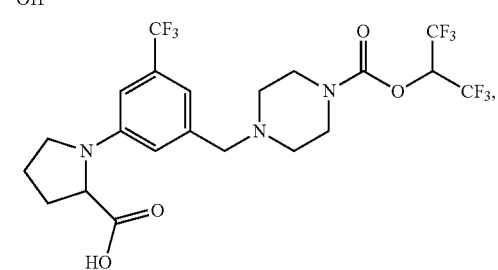

-continued
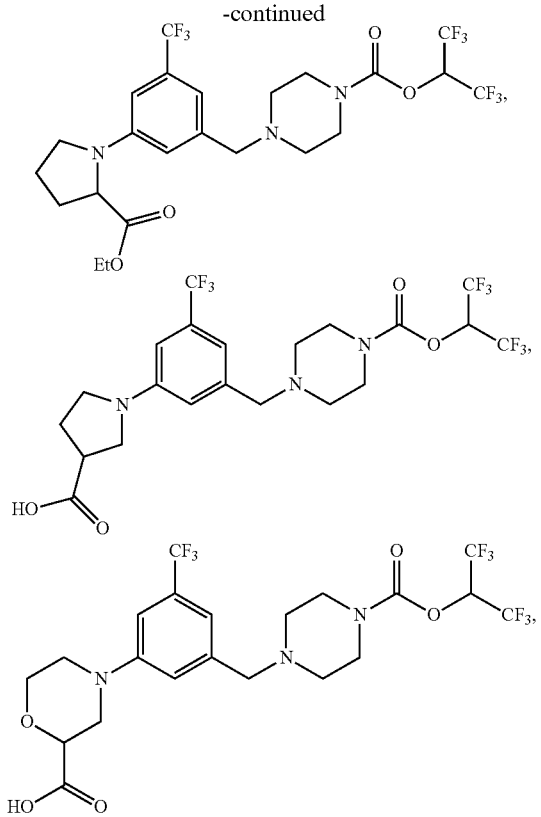
-continued
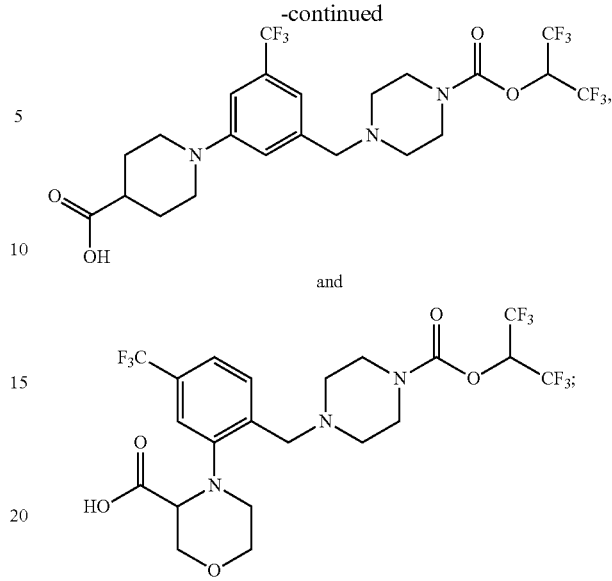
or a solvate, hydrate, N-oxide, stereoisomer, or a pharmaceutically acceptable salt thereof.
15. The method of claim 1, wherein the pain is neuropathic pain.
16. The method of claim 14, wherein the pain is neuropathic pain.
* * * * *